United States Patent [19]
Cochran et al.

[11] Patent Number: 5,223,424
[45] Date of Patent: Jun. 29, 1993

[54] ATTENUATED HERPESVIRUSES AND HERPESVIRUSES WHICH INCLUDE FOREIGN DNA ENCODING AN AMINO ACID SEQUENCE

[75] Inventors: Mark D. Cochran, Carlsbad; Christina H. Chiang; Richard D. MacDonald, both of San Diego, Calif.

[73] Assignee: Prutech Research And Development, San Jose, Calif. ; a part interest

[21] Appl. No.: 225,032

[22] Filed: Jul. 27, 1988

Related U.S. Application Data

[63] Continuation-in-part of Ser. No. 78,519, Jul. 27, 1987, abandoned, and a continuation-in-part of Ser. No. 933,107, Nov. 20, 1986, abandoned, and a continuation-in-part of Ser. No. 902,887, Sep. 2, 1986, abandoned, and a continuation-in-part of Ser. No. 887,140, Jul. 17, 1986, abandoned, and a continuation-in-part of Ser. No. 823,102, Jan. 27, 1986, Pat. No. 5,068,192, and a continuation-in-part of Ser. No. 773,430, Sep. 6, 1985, Pat. No. 4,877,737.

[51] Int. Cl.$^5$ .............. C12N 7/04; C12N 7/01; C12N 15/86
[52] U.S. Cl. .................. 435/236; 435/235.1; 435/320.1
[58] Field of Search .............. 435/320.1, 235.1

[56] References Cited

U.S. PATENT DOCUMENTS

| | | | |
|---|---|---|---|
| 4,680,176 | 7/1987 | Berns et al. | 424/89 |
| 4,999,296 | 3/1991 | Kit et al. | 435/235.1 |

*Primary Examiner*—Richard A. Schwartz
*Assistant Examiner*—Philip W. Carter
*Attorney, Agent, or Firm*—John P. White

[57] ABSTRACT

The present invention provides a recombinant fusion protein comprising an antigenic amino acid sequence fused to at least a portion of the gpX glycoprotein from pseudorabies virus. Such a protein may be formulated into a vaccine and delivered to an animal using a live herpesvirus vector adapted to express the fusion protein.

7 Claims, 82 Drawing Sheets

Figure 10A

```
      PstI
  1   CTGCAGGGGG  GGGGGGGGGG  GGGGGGTTTA  AAAGAGAGAA  TTTCCGTTTG  GCTATCGGAT
                                  DraI                               EcoRV
 61   AGCTCCTTTT  AATGTATGGT  ATTGAATATA  CCAAAGTTCT  AACTTTTTTG  ATATCGCTTG
                  METTyrGly-  IleGluTyrT- hrThrValLe- uThrPheLeu- IleSer.....

121   TATTTGTCAA  TTATATATTG  AAATCAGTTA  CTAGAACAAT  GGACTTTATC  ATTTATAGAT
181   TCTTATTGGT  TATAGTCGTA  CTTGCACCGC  TCATTAAAGC  TCAAAATTAC  GGAATTAATT
                                                           EcoRI
241   TACCAATAAC  TGGATCTATG  GATACGCCAT  ATATGAATTC  AACTACAAGT  GAAACATTTT
301   TGACTTCGAC  ATTATGTCTA  TATTATCCAA  ATGAAGCAGC  TACAGAAATT  GCAGATACAA
361   AATGGACAGA  AACATTGTCG  CAGTTGTTTT  TAACAAAAGG  ATGGCCAACA  GGGTCAGTTT

DraI
421   ATTTTAAAGG  ATATGCAGAT  ATTGCGTCAT  TTTCTGTAGA  ACCGCAGTTA  TACTGCGACT
481   ATAATATTGT  ACTAATGAAA  TATGATGGAA  ATTTACAGTT  AGACATGTCT  GAATTGGCTG
541   ATTTAATATT  GAATGAATGG  CTATGTAATC  CAATGGATAT  AATGCTATAT  TATTATCAGC
```

Figure 10B

```
                                    EcoRV
 601  AAACAGATGA  AGCTAATAAA  TGGATATCAA  TGGGTACATC  ATGTACGATT  AAAGTATGTC
 661  CTCTAAATAC  GCAGACTCTC  GGGATAGGAT  GTTCGACTAC  AGACATAAAT  TCATTTGAAA
 721  CAGTGGCCAA  TGCAGAGAAA  TTAGCTATAA  CTGATGTTGT  CGATGGAGTC  AATCATAAAT
 781  TAGACGTAAC  AACGAGTACA  TGTACTATAA  GAAATTGTAA  AAAACTTGGA  CCAAGAGAAA
 841  ATGTCGCTGT  AATTCAGGTA  GGAGGTCCAA  ACATACTCGA  CATAACAGCT  GATCCAACAA
 901  CTGCACCACA  AACTGAAAGA  ATGATGCGTA  TAAATTGGAA  GAGATGGTGG  CAAGTCTTTT
 961  ATACAATAGT  TGATTATGTC  AATCAAATTG  TACAAGTCAT  GTCCAAGCGA  TCACGCTCCT
                                            XbaI
1021  TAGATTCTGC  TGCCTTTTAT  TACCGAGTCT  AGATATATCT  TAGATTAGAA  TTGTATGATG
      ...SerAl-  aAlaPheTyr-  TyrArgVal----
        PstI
1081  TGACCTGCAG
```

Figure 11A

```
  1  CTGATGAAAA ATTCATAAAA GAAACTGAAC ACGCAAAAGA CTACGGAGGT AAAATTGGAC
 61  ATTACTTCTT CAGAGCAAAG CGTGCCTTTG CTCCAAAACT CTCAGAAACA GACTCACCAA
121  CTACATCTCA ACAACCAGAG GTAAGAAGAT CGCCGAGAAA ACACCCAGGG TCTAAACCAC
181  CAGGAAAAAG ACCTGCTCCA AGACATATTT TTATAAACTT AGCTAAAAAA AAAGCTAAAG
241  GGACATCTAA TACAAACTCT AACTCAATGA GTGAAAATGT GGAACAACAC AACCCTATTA
                                     METS-erGluAsnVa-lGluGlnHis AsnPro.....

301  ATGCAGGCAC TGAATTGTCT GCAACACGGAA ATGAATCTGG GGGTGGGGGC GGCGGTGGCG
                                          AccI
361  GGGTAGGGG  TGCTGGGGGG GTTGGTGTGT CTACAGGTAG TTTCAATAAT CAAACAGAAT
421  TTCAATACTT GGGGAGGGC  TTGGTTAGAA TCACTGCACA CGCATCAAGA CTCATACATC

RsaI
481  TAAATATGCC AGAACACGAA ACATACAAAA GAATACATGT ACTAAATTCA GAATCAGGGG

RsaI
541  TGGCGGGACA AATGGTACAA GACGATGCAC ACACACAAAT GGTAACACCT TGGTCACTAA
601  TAGATCGTAA CGCATGGGGA GTGTGGTTCA ATCCAGCGGA CTGGCAGTTA ATATCCAACA

RsaI
661  ACATGACAGA AATAAACTTA GTTAGTTTTG AACAAGAAAT ATTCAATGTA GTACTTAAAA
721  CAATTACAGA ATCAGCAACC TCACCACCAT CCAAAATATA TAATAATGAT CTAACTGCAA
781  GCTTAATGGT CGCACTGAC  ACCAATAACA CACTTCCATA CACCACCAGCA GCACCTAGAA
841  GTGAAACACT TGGTTTTTAT CCATGGTTAC CTACAAAACC AACTCAATAC AGATATTACC
901  TATCATGCAT CAGAAACCTA AATCCACCAA CATACACTGG ACAATCACAA CAAATAACAG
                                                                   RsaI
```

Figure 11B

```
 961  ACTCAATACA AACAGGACTA CACAGTGACA TTATGTTCTA CACAATAGAA AATGCAGTAC
1021  CAATTCATCT TCTAAGAACT GGAGATGAAT TCTCCACAGG AATATATCAC TTTGACACAA
1081  AACCATTAAA ATTAACTCAC TCATGGCAAA CAAACAGATC TCTAGGACTG CCTCCAAAAC
1141  TACTAACTGA ACCTACCACA GAAGGAGACC AACACCCAGG AACACTACCA GCAGCTAACA
1201  CAAGAAAAGG TTATCACCAA ACAATTAATA ATAGCTACAC AGAAGCAACA GCACTTAGGC
1261  CAGCTCAGGT AGGATATAAT ACACCATACA TGAATTTTGA CTACTCCAAT GGTGGACCAT
1321  TTCTAACTCC TATAGTACCA ACAGCAGACA CACAATATTA TGATGATGAA CCAAATGGTG
1381  CTATAAGATT TACAATGGGT TACCAACATG CACACTTAAC CACATCTTCA CAAGAGCTAG
1441  AAGATACAC ATTCAATCCA CAAAGTAAAT GTGGAAGAGC TCCAAAGCAA CAATTTAATC
1501  AACAGGCACC ACTAAACCTA GAAAATACAA ATAATGGAAC ACTTTTACCT TCAGATCCAA
1561  TAGGAGGGAA ATCTAACAAG CATTTCATGA ATACACTCAA TACATATGA CCATTAACAG
1621  CACTAAACAA TACTGCACCT GTATTCCAA ATGGTCAAAT ATGGGATAAA GAACTTGATA
1681  CAGATCTAAA ACCTAGACTA CATGTTACAG CTCCATTTGT TTGTAAAAAC AATCCACCAG
1741  GACAACTATT TGTAAAAATA GCACCAAACC TAACAGATGA TTTCAATGCT GACTCTCCTC
1801  AACAACCTAG AATAATAACT TTTGGTGGAA AGGAACACTA ACATTCACAG
1861  CAAAAATGAG ATCCAGTAAT ATGTGGAACC CTATTCAACA ACACACAACA ACAGCAGAAA
1921  ACATTCGTAA ATATATTCCT ACAAATATTG GTGGTATAAA AATGTTTCCA GAATATTCAC
1981  AACTTATACC AAGAAAATTA TACTAGAAAT AACTCTGTAA ATAAAAACTC AGTTACTTGG
      ..LeuIlePr-oArgLysLeu Tyr---
                 Rsal
2041  TTAATCATGT ACTACTATCA TG
```

BamHI fragments

BamHI #16

FIG. 22A

| FIGURE 22A |
| FIGURE 22B |
| FIGURE 22C |
| FIGURE 22D |
| FIGURE 22E |

```
GGGTGTGTCTCGAACGGTGTAATCTCTACAAGTGAATTACCTGATGCCATTACTAC
TAATGTCGTAAGTATACTCAGTGTGTGTCAATACATTGTACTACTACACACAAATG
CGTGTATTCATTAGGAGCTCCTGCTCCTGGTCGTGTACTGTATTAAGAAGATGGT
TACCAGATGATCGCCATATGTCTTGATAATGCTTGAGGATTAGCTTCAGTGTTAC
AGGTGATTGTACTGTCTTTACATTGAAGATAAGTTTCTGATTTATATGATGGCTCC
ACAAATCAATGACGGTGAAAACACGTCTGTTCTTACTATATAAATGTTCATTAAAG
AGAAACTGTCACTGTGATCCTGTCCCATTAAATCACGGAATTTGTTGGAATAAAGATTTATGA
ATTGATTCAAAGATTTAACTACTTGGACTGTATTGTTAACACGTCATCATCAGAAGGCTTT
CTGATTGGTATTAACTACTTGGAGAAACTCTACATATGCCTGCAAATGGCATGCCA
ATTATATATTTTGGAGAACTCTACAATTATGCTCATCACATAACTCAGTCGTCCTAATT
CAAGTCGTTGTAACAAGCCACTTATTGCTTAAGAAAAGAATTGAATGAATGTCATTCGA
TTACTAAGGAAGGGTAGTTGCTCATTGAAATAATAAGTTACTAACTTGGTTACCACTTCGTTA
ACACCACCATGAAAATTATTGTCCTGTAATCCCATTGATTTATGAGACAATTTCCTTGT
METLysLysLeuPheVal..........

TCTAAATTGACTAATAGAACTATAGGTAACCATTGAAACCTTCCTTCTAAATTATAGTA
GTAGGTTATCACCTAATTCAGATGCGTGTTAGTGTGTCATTATTTCCTACTACTTGGTTAATTG
CATTCGCAATAATAGTAGTGCCTTTATGCCATTGAAAATCTTAAGCATTGTATGGATTATGCT
ACAGAAAATATCACTTCGAATCACAAACAACGGTAGTCGTTAAACGGTTAATGGATACCCATCA
```

FIGURE 22B

```
CAGTTACAACAACCCGCAATTTTAATTCTGCTGAAGGTGCTATTATATGCATTTGCAAGGGCTCACCACC
TACTACCACCAGAATCTAGTTGACTTGCAATTGGGGTAGTGAGTGCAGGTTAAACCATAAGTTCCCT
ATATGTCCTTCTAATTCAGAGGCAAATTGTGTAATATGCTAATGCTGTATGCCTACAATGGTTTGCAGATGCGG
TTGTTGCCTTATTTACATGGTCTGCTAGTTACCGTATTAGTTGTGAAAATCAATGGTCTGGCACTGTTACACT
TGGTGATATGCGTCCGACTACATTAGAACCGCTGGCACGTTTGTAGACCTTGTGGTTTAATCCTGTT
TATGATGTCAGTTATTATTAGAGTAATAAAAATGTACTACCGTAGTTCCAATTGCACTGATCAAT
GCGCTAGTTATGTGGCTAATGTTTTTACTACACAGCCAGGAGGCTTTATACCATCAGATTTAGTTTAA
TAATTGGTTCCTTCTAACTAATAGCTCCACGTTGGTTAGTGGTTAAATTAGTTACCAAACAGCCGTTATTA
GTTAATGCTTATGGCCAGTCCCTGCTGTTTTAAATAACACTTCTACATTTGTTTTGAAGGTGCTGGCT
TTGATCAATGTAATGTAATCAGGTAAGGGTGCCACAGTGTTTCATTGAACAACGGGTGGTCACTCTTGAAATC
AAATGTACAATCAGTGAGTGATACAGTGACTCGAGCTTTTATGCCACAGTCTCTTACGTATCTAGAACATTACCACCTAG
TCATGTTATATGATAATCAGTGAGTGATACAGTGACTCGAGCTATATGTTACAATTTCTTTAGCACATTT
ATGGACCACCGTACTGTTACTGTATATGGGGCCAGTTGGTGACCATTGGTGATAGTGACGTTTTCTGACAATAGCTTACACAT
TGTCAAGGAGATTGCTATTAGTAGTAAGTGGGGCCAGTTGGTGACCATTGGTGATAGTGACGTTTTCTGACAATAGCTTACACAT
CCTATTGATTGTATATCTTTTAATTGACATTGGTGATAGTGACGTTTTCTGACAATAGCTTACACAT
CGTACACTGAAGCATTAGTAGTACAAGTTGAAACACAGCTATTACAAGGTGACGTATTGTAATAGTTACGT
TAATAACATTAAATGCTCTCAACTTGCTCAATTTGAATAATGGATTTTATCCTGTTTCTTCAAGTGAA
GTTGGTCTTGTCAATAAGAGTCGTTGTGTTGTTACTACCTAGCTTTTACACACTACCTATTGTTAACATAACTA
TTGGTCTTGATCGTACGAAGCGTAGTGTTATGCTGTCAACCCATAGCCTCAACATTTTCAGTTTATGTTACATTACACTACC
AATGCGGATAACAACACCGATGTGTACTGTATTCGTTCTGACCAATTTCGTTCTGACCAATTTTCAGTTTATGTTCATTCTACTT
GCAAAGTGCTTATGGGGACAATGTTTTAAGCGAACTGCACGCGAACGTTTAGATGCCACAGCTGTTA
```

FIGURE 22C

```
TAAAAACTGGTACTGTGCCTTCTCATTTGATAAATTGAACAATTACTTAACTTTAACAAGTTCTGTTT
GTCGTTGAGTTCCTGTTGGTGCTAATTGTAAGTTTGATTGTAGCTGCCCGTACAAGAACCAATGATCAGGTT
GTTAGAAGTTTGTATGTAATATATGAAGAAGGAGACAACATAGTGGGTTGTACCGTCTGATATATAGTGGTT
TACACGATTGTCAGTGCTACACCTAGATTCCTGCACAGATTACAAATACTATATGTAGAACTGGTGTGG
TATTATTAGACAAACTAACAGGAGCTACTTAGTGCTTATATTACACATCACTATCAGGTGATTTGTTA
GGTTTTAAAAATGTAGTGATGGTGTCATCTCTGTAACGCCATGTGATGTAAGCGCACAAGCAGCTG
TTATTGATGGTACCATAGTTGGGCTATCACTTCACTCTATAAACAGTGAACTGTTAGTCTAACACATTGGAC
AACAACACCTAATTTTATACTACTCTATATAATACACATGATAGGACTCGTGGCACTGCAATTGAC
AGTAATGATGTTGATTGTGAACCTGTCATAACCTATTCTAACATAGGTGTTTTGTAAAATGGTGCTTTGG
TTTTTATTAACGTCACACATTCGATGGAGACGTCAACAATTAGCAATGTAAGTCACGATACCTAC
AACTTTACTATATCCGTGCAAGTGCAATATATTCAGGTTTACACTACACCAGTGTCAATAGACTGTTCA
AGATATGTTGTAATGGCAACCCTAGTGTAACAAATTGTTAACACATAGTTTCTGCATGTCAACTA
TTGAGCAAGCATTGCAATGGGTGCCAGACTTGAAACATGAAGTTGCTTCCATGTTATTTGTTTCTGAA
```

FIGURE 22D

```
ATGCCCTGAAATTGGCTTCTGTCGAAGATTGAATAGTTCGGGAACTTTAGATCCTATTTACAAAGAATGG
CCTAATATAGGTGGCCTCTTGGCTAGAGAAGTTCTAAATACATACTTCCGTCCGATAATAGCAAACGTAAGT
ATCGTTCAGCTATAGAGGACTGCTTTTGCTAAGGTTGTAACGTCTGGTTTAGTACAGTTGATGAAGA
TATAAACGTTGTACAGGTGGTTATGACATAGCTGACTTAGTATGTGCTCAATACTACAATGGCATCATG
GTGCTACCTGGTGTGCCTAATGCTGACAAATGACTATGTACACAGCATCCCTCGCAGGTGGTATATAT
TAGGTGCACTTGGTGAGGCGCCGTATACCTTTTGCCAGTAGCAGTTCAGCTAGACTTAATTATGT
TGCTCTACAAACTGATGTATTGAACAAAACCAGCAGATCCTGGCTAGTGCTTTCAATCAAGCTATTGGT
AACATTACACAGTTAAGGTTAATGTCTATACATCAAACTTCACGAGGTCTGCAACTGTTGC
TAAAGCATTGGCAAAGTGCAAGATGTTGTACAACATACAAGGGCAAGCTTTAAGCCACCTACAGTACA
ATTGCAAATAATTTCCAAGCCATTAGTAGTTCTATTAGTGACATTTATAATAGGCTTGATGAATTGAGT
GCTGATGCACAAGTTGACAGGCTTGACAGGAAGACTTACAGCACACTTCATTTGTGTCTCAGACTC
TAACCAGACAACAAGCCGAGTTAGGGCGAGTTAGGGCCAAAGACAACTGCCAAAGACAAGGTTAATGCGTTAGGTC
TCAGTCTCAGAGATTCGGATTCTGTGTGTTCACATAGTGCTATTACCAACGGCTTGTCGTTGTTTTCTGTAATCT
GGCATGATCTCTTTCACATAGTGCCACTTGTCGTTGTCCAGCTGACTTTGTTTCTGATTTCT
GTGCTTTAGATGGTGATCGCAATGTGCCACTTGTCGTTAAAGATGTCCAGCTGACTTTGTTTCTGTAATCT
AGATGACAAGTTCTATTGAACCCCAGAACTGTATCAGCCTAGTGGCAACTAGTTCTGATTTGTT
CAAATTGAGGTGCGATGTGCTGTTGTTGTTAATGCAACTGTAAGTGATTTGCCTAGTATATACCTGATT
ATATTGATATTAATCAGACTGTTCAAGACATATTAGAAATTTAGACCAAATTTAGAGACTGTACCTGAGTT
```

FIGURE 22E

```
GACATTTGACATTTTTAACGCAACCTATTTAAACCTGACTGGTGAAATTGATGACTTAGAATTTAGTCA
GAAAAGCTACATAACACTACTGTAGAACTTGCCATTCTTATTGACAACATTAACAATACATTAGTCAATC
TTGAATGGCTCAATAGAATTGAAACCTATGTAAATGGCCTTGGCTTGTGTGGCTACTAATAGGCTTAG
TAGTAATATTTGCATACCATTACTGCTATTTTGCTGTTGTAGTACAGGTTGCTGTGGATGCATAGGTTG
.........ThrAlaIleLeuLeuLeu---

TTTAGGAAGTGTGTTGTCACTCTATATGCAGTAGAAGACAATTTGAAAATTACGAACCTATTGAAAAGTG
CACGTCCATTAAATTTAAATGTTAATTTTATTATCTGCTATAATAGCATTGTTAAGATGATGAA
TAAAGTCCTTAAGAACTAAACTTTCGAGTCATTACAGGTCCTGTATGGACATGCAAATCCATTAATACA
TCCGTAGATGCCTGACTTGACGAACTTGATGTGCATACTGCTGTAACTCTTAAGTAG
```

FIGURE 24A

| FIGURE 24A |
|---|
| FIGURE 24B |

```
AGGAACAAAGTTGTTCAACACAGCAGCAGCCAACAGACCCAAAGGCAGGCAGACACCGAACCCA
AATGGAAATATTGGAAACACACAACCAACAATGACAAAACAACCGAAACAACCGAGAGGCCAA
      MetGluTyrTrpLys..........
ACACAGTAGCAAGGTTACAAATATCATAATGTACACCTTCTGGACAATACATCAACAATATTAGTC
ATTTTTATAATGATATATTGACAAACTTAATTCAAGAGAACATCATAAATTAATGTGCAGAAATAA
GAAAGAATTCGCGGCAATAGACACCAAGATTCAGAGACTCAGAGTCATGTTGGAACCTCAATACAGTC
AGGAATAATACAAGACTTCTCACAAACTATCCAAAACTATCCAAACTATCCACTAACACAA
CAAATGTCAGATCTCAGAAAATTATCAATGATCTAACAAATAAAGAACATCAAGAAGTGCCAATAC
AGAGAATGACTACTTCATGATAGAGGGTATAGAAGGTCTCTGGAGGTGTACATCTGGTAA
CCCATCTCTAACAGTAGTCTAAGATAAGTAATAACCAGCGCCCAGGTTAATTAGCAACATCTACTACA
GTAATGGCTGTATTAGAATAGTCCATGTTAGCCAATCAATGTTAACTCTACCGCTTACACCTCTAATCTTA
TCACCCAGGCCTGTACCTGGTAATACAGAGTCTTAAATCAGATACTACAAATAGGGATAATAGAATAATTC
GGACCTAGTACCACTATTGCCACTAGTTTATCGTATGCCAACACCAAAGTTGATGAGAGATCCGATT
TCTCTGGCACTAACAGTAGTCCTGGTAATACAGATGTCTAACACACAAAGTTGATGAGAGATCCGATT
ATGCATCAACAGTAGTCTATTGAGGATATTGTCACTATTGCTACTGATCAGTAGGACCAGAATC
GTTTACAAATAATAATAAACCGTATCGATAAACCGTATCATCAGTAGACCGAGTGTAT
TATTTATATGGGTAAGTATTATCTTCTGCAAACACACAGAGACTTAGCATGAGCGAGACGTAAATAT
GTAATACAACTCGTTGTCCTGGCAAATACATGAGCAATGAGCATGAAAACGGAGACGGTAATAT
AAATAGGAGAATGGTAAACTCTATTATTGTTGTTGATAAAGCCATGATCAACTTTTATTAGTGACAGAATAT
TGGACTATTCCAATGAGCCAACAAGTTGGCACAGTTTACAGTTAGGGGTAATTACAGTGGACAGAATAT
ACATATACTACTAGATCCAACAAGTTGGCACAGTAAATTACAGTGGGGTAATTACAGATATTTCTGATTATAA
```

FIGURE 24A

```
TAATATAAGAATAAATTGGACTTGGAGCATAATGTACCATCACGGCCAGGAAATGATGAATGTCCATGGGGT
CATTCATGCCCAGACGATGTATAACAGGAGTTTACACTGCATATCCGCTAAACCCATGCGGGAGTG
TTGTATCATCAGTAATTCTTGACTCACAAAGTCTAGAGAAACCCAATCATTACCTACTCAACAGCTAC
AATAGAATAAATGAATTAGCTATATAACAGAACACTTCCAGCTGCATATACAACAAATTGTATC
ACACATTATGATAAAGGGTATTGTTTTCATATAGTAGAAATAAATCACAGAAGTTTGAATACGTTTCAAC
CTATGTTATTCAAACAGAAGTTCCAAAACTGCAGCTAAATGATCATCGCATATCGGATCGCCAAGATG
   .....ProLysAsnCysSer----

ACATTAAAGAGACCACCAGAGACAACACAGGAGATGATGCAAGATATAAAGGAATAAT
```

| FIGURE 27A |
| FIGURE 27B |
| FIGURE 27C |

```
CGATACGATCGGTCTGACCCCGGCCAGTCACCCCGGGACACGGCCGTTGTTCCAGGATAGAACT
CCTCCTTCTACACCCTATCATTGATCAGTAGGTCAGATCGTAGAGTCAGCAAACGATGACAAACCTG
                                              METThrAsn...

CAAGATCAACCCAACAGATTGTTCCGTTCATACGGAGCCTTCTGATCGAACAACCCGGACCCGCTCCA
TTCCGACGACACACCCTGAGAGCACACTCTCAGTCGATCTCGAGACCTCGACCTACAATTGACTGTGGGGA
CACAGGGTCAGGGCTAATTGTCTTTTCCCTGGATTCCGTGGCTCAATTGTGGGTCTCACTACACACTG
CAGAGCCAATGGGCTACAAGTTCGATCGAGGAACTACAGCCCAGAACCTACACCGGCCAGTACAACT
ACTGCAGGCTAGTGAGTGAGTCTCAAGCACACTCTCTGGCGTTTATGCACTAAA
CGGCACCATAAACGCCGTGACCTTCCAAGGAAGCCCTGAACTGAAACGTCTAGTAGGGAAGGGGTCACCGTCCTTG
ATGTCTGCAACAGCCAACATCATATGATCTTGGTATGTGACACAGCCTTGGACACGTTCCCAGTCAGATGATTAC
GCTTACCACCACTCATATGATCTTGGTATGTGACACAGCCTACACCATAACTGCAGCGATGATTAC
AAAAATGTAGCCACACATGTCACAACCAGGTGCGGTAACAATCACACTGTTCTCAGCCAACATTGATGCCATCA
CAATTCTCATCACAGTACCAGGTGCGGTAACAATCACACTGTTCTCAGCCAACATTGATGCCATCA
CAAGCCTCAGCGTTGGCGGAGAGCGTCTGTGTTTCGAACAAGCCGTCCAACAAGCCGGGCGCCACCAT
CTACCTAGCCTTTGATGGGACAACCAGGCGTGTGCCCGCAAACACTCCAGGCCTGGCCTGACGACC
GGCACCGACAACACCTTATGCCATTCAATTCTGTGATTCCAGGGATAACCCAGCCAATCACATCCA
TCAAACTGGAGATAGTGACCTCCAAAGTGCTGCAGGCCGATCAGATGTATGTCGGCAAGAGG
CAGCCCTAGCAGTGACGATCCATGGTGGGCAACTACTATCCCGTCCCGTCACGCTAGTGCCCTAC
```

FIGURE 27B

```
GAAAGAGTGGCAACAGGATCCGTCGTTACGGTCCGTCGGGGTGAGCTGAGCAACTTCGAGCTGATCCCAATCCTG
AACTAGCAAGAACCTGGTTACAGAATACGGCCGATTTGACCCAGGAGCCATGAACTACACAAATTGAT
ACTGAGTGAGAGGACCGTCTTGGCATCAAGACCGTCTGCCAACAAGGAGTACACTGACTTCGTGAA
TACTTCATCGAGGTGCCCGACCTCAACTCTCCCCTGAAGATTGCAGGAGCATTCGGCTTCAAAGACATAA
TCCCGGCCATAAGGAGGATAGCTGTGCCGGTGTCTCCACATTGTCCCGCTGCCGCTCCCCTAGCCCA
TGCAATTGGGGAAAAGCAAGGTGTAGACTACCTGCTGGGCGATGAGGCACAGGCTGCTTCAGAACTGCTCGAGCC
GCGTCAGGAAAAGCAAGGCTGCCTCAGGCCCGCATAAGGCAGCAGCTGACTCTCGCCGCCGACAAGGGGTACG
AGGTAGTCGGCGAATCTATTCCAGGTGCCCCAGAATCCCGTAGTCGACGATTCTTGACTTGCACCTGGGT
ACTCCGCGGTGCACACAACCTCGACTCGGTTGTTAAGAGAGGGTGCCACGCTATTCCTGTGGTTATTACG
ACAGTGGAAGACGCCATGACACCCAAAGCATTGAAACAGCAAAATGTTGCTGTCATTGAAGGCGTGCGAG
AAGACCTCCAACCTCCATCTCCAAAGAGATATCCTTCATAGCGAACTCTCTCTGACACAGAGTCTATGGATA
TGCTCCAGATGGGTACTCTCCACTGGAGACTACACCGTGTCCCAATAGATGGAAATCTAGCCATAG
GACGACAGCATTATGCTGTCCAAAGATCTCCATACCTCTATTGTGGGAAACAGTGGAAATCTAGCCATAG
CTTACATGGATGTGTTTCGACCCAAAGTCGCCATATGACCGGACTCTATGCTGCCATTGTCAATGCTGTGTGG
CGAGATTGAGAAGTAAGCTTTAGAAGCACCAGCTCGCCACTGCCACACCAGCCGACTTGGCCTTAAGTTGCT
GGTCCCGGAGCATTCGATGTAAACACCCCCTACCTCAACGTTCATCAACGTTTCCCTCACAATC
CACGCGGACTGGACAGGCTCCCCTACCTCAACCTCAACGCTTCATCCCAATGCAGGACGCCAGTACCA
CCTTGCCATGGCTGCATCAGAGTTCAAATGCCACTCTGCACTCAGTGTGTTCATGTGGCTGGAAGAGAATGGAAGCA
GCAGCCAACGTGGACCCACTATTCCAAATCCAGCGACCCGAACGCCCATCGAACGCCCATCGAATCGGATTG
TGACCGACATGCCAAGCTCGACCAAGTCGCAAGGGCCAAGTGCGAAATTTTTTGCAAACGC
ACCACAAGCAGGCAGGCCAAGTGCGAAGGGCCAAGTACGGGACCAGGCTCACGGAGGTGGAGGCTCGGGGC
```

FIGURE 27C

CCCACCAGAGGAAGCACAGAGGGAAAAAGACACACGGATCTCAAAGAAGATGGAGACATGGGCATCT
ACTTTGCAACACCAGAATGGGTAGCACTCAATGGGCACCGAGGGCCAGCTCAGCTAAAGTACGG
GCAGAACACAGAGAAATACCGGACCCAAACGAGGACTATCTAGACTGAGAGAAGAGCCGG
TTGGCATCAGAAGAACAAATCCTAAGGGCAGCTACGTCGATCTCAGGACACAGGCAGAGCCAC
CCCAAGCTTTCATAGAGAAGTTGCCAAAGTCTATGAAATCAACCATGGACGTGCCAAACCAAGAACA
GATGAAAGATCTGCTCTTGACTGCGATGGAGATGAAGCATCGCAATCCCAGGCGTCTACCAAGCCC
AAGCCAAACCCAATGCTCCAACACAGAGACCCCTGGTCGGGTGGGCCCTGATCAGGACCGTCTCTG
ATGAGGACCTTGAGTGAGGCTCCTGGAGTCTCCGACAACACCCGGCAGGTGTGACACAATTCGGCC
GluAspLeuGlu---

TTACAACATCCCAAATTGGATCCGTTCGGGGGTCCCC

```
1-GGATCCCGTCGAATGGAGGAGGATATTAATTCCGATTCCTAGGTATGCATAATCCGACCCC--60
   GGTACTCCGTATAGACCCGGCCACTCGGCCAACCCTCTACATTCTTTCGTTGCCTGGTAT
   TCGATTGGAATTGAACGTGACGTCAAGAGCGAAGTTGGACCATTCATCGTCTGAAGGGGG
   TCGACTATAGAGTCACACAAATTCTCCTGTATTGTTAAGGAATACGAATACTCTTCT
   CGGTCGCAGATTATATCAGTATTTGTGAGAAGAGTTGCCGGTGCGCTTCGGAGAACTA
301-GTGCTTTCAGTCGTCGTCGGTACAGCTGTCTTGTGGCGACAGTTGTAGATAATTCGGTCGTA-360
   GGCGAATTGGGCACCTCTGACAAAGGAACGCCATCGGCCGAAATGGAGAAGGGTTGAA
   GTTAGGATATATGGTTATGACGTTATGCCCACCCATGCCAGCGCAGTACGCGTAGAACGCGCATGT
   GACAGAAACTAGAAATATGCCCATCTCAGCGCGTAGAACAAGAGGTTTGCTGTAA
   TGGAAACCATATACTTGCGGTTCTCGAACAAGTTTCGATAGATGCGTAATATGGTATAA
601-ATGGTCTTTACCCGCCCGCAATAAACAACAAGTTATTGTTAATTCGAGTCCTCATTGTTTTC--660
   GACCGCTCAATAAACATCCGCCAGCATGGGCGATGCGCAGACCGATCTATCACGATAGTGGTTA
   AAAGAGCGTTCCGCCAAGTAAGCATCCCCGGAATAATGAAGCCCAGTACAGATTTCACGACTGGC
   TAGCACGCAAGTAAGCATCCCCGGAATAATGAAGCCCAGTACAGATTTCACGACTGGC
   TGCTGCCAATTGTTGACACCCTTATTAGTAGTAGCGCGAAATATGATACATGTAAACATGA
901-CATCGCAGCGAACTCGCGGCACCGATTATCATATCAAATTGTAGCCCTATAATTGACCACATCCAGCCAA--961
   TGCAATGCCAGTGCACTGGAATACATAGTGACGATAGCGACGAATTCCAAGACAAGCCCGTACATGCC
   GTTGTTGCTGGATGACAGTCCAATCGTGACGAATTTTAATGCCCCATATATTATGGAGCGC
   TTGTAATGACTGAAGCATGAACCCCATGGCATAACATAGAAATATTGACGAATAATGCC
   AATAATCAGCGGTTGTGTAAGCCCATGGCATAACATAGAAATATTGACGAATAATGCC
1201-TTTAGCTGCGTCAAACTATATACGTCTTTTCATAAGCATATCGGCACCGGGAGAAGG--1261
   GATTGTGTAACCATGTCCGAGACGAGAAGGGCGAAGTATAGTCCTCGCGCAATTGCG
   ATAATAGCAAGTGGATAATAATGTAGCGCTTGCATCTCTAGCGATATTTATAGCCAATAT
   TGTATAGACTGCAAGAAACCCCGCGAGAGGATTGGGTATGTTTGGTATTGTTATACCG
   AGTAATGTTCCGGTGAAGCATGAAAATCCGAAGTCAAGTCCCCTGCCGTT
1501-GAAATGCAGACATAGTTGTGGGATGTAATTATTGCCCCGAGCATAACACGCCAAA--1561
```

FIGURE 30B

```
     GATGTTACTTCGATTATCCGCAATGCAGTTTGTAAGTAGTATTACTGATGGCAAGCGC
     TCGTTATTGATCAGTGTTTCCGCAACGAAGCGATTATAGCAAATATAAACTGCCGGC
     TTGCCCACTAGCATAAGCGTTCCGAAGTCTTATCGTAAGTCGTGCAGCAACGTAGCG
     ATGAATCCGGCAATTACACATACCGTACAGTTCCGTAAGCTCTGTTTGATCGATAGC
1801-GGAATTAATGCCACTCACTACTACCGACACGGTAACAGTAACTGCAGCGATGCACACTAAGGAA-1861
     CATACACTGATCATCACTACCGTATACACCTTCTTGCCATTTGTCGATGTCCTCTCCC
     GCAGTGCATTGGCGATGTATAAGCACTTAGCCAGCTGTTATAAGTCTCAAGC
     GGAGCTGCAGATGTATAAGCTGTGTGGAGGACTCGCTGCTCCGGAAGCATATTTTCT
     TCTGCAAAGCTGCGCCGGCGTTTAGTTAACGTATGAGTGTCACCGATCTGTCGACCCGT
2101-GAAGGTTGGCCCAGCCCCACCTGCCCCTCTAACCAGGATGCCGGGTTTGTCTGGCATTTTAT-2161
     TGGGTATCCGCTCTGGTGTTTCCTTTGGGAAATATTCGTTGATGCGTTTGCTCGATT
     TTCTTGAAGTAGCCTGCGATACTCTCTCCAGTTCATCATATGTCATACAGTCTGTGTTACAA
     GCACCATCAACGCGGCCTTACTTCTCCAGATACTGAGTCCATCTACTACTGCAAACTTAT
     AACAGGAATGCCGTAGGACTTCCAATGCGTGTGCCCGAATACTAGCGGCGATCGC
2401-AAGTTGTATAAACCCCAGATCAACTCCCGACGTACCCGCCTTGATTTTATTGACGATAT-2461
     TTCTAAATGCACTAGTATCTTCCAATGCAACACAAAGGTTTACCACTTCCATAGCCG
     TTAAATAGTGTTTTTATTGCCTTCTTCTTCTGCATGCTACTACGAGAGCTAGGTAGC
     CGAGGTTGGAGGGTTGTAAGGATACTGAGTCATGGCAGTCCCATCTACTTGCAAACTTAT
     AACAGTACAAGCCTTCCAGTTTTAAAGAGAATACAAGTTC
2701-TTCGTGTTGCAGTTTTGAGTCGACGGCCTGATTTTGTCAATTGTTGTTGTTAGAG-2761
     AAAGGTAACATCGGGAGTTTTTGGGGAAAATTGTAGACCATTCCAGAGCTCATATT
     TAATGATTGTATTCGATACTGAACCACCGTCGGTCATGTATGTACGCTTGATTAAAT
     GCCTACATCGAGGCTCTCCCGCGAAGGTAAAGGAGACGTCAATTGCCCTTCTCTTTCAC
     ATTTGAATGCATCTAAAGAGTGCGTCTGGAATCAGTTAATGCTAGAAACATCGCAGTTG
3001-GCCCATGCCATTCATATTCGTCGAAGAATCACGGTCGATTGGAAXAAAAATGCGCTGTC-3061
     CGCAGACGTAACATCCCTTGTACAATGACCATGCCATATGAGCCTGTCACAAT
     ACAACTGACGATCGATTTCAACGATGCCGATATAGTCATGAATTTTTCCCCTGCCATAT
     AATCCTCCATTTCTTTTGCATATCCTGCATGTATGAGCCCTCCTGCAGTGGTCACA
     TGCGACAGTTATTCCTGCCATCATAAAACCCCTTTCTGAACACCGATGGGTGGACAA
3301-ATTATCGTCCCGCGTTGTATGTGTAGAAGCTCGGATCC-3335
```

FIGURE 34A

```
ACA TCT AAT ACA AAC TCT AAC TCA ATG AGT GAA AAT GTG GAA CAA CAC AAC CCT ATT AAT
                                Met Ser Glu Asn Val Glu Gln His Asn Pro Ile Asn

GCA GGC ACT GAA TTG TCT GCA ACA GGA AAT GAA TCT GGG GGT GGC GGT GGC GGG
Ala Gly Thr Glu Leu Ser Ala Thr Gly Asn Glu Ser Gly Gly Gly Gly Gly Gly

GGT AGG GGT GCT GGG GTT GGT GTG TCT ACA GGT AGT TTC AAT CAA ACA GAA TTT
Gly Arg Gly Ala Gly Val Gly Val Ser Thr Gly Ser Phe Asn Gln Thr Glu Phe

CAA TAC TTG GGG GAG GGC TTG GTT AGA ATC ACT GCA CAC GCA TCA AGA CTC ATA CAT CTA
Gln Tyr Leu Gly Glu Gly Leu Val Arg Ile Thr Ala His Ala Ser Arg Leu Ile His Leu

AAT ATG CCA GAA CAC GAA CAC GAA ATA CAT GTA CTA AAT TCA GAA TCA GGG GTG
Asn Met Pro Glu His Glu His Glu Ile His Val Leu Asn Ser Glu Ser Gly Val

GCG GGA CAA ATG GTA GAT GAT GCA CAC ACA CAA ATG CCT TGG TCA ACA CCT TGG TCA ATA
Ala Gly Gln Met Val Asp Asp Ala His Thr Gln Met Pro Trp Ser Thr Pro Trp Ser Ile

GAT CGT AAC GCA TGG GGA GTG TGG TTC AAT CCA GCG GAC TGG CAG TTA ATA TCC AAC AAC
Asp Arg Asn Ala Trp Gly Val Trp Phe Asn Pro Ala Asp Trp Gln Leu Ile Ser Asn Asn

ATG ACA ACA GAA ATA AAC TTA GTT AGT TTT TGA CAA GAA ATA TTC AAT GTA GTA CTT AAA ACA
Met Thr Thr Glu Ile Asn Leu Val Ser Phe *   Gln Glu Ile Phe Asn Val Val Leu Lys Thr

ATT ACA GAA TCA GCA ACC TCA CCA CCA TCC AAA ATA TAT AAT AAT GAT CTA ACT GCA AGC
Ile Thr Glu Ser Ala Thr Ser Pro Pro Ser Lys Ile Tyr Asn Asn Asp Leu Thr Ala Ser
```

FIGURE 34B

```
TTA  ATG  GTC  GCA  CTA  GAC  ACC  AAT  AAC  ACA  CTT  CCA  TAC  ACA  CCA  GCA  CCT  AGA  AGT
Leu  Met  Val  Ala  Leu  Asp  Thr  Asn  Asn  Thr  Leu  Pro  Tyr  Thr  Pro  Ala  Pro  Arg  Ser

GAA  ACA  CTT  GGT  TTT  CCA  TGG  CCA  TTA  CCT  ACA  AAA  CCA  ACT  CAA  TAC  AGA  TAT  TAC  CTA
Glu  Thr  Leu  Gly  Phe  Pro  Trp  Pro  Leu  Pro  Thr  Lys  Pro  Thr  Gln  Tyr  Arg  Tyr  Tyr  Leu

TCA  TGC  ATC  AGA  AAC  CTA  AAT  CCA  CCA  ACA  TAC  ACT  GGA  CAA  TCA  CAA  CAA  ATA  ACA  GAC
Ser  Cys  Ile  Arg  Asn  Leu  Asn  Pro  Pro  Thr  Tyr  Thr  Gly  Gln  Ser  Gln  Gln  Ile  Thr  Asp

TCA  ATA  CAA  ACA  GGA  CTA  CAC  AGT  GAC  ATT  ATG  TTC  TAC  ACA  ATA  GAA  AAT  GCA  GTA  CCA
Ser  Ile  Gln  Thr  Gly  Leu  His  Ser  Asp  Ile  Met  Phe  Tyr  Thr  Ile  Glu  Asn  Ala  Val  Pro

ATT  CAT  CTT  CTA  AGA  ACA  ACA  GGA  GAT  GAA  TTC  TCC  ACA  GGA  ATA  TAT  CAC  TTT  GAC  ACA  AAA
Ile  His  Leu  Leu  Arg  Thr  Thr  Gly  Asp  Glu  Phe  Ser  Thr  Gly  Ile  Tyr  His  Phe  Asp  Thr  Lys

CCA  TTA  AAA  TTA  ACT  CAC  TCA  CAA  TGG  CAA  ACA  AAC  AGA  TCT  CTA  GGA  CTG  CCT  CCA  AAA  CTA
Pro  Leu  Lys  Leu  Thr  His  Ser  Gln  Trp  Gln  Thr  Asn  Arg  Ser  Leu  Gly  Leu  Pro  Pro  Lys  Leu

CTA  ACT  GAA  CCT  ACC  ACA  GAA  GAC  CAA  CAC  CCA  GGA  ACA  CTA  CCA  GGA  GCT  AAC  ACA
Leu  Thr  Glu  Pro  Thr  Thr  Glu  Asp  Gln  His  Pro  Gly  Thr  Leu  Pro  Gly  Ala  Asn  Thr

AGA  AAA  GGT  TAT  CAC  CAA  ACA  ATT  AAT  AGC  TAC  ACA  GAA  GCA  ACA  GCA  CTT  AGG  CCA
Arg  Lys  Gly  Tyr  His  Gln  Thr  Ile  Asn  Ser  Tyr  Thr  Glu  Ala  Thr  Ala  Leu  Arg  Pro
```

FIGURE 34C

```
GCT CAG GTA TAT AAT ACA CCA TAC ATG AAT TTT GAC TAC TCC AAT GGT GGA CCA TTT
Ala Gln Val Tyr Asn Thr Pro Tyr Met Asn Phe Asp Tyr Ser Asn Gly Gly Pro Phe

CTA ACT CCT ATA GTA CCA GCA ACA GAC GCA ACA TAT GAT TAT GAT GAA CCA AAT GGT GCT
Leu Thr Pro Ile Val Pro Thr Ala Asp Thr Gln Tyr Asp Asp Tyr Glu Pro Asn Gly Ala

ATA AGA TTT ACA ATG GGT TAC CAA CAT GGA CAC TTA ACC ACA TCT TCA CAA GAG CTA GAA
Ile Arg Phe Thr Met Gly Tyr Gln His Gly His Leu Thr Thr Ser Ser Gln Glu Leu Glu

AGA TAC ACA TTC AAT CCA CAA AGT AAA TGT GGA AGA GCT CCA AAG CAA CAA TTT AAT CAA
Arg Tyr Thr Phe Asn Pro Gln Ser Lys Cys Gly Arg Ala Pro Lys Gln Gln Phe Asn Gln

CAG GCA CCA CTA AAC CTA GAA AAT ACA AAT GGA ACA CTT TTA CCT TCA GAT CCA ATA
Gln Ala Pro Leu Asn Leu Glu Asn Thr Asn Gly Thr Leu Leu Pro Ser Asp Pro Ile

*** *** *** *** *** *** *** *** *** *** *** *** *** *** *** *** *** *** ***
GGA AAA TCT AAC AAG CAT TTC ATG AAT ACA CTC AAT ACA TAT GGA CCA TTA ACA GCA
Gly Lys Ser Asn Lys His Phe Met Asn Thr Leu Asn Thr Tyr Gly Pro Leu Thr Ala

*** *** *** *** *** *** *** *** *** *** *** *** *** *** *** *** *** *** ***
CTA AAC AAT ACT GCA CCT GTA TTT CCA CAA AAT GGT CAA ATA TGG GAT AAA GAA CTT GAT ACA
Leu Asn Asn Thr Ala Pro Val Phe Pro Gln Asn Gly Gln Ile Trp Asp Lys Glu Leu Asp Thr
```

FIGURE 34D

```
GAT CTA AAA CCT AGA CTA CAT GTT ACA GCT CCA TTT GTT TGT AAA AAC AAT CCA GGA
Asp Leu Lys Pro Arg Leu His Val Thr Ala Pro Phe Val Cys Lys Asn Asn Pro Gly

CAA CTA TTT GTA AAA ATA GCA CCA AAC CTA ACA GAT GAT TTC AAT GCT GCT GAC TCT CCT CAA
Gln Leu Phe Val Lys Ile Ala Pro Asn Leu Thr Asp Asp Phe Asn Ala Asp Ser Pro Gln

CAA CCT AGA ATA ATA ACT GAT TCA AAC TTT TGG TGG AAA GGA ACA CTA TTC ACA GCA
Gln Pro Arg Ile Ile Thr Asp Ser Asn Phe Trp Trp Lys Gly Thr Leu Phe Thr Ala

AAA ATG AGA TCC AGT AAT ATG TGG AAC CCT ATT CAA CAA CAC ACA ACA ACA GCA GAA AAC
Lys Met Arg Ser Ser Asn Met Trp Asn Pro Ile Gln Gln His Thr Thr Thr Ala Glu Asn

ATT CGT AAA TAT ATT CCT ACA AAT ATT GGT GGT ATA AAA ATG TTT CCA GAA TAT TCA CAA
Ile Arg Lys Tyr Ile Pro Thr Asn Ile Gly Gly Ile Lys Met Phe Pro Glu Tyr Ser Gln

CTT ATA CCA AGA AAA TTA TAC TAG AAA TAA CTC TGT AAA TAA CTC AGT TAC TTG GTT
Leu Ile Pro Arg Lys Leu Tyr ---

AAT CAT GTA CTA TCA TG
```

FIGURE 35A

```
          10                  20                  30                  40                  50
           *                   *                   *                   *                   *
ATA GGA GGG AAA TCT AAC AAG CAT TTC ATG AAT ACA CTC AAT ACA TAT GGA CCA TTA
Ile Gly Gly Lys Ser Asn Lys His Phe Met Asn Thr Leu Asn Thr Tyr Gly Pro Leu 60                  70                  80                  90                 100                 110
           *                   *                   *                   *                   *                   *
ACA GCA CTA AAC AAT ACT GCA CCT GTA TTT CCA AAT GGT CAA ATA TGG GAT AAA GAA
Thr Ala Leu Asn Asn Thr Ala Pro Val Phe Pro Asn Gly Gln Ile Trp Asp Lys Glu

120
          *
CTT GAT ACA
Leu Asp Thr
```

FIGURE 35B

```
         10          20          30          40          50
          *           *           *           *           *
ATC GGC GGC AAG TCG AAC AAG CAC TTC ATG AAC ACG CTG AAC ACG TAC GGG CCG CTG
Ile Gly Gly Lys Ser Asn Lys His Phe Met Asn Thr Leu Asn Thr Tyr Gly Pro Leu 60          70          80          90         100         110
          *           *           *           *           *           *
ACC GCG CTG AAC AAC ACC GCC CCC GTG TTC CCG AAC GGG CAG ATC TGG GAC AAG GAG
Thr Ala Leu Asn Asn Thr Ala Pro Val Phe Pro Asn Gly Gln Ile Trp Asp Lys Glu

120
          *
TTG GAC ACC
Leu Asp Thr
```

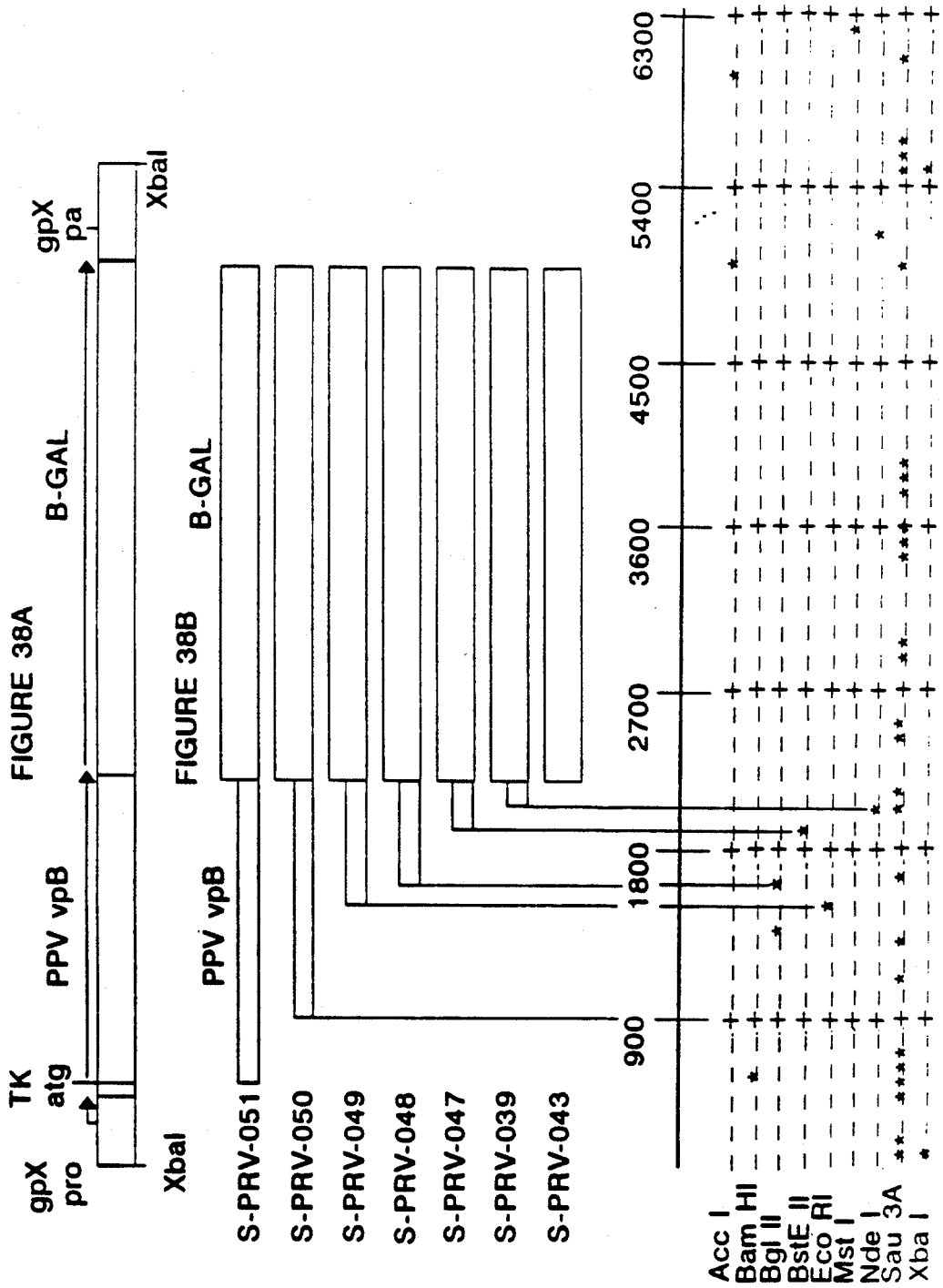

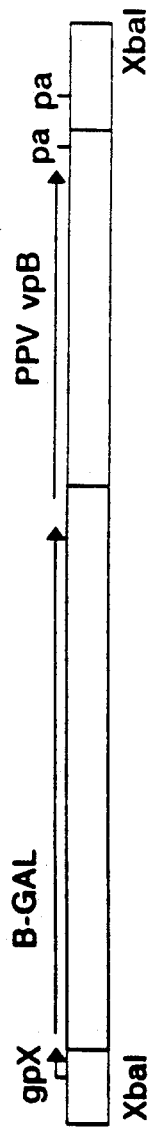
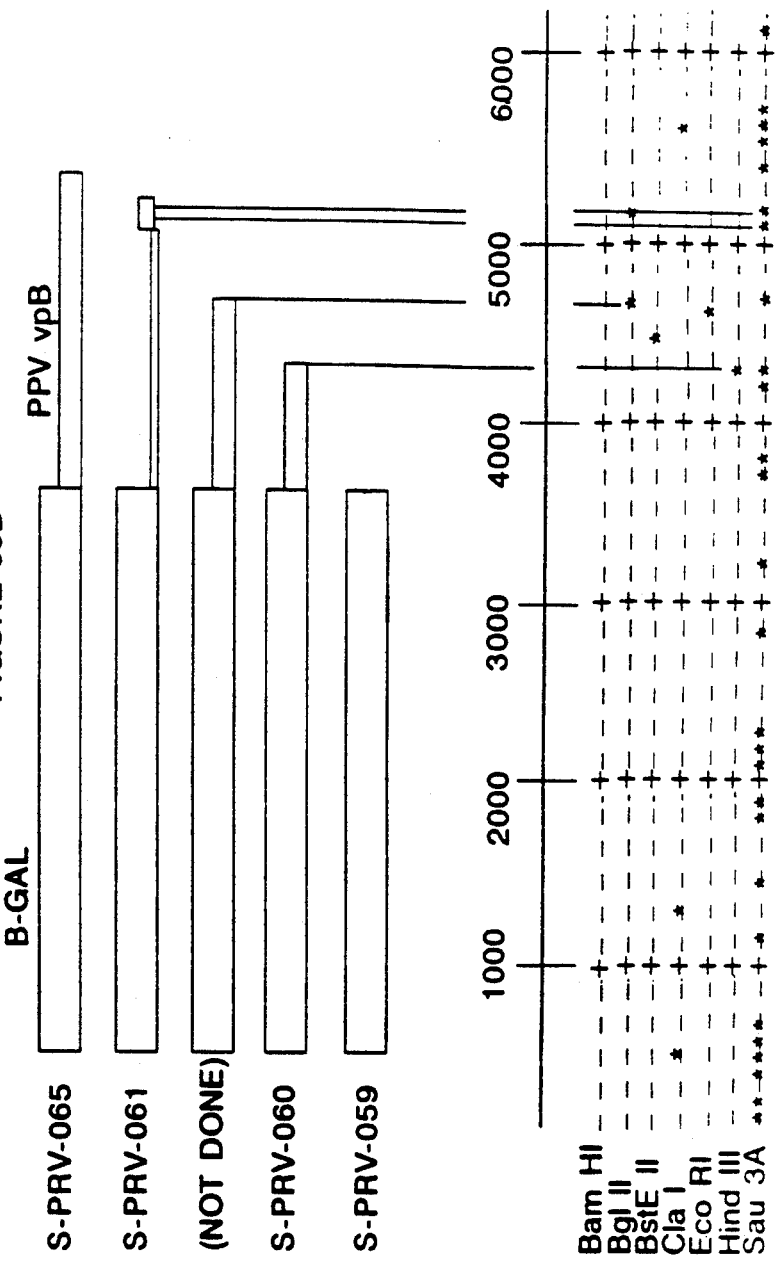
FIGURE 39A
FIGURE 39B

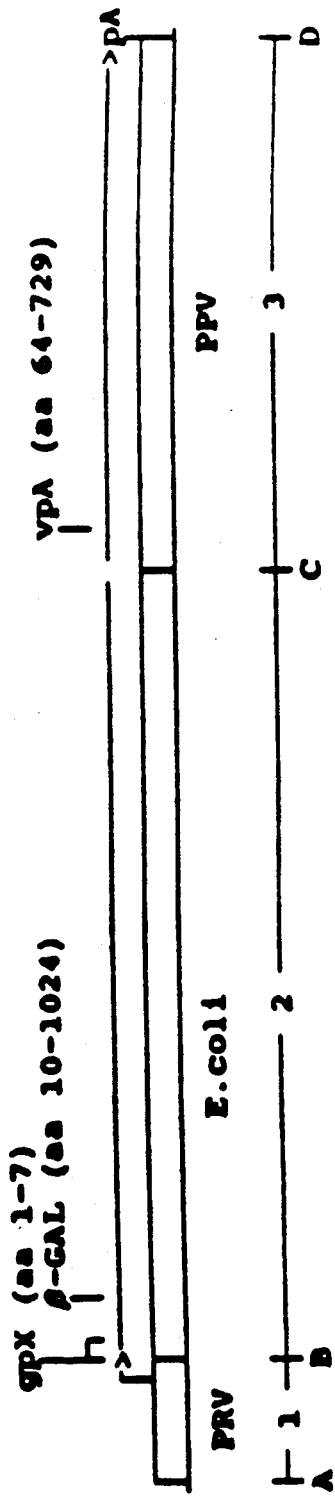
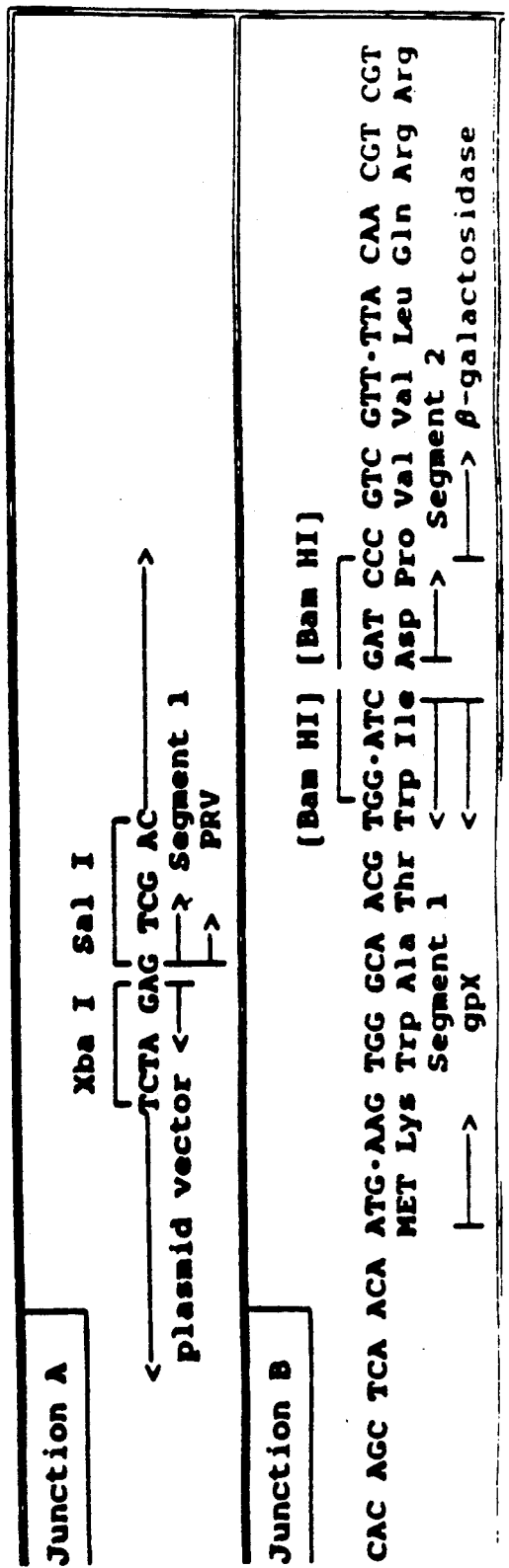
FIGURE 40A
FIGURE 40B

FIGURE 40B

Junction C

```
                                                    Pvu II
GAC GAC TCC TGG AGC·CCG TCA GTA TCG GCG·GAA ATC CAG CTG AGC·GCC GGT CGC TAC
Asp Asp Ser Trp Ser Pro Ser Val Ser Pro Ala Glu Ile Gln Leu Ser Ala Gly Arg Tyr
                    Segment 2 <──┤├──> Synthetic DNA

[Pvu II]
CAT·TAC CAG TTG GTC GTC TGG·TGT CAA AAA GAT CCC·CCT GAT GAA AAA TTC·ATA AAA GAA
His Tyr Gln Leu Val Val Trp Cys Gln Lys Asp Pro Pro Asp Glu Lys Phe Ile Lys Glu
              Synthetic DNA <──┤├──> Segment 3
    β-galactosidase <──┤         ├──> vpA
```

Junction D

```
                                                            Poly A sigan1
TCA CAA CTT ATA CCA·AGA AAA TTA TAC TAG·AAA TAA CTC TGT AAA·TAA AAA CTC AGT
Ser Gln Leu Ile Pro Arg Lys Leu Tyr ───
                vpA <──┤

[Rsa I]                             Xba I
TAC·TTG GTT AAT CAT GTG·ACC TGC AGG TCG ACT·CTA GA ────>
Segment 3 <──┤├──> Synthetic DNA
PPV       <──┤├──> plasmid vector
```

FIGURE 43A
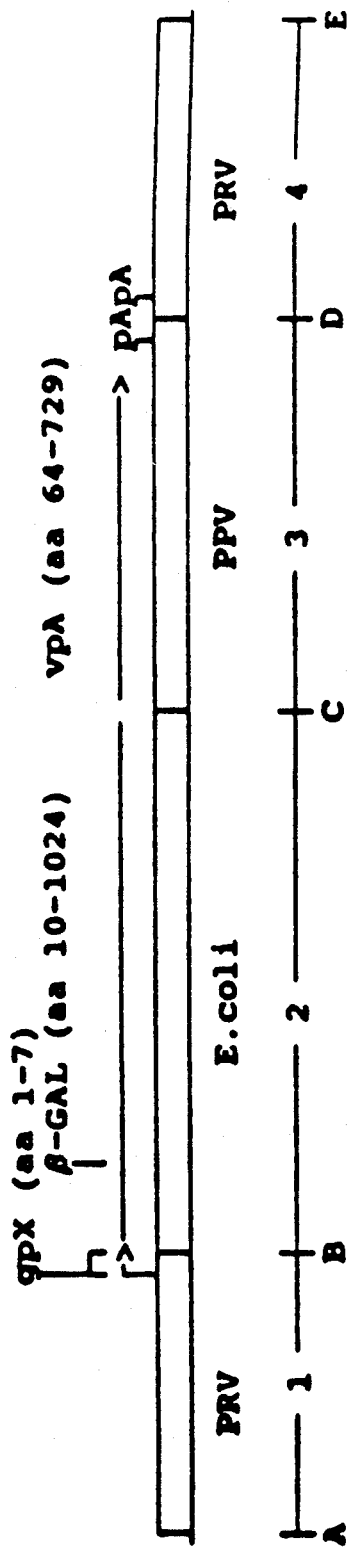
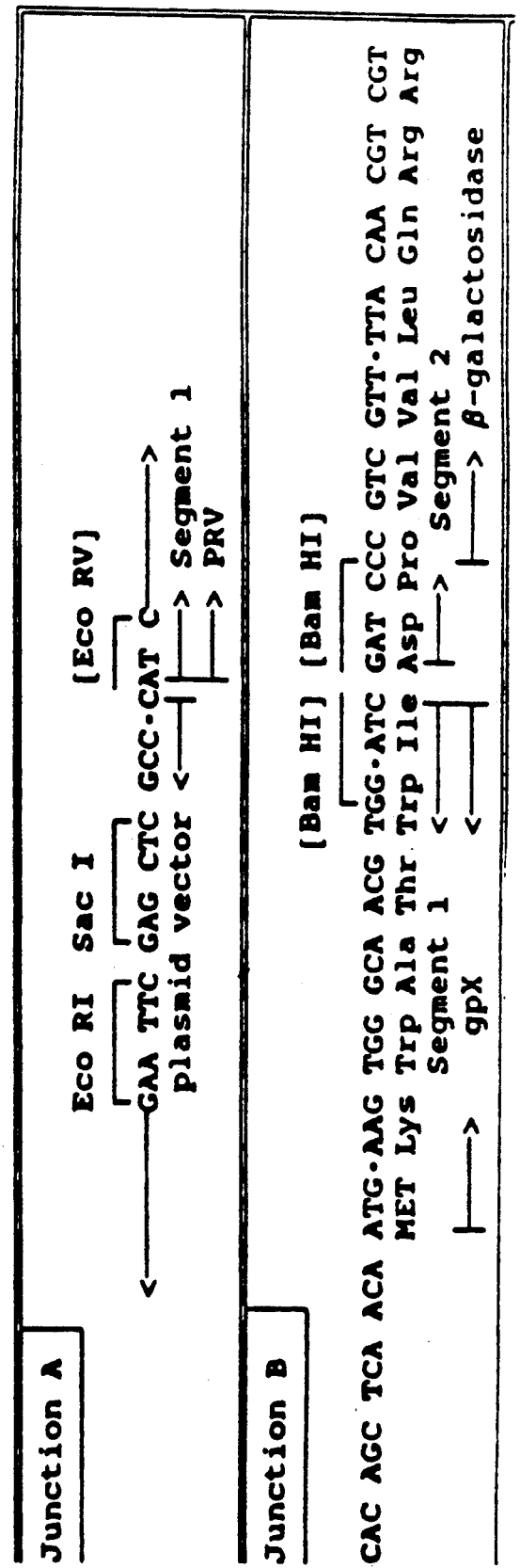

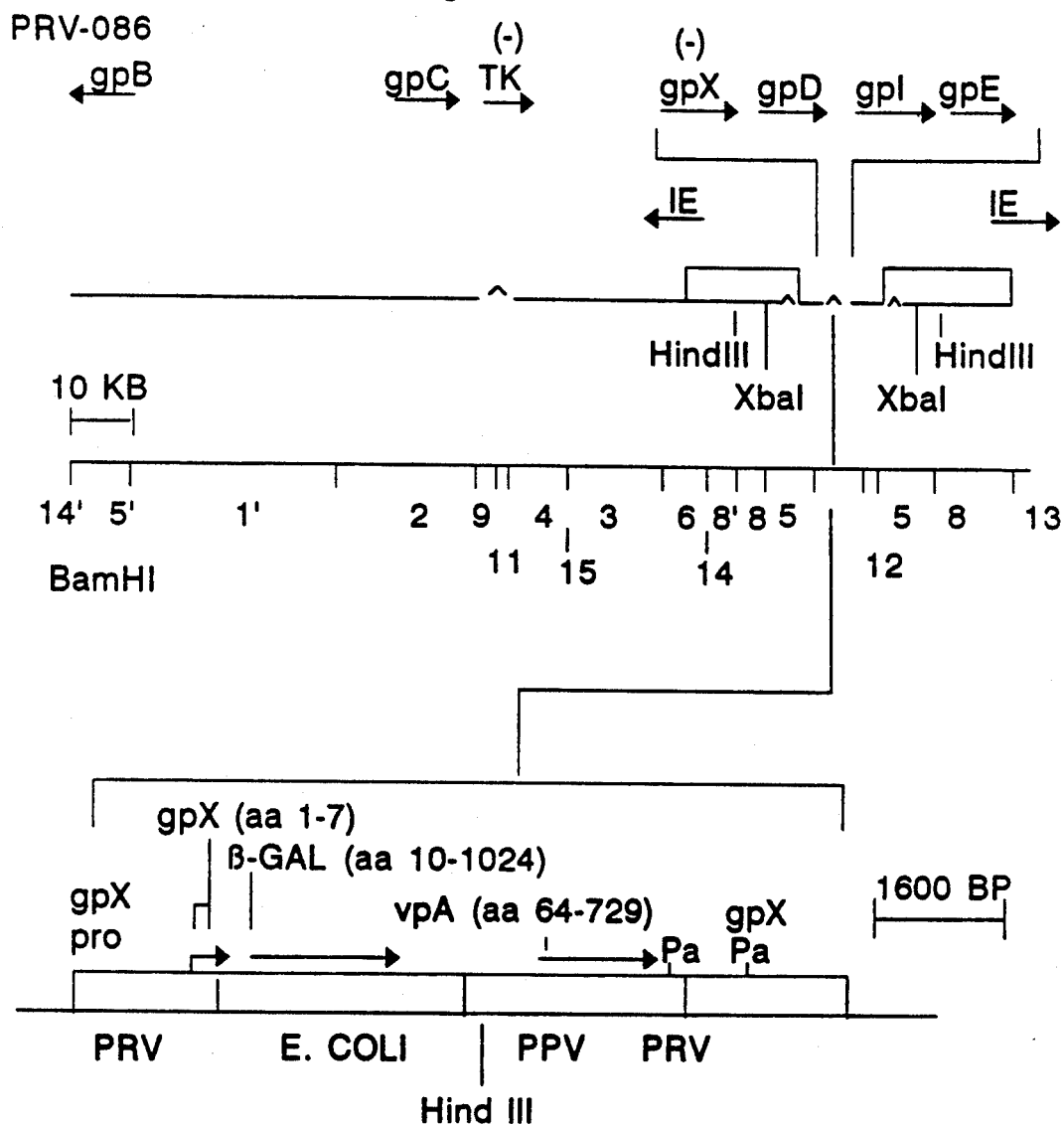

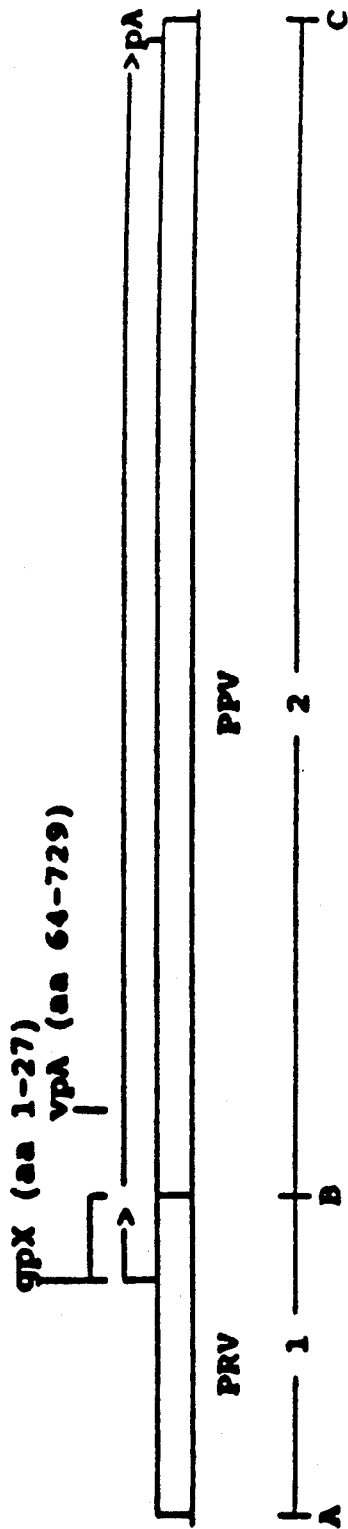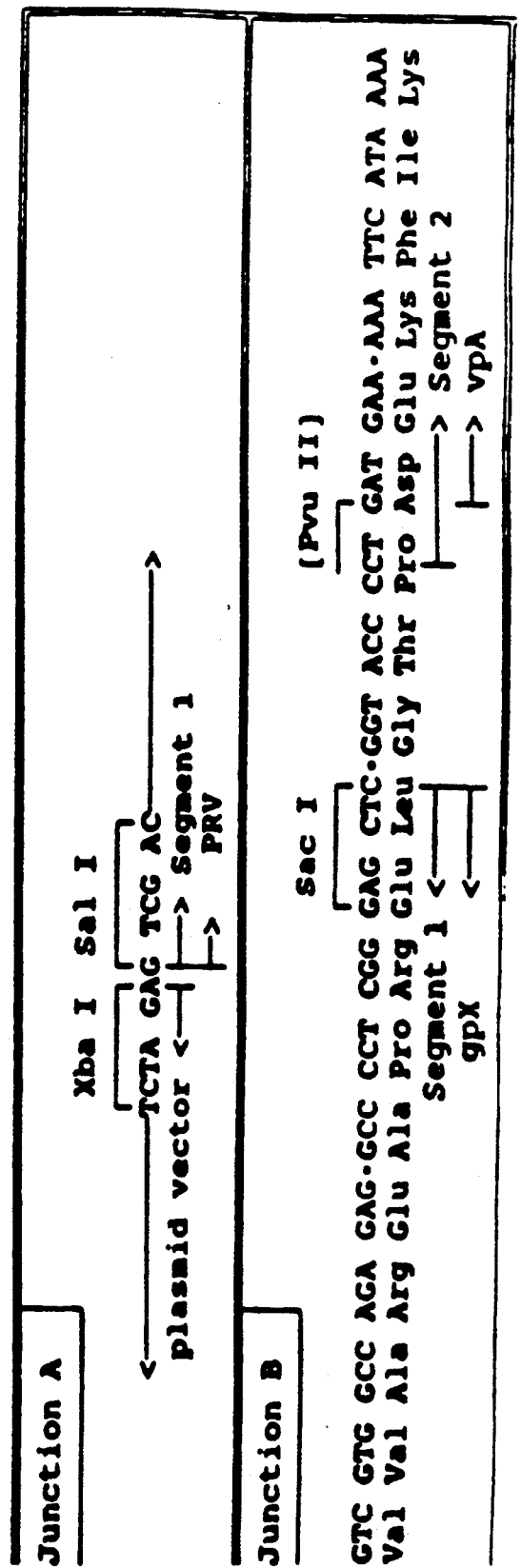
FIGURE 45A

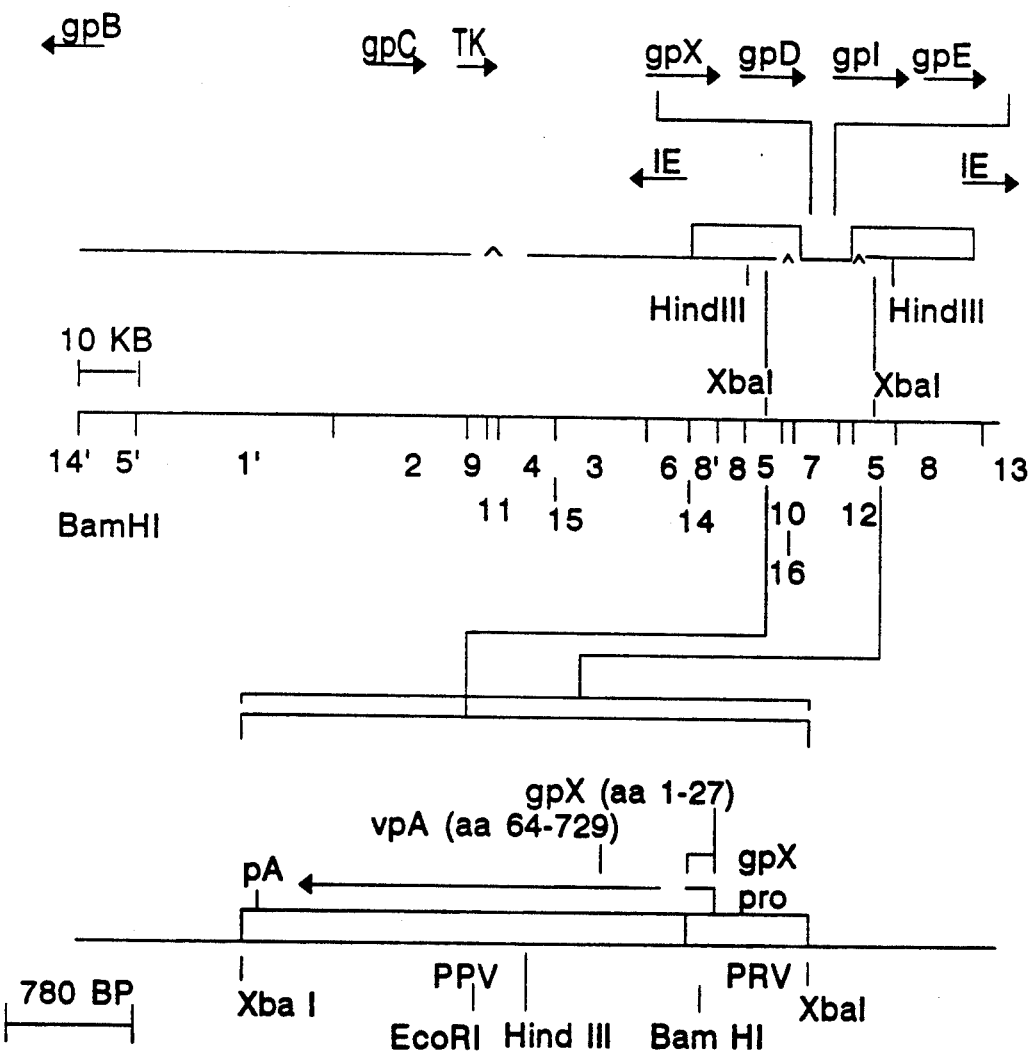

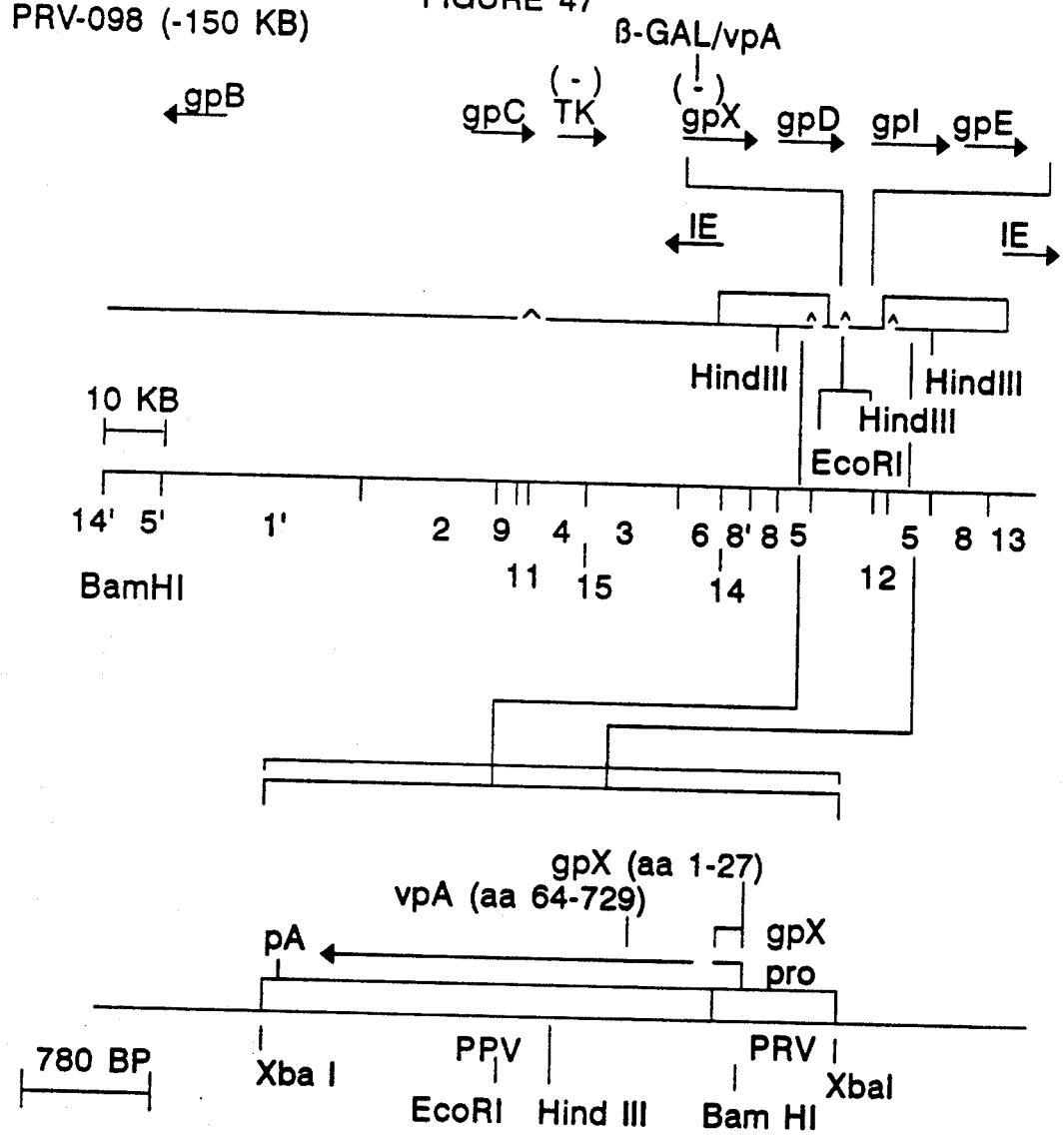

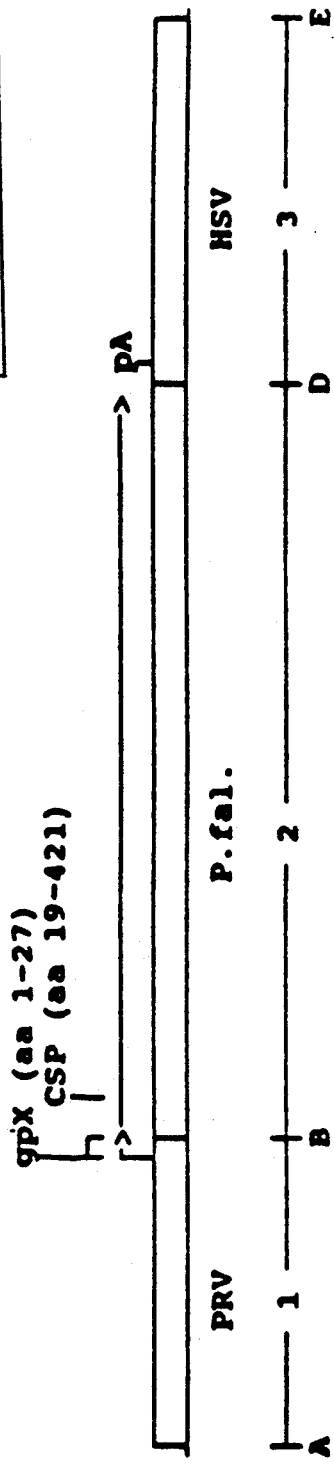
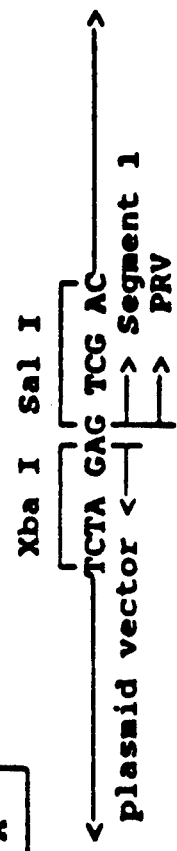
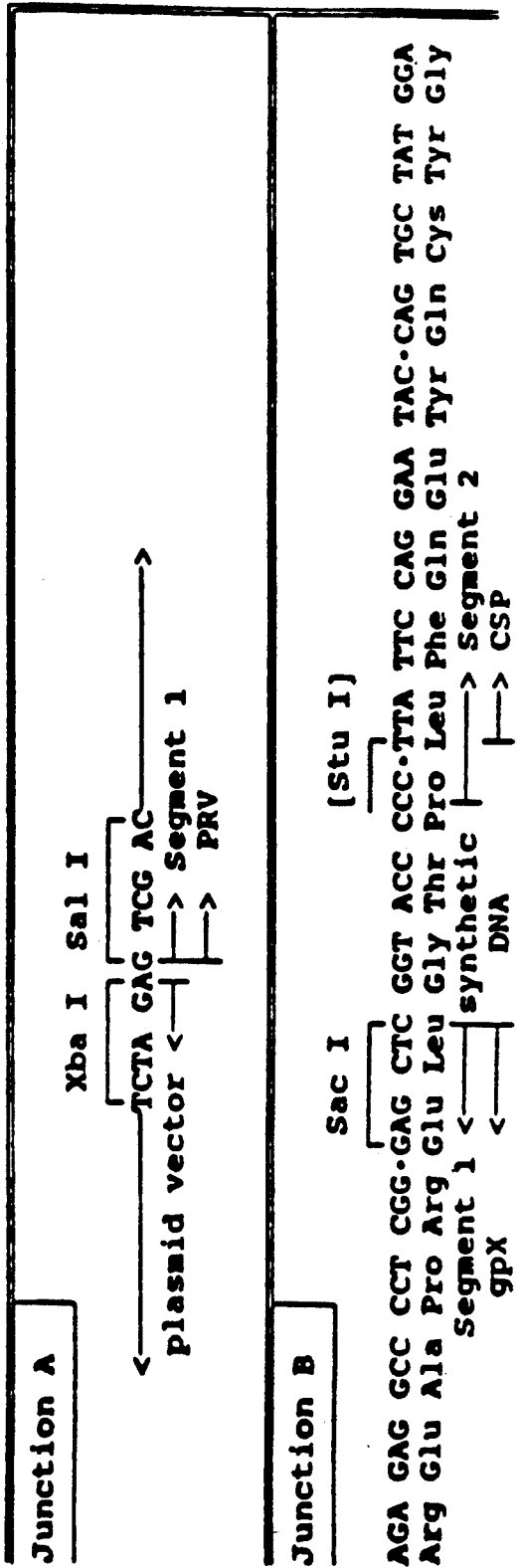
FIGURE 48A

FIGURE 51A
FIGURE 51B
FIGURE 51A
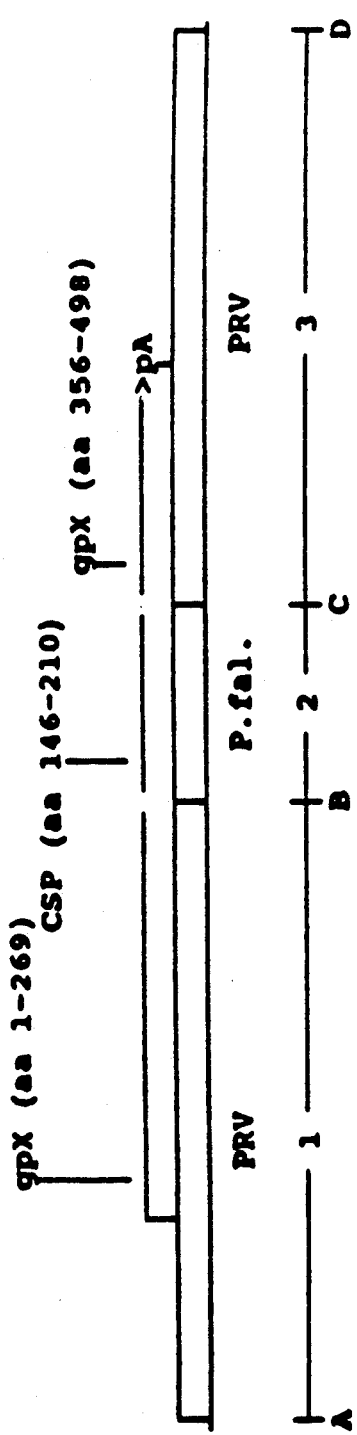
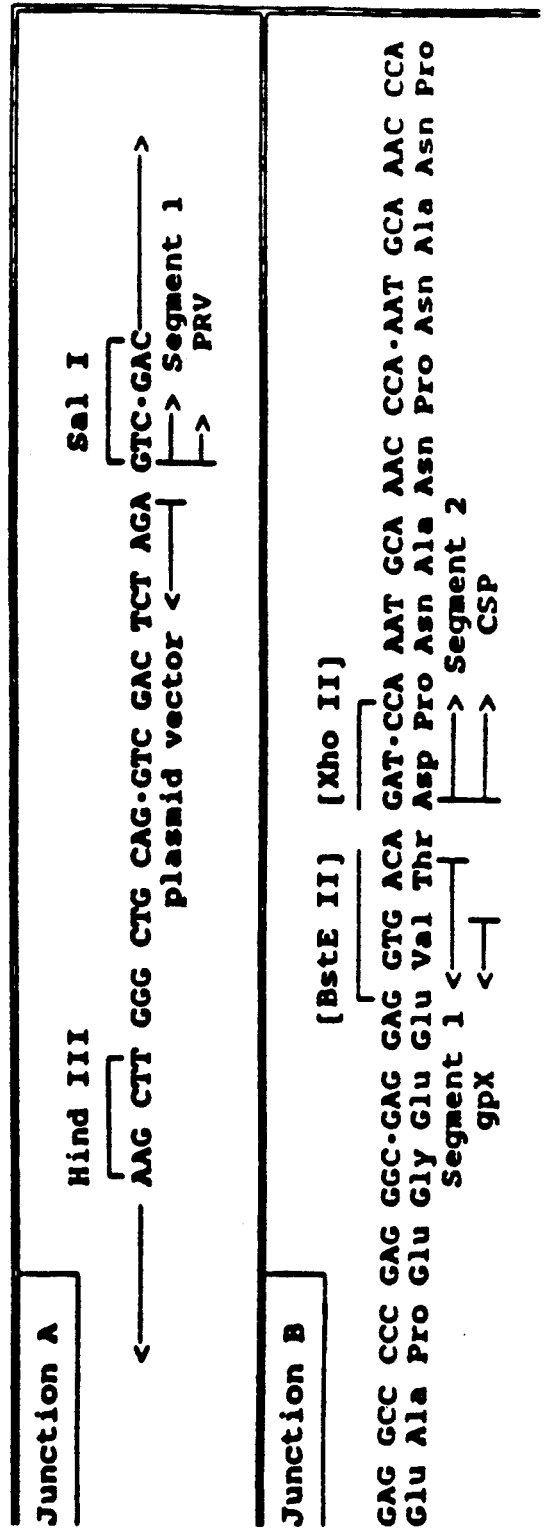

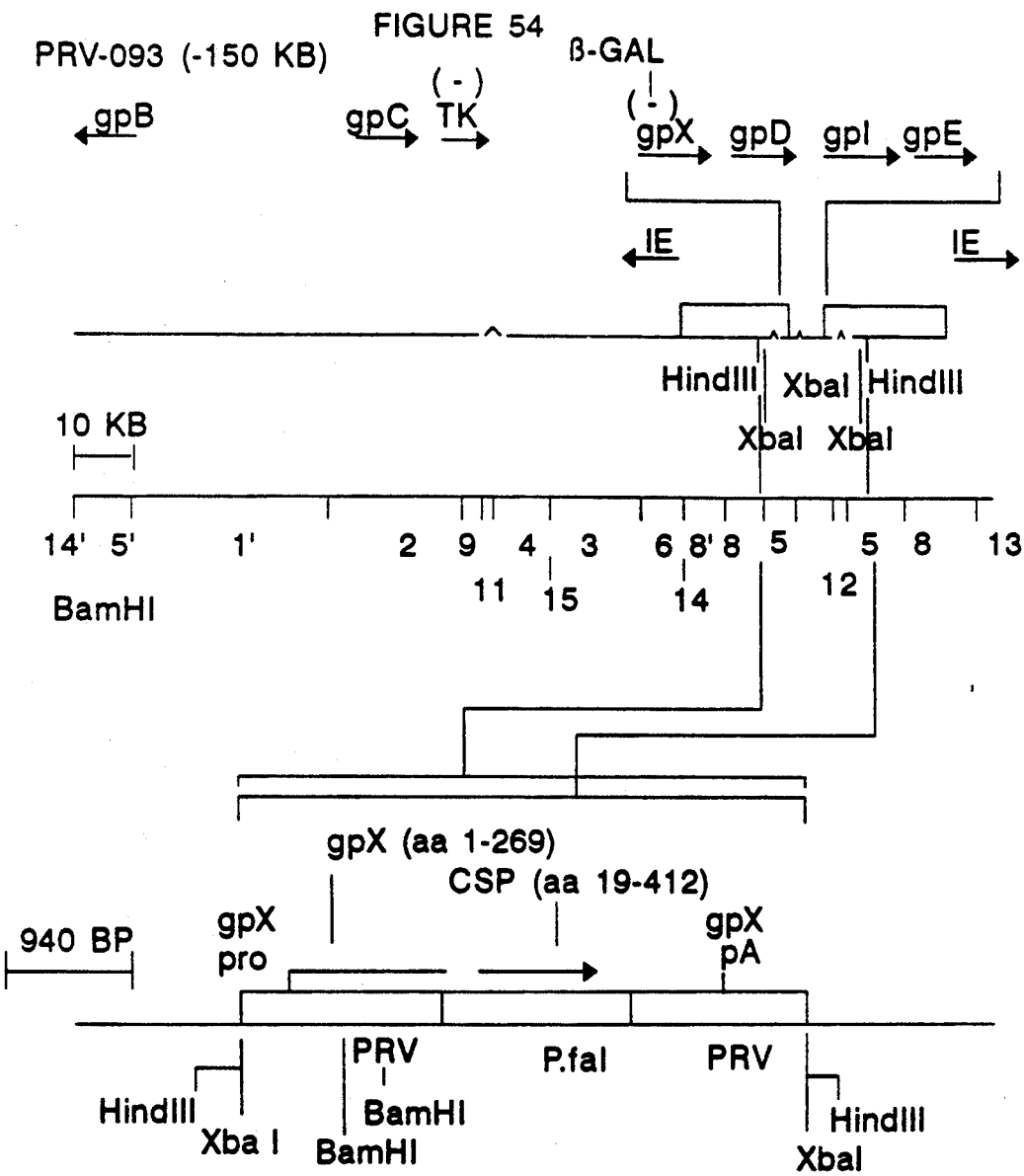

5,223,424

ATTENUATED HERPESVIRUSES AND HERPESVIRUSES WHICH INCLUDE FOREIGN DNA ENCODING AN AMINO ACID SEQUENCE

This application is a continuation-in-part of U.S. Ser. No. 078,519, filed Jul. 27, 1987, now abandoned, U.S. Ser. No. 933,107, filed Nov. 20, 1986, now abandoned, U.S. Ser. No. 902,887, filed Sep. 2, 1986, now abandoned, U.S. Ser. No. 887,140, filed Jul. 17, 1986, now abandoned, U.S. Ser. No. 823,102, filed Jan. 27, 1986, now U.S. Pat. No. 5,068,192 and U.S. Ser. No. 773,430, filed Sep. 6, 1985, now U.S. Pat. No. 4,877,737, the contents of each of which are hereby incorporated by reference into the present application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The advent of recombinant DNA techniques has made it possible to manipulate the naturally occurring DNA sequences within an organism (the genome) in order to change in some manner the functions of the organism through genetic engineering. The present invention concerns organisms defined as viruses that infect animals and contain DNA as their genetic material; specifically viruses belonging to the herpesvirus group (herpesviruses (23). This group of viruses comprise a number of pathogenic agents that infect and cause disease in a number of target species: swine, cattle, chickens, horses, dogs, cats, etc. Each herpesvirus is specific for its host species, but they are all related in the structure of their genomes, their mode of replication, and to some extent in the pathology they cause in the host animal and in the mechanism of the host immune response to the virus infection.

The types of genetic engineering that have been performed on these herpesviruses consist of cloning parts of the virus DNA into plasmids in bacteria, reconstructing the virus DNA while in the cloned state so that the DNA contains deletions of certain sequences, and furthermore adding foreign DNA sequences either in place of the deletions or at sites removed from the deletions. The usual method is to make insertions of the foreign DNA into the viral sequences, although the foreign DNA could be attached to the end of the viral DNA as well. One utility of the addition of foreign sequences is achieved when the foreign sequence encodes a foreign protein that is expressed during viral infection of the animal. A virus with these characteristics is referred to as a vector, because it becomes a living vector which will carry and express the foreign protein in the animal. In effect it becomes an elaborate delivery system for the foreign protein.

The prior art for this invention stems first from the ability to clone and analyze DNA while in the bacterial plasmids. The techniques that are available for the most part are detailed in Maniatis et al. (1). This publication gives state-of-the-art general recombinant DNA techniques.

The application of recombinant DNA techniques to animal viruses has a relatively recent history from about 1980. The first viruses to be engineered have been the smallest ones—the papovaviruses. These viruses contain 3,000–4,000 base pairs (bp) of DNA in their genome. Their small size makes analysis of their genomes relatively easy and in fact most of the ones studied (SV40, polyoma, bovine papilloma) have been entirely sequenced. Because these virus particles are small and cannot accommodate much extra DNA, and because their DNA is tightly packed with essential sequences (that is, sequences required for replication), it has not been possible to engineer these viruses as live vectors for foreign gene expression. Their entire use in genetic engineering has been as defective replicons for the expression of foreign genes in animal cells in culture (roughly analgous to plasmids in bacterial systems) or to their use in mixed populations of virions in which wild type virus acts as a helper for the virus that has replaced an essential piece of DNA with a foreign gene. The studies on papovaviruses do not suggest or teach the concept of living virus vectors as delivery systems for host animals.

The next largest DNA animal viruses are the adenoviruses. In these viruses there is a small amount of nonessential DNA that can be replaced by foreign sequences. The only foreign genes that seem to have been expressed in adenoviruses are the T-antigen genes from papovaviruses (2,3,4,5), and the herpes simplex virus thymidine kinase gene (28). It is possible, given this initial success, to envision the insertion of other small foreign genes into adenoviruses. However the techniques used in adenoviruses do not teach how to obtain the same result with herpesviruses. In particular, these results do not identify the nonessential regions in herpesviruses wherein foreign DNA can be inserted, nor do they teach how to achieve the expression of the foreign genes in herpesviruses, e.g. which promoter signals and termination signals to use.

Another group of animal viruses that have been engineered are the poxviruses. One member of this group, vaccinia, has been the subject of much research on foreign gene expression. Poxviruses are large DNA-containing viruses that replicate in the cytoplasm of infected cells. They have a structure that is very unique among viruses—they do not contain any capsid that is based upon icosahedral symmetry or helical symmetry. In theorizing on the origin of viruses, the poxviruses are the most likely ones to have originated from bacterial-like microorganisms through the loss of function and degeneration. In pat due to this uniqueness, the advances made in the genetic engineering of poxviruses cannot be directly extrapolated to other viral systems, including herpesviruses. Vaccinia recombinant virus constructs have been made in a number of laboratories that express the following inserted foreign genes: herpes simplex virus thymidine kinase gene (6,7), hepatitis B surface antigen (8,9,29), herpes simplex virus glycoprotein D gene (8,29), influenza hemagglutinin gene (10, 11), malaria antigen gene (12), and vesicular stomatitis glycoprotein G gene (13). The general overall features of the vaccinia recombinant DNA work are similar to the techniques used for all the viruses, especially as they relate to the techniques in reference (1). However in detail, the vaccinia techniques do not teach how to engineer herpesviruses.

Vaccinia DNA is not infectious, so the incorporation of foreign DNA must involve an infection/transfection step that is not appropriate to other viruses, and vaccinia has unique stability characteristics that make screening easier. In addition, the signal sequence used by promoters in vaccinia are unique and will not work in other viruses. The utility of vaccinia as a vaccine vector is in question because of its close relationship to human smallpox and its known pathogenicity to humans. The use of host-specific herpesviruses promises to be a better solution to animal vaccination.

Herpesviruses contain 100,000 to 150,000 base pairs of DNA as their genetic material, and several areas of the genome have been identified that are dispensible for the replication of virus in vitro in cell culture. Modifications of these regions of the DNA are known to lower the pathogenicity of the virus, i.e. to attenuate the virus, for an animal species. For example, inactivation of the thymidine kinase gene renders human herpes simplex virus non-pathogenic (45), and pseudorabies virus of swine non-pathogenic (46 and 47).

Removal of part of the repeat region renders human herpes simplex virus non-pathogenic (48 and 49). A repeat region has been identified in Marek's disease virus that is associated with viral oncogenicity (50). A region in herpesvirus saimiri has similarly been correlated with oncogenicity (51). However, modifications in these repeat regions do not teach the construction of attenuated pseudorabies viruses with deletions in repeat sequences.

The degree of attenuation of a virus is important in the utility of the virus as a vaccine. Deletions which cause too much attenuation of the virus will result in a vaccine that fails to elicit an adequate immune response.

The herpesviruses are known to cause a variety of latent and recurrent infections in human and other vertebrates and are even known to infect a fungus and an oyster. Among the conditions associated with herpesvirus infections are fever blisters caused by herpes simplex type 1, genital herpes causes by herpes simplex type 2, and chickenpox in children and shingles in adults cause by herpes zoster infection. Pseudorabies virus (PRV), a Class D herpesvirus, induces Aujesky's disease, an acute and often fatal nervous condition, in domestic and wild animals.

Among the herpesviruses, only herpes simplex of humans and, to a limited extend, herpes saimiri of monkeys have been engineered to contain foreign DNA sequences previous to this disclosure. The earliest work on the genetic manipulation of herpes simplex virus involved the rescue of temperature sensitive mutants of the virus using purified restriction fragments of DNA (14). This work did not involve cloning of the DNA fragments into the viral genome. The first use of recombinant DNA to manipulate herpes simplex virus involved cloning a piece of DNA from the L-S junction region into the unique long region of the DNA, specifically into the thymidine kinase gene (15). This insert was not a foreign piece of DNA, rather it was a naturally occurring piece of herpesvirus DNA that was duplicated at another place in the genome. This piece of DNA was not engineered to specifically express any protein, and thus it did not teach how to express protein in herpesviruses. The manipulation of herpes simplex next involved the creation of deletions in the virus genome by a combination of recombinant DNA and thymidine kinase selection. The first step was to make a specific deletion of the thymidine kinase gene (16). The next step involved the insertion of the thymidine kinase gene into the genome at a specific site, and then the thymidine kinase gene and the flanking DNA at the new site were deleted by a selection against thymidine kinase (17). In this manner herpes simplex alpha-22 gene has been deleted (17). In the most recent refinement of this technique, 15,000 bp sequence of DNA has been deleted from the internal repeat of herpes simplex virus (18).

The insertion of genes that encode protein into primate herpesviruses have involved seven cases: the insertion of herpes simplex glycoprotein C back into a naturally occurring deletion mutant of this gene in herpes simplex virus (19); the insertion of glycoprotein D of herpes simplex type 2 into herpes simplex type 1 (20), again with no manipulation of promoters since the gene is not really 'foreign'; the insertion of hepatitis B surface antigen into herpes simplex virus under the control of the herpes simplex ICP4 promoter (21); and the insertion of bovine growth hormone into herpes saimiri virus with an SV40 promoter that in fact didn't work in that system (an endogenous upstream promoter served to transcribe the gene) (22). Two additional cases of foreign genes (chicken ovalbumin gene and Epstein-Barr virus nuclear antigen) have been inserted into herpes simplex virus (30), and glycoprotein X of pseudorabies virus has been inserted into herpes simplex virus (31).

These limited cases of deletion and insertion of genes into herpesviruses demonstrate that it is possible to genetically engineer herpesvirus genomes by recombinant DNA techniques. The methods that have been used to inset genes involve homologous recombination between the viral DNA cloned on plasmids and purified viral DNA transfected into the same animal cell. In aggregate this is referred to as the homologous recombination technique. This technique with minor modifications has been adaptable to other herpesviruses that we have engineered. However, the extent to which one can generalize the location of the deletion and the sites for insertion of foreign genes is not obvious from these previous studies. Furthermore, it is also not obvious that non-primate herpesviruses are amenable to the same techniques as the primate herpesviruses, and that one could establish a targeted approach to the deletion, insertion, and expression of foreign genes.

Infectious bovine rhinotracheitis (IBR) virus, an alpha-herpesvirus with a class D genome, is an important pathogen of cattle. It has been associated with respiratory, ocular, reproductive, central nervous system, enteric, neonatal and dermal diseases (37). Cattle are the normal hosts of IBR virus, however it also infects goats, swine, water buffalo, wildebeest, mink and ferrets. Experimental infections have been established in muledeer, goats, swine, ferrets and rabbits (38).

Conventional modified live virus vaccines have been widely used to control diseases caused by IBR. These vaccine viruses may revert to virulence, however. More recently, killed virus IBR vaccines have been used, but their efficacy appears to be marginal.

IBR has been analyzed at the molecular level as reviewed in (39). A restriction map of the genome is available in this reference, which will aid in the genetic engineering of IBR according to the methods provided by the present invention. No evidence has been presented that IBR has been engineered to contain a deletion or an insertion of foreign DNA.

Marek's disease virus (MDV) causes fowl paralysis, a common lymphoproliferative disease of chickens. The disease occurs most commonly in young chickens between 2 and 5 months of age. The prominant clinical signs are progressive paralysis of one or more of the extremeties, incoordination due to paralysis of legs, drooping of the limb due to wing involvement, and a lowered head position due to involvement of the neck muscles. In acute cases, severe depression may result. In the case of highly oncogenic strains, there is characteristic bursal and thymic atrophy. In addition, there are lymphoid tumors affecting the gonads, lungs, liver, spleen, kidney and thymus (37).

All chicks are vaccinated against MDV at one day of age to protect the chick against MDV for its lifetime. One vaccine method for MDV involves using turkey herpesvirus (HVT). It would be advantageous to incorporate other antigens into this vaccination at one day of age, but efforts to combine vaccines have not proven satisfactory to date due to competition and immunosuppression between pathogens. The multivalent vaccines engineered in this invention are a novel way to simultaneously vaccinate against a number of different pathogens.

A restriction map of both MDV (43) and HVT (34) are available in the literature. There is no evidence to suggest that anyone has successfully created a deletion or insertion of foreign DNA into MDV or HVT prior to this disclosure.

Other herpesviruses contemplated to be amenable to these procedures are feline herpesvirus (FHV), equine herpesvirus (EHV), and canine herpesvirus (CHV). These pathogens cause disease in each of their respective hosts. Feline herpesvirus causes feline rhinotracheitis, an acute upper respiratory tract infection characterized by fever, pronounced sneezing, nasal and lacrimal secretions, and depression. The virus may cause corneal ulceration and abortion. The nasal passages and turbinates show focal necrosis, and the tonsils are enlarged and hemmorhagic. Equine herpesvirus causes rhinopneumonitis, abortion, exanthema of the genitals and occasionally neurologic disease. The acute disease is characterized by fever, anorexia and a profuse, serous nasal discharge. The neurologic symptoms, when present, consist of ataxia, weakness and paralysis. Canine herpesvirus causes severe illness in young puppies, where mortality may reach 80%. The disease is characterized by viremia, anorexia, respiratory illness, abdominal pain, vomiting and incessant crying. Generally, there is no fever. The principal lesions are disseminated necrosis and hemorrhages in the kidneys, liver and lungs.

The molecular biology of the feline, equine and canine herpesviruses are in their initial phases. Partial restriction maps are available for equine herpesvirus, and in progress in at least one lab for the feline herpesvirus. Beyond this type of genome analysis, no evidence for the deletion or insertion of foreign genes into these viruses is available.

The present invention involves the use of genetically engineered herpesvirus to protect animals against disease. It is not obvious which deletions in herpesviruses would serve to attenuate the virus to the proper degree. Even testing vaccine candidates in animal models, e.g. mice, does not serve as a valid predictor of the safety and efficacy of the vaccine in the target animal species, e.g. swine.

Another subject of the present invention is a vaccine for pseudorabies virus (herpesvirus suis, suid herpesvirus 1, or Aujesky's disease virus) disease of swine. Swine are the natural host of pseudorabies virus in which infection in older animals is commonly inapparent but may be characterized by fever, convulsions, and death particularly in younger animals. Pseudorabies also infects cattle, sheep, dogs, cats, ferrets, foxes, and rates (37) where the infection usually results in death. Death is usually preceded by intense pruritus, mania, encephalitis, paralysis, and coma. Traditional live vaccines are available for use in swine, but they are lethal for the other animals. An improved vaccine for pseudorabies would induce a more reliable immune response in swine, would be specifically attenuated to be incapable of reversion to virulence, and would not cause disease in other hosts.

Pseudorabies virus, an alpha-herpesvirus of swine, has a genome of class D (23); that is it contains two copies of a single repeat region, one located between the unique long and unique short DNA region and one at the terminus of the unique short region (see FIG. 1). Herpes simplex virus is an alpha-herpesvirus with a class E genome (23); that is it contains two copies of each of two repeats. Herpes saimiri is a gamma-herpesvirus with a class B genome; that is, it contains numerous reiterations of the same sequence at both termini (23). As the genome structure differs significantly between these different classes of herpesviruses, and because the different viruses attack different cells within their hosts and elicit different pathologies, it is necessary in each instance to establish which specific regions can be removed in order to attenuate and which regions can be altered to express foreign genes.

Pseudorabies virus has been studied using the tools of molecular biology including the use of recombinant DNA techniques. BamHI, KpnI, and BglII restriction maps of the virus genome have been published (24, 27). DNA transfection procedures have been utilized to rescue temperature sensitive and deletion mutants of the virus by the homologous recombination procedure (24). There are two examples of deletions that have been made in the pseudorabies virus genome—one is a thymidine kinase gene deletion (25), also disclosed in U.S. Pat. No. 4,514,497 entitled "Modified Live Pseudorabies Viruses". This patent teaches thymidine kinase deletions only and does not suggest other attenuating deletions, nor does it suggest insertion of foreign DNA sequences. The other reference involves the deletion of a small DNA sequence around a HindIII restriction site in the repeat region (26) upon which European Patent Publication no. 0141458, published on May 15, 1985, corresponding to European Patent Application No. 84201474.8, filed on Oct. 12, 1984 is based. This patent application does not teach or suggest attenuating deletions nor does it teach or suggest he insertion of DNA sequences into pseudorabies virus.

The present invention concerns deletions which have been introduced into the pseudorabies virus genome at sites previously undisclosed. Foreign DNA sequences have also been introduced into the attenuated pseudorabies virus genome and expressed as proteins. One embodiment of the invention concerns a vaccine useful for preventing pseudorabies and other swine diseases with a single inoculum.

Other relevant pseudorabies literature disclosed herein, concerns the presence of naturally-occurring deletions in the genome of two vaccine strains of pseudorabies viruses (27). These deletions are responsible, at least in part, for the attenuated nature of these vaccines however they do not occur in a repeat sequence and do not suggest the attenuation of pseudorabies virus by deleting a portion of a repeat sequence. Such naturally-occurring deletions do not teach methods for making these deletions starting with wild type pseudorabies virus DNA, nor do they suggest other locations at which to make attenuating deletions. There are no examples of naturally-occurring insertions of foreign DNA in herpesviruses.

The natural host of pseudorabies virus is swine, in which infection is commonly inapparent but may be characterized by fever, convulsions and paralysis. Pseudorabies virus also infects cattle, sheep, dogs, cats, foxes and mink, where infection usually results in death of the host. The predominant visible feature of pseudorabies viral infection is intense pruritis generally resulting in host mutilation of the involved area. Violent excitement, fits and paralysis, all symptoms of encephalomyelitis, precede death which usually occurs within a few days following onset of clinical signs.

Pseudorabies virus disease in swine is of serious concern to governmental bodies worldwide. In the United States, swine form infected herds cannot be sold except to slaughterhouses. Several individual states have separately enacted eradication control practices against pseudorabies. At the current time, any animal vaccinated for pseudorabies disease is treated as though it were infected with pseudorabies virus and is subject to the same regulatory constraints. This is due primarily to the lack of a diagnostic test to differentiate vaccinated from infected animals.

The research and development trend among traditional vaccine manufacturers has generally emphasized research leading to vaccines that are based upon virus subunits rather than live viruses. This departure from live virus vaccines is due partly to the recognized safety aspect of subunit vaccines, and their unlikelihood of containing infections live viruses. Another reason for developing a subunit vaccine has been to allow for the development of a diagnostic test that would accompany the vaccine and would differentiate vaccinated from infected animals, thereby escaping from the regulatory burden following use of other vaccines. Subunit vaccines also have limitation. They contain a limited number of viral antigens compared to those produced by live viruses. This paucity of antigens produces a weak immune response of short duration in the vaccinated animal at considerably greater cost than a live virus vaccination. However, the limited spectrum of antigens in the subunit vaccine allows the vaccinated swine to be distinguished from swine which have been infected with the wild-type virus. The ability to distinguish vaccinated from infected swine is a crucial property of a pseudorabies vaccine because none of the know vaccines prevent the vaccinated animals from being super-infected by the wild-type virus. While the vaccinated animals do not become sick upon super-infection, there is strong evidence that they may become carriers of the wild-type virus and pass the wild-type virus to other swine.

In any eradication program aimed at eliminating pseudorabies virus, a vaccine provided with characteristics which would allow vaccinated animals to be distinguished from animals infected with wild-type virus would be advantageous. The subunit vaccines have high cost and poor efficacy but an animal vaccinated with this type of vaccine will produce antibodies only to the limited spectrum of antigens present in the vaccine. By sampling the serum of the swine, it is possible to show that the vaccinated animal has antibodies only to the antigens contained in the vaccine while an animal infected with the wild-type virus would have antibodies against a wider range of antigens. A subunit vaccine used in this way to differentiate vaccinated from pseudorabies infected animals has been disclosed in European Patent Application No. 8540074.4, filed on Sep. 4, 1985, published Nov. 27, 1985 as European Publication No. 0162738 and entitled "Production of Pseudorabies Virus Subunit Vaccines". This published patent application does not teach or suggest the construction or use of a similar diagnostic test in conjunction with a live virus vaccine. The vaccination of an animal with a live virus which would resulting an immune response distinguishable from wild-type infection would also have the further advantages of low cost and high efficacy associated with live virus vaccines.

Deletions in genes coding for viral antigens have been described previously. A spontaneous deletion in the glycoprotein C gene of herpes simplex virus (52), a spontaneous deletion in the glycoprotein A gene of Marek's disease virus (53) a spontaneous deletion in the glycoprotein A gene (also called glycoprotein gI) of PRV (27,55) and the absence or greatly reduced amount of glycoprotein gIII in some PRV mutants (54) are known. However, all of these deletions arose spontaneously in an uncontrolled process. Hence, it has not been possible to direct deletions to DNA encoding for specific antigens to control the deletion process and direct the deletions to antigens particularly suitable as diagnostic markers.

The presence or absence of particular antigens in any infectious disease can be exploited as a diagnostic test for the infectious disease agent. This presence or absence forms the basis for all immunolgocial diagnositc tests, which differ only in the details of their specific immunological approach. Publications pertinent to the current invention include Wathan and Wathan (54) who reported that either the gI gene or the gIII gene could be deleted from PRV and suggested that the resulting virus could be used for distinguishing vaccinated from infected swine. However, they did not describe the methodology necessary to create the vaccine, they did not demonstrate the utility of such a vaccine in serological tests and they did not in any other way prove the feasibility of such a vaccine.

Van Oirschot, et al. (56), have used a special monoclonal-based immunological detection system for gI of PRV and have shown that pigs inoculated with naturally-occuring vaccine strains which are missing at least a portion of the gI gene can be differentiated from pigs infected by wild-type PRV. However, this diagnostic test may be used for any of several vaccines against PRV that are already existing in both Europe and the U.S. without differentiating which vaccine was used. This limits the usefulness of this diagnostic, since the vaccines which are detectable have differing biological and virulence properties.

The approach of deleting a gent to attenuate a virus coupled with a diagnostic for that gene, provides a vaccine that can be differentiated from any of the currently used PRV vaccines and from wild-type PRV. It is important to be able to differentiate a new, safer vaccine from those currently used because pigs receiving the current vaccines are all regulated during eradication programs to the same extent as those infected with wild-type PRV.

Antigens of choice for the purpose of a diagnostic marker would have the following characteristics: 1) the antigens and their genes would be non-essential for the production of infectious virus in tissue culture; and 2) the antigen would elicit a major serological response in the animal, but is preferably not an important neutralizing antigen.

The present invention therefore involves the ability to attenuate pseudorabies virus of swine to create a live virus vaccine and the ability to distinguish whether an animal has been given the vaccination or whether the animal has been infected by wild-type pseudorabies virus.

SUMMARY OF THE INVENTION

The present invention provides a recombinant fusion protein comprising an antigenic amino acid sequence fused to at least a portion of the gpX glycoprotein from pseudorabies virus.

Also provided is a recombinant fusion protein comprising the *E. coli* b galactosidase gene fused at its carboxy terminus to an antigenic amino acid sequence and delivered to an animal using a live herpesvirus vector adapted to express the fusion protein.

The present invention further provides an infectious bovine rhinotracheitis virus which includes a foreign DNA sequence which encodes the *Escherichia coli* beta-galactosidase and neomycin resistance genes, and the parainfluenzae -3, PI-3, virus fusion gene, F.

Further provided is a herpesvirus of turkeys which includes a foreign DNA sequence which encodes the *Escherichia coli* beta-galactosidase gene and the infectious bursal disease virus, IBDV, large segment of RNA.

Also provided is herpesvirus of turkeys which includes a foreign DNA sequence which encodes the *Escherichia coli* beta-galactosidase gene and the Marek's disease virus, MDV, glycoprotein A, gp A, gene.

Furthermore, the present invention provides an attenuated, hybrid, nonprimate herpesvirus which comprises a pseudorabies virus from which has been deleted the TK gene and a portion of the repeat region, and into which has been inserted a foreign DNA sequence which encodes the transmissible gastroenteritis, TGE, virus gp195 gene.

BRIEF DESCRIPTION OF THE FIGURES

Throughout this application various herpesviruses are described, at least in part, by reference to ATCC Accession Numbers. These herpesviruses have been deposited with the American Type Culture Collection (ATCC) 12301 Parklawn Drive, Rockville, Md. 20852. These deposits were made pursuant to the Budapest Treaty on The International Recognition of the Deposit of Microorganisms for the Purposes of Patent Procedure.

FIG. 10A and 10B Swine rotavirus gp38 Gene Sequence in pSY565.

FIG. 11A and 11B Swine parvovirus B gene sequence in pSY875.

FIG. 35 Translation of two versions of the sw vpA=viral protein A; PRV =pseudorabies virus; PPV=porcine parvovirus; KB=kilo base pairs; BP=base pairs; kd=kilo daltons; pA=Poly A addition signal; aa=amino acids.

Abbreviations: gpX=glycoprotein X; CSP=circumsporozoite protein; vpA=viral protein A; PRV=pseudorabies virus; P.fal. =Plasmodium falciparum; pA=Poly A addition signal; aa=amino acids.

Figure 49:
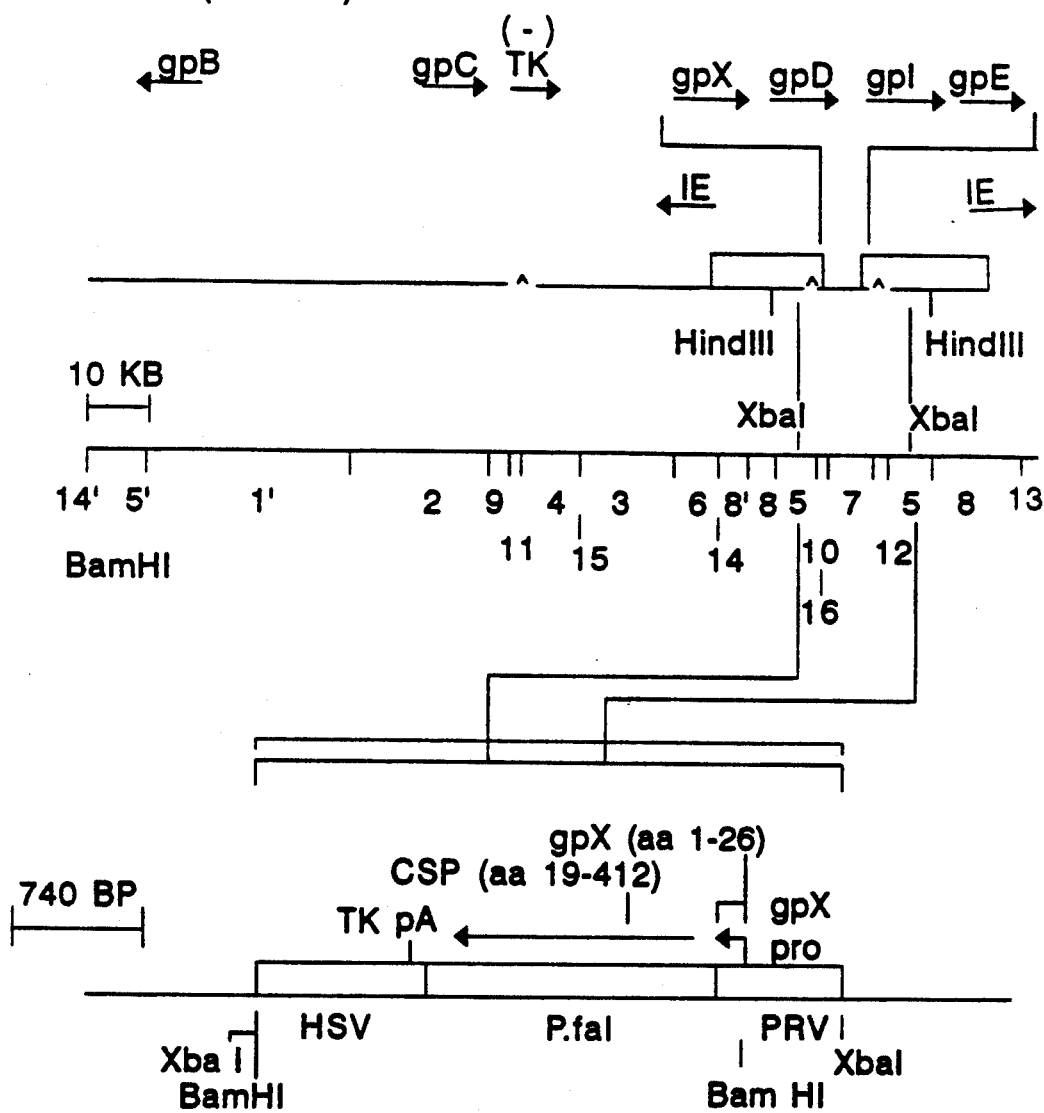
Figure 50:
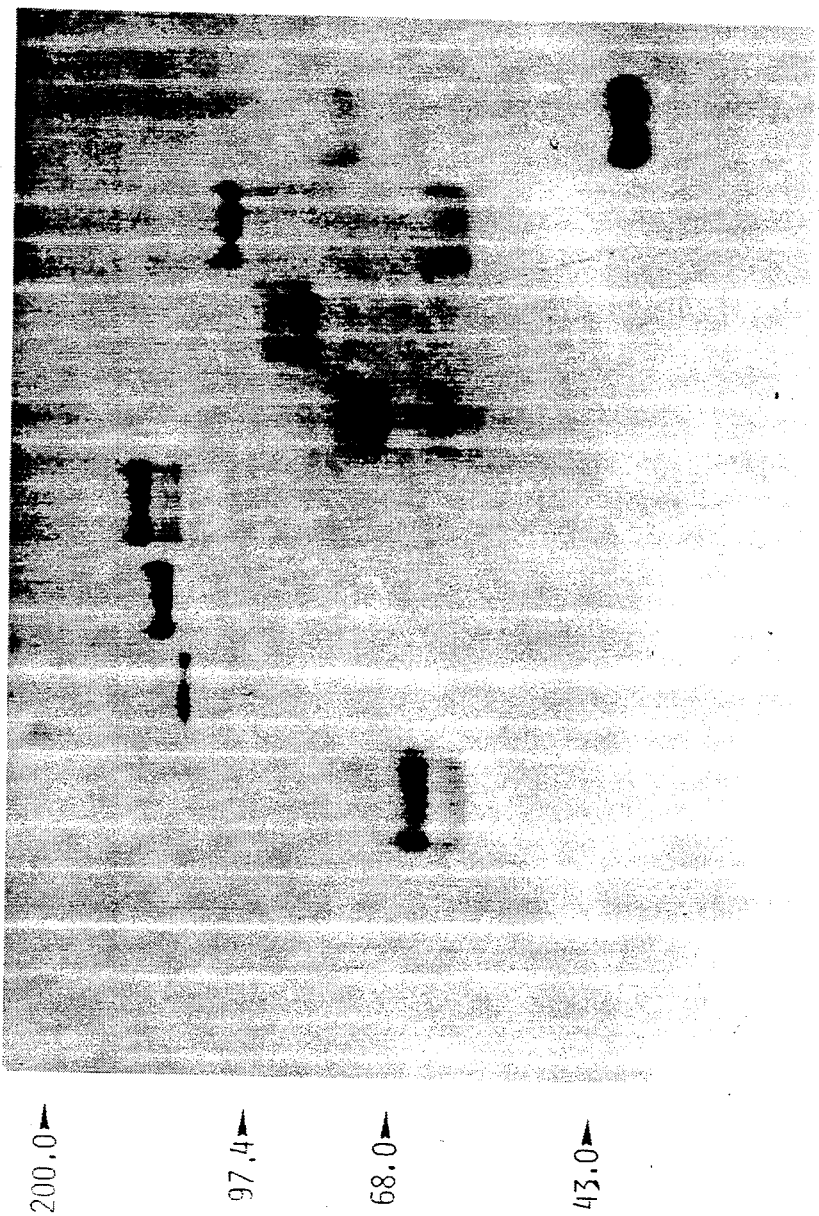

FIG. 49 Structure of S-PRV-066 and summary of foreign genes expressed by the recombinant virus.

Abbreviations: gp=glycoprotein; TK=thymidine kinase; IE=immediate early; CSP =circumsporozoite protein; vpA=viral protein A; PRV=pseudorabies virus; P.fal. =Plasmodium falciparum; KB=kilo daltons; pA=Poly A addition signal; aa=amino acids.

FIG. 50 Western Blot of lysates prepared from recombinant pseudorabies viruses expressing -galactosidase fusion proteins.

FIG. 51 Description of the DNA insertion in plasmid PSY1373. Restriction enzymes indicated are those present in the source DNAs mentioned in the text. Restriction enzymes enclosed in brackets indicate sites which were destroyed in the creation of segment junctions.

Abbreviations: gpX=glycoprotein X; CSP=circumsporozoite protein; vpA=viral protein A; PRV=pseudorabies virus; P.fal. =*Plasmodium falciparum*; pA=Poly A addition signal; aa=amino acids.

FIG. 52 Structure of S-PRV-088 and summary of foreign genes expressed by the recombinant virus.

Abbreviations: gp=glycoprotein; TK=thymidine kinase; IE=immediate early; CSP =circumsporozoite protein; vpA=viral protein A; PRV=pseudorabies virus; P.fal. =*Plasmodium falciparum*; KB=kilo base pairs; BP=base pairs; kd=kilo daltons; pA=Poly A addition signal; aa=amino acids.

FIG 53 Description of the DNA insertion in plasmid 181-66.26. Restriction enzymes indicated are those present in the source DNAs mentioned in the text. Restriction enzymes enclosed in brackets indicate sites which were destroyed in the creation of segment junctions.

Abbreviations: gpX=glycoprotein X; CSP=circumsporozoite protein; vpA=viral protein A; PRV=pseudorabies virus; P.fal. =*Plasmodium falciparum*; pA=Poly A addition signal; aa=amino acids.

FIG. 54 Structure of S-PRV-093 and summary of foreign genes expressed by the recombinant virus.

Abbreviations: gp=glycoprotein; TK=thymidine kinase; IE=immediate early; CSP =circumsporozoite protein; vpA=viral protein A; PRV=pseudorabies virus; P.fal. =Plasmodium falciparum; KB=kilo base pairs; BP=base pairs; kd=kilo daltons; pA=Poly A addition signal; aa=amino acids.

DETAILED DESCRIPTION OF THE INVENTION

The present invention provides a hybrid nonprimate herpesvirus comprising DNA which includes a sequence essential for viral replication of the hybrid, nonprimate herpesvirus, at least a portion of which is present in a sequence essential for replication of a naturally-occurring nonprimate herpesvirus and at least one foreign DNA sequence. The sequence essential for viral replication of the hybrid, nonprimate herpesvirus may be derived from a naturally-occurring nonprimate herpesvirus.

The foreign DNA sequence may be adapted for expression in a host and encode an amino acid sequence. In one embodiment of the invention, the foreign DNA sequence is adapted for expression by a herpesvirus promoter. The herpesvirus promoter may be an endogenous upstream herpesvirus promoter or an inserted upstream herpesvirus promoter. Examples of such herpesvirus promoters include, but are not limited to, the herpes simplex type ICP4 protein promoter, the pseudorabies thymidine kinase promoter, the pseudorabies immediate early gene promoter, the pseudorabies glycoprotein X promoter or the pseudorabies glycoprotein 92 promoter.

The amino acid sequence encoded by the foreign DNA sequence may be a polypeptide. Furthermore, the polypeptide may be a protein. In one embodiment of the invention, the protein, when expressed in the host, is antigenic. In a further embodiment of the invention, the protein is swine rotavirus glycoprotein 38. In yet another embodiment of the invention, the protein is bovine rotavirus glycorprotein 38. In yet a further embodiment of the invention, the protein is swine parvovirus B capsid protein.

The hybrid, nonprimate herpesvirus may comprise DNA of which at least a portion is present in a sequence essential for replication of a naturally-occurring alpha-herpesvirus. The alpha-herpesvirus may be a pseudorabies virus, infectious bovine rhinotracheitis virus, equine herpesvirus I, feline herpesvirus I or canine herpesvirus I. Additionally the alpha-herpesvirus may be a class D herpesvirus. The class D herpesvirus may be psuedorabies virus, infectious bovine rhinotracheitis virus, equine herpesvirus I, feline herpesvirus I or canine herpesvirus I. In one embodiment of the invention, the alpha-herpesvirus is an infectious bovine rhinotracheitis virus and the foreign DNA encodes the *Escherichia coli* neomycin resistance gene. This foreign DNA sequence may also be under the control of an inserted pseudorabies virus glycoprotein X promoter. Such a virus has been constructed, designated S-IBR-004, and deposited with the ATCC under Accession No. VR 2134.

In another embodiment of the invention, the alpha-herpesvirus is an infectious bovine rhinotracheitis virus with a deletion in the unique short sequence. Furthermore, the foreign DNA sequence may encode the bovine rotavirus glycoprotein 38 gene. This virus, designated S-IBR008, has under constructed and deposited with the ATCC under Accession No. VR 2141.

Additionally the hybrid, nonprimate herpesvirus may comprise DNA of which at least a portion is present in a sequence essential for replication of a naturally-occurring gamma-herpesvirus. The gamma-herpesvirus may be Marek's disease virus or herpesvirus of turkeys. Moreover the gamma-herpesvirus may be a class E herpesvirus. The class E herpesvirus may be Marek's disease virus or herpesvirus of turkeys.

Also provided is an attenuated, nonprimate herpesvirus comprising DNA which includes a sequence essential for viral replication of the attenuated, nonprimate herpesvirus, at least a portion of which is present in a sequence essential for replication of a naturally-occurring nonprimate herpesvirus, from which at least a portion of a repeat sequence has been deleted. The sequence essential for viral replication of the attenuated, nonprimate herpesvirus may be derived from a naturally-occurring nonprimate herpesvirus.

The deleted portion of the repeat sequence may include a portion of a repeat sequence other than a junction region or may include a junction region. Additionally, the deleted portion of the repeat sequence may comprise a nonessential sequence of one repeat sequence or both repeat sequences. Furthermore at least a portion of the essential sequence of a repeat may be deleted. In one embodiment of the invention, one entire repeat may be deleted. Moreover, a sequence not located within a repeat may additionally be deleted. In one embodiment of the invention the deleted sequence not located within a repeat is at least a portion of a gene.

The attenuated nonprimate herpesvirus may comprise DNA at least a portion of which is present in a sequence essential for replication of a naturally-occurring alpha-herpesvirus. The alpha-herpesvirus may be a pseudorabies virus, infectious bovine rhinotracheitis virus, equine herpesvirus I, feline herpesvirus I or canine herpesvirus I. Additionally, the alpha-herpesvirus may be a class D herpesvirus. The class D herpesvirus may be a pseudorabies virus, infectious bovine rhinotracheitis virus, equine herpesvirus, I, feline herpesvirus I or canine herpesvirus I. In one embodiment of the invention, the alpha-herpesvirus is an infectious bovine rhinotracheitis virus. In another embodiment of the invention, the attenuated, nonprimate herpesvirus comprises an infectious bovine rhinotracheitis virus from which has been deleted at least a portion of both repeat sequences. This virus has been constructed, designated S-IBR-002, and deposited under ATCC Accession No. VR 2140.

Further provided is an attenuated, hybrid, nonprimate herpesvirus comprising DNA which includes a sequence essential for viral replication of the attenuated, hybrid, nonprimate herpesvirus, at least a portion of which is present in a sequence essential for replication f a naturally-occurring nonprimate, herpesvirus and at least one foreign DNA sequence. The sequence essential for viral replication of the attenuated, hybrid, nonprimate virus may be derived from a naturally-occurring nonprimate herpesvirus. Furthermore, at least a portion of a repeat sequence of the attenuated, hybrid, nonprimate herpesvirus may be deleted.

The foreign DNA sequence may be adapted for expression in a host and encode an amino acid sequence. Additionally, the foreign DNA sequence may be adapted for expression by a herpesvirus promoter. The herpesvirus promoter may be an endogenous upstream promoter or an inserted upstream herpesvirus promoter. The herpesvirus promoter may be the herpes simplex type ICP4 protein promoter, the herpes simplex type I thymidine kinase promoter, the pseudorabies immediate early gene promoter, the pseudorabies glycoprotein X promoter or the pseudorabies glycoprotein 92 promoter.

The amino acid sequence encoded by the foreign DNA sequence may be a polypeptide. Additionally the polypeptide may be a protein. Furthermore the protein, when expressed in a host, may be antigenic. In one embodiment of the invention the protein is swine rotavirus glycoprotein 38. In another embodiment, the protein is bovine rotavirus glycoprotein 38. In a further embodiment of the invention, the protein is swine parvovirus B capsid protein.

The attenuated, hybrid, nonprimate herpesvirus may comprise DNA, at least a portion of which is present in a sequence essential for replication of a naturally-occurring alpha-herpesvirus. The alpha-herpesvirus may be a pseudorabies virus, infectious bovine rhinotracheitis virus, equine herpesvirus I, feline herpesvirus I or canine herpesvirus I. Additionally, the alpha-herpesvirus may be a class D herpesvirus. The class D herpesvirus may be pseudorabies virus, infectious bovine rhinotracheitis virus, equine herpesvirus I, feline herpesvirus I or canine herpesvirus I.

Furthermore the attenuated, hybrid, nonprimate herpesvirus may comprise DNA, at least a portion of which is present in a sequence essential for replication of a naturally-occurring gamma-herpesvirus. The gamma-herpesvirus may be Marek's disease virus or herpesvirus of turkeys. Additionally the gamma-herpesvirus may be a class E herpesvirus. The class E herpesvirus may be Marek's disease virus or herpesvirus of turkeys.

The present invention also provides a vaccine useful for immunizing an animal against a herpesvirus disease. This vaccine comprises an effective immunizing amount of a hybrid, nonprimate herpesvirus of the present invention and a suitable carrier.

Also provided is a multivalent vaccine useful for immunizing an animal against at least one pathogen. This vaccine comprises an effective immunizing amount of a hybrid, nonprimate herpesvirus of the present invention which includes a foreign DNA sequence encoding a protein which, when expressed in the host, is antigenic and a suitable carrier.

Furthermore, the present invention provides a vaccine useful for immunizing an animal against a herpesvirus disease which comprises an effective immunizing amount of an attenuated, nonprimate herpesvirus provided by the invention and a suitable carrier. Another vaccine useful for immunizing an animal against a herpesvirus disease is also provided. This vaccine comprises an effective immunizing amount of an attenuated, hybrid, nonprimate herpesvirus of the present invention and a suitable carrier.

Moreover, a multivalent vaccine useful for immunizing an animal against at least one pathogen is provided. This vaccine comprises an effective immunizing amount of an attenuated, hybrid, nonprimate herpesvirus which includes at least one foreign DNA sequence encoding a protein which, when expressed in the host, is antigenic and a suitable carrier.

Methods of immunizing animals against herpesvirus diseases and methods of immunizing an animal against at least one pathogen are provided. These methods comprise administering to the animal a suitable dose of a vaccine of the present invention. The animals which may be immunized include, but are not limited to, bovine animals, sheep and goats.

Methods of identifying the hybrid, nonprimate herpesviruses are provided. In one embodiment of the invention, the foreign DNA sequence in the virus is detected. In another embodiment of the invention, the presence of the expressed polypeptide in the host animal or host cell is detected. In yet another embodiment of the invention, the presence of the expressed protein in the host animal or host cell is detected.

Furthermore, methods of identifying an attenuated, hybrid, nonprimate herpesvirus of the invention are provided. In one embodiment of the invention, the foreign DNA sequence is detected. In another embodiment of the invention, the presence of the expressed polypeptide in the host animal or host cell is detected. In yet a third embodiment of the invention, the presence of the expressed protein in the host animal or host cell is detected.

The presence invention further provides a method of producing in an animal a gene product for purposes other than immunization. This method comprises administering to the animal a suitable quantity of a hybrid, nonprimate herpesvirus of the present invention which includes a foreign DNA sequence adapted for expression in a host, the foreign DNA sequence of which expresses the gene product. Additionally, a gene product may be produced in an animal for purposes other than immunization by administering to the animal a suitable quantity of an attenuated, hybrid, nonprimate herpesvirus which includes a foreign DNA sequence adapted for expression in a host, the foreign DNA sequence of which expresses the gene product.

Methods of preparing an attenuated, hybrid, nonprimate herpesvirus of the present invention are also provided. One method comprises isolating naturally-occurring nonprimate herpesvirus viral DNA and using restriction enzyme digestion to produce DNA restriction fragments. These restriction fragments are purified by agarose gel electrophoresis to obtain specific DNA fragments which are treated with appropriate enzymes, known to those skilled in the art, to produce modified viral DNA fragments. These modified DNA fragments are capable of binding to bacterial plasmid DNA sequences. Suitable bacterial plasmids are separately treated with appropriate restriction enzymes, known to those skilled in the art, to produce bacterial plasmid DNA sequences capable of binding to modified viral DNA fragments. These bacterial plasmid sequences are then combined with the modified viral DNA fragments under suitable conditions to allow the viral DNA to bind the bacterial DNA and form a viral-bacterial plasmid.

The viral-bacterial DNA plasmid is then mapped by restriction enzymes to generate a restriction map of the viral DNA insert. The viral-bacterial DNA plasmid is then treated with a restriction enzyme known in the art to cause at least one deletion in the viral DNA sequence of the viral-bacterial DNA plasmid. This plasmid, containing at least one deletion in the viral DNA sequence, is transfected with naturally-occurring nonprimate herpesviral DNA into animal cells. The animal cells are maintained under suitable conditions to allow the naturally-occurring nonprimate herpesviral DNA to regenerate herpesviruses and a small percent of viruses which have recombined with the viral-foreign DNA sequence of the viral-bacterial-foreign DNA plasmid. Some of these recombined viruses have deletions in their genome as a result of deletions in the viral DNA insert of the plasmid. The viruses are identified and subsequently plaque purified away from the undesired viruses.

In another embodiment of the invention, naturally-occurring nonprimate herpes viral DNA is isolated and digested with appropriate restriction enzymes to produce viral restriction fragments. Separately, foreign DNA is digested with appropriate enzymes to produce foreign DNA restriction fragments. The foreign DNA restriction fragments are mixed with the viral DNA restriction fragments under suitable conditions so as to allow the fragments to join together to produce viral-foreign DNA fragments. Animal cells are transfected with the viral-foreign DNA fragments and maintained under suitable conditions so as to allow the foreign DNA fragments to regenerate herpesviruses and a small percent of viruses which have includes foreign DNA fragments into their genome. Herpesviruses which have included desired foreign DNA fragments into their genome are identified and plaque purified away from undesired herpesviruses.

In still another embodiment, this invention provides a recombinant fusion protein comprising an antigenic amino acid sequence, e.g. a foreign antigen or epitope, fused to at least a portion of the gpX protein from pseudorabies virus, such as the amino terminal transmembrane signal sequence from the gpX glycoprotein. Thus, the antigenic amino acid sequence may be inserted into an internal portion of the gpX glycoprotein, such that the gpX/antigenic amino acid sequence boundary is in frame only on the amino terminal side or such that both gpX/antigenic amino acid sequence boundaries are in frame (an embedded fusion) with each other.

A recombinant fusion protein in accordance with the teachings of the subject invention may be delivered to an animal using a live herpes vector adapted to express the fusion protein and, for example, may comprise as the antigenic amino acid sequence all or part of swine parvovirus capsid protein or the malaria CSP protein, particularly the malaria CSP repeat region.

In a particular embodiment of the invention the recombinant fusion protein comprises the *E. coli* beta galactosidase gene fused at its carboxy terminus to an antigenic amino acid sequence and is delivered to an animal using a live herpesvirus vector adapted to express the fusion protein.

Effective immunizing amounts of the recombinant fusion proteins of this invention may be formulated into vaccines using methods well known to those skilled in the art.

In yet another embodiment of the invention, an infectious bovine rhinotracheitis virus includes a foreign DNA sequence which encodes the *Escherichia coli* beta-galactosidase and neomycin resistance genes, and the parainfluenzae -3, PI-3, virus hemagglutinin gene, HN. One such virus, designated S-IBR-018, has been constructed and deposited with the ATCC under Accession No. VR 2180.

Also provided is an infectious bovine rhinotracheitis virus which includes a foreign DNA sequence which encodes the *Escherichia coli* beta-galactosidase and neomycin resistance genes, and the parainfluenzae -3, PI-3, virus fusion gene, F. One such virus which has been constructed is designated S-IBR-019.

Further provided is a herpesvirus of turkeys which includes a foreign DNA sequence which encodes the *Escherichia coli* beta-galactosidase gene and the infectious bursal disease virus, IBDV, large segment of RNA. One such virus, designated S-HVT-003, has been constructed and deposited with the ATCC under Accession No. VR 2178.

In another embodiment of the invention, a herpesvirus of turkeys which includes a foreign DNA sequence encodes the *Escherichia coli* beta-galactosidase gene and the Marek's disease virus, MDV, glycoprotein A, gp A, gene. One such virus has been designated S-HVT-004.

The attenuated, hybrid, nonprimate herpesvirus may comprise a pseudorabies virus from which has been deleted the TK gene and a portion of the repeat region, and into which has been inserted a foreign DNA sequence which encodes the transmissible gastroenteritis, TGE, virus gp195 gene. This virus, designated S-PRV-055, has been constructed and deposited with the ATCC under Accession No. VR 2179.

This invention further provides attenuated pseudorabies viruses designated S-PRV-065 (ATCC No. VR 2215); S-PRV-086 (ATCC No. VR 2216); S-PRV-040 (ATCC No. VR 2214; S-PRV-098 (ATCC No. VR 2219); S-PRV-066; S-PRV-088 (ATCC No. VR 2217); and S-PRV-093 (ATCC No. VR 2218).

The present invention discloses that expression of foreign antigens in herpesviruses is in large part determined by the sequence of DNA encoding the foreign antigen. In particular, the "triplet" frequencies of the codons used in the gene itself and the position of these "triplet" frequencies within the intact messenger RNA becomes the crucial factors in the expression of all foreign antigens within herpesviruses. Some foreign antigens have these sequences naturally and do not need to be changed, but most do not. The actual biological basis for this effect is still largely unknown, but a computer-modelling test has been derived that can be used to predict the expression of a foreign antigen in herpesviruses. The present invention discloses expression of foreign antigens that had low or no expression using only herpesvirus regulatory signals known in the art, but became much improved in expression when the present invention was applied.

The present invention may be practiced by one of the following:

1. directly synthesizing the gene for the foreign antigen substituting wherever possible in the coding region nucleotide triplets (codons) that are favored within the herpesvirus genome, then using this synthetic gene to express the foreign protein in the herpesvirus vector; or 2. by making a fusion between a gene that already has the favored herpesvirus triplet nucleotide (codons) followed by a foreign antigen gene that does not have the favored triplet frequencies, and positioning the favored gene so that it is translated first in the fusion (thereby competing successfully for ribosomes) followed by the foreign gene which utilizes these same ribosomes.

The present invention discloses the means to determine if a gene is favorable or unfavorable within the herpesvirus context, and then discloses how to synthesize a gene that is more favorable starting with a gene that is unfavorable. Secondly, it discloses a class of genes that are already favorable, and demonstrates how fusions of these genes with unfavorable genes can be used to drive the expression of the unfavorable part of the fusion.

Materials and Methods

GROWTH OF HERPESVIRUS IN TISSUE CULTURE. All of the herpesviruses under discussion were grown in tissue culture cells. Unless otherwise noted, the cells used were: Vero cells for PRV; MDBK cells for IBR; CEF cells for HVT; Crandall feline kidney cells for FHV. Vero cells are suitable for EHV and MDCK cells are suitable for CHV.

PREPARATION OF HERPESVIRUS STOCK SAMPLES. Herpesvirus stock samples were prepared by infecting tissue culture cells at a multiplicity of infection of 0.01 PFU/cell in Dulbecco's Modified Eagle Medium (DMEM) containing 2 mM glutamine, 100 units/ml penicillin, 100 units/ml streptomycin (these components were obtained from Irvine Scientific or equivalent supplier, and hereafter are referred to as complete DME medium) plus 1% fetal bovine serum. After cytopathic effect was complete, the medium and cells were harvested and the cells were pelleted at 300 rpm for 5 minutes in a clinical centrifuge. For all herpesviruses except HVT, the cells were resuspended in 1/10 the original volume of medium, and an equal volume of 2 times autoclaved skim milk (9% skim milk powder in $H_2O$ wgt/vol) was added. The virus sample was frozen and thawed 2 times, aliquoted, and stored frozen at $-70°$ C. The titer was usually about $10^8$ plaque forming units per ml. For HVT, infected cells were resuspended in complete medium containing 20% fetal bovine serum, 10% DMSO and stored frozen at $-70°$ C.

PREPARATION OF HERPESVIRUS DNA. For herpesvirus DNA preparation, a confluent monolayer of tissue culture cells in a 25 $cm^2$ flask or a 60 mm petri dish was infected with 100 microliters of virus sample in 1 ml medium. Adsorption proceeded for 1-2 hours at 37° C. in a humidified incubator with 5% $CO_2$ in air. After adsorption, 4 mls of complete DME medium plus 1% fetal bovine serum were added. After overnight incubation, or when the cells were showing 100% cytopathic effect, the cells were scraped into the medium with a cell scraper (Costar brand). The cells and medium were centrifuged at 3000 rpm for 5 minutes in a clinical centrifuge. The medium was decanted, and the cell pellet was gently resuspended in 0.5 ml solution containing 0.01M Tris pH 7.5, 1 mM EDTA, and 0.5% Nonidet P-40 (NP40, an ionic detergent comprising an octyl phenol ethylene oxide condensate containing an average of 9 moles ethylene oxide per molecule, purchased from Sigma Chemical Co., St. Louis, Mo.). The sample was incubated at room temperature for 10 minutes. Ten microliters of a stock solution of RNase A (Sigma) were added (stock was 10 mg/ml, boiled for 10 minutes to inactivate DNAase). The sample was centrifuged for 5 minutes at 3000 rpm in a clinical centrifuge to pellet nuclei. The DNA pellet was removed with a pasteur pipette or wooden stick and discarded. The supernatant fluid was decanted into a 1.5 ml Eppendorf tube containing 25 microliters of 20% medium dodecyl sulfate (Sigma) and 25 microliters proteinase-K (10 mg/ml; Boehringer Mannheim supplier). The sample was mixed and incubated at 37° C. for 30-60 minutes. An equal volume of water-saturated phenol was added and the sample was mixed on a vortex mixer for 1 minute. The sample was centrifuged in an Eppendorf minifuge for 5 minutes at full speed. The upper aqueous phase was removed to a new Eppendorf tube, and two volumes of $-20°$ C. absolute ethanol were added and the tube put at $-20°$ C. for 30 minutes to precipitate nucleic acid. The sample was centrifuged in an Eppendorf centrifuge at 4° C. for 5 minutes. The supernatant was decanted, and the pellet was washed one time with cold 80% ethanol. The pellet was dried in a lyophilizer, and rehydrated in 17 microliters H2O. For the preparation of larger amounts of DNA, the procedure was scaled up to start with a 850 cm2 roller bottle of Vero cells. The DNA was stored in H2O or in 0.01M Tris pH 7.5, 1 mM EDTA at $-20°$ C. or $+4°$ C.

PREPARATION OF HERPES VIRUS OF TURKEY DNA. All manipulations requiring herpes virus of turkey (HVT) were made using strain FC-126 (ATCC #584-C). For the preparation of HVT viral DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% $CO_2$ in air. Best DNA yields were obtained by harvesting monolayers which were maximally infected, but showing incomplete cell lysis (typically 5-7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments). The resultant pellet was resuspended in cold PBS (20 ml/Roller Bottle) and subjected to another centrifugation for 10 minutes at 3000 rpm in the cods. After decanting the PBS, the cellular pellet was resuspended in 4 ml/ roller bottle of RSB buffer (10 mM Tris pH 7.5, 1 mM EDTA, and 1.5 mM $MgCl_2$). NP40 (Nonidet P-40; Sigma) was added to the sample to a final concentration of 0.5% and allowed to incubate on ice for 15 minutes with occasional mixing. The sample was centrifuged for 10 minutes at 3000 rpm in the cold to pellet the nuclei and remove cellular debris. The supernatant fluid was carefully transferred to a 15 ml Corex centrifuge tube. Both EDTA (0.5M pH 8.0) and SDS (sodium dodecyl sulfate; stock 20%) were added to the sample to final concentrations of 5 mM and 1%, respectively. One hundred microliters of proteinase-K (10 mg/ml; Boehringer Mannheim) was added per 4 milliliters of sample, mixed, and incubated at 45° C. for 1-2 hours. After this period, an equal volume of water-saturated phenol was added to the sample and gently mixed by hand. The sample was spun in a clinical centrifuge for 5 minutes at 3000 rpm to separate the phases. NaOAc was added to the upper aqueous phase to a final concentration of 0.3M (stock solution 3M pH 5.2), and the nucleic acid precipitated at $-70°$ C. for 30 minutes after the addition of 2.5 volumes of cold absolute ethanol. DNA in the sample was pelleted by spinning for 20 minutes at 8000 rpm in an HB-4 rotor at 5° C. The supernatant was carefully removed and the DNA pellet washed once with 25 ml of 80% ethanol. The DNA pellet was dried briefly by vacuum (2-3 minutes), and resuspended in 50 microliters/roller bottle of infected cells of $T_{10}E_1$ buffer (10 mM Tris pH 7.5, 1 mM EDTA). Typically, yields of viral DNA ranged between 5-10 micrograms/roller bottle of infected cells. All viral DNA was stored at approximately 10° C.

PREPARATION HERPESVIRUS CELLYSATES. For cell lysate preparation, a confluent monolayer of tissue culture cells in a 25 cm flask or a 60 mm petri dish was infected with 100 microliters of virus sample in 1 ml of medium. Adsorption proceeded for 1-2 hours at 37° C. in a humidified incubator with 5% $CO^2$ in air. After adsorption, 4 mls of medium were added. After overnight incubation, or when cells were showing 100% cytopathic effect, the cells were scraped into the medium with a cells scraper (Costar brand). The cells and medium were centrifuged at 3000 rpm for 5 minutes in a clinical centrifuge. The medium was decanted, and the cell pellet was suspended in 250 microliters of disruption buffer (2% sodium dodecyl sulfate, 2% beta-mercapto-ethanol). The samples were sonicated for 30 seconds on ice and stored at $-20°$ C.

PHENOL EXTRACTION. Phenol extraction was performed on any convenient volume of DNA sample, typically between 100 microliters to 1 ml. The DNA sample was diluted in 0.01M Tris pH 7.5, 1 mM EDTA and an equal volume of water saturated phenol was added. The sample was mixed briefly on a vortex mixer and placed on ice for 3 minutes. After centrifugation for 3 minutes in a microfuge, the aqueous layer was removed to a new tube and was precipitated by ethanol.

ETHANOL PRECIPITATION. DNA in a sample was concentrated by ethanol precipitation. To the DNA sample were added 1/10 volume of 3M sodium acetate, pH 7.5 and 3 volumes of cold ethanol. The DNA was precipitated for 30 minutes at $-70°$ C. or overnight at $-20°$ C. and then pelleted by centrifugation in the microfuge for 15 minutes at 4° C. The pellet was washed once with 200 microliters of cold 80% ethanol and pelleted again for 10 minutes at 4° C. After air drying or lyophilization, the pellets were resuspended in the appropriate buffer or $H_2O$.

RESTRICTION ENZYME DIGESTION. DNA was cut by restriction enzymes using the buffer recommended by the manufacturer (International Biotechnologies Inc. New Haven, Conn. (IBI), Bethesda Research Laboratories, Bethesda, Md. (BRL), and New England Biolabs, Beverly, Mass.). Whenever possible, the concentration of DNA was kept below 1 microgram/50 microliters. Incubation was at 37° C. for 1-4 hours.

AGAROSE GEL ELECTROPHORESIS OF DNA. To visualize the restriction pattern of the DNA, 5 microliters of loading buffer (5× electrophoresis buffer, 0.01% bromphenol blue dye, 50 mM EDTA, and 50% glycerol) were added. The sample was loaded into a lane in a horizontal submarine electrophoresis unit containing a 0.6% agarose gel. The electrophoresis buffer was 40 mM Tris, 10 mM EDTA, adjusted to pH 7.8 with acetic acid, and with or without 0.5 micrograms/ml ethidium bromide. The gel was run at 40-50 V for 18 hours, and the gel was removed and stained with 0.5 micrograms/ml ethidium bromide for 30 minutes. The DNA bands were visualized on a long wavelength UV transilluminator.

PHOSPHATASE TREATMENT OF DNA. Phosphatase treatment of DNA was performed by adding 1 microliter (25 units) of calf intestinal phosphatase (Boehringer Mannheim) directly to the restriction enzyme digestion reactions and continuing the incubation for 30 minutes at 37° C. The phosphatase was inactivated for 60 minutes at 65° C. prior to phenol extraction.

POLYMERASE FILL-IN REACTION. DNA was resuspended in buffer containing 50 mM Tris pH 7.4, 50 mM KCl, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

EXONUCLEASE RESECTION REACTION. DNA was resuspended in 100 microliters of 60 mM Tris pH 8.0, 0.66 mM $MgCl_2$, 1 mM beta-mercaptoethanol. The sample was warmed to 30° C. for 5 minutes, and 10 units of lambda exonculease III (BRL) were added. At frequent time intervals (e.g. every 2.5 minutes), 10 microliter aliquots were diluted into 100 microliters of 30 mM sodium acetate pH 4.5, 250 mM NaCl, 1 mM $ZnSO_4$, 4 micrograms/100 microliters yeast tRNA, 30 units/100 microliters S1 nuclease. After 45 minutes at 30° C., 15 microliters of stop buffer consisting of 625 mM Tris pH 9.0, 150 mM EDTA, 1% SDS were added. The samples were then phenol extracted and ethanol precipitated as above. The DNA digestion products were then analyzed and purified by agarose gel electrophoresis.

PHENOL EXTRACTION OF DNA FROM AGAROSE. DNA bands cut from low melting point agarose gels were diluted to less than 0.5% agarose to a final concentration of 0.3M sodium acetate. The samples were heated to 65° C. to melt the agarose and then cooled to 37° C. for 5 minutes. An equal volume of phenol was added and the sample was phenol extracted three times (see PHENOL EXTRACTION). The DNA was then ethanol precipitated and the pellet resuspended at a concentration of 3-6 fmole DNA/microliter.

LIGATION. DNA was jointed together by the action of the enzyme T4 DNA ligase (BRL). Ligation reaction contained 10 fmoles DNA, 20 mM Tris pH 7.5, 10 mM $MgCl_2$, 10 mM dithiothreitol (DTT), 200 micromolar ATP, and 20 units T4 DNA ligase in 10 microliters final reaction volume. The ligation was allowed to proceed for 3-16 hours at 15° C. Typically DNA fragments to be ligated together were added at an equal molar ratio. Typically two different DNA fragments were joined during ligation, but joining of three or four different DNAs at once was also possible.

RESTRICTION MAPPING OF DNA. Restriction mapping of DNA was performed as detailed in Maniatis et al. (1). Once it was cloned, the DNA was digested with a number of different restriction enzymes and the DNAs were analyzed on agarose gels and the sizes of the resulting fragments were measured. A double digest with two different restriction enzymes was performed on the same DNA sample to aid in the interpretation of the maps. Another approach used was to cut the DNA with a restriction enzyme that has a single unique site in the DNA, label the end of the DNA with $^{32}P$ using T4 DNA kinase or Klenow DNA polymerase (see POLYMERASE FILL-IN REACTION) and then cut the DNA with other restriction enzymes at low temperature or for short times so that only partial digestion occurred. The subsequent analysis of the partial digestion fragments on agarose gels served to order the restriction sites on the map. All of these mapping procedures are well understood by those skilled in the art and are detailed in Maniatis et al. (1). The most complete restriction maps can only be composed once the DNA has been sequenced, and the sequence is then analyzed by a computer searching for all the known restriction enzyme sites. Some of our maps have been generated from sequence information.

SOUTHERN BLOTTING OF DNA. The general procedure for Southern blotting was taken from Maniatis et al. (1). DNA was blotted to nitrocellulose filters (S&S BA85) in 20× SSC (1× SSC=0.15M NaCl, 0.015M sodium citrate, pH 7.0), and prehybridized in hybridization solution consisting of 30% formamide, 1× Denhardt's solution (0.02% polyvinylpyrrolidone (PVP), 0.02% bovine serum albumin (BSA), 0.02% Ficoll), 6× SSC, 50 mM $NaH_2PO_4$, pH 6.8, 200 micrograms/ml salmon sperm DNA for 4-24 hours at 55° C. Labeled probe DNA was added that had been labelled by nick translation using a kit from Bethesda Research Laboratories (BRL) and one $^{32}P$-labeled nucleotide. The probe DNA was separated from the unincorporated nucleotides by NACS column (BRL) or on a Sephadex G50 column (Pharmacia). After overnight hybridization at 55° C., the filter was washed once with 2× SSC at room temperature followed by two washes with 0.01× SSC, 0.1% sodium dodecyl sulfate (SDS) for 30 minutes at 55° C. The filter was dried and autoradiographed.

DNA TRANSFECTION FOR GENERATING RECOMBINANT VIRUS. The method is based upon the calcium phosphate DNA precipitation procedure of Graham and Van der Eb (32) with the following modifications. For transfection into animal cells, 0.1-0.2 micrograms of plasmid DNA containing the foreign DNA flanked by appropriate herpesvirus cloned sequences (the homovector) were mixed with 0.3 micrograms of intact DNA. Both DNAs were stored either in $H_2O$ or 0.01M Tris pH 7.5, 1 mM EDTA and the final volume should be less than 0.25 ml. To the mixture was added an equal volume of 2× HEPES buffered saline (10 g N-2-hydroxyethyl piperazine N'-2-ethanesulfonic acid (HEPES), 16 g, NaCl, 0.74 g KCl, 0.25 g $Na_2HPO_4 \cdot 2 \cdot H_2O$, 2 g dextrose per liter $H_2O$ and buffered with NaOH to pH 7.4). The mixture was then diluted to 0.5 ml by the addition of the appropriate volume of 1× HEPES buffered saline (prepared by diluting the above solution 1:1 with $H_2O$). After mixing, 35 microliters of 2.2M $CaCl_2$ were added to the DNA mixture and mixed.

The mixture was incubated at room temperature for 30 minutes. Medium was removed from an 80% confluent monolayer of rabbit skin cells, Vero cells, or CEF cells growing in a 25 $cm^2$ flask, and the DNA mixture was added to the flask and distributed over the cells. After a 30 minute incubation at room temperature, 5 mls of complete DME medium plus 10% fetal bovine serum were added. The cells were incubated for 5 hours at 37° C. in a humidified incubator containing 5% $CO_2$ in air. The medium was changed at 5 hours either with or without a glycerol shock. When used, the glycerol shock consisted of removing the medium and adding DME containing 20% glycerol for 3 minutes at room temperature, followed by a wash with 10% glycerol in DME, and a wash in 5% glycerol in DME, followed by the addition of fresh complete DME medium plus 10% fetal bovine serum. The cells were incubated at 37° C. as above for 3-4 days until cytopathic effect from the virus was 50-100%. Virus was harvested as described above for the preparation of virus stocks. This stock was referred to as a transfection stock and it was subsequently screened for recombinant virus either with or without a selection mechanism to enrich for recombinant plaques as described below.

DNA COTRANSFECTION FOR GENERATING RECOMBINANT HVT VIRUS. The method is based upon the polybrene-DMSO procedure of Kawai and Nishizawa (Mol and Cell bio., vol 4, pages 1172-1174, 19840 with the following modifications. Generation of recombinant HVT virus is dependent upon homologous recombination between HVT viral DNA and the plasmid homology vector containing the desired foreign DNA flanked by the appropriate herpesvirus cloned sequences. Transfections were carried out in 6 cm plates (Corning plastic) of 50% confluent primary chick embryo fibroblast (CEF) cells. The cells were plated out the day before in CEF growth media (1× F10/199, 5%, fetal calf serum, 2% glutamine, 1% non-essential amino acids, and 2% penicillin/streptomycin) containing 4 micrograms/milliliter polybrene (stock 4 mg/ml in 1× HBSS). For cotransfections into CEF cells, 5 micrograms of the plasmid homology vector was mixed with 5 micrograms of intact HVT DNA, and suspended in 1 ml of CEF media containing 30 micrograms/milliliter polybrene (stock 4 mg/ml in 1× HBSS). The DNA-polybrene suspension (1 ml) was then added to a 6 cm plate of CEF cells from which the media had been aspirated, and incubated at 39° C. for 30 minutes. The plates were rocked periodically during this time to redistribute the inoculum. After this period, 4 ml of CEF growth media was added directly to each plate, and incubated an additional 2.5 hours at 39° C. At this time, the media was removed from each plate, and the cells shocked with 2 ml of 30% DMSO (Dimethyl Sulfoxide, J. T. Baker Chemical Co.) in 1× HBSS for 4 minutes at room temperature. The 30 % DMSO was carefully removed and the monolayers washed once with 1× HBSS at room temperature. The cells were then incubated at 39° C. after the addition of 5 mls of CEF growth media. The next day, The media was changed to remove any last traces of DMSO and to stimulate cell growth. Cytopathic effect from the virus becomes apparent within 6 days. Generation of a high titer stock (80%-90% CPE) can usually be made within 1 week from this date. HVT stock samples were prepared by resuspending the infected cells in CEF growth media containing 20% fetal calf serum, 10% DMSO and stored at −70° C.

DIRECT LIGATION PROCEDURE FOR GENERATING RECOMBINANT HERPESVIRUSES. Rather than using homovectors and relying upon homologous recombination to generate recombinant virus, the technique of direct ligation was developed to insert foreign genes into herpesviruses. In this instance, the cloned foreign gene did not require flanking herpesvirus DNA sequences but only required that it have restriction sites available to cut out the foreign gene fragment from the plasmid vector. A compatible restriction enzyme was used to cut the herpesvirus DNA. A requirement of the technique was that the restriction enzyme used to cut the herpesvirus DNA must cut at a limited number of sites, preferably less than 'sites. For PRV DNA, we have used xbaI, which cut PRV DNA in two places, and contemplate the use of HindIII (2 cuts), EcoRV (2 or 3 cuts) or NdeI (3-5 cuts). The herpesvirus DNA was mixed with a 30-fold molar excess of plasmid DNA, and the mixture was cut with the appropriate restriction enzyme. The DNA mixture was phenol extracted and ethanol precipitated to remove restriction enzymes, and ligated together according to the ligation procedure detailed above. The ligated DNA mixture was then phenol extracted, ethanol precipitated, and resuspended in 298 microliters 0.01M Tris pH 7.5, 1 mM EDTA. Forty-two microliters of 2M $CaCl_2$ were added, followed by an equal volume of 1× HEPES buffered saline (see above), and the sample was used to transfect animal cells as described above.

The virus in the transfection stock was then screened for foreign DNA inserts as described below. The advantage of the direct ligation technique was that is required less construction of sub-clones in the plasmid state, and that the recombinant virus was present in the transfection stock at a much higher frequency than with homologous recombination.

HAT SELECTION F RECOMBINANT HERPESVIRUS EXPRESSING THYMIDINE KINASE. Deletion mutants of herpesviruses which suffered deletions in the thymidine kinase (TK) gene were constructed. These PRV strains have been designated S-PRV-002 and S-PRV-003 and have been deposited with the ATCC under Accession No. VR 2107 and VR 2108 respectively. These TK minus (TK-) viruses have been used as recipients for the insertion of the foreign herpes simplex type 1 (HSV-1) TK gene. One HSV-1 TK gene that we have used contains the HSV-1 ICP4 promoter and was from B. Roizman (16). It was sub-cloned to lie between two flanking regions of PRV DNA, for example by insertion of the TK gene into PRV BamHI #5 fragment between XbaI and HpaI sites. The plasmid construct was then transfected with the PRV TK- DNA to yield recombinant virus. The transfection stock was enriched for TK-containing virus by the HAT selection procedure described in 35). The transfection stock was used to infect monolayers of 143 TK- cells in 60 mm culture dishes that had been preincubated in HAT medium for 16 hours at 37° C. (HAT medium: medium 199 containing 2 mM glutamine, 100 units/ml penicillin, 100 units/ml streptomycin, 10% fetal bovine serum, $5 \times 10^{-5}$M hypoxanthine, $10^{-5}$M thymidine, $5 \times 10^{-6}$M aminopterin). Samples of the transfection stock virus were infected into the 143 TK- cells using $10^{-3}$ to $10^{-7}$ dilutions of virus. After one or two days at 37° C. the dished inoculated with the highest dilution of virus and still showing virus plaques were harvested for virus stocks, and the selection was repeated a second time. The virus stock harvested from the second HAT selection was used in a plaque assay and individual plaques were picked and tested for foreign DNA inserts as described below.

BROMODEOXYURIDINE SELECTION OF RECOMBINANT HERPESVIRUS. In order to insert a foreign gene in place of a TK gene already present in the herpesvirus genome, the foreign gene was cloned in plasmids so that it contained the same flanking homology regions as the TK genes. These flanking regions could be part of the TK gene itself, or parts of the herpesvirus that flank the TK gene. In either case, the plasmid DNA containing the foreign gene was transfected with intact herpesvirus genomic DNA containing the HSV-1 TK gene. The transfection stock of recombinant virus was grown for two selections in 143 TK- cells in the presence of 40 micrograms/ml bromodeoxyuridine (BUDR, Sigma) in complete DME medium plus 10% fetal bovine serum. The drug BUDR is an analogue of thymidine that is recognized by the viral enzyme thymidine kinase (TK) and is ultimately incorporated into DNA. When incorporated into the DNA, BUDR is mutagenic and lethal and thus selects against viruses that have an active TK gene. By this selection method, viruses that had exchanged their TK gene for a foreign gene by homologous recombination were enriched in the population. Screening for the recombinant viruses was then performed by one of the techniques detailed below.

HYBRIDIZATION SCREEN FOR RECOMBINANT HERPESVIRUS. One procedure used is described in (36). The technique involved doing a plaque assay on PRV under agarose, removing the agarose once plaques had formed, and lifting the cell monolayer from the dish onto a nitrocellulose membrane filter. The filter was then processed through the Southern procedure for DNA hybridization as detailed above. The DNA probe used in the procedure was made from the foreign gene that had been inserted into the virus. Thus plaques that contain the foreign gene were identified, and they were picked from the agarose overlay that had been saved.

BLUOGAL SCREEN FOR RECOMBINANT HERPESVIRUS. When the foreign gene encoded the enzyme beta-galactosidase, the plaques that contained the gene were visualized more easily. The chemical Bluogal~ (BRL) was incorporated at the level of 200-300 micrograms/ml into the agarose overlay during the plaque assay, and the plaques that expressed active beta -galactosidase turned blue. The blue plaques were then picked and purified by further blue plaque isolations. Other foreign genes were inserted by homologous recombination such that they replaced the beta-galactosidase gene; in this instance non-blue plaques were picked for purification of the recombinant virus.

ANTIBODY SCREEN FOR RECOMBINANT HERPESVIRUS. A Third method for screening the recombinant virus stock was to look directly for the expression of the foreign gene with antibodies. Herpesvirus plaques were spotted and picked by inserting a toothpick through the agarose above the plaque and scraping the plaque area on the dish. Viruses were then rinsed from the toothpick by inserting the toothpick into a well of a 96-well microtiter dish (Falcon Plastics) containing a confluent monolayer of tissue culture cells that had been washed 3 times in DME medium without serum. It was important for the virus to grow without serum at this stage to allow the immunological procedure to work. After cytopathic effect was complete, the plates were put at $-70°$ C. to freeze and lyse the cells. The medium was thawed, and the freeze/thaw procedure was repeated a second time. Then 50-100 microliters of medium were removed from each well and filtered under vacuum through a nitrocellulose membrane (S&S BA85) using a DotBlot~ apparatus (BRL). The filter blots were soaked in a blocking solution of 0.01M Tris pH 7.5, 0.1M NaCl, 3% bovine serum albumin at room temperature for two hours with shaking. The filter blots were then placed in a sealable bag (Sears-A-Meal ® or equivalent), and 10 mls of the blocking solution that contained 10 microliters of antibody specific for the foreign protein were added. After overnight incubation at room temperature with shaking, the blot was washed 3 times with 100 mls 0.01M Tris, pH 7.5, 0.1M NaCl, 0.05% Tween 20 detergent (Sigma). The blot was put in another sealable bag and 10 mls blocking solution containing $10^6$ counts per minute of $^{125}$I-protein A (New England Nuclear) were added. After allowing the protein A to bind to the antibody for 2 hours at room temperature with shaking, the blot was washed as above, dried, and overlayed with an x-ray film and an intensifying screen (Dupont) and autoradiographed for 1-3 days at $-70°$ C. The film was developed by standard procedures. Virus from the positive wells which contained the recombinant virus was further purified.

WESTERN BLOTTING PROCEDURE. Samples of cell lysates, positive controls and protein standards were run on a polyacrylamide gel according to the procedure of Laemmli (42). After electrophoresis, the gel was soaked in a transfer buffer (0.025M Tris base, 0.192M glycine, 20% methanol) plus 0.1% SDS for 20 minutes. The stacking el portion was removed and the separation gel was placed onto Whatman 3 mm paper. A matching-sized piece of nitrocellulose filter was prewet in the transfer buffer and placed onto the polyacrylamide gel to cover the gel completely and make intimate contact. A prewet piece of Whatman 3 mm paper was placed on top of the nitrocellulose filter to create a "sandwich", and the sandwich was placed into an electrophoretic transfer device (Biorad). The sandwich was completely submersed in transfer buffer. The electrophoretic transfer was carried out for 3 hours at 250 milliamps. After transfer, the nitrocellulose filter was removed from the assembly and placed in a dish containing 50 mls of blocking buffer (50 mg/ml bovine serum albumin, 10 mM magnesium chloride, 100 mM potassium chloride, 1 mM calcium chloride, 10 mM imidazole pH 7.0, 0.3% Tween-20, 0.02% sodium azide). The nitrocellulose blot was incubated for 1-2 hours in the blocking buffer at room temperature on a shaker. The blot was then placed in a sealable bag containing 15 mls of the blocking buffer plus the specific antiserum as a probe and incubated overnight at $37°$ C. on a shaker. The blot was then removed from the probe solution and rinsed with 5-6 changes of phosphate buffered saline over a period of 1 hours. The phosphate buffered saline was removed and 50 mls of blocking buffer containing $5 \times 10^5$ cpm of $^{125}$I labeled protein A (Amersham) were added. The blot was incubated for 1 hour with the labeled protein A solution, the labeled protein A solution was removed and the blot was rinsed with 5-6 changes of phosphate buffered saline solution containing 0.3% Tween-20. The blot was air dried and autoradiographed overnight with an intensifying screen.

METHOD FOR cDNA CLONING SWINE ROTAVIRUS gp38 GENE VIRUS GROWTH. The OSU strain of porcine rotavirus (ATCC VR-892) was propagated on MA-104 cells (Rhesus monkey kidney cells from MA Bioproducts). Confluent monolayers were infected at a multiplicity of infection of greater than 10 in DMEM containing 5 micrograms/ml trypsin. Cells were incubated with the virus for 48 hours or until a cytopathic effect was obtained. Media and cell debris were collected and centrifuged at $10,000 \times g$ for 20 minutes at $4°$ C. The supernatant containing the rotavirus was then centrifuged at $10,000 \times g$ in a preparative Beckman Ti45 rotor at $4°$ C. Virus pellets were resuspended in SM medium (50 mM Tris-HCl pH 7.5, 100 mM KCL, 10 mM MgCl$_2$) and homogenized lightly in a Dounce-type homogenizer. The resuspended virus was centrifuged at $10,000 \times g$ for 10 minutes then loaded onto 25-50% CsCl gradients in SM buffer. Gradients were centrifuged at $100,000 \times g$ for 4 hours at $20°$ C. The two blue-white bands representing intact virions and cores of rotavirus were collected, diluted, and the CsCl gradient procedure was repeated a second time. Virus obtained from the second gradient was dialyzed overnight against SM buffer at $4°$ C.

VIRAL RNA ISOLATION. Dialyzed swine rotavirus was twice extracted with an equal volume of SDS/phenol then twice more with chloroform: isoamylalcohol (24:1). The double stranded RNA was precipitated with ethanol in the presence of 0.2M sodium acetate, centrifuged and resuspended in water. The yield was typically 100 micrograms from 1,000 cm$^2$ of infected cells.

SYNTHESIS AND CLONING OF gp38 cDNA. 160 micrograms of double-stranded swine rotavirus RNA obtained from the above procedure was mixed with one microgram each of two synthetic oligo nucleotide primers in a volume of 160 microliters (sequences of primers were: 5'-GGGAATTCTGCAGGT-CACATCATACAATTCTAATCTAAG-3'and 5'-GGGAATTCTGCAGGCT-TAAAAGAGAGAATTTCCGTTTGGCTA-3') derived from the published sequence of bovine rotavirus (24). The RNA-primer mixture was boiled for 3 minutes in a water bath then chilled on ice. Additions of 25 microliters of 1M Tris-HCl pH 8.3, 35 micro-liters of 1M KCl, 10 microliters of 0.25M MgCl$_2$, 7 microliters of 0.7M 2-mercaptoethanol, 7 microliters of 20 mM dNTP's and 6 microliters of reverse transcriptase (100 units) were made sequentially. The reaction was incubated at 42° C. for 1.5 hours then 10 microliters of 0.5M EDTA pH 8.0 was added and the solution was extracted once with chloroform: phenol (1:1). The aqueous layer was removed and to it 250 microliters of 4M ammonium acetate and 1.0 ml of 95% ethanol was added, the mixture was frozen in dry ice and centrifuged in the cold. The resulting pellet was resuspended in 100 microliters of 10 mM Tris-HC1 pH 7.5 and the ammonium acetate precipitation procedure was repeated. The pellet was resuspended in 100 microliters of 0.3M KOH and incubated at room temperature overnight then at 37° C. for 2 hours. The solution was brought to neutral pH by addition of 10 microliters of 3.0M HC1 and 25 microliters of 1.0M Tris-HC1 pH 7.5. The resulting single-stranded cDNA was then precipitated two times by the above described ammonium acetate-ethanol procedure. The pellet obtained was resuspended in 50 microliters of 10 mM Tris-HC1 pH 7.5, 100 mM NaCl, 1 mM EDTA, boiled in a water bath for 2 minutes then incubated at 59° C. for 16 hours. The solution was lyophilized to a volume of 15 microliters and the resulting double-stranded cDNA was run on a 1.0% agarose gel (Sigma agarose Type II). The ethidium bromide stained DNA migrating at 1,000–1,100 base pair length was excised from the gel and electroeluted in a CBS electroeluter device. The solution was lyophilized, and the cDNA was resuspended in 25 microliters of water. To this solution was added 2 microliters of 1.0M Tris-HC1 pH 7.5, 2 microliters of 1M KC1, 1 microliter of 0.25M $MgCl_2$, 1 microliter of 20 mM dNTP's and 5 units of *E. coli* DNA polymerase I. The reaction was incubated at room temperature for 15 minutes, then chloroform/phenol extracted and ammonium acetate-ethanol precipitated as described above. The resulting cDNA was tailed with dCTP using terminal deoxynucleotide transferase (BRL buffer and enzyme used). The reaction was stopped with 2 microliters of 0.5M EDTA, chloroform/phenol extracted and precipitated with sodium acetate in the presence of 10 micrograms of carrier tRNA. The resuspended cDNA was mixed with 200 ng of dGMP-tailed Pst I cut pBR322 (BRL catalog #5355SA) in 200 microliters of 10 mM tris-HC1 pH 7.5, 100 mM NaCl, 1 mM EDTA, heated to 65° C. for 5 minutes then 57° C. for 2 hours. The annealed cDNA-vector pBR322 was transformed onto *E. coli* DH-1 cells prepared for high efficiency transformation. Colonies that showed sensitivity to ampicillin and tetracycline resistance were grown and DNA was prepared and cut with Pst I to determine the size of the cDNA insert. Several clones having Pst I inserts of 1,050–1,100 base pairs were analyzed and found to have identical restriction enzyme digest patterns. The largest clone was designated pSY565 and has been deposited with the ATCC under accession number 53,340. For one of these clones, the 1,100 base pair Pst I insert was subcloned into a M13 phage sequencing vector. The entire DNA sequence of this clone was determined and is shown in FIG. 10A and 10B. The location of the gp38 open reading frame was determined from the amino acid homology to human and bovine sequences already published (44).

METHOD FOR cDNA CLONING BOVINE ROTAVIRUS gp38 GENE VIRUS GROWTH. The Calf Nebraska strain of bovine rotavirus (USDA) was propagated on MA-104 cells (Rhesus monkey kidney cells from MA Bioproducts). Confluent monolayers were infected at a multiplicity of infection of greater than 10 in DMEM containing 5 micrograms/ml trypsin. Cells were incubated with virus for 48 hours or until a cytopathic effect was obtained. Media and cell debris were collected and centrifuged at 10,000×g for 20 minutes at 4° C. The supernatant containing the rotavirus was then centrifuged at 10,000×g in a preparative Beckman Ti45 rotor at 4° C. Virus pellets were resuspended in SM medium (50 mM Tris-HC1 pH 7.5, 100 mM KCL, 10 mM $MgCl_2$) and homogenized lightly in a Dounce-type homogenizer. The resuspended virus was centrifuged at 10,000×g for 10 minutes then loaded onto 25–50% CsCl gradients in SM buffer. Gradients were centrifuged at 100,000×g for 4 hours at 20° C. The two blue-white bands representing intact virions and cores of rotavirus were collected, diluted, and the CsCl gradient procedure was repeated a second time. Virus obtained from the second gradient was dialyzed overnight against SM buffer at 4° C.

VIRAL RNA ISOLATION. Dialyzed bovine rotavirus was twice extracted with an equal volume of SDS/phenol then twice more with chloroform: isoamylalcohol (24:1). The double stranded RNA was precipitated with ethanol in the presence of 0.2M sodium acetate, centrifuged and resuspended in water. The yield was typically 100 micrograms from 1,000 $cm^2$ of infected cells.

SYTHESIS AND CLONING OF gp38 cDNA. 160 micrograms of double-stranded bovine rotavirus RNA obtained from the above procedure was mixed with one microgram each of two synthetic oligo nucleotide primers in a volume of 160 microliters (sequences of primers were: 5'-GGGAATTCTGCAGGTCACATCATACAATTCTAATCTAAG-3' and 5'-GGGAATTCTGCAGGCTTTAAAGAGAGAATTTCCGTTTGGCTA-3') derived from the published sequence of bovine rotavirus (24). The RNA-primer mixture was boiled for 3 minutes in a water bath then chilled on ice. Additions of 25 microliters of 1M Tris-HC1 pH 8.3, 35 microliters of 1M KC1, 10 microliters of 0.25M $MgCl_2$, 7 microliters of 0.7 m 2-mercaptoethanol, 7 microliters of 20 mM dNTP's, and 6 microliters of reverse transcriptase (100 units) were made sequentially. The reaction was incubated at 42° C. for 1.5 hours then 10 microliters of 0.5M EDTA pH 8.0 was added and the solution was extracted once with chloroform: phenol (1:1). The aqueous layer was removed and to it 250 microliters of 4M ammonium acetate and 1.0 ml of 95% ethanol was added, the mixture was frozen in dry ice and centrifuged in the cold. The resulting pellet was resuspended in 100 microliters of 10 mM Tris-HC1 pH 7.5 and the ammonium acetate precipitation procedure was repeated. The pellet was resuspended in 100 microliters of 0.3M KOH and incubated at room temperature overnight then at 37° C. for 2 hours. The solution was brought to neutral pH by addition of 10 microliters of 3.0M HC1 and 25 microliters of 1.0M Tris-HC1 pH 7.5. The resulting single-stranded cDNA was then precipitated two times by the above described ammonium acetate-ethanol procedure. The pellet obtained was resuspended in 50 microliters of 10 mM Tris-HC1 pH 7.5, 100 mM NaCl, 1 mM EDTA, boiled in a water bath for 2 minutes then incubated at 59° C. for 16 hours. The solution was lyophilized to a volume of 15 microliters and the resulting double-stranded cDNA was run on a 1.0% agarose gel (Sigma agarose Type II). The ethidium bromide stained DNA migrating at 1,000–1,100 base pair length was excised from the gel and electroeluted in a CBS electroeluter device. The solution was lyophilized, and the cDNA was resuspended in 25 microliters of water. To this solution was added 2 microliters of 1.0M Tris-HCl pH 7.5, 2 microliters of 1M KCl, 1 microliter of 0.25M $MgCl_2$, 1 microliter of 20 mM dNTP's, and 5 units of *E. coli* DNA polymerase I. The reaction was incubated at room temperature for 15 minutes, then chloroform/phenol extracted and ammonium acetate-ethanol precipitated as described above. The resulting cDNA was tailed with dCTP using terminal deoxynucleotide transferase (BRL buffer and enzyme used). The reaction was stopped with 2 microliters of 0.5M EDTA, chloroform/phenol extracted and precipitated with sodium acetate in the presence of 10 micrograms of carrier tRNA. The resuspended cDNA was mixed with 200 ng of dGMP-tailed Pst I cut pBR322 (BRL catalog #5355SA) in 200 microliters of 10 mM Tris-HCl pH 7.5, 100 mM NaCl, 1 mM EDTA, heated to 65° C. for 5 minutes then 57° C. for 2 hours. The annealed cDNA-vector pBR322 was transformed onto *E. coli* DH-1 cells prepared for high efficiency transformation. Colonies that showed sensitivity to ampicillin and tetracycline resistance were grown and DNA was prepared and cut with Pst I to determine the size of the cDNA insert. Several clones having Pst I inserts of 1,050–1,100 base pairs were analyzed and found to have identical restriction enzyme digest patterns. For one of these clones, the 1,100 base pair Pst I insert was subcloned into a M13 phage sequencing vector. Part of the DNA sequence of this clone was determined and was found to be identical to the published sequence (24).

SELECTION OF G418 RESISTANT HERPESVIRUS. The antibiotic G418 (GIBCO) has a wide range of inhibitory activity on protein synthesis. The recombinant virus, however, expressed the aminoglycoside 3'-phosphotransferase, encoded by the NEO gene, upon acquiring the foreign gene and became resistant to G418. The transfection stocks of recombinant viruses were grown on MDBK (for IBR virus), Vero (for PRV) or QT35 (for HVT) cells in the presence of 500 micrograms/ml G418 in complete DME medium plus 1% fetal bovine serum. After one or two days at 37° C., plaques from the dishes inoculated with the highest dilution of virus were picked for virus stocks. The selection was repeated a second or third time. The virus stocks generated from the G418 selection were tested for NEO gene insertion by the SOUTHERN BLOTTING OF DNA hybridization procedure described above.

PURIFICATION OF gpX. gpX was purified from the tissue culture medium of infected Vero cells grown in complete DME plus 1% fetal bovine serum. Confluent Vero cells were infected at a multiplicity of infection equal to 5, with wild-type, Iowa S-62 strain pseudorabies virus. The viral proteins were radiolabelled with $^{14}C$ glucosamine and/or $^{35}S$ methionine by adding the appropirate label to the flask eight hours after infection. The cells and media were harvested at twenty hours post infection, when the cells showed considerable cytopathic effect and the fluids were centrifuged.

The supernatant fluid was concentrated 10× and dialyzed against 0.02M sodium sulfate/0.01M sodium phosphate buffer, pH 7.2 (16 hours, 0° C.), then against two changes of 0.01M sodium phosphate buffer, pH 7.2 (24 hours, 0° C.). The dialysate was treated for 30 minutes at 0° C. with 70% perchloric acid to a final concentration of 0.2M perchloric acid, then centrifuged at 10,000 rpm for 25 minutes. The supernatant fluid was then dialyzed against 0.02M Tris, pH 8.5.

Purification was carried out by high performance liquid chromatography on a Beckman Model 334 HPCL.

The acid-soluble proteins were separated on a Biogel TSK D AE 5-PW column (75×75 mm) using a 60 minute linear gradient, flow rate 0.8 ml/minute. Starting buffer was 0.02M Tris, pH 8.5, limit buffer was 0.02M Tris, pH 7.0 containing 0.75M NaCl.

The gpX eluted as a major radioactive peak at 65% of the limit buffer. The recovered material represented 25% of the applied radioactivity.

ELISA ASSAY. A standard enzyme-linked immunosorbent assay (ELISA) protocol was used to determine the immune status of swine following vaccination and challenge.

A purified gpX antigen solution (40 microliters) was allowed to a orb to the wells of polycarbonate microtiter dishes for 2 hours at room temperature. The antigen was in a (0.015M) carbonate-(0.04M) bicarbonate buffer, pH 9.6. The coated wells were rinsed 3 times with ELISA was solution (0.05% Tween 20 non-ionic detergent in phosphate buffered saline, pH 7.5).

Forty microliters of serum containing gpX antibody (diluted 1 to 10 in Tris buffer containing 1% bovine serum albumin and 0.05% Tween 20) were added to the wells and incubated 1 hour at 37° C.

The anti-serum was removed and the wells were washed 3 times with ELISA wash solution. A solution containing Staphylococcal protein A coupled to horseradish peroxidase (Bio-Rad) (diluted 1:10,000 in the Tris/BSA/Tween buffer described above) was added (50 microliters) to visualize the wells containing antibody against the specific antigen. The solution was incubated 1 hour at 37° C., then removed and the wells were washed 3 times with ELISA wash solution. 100 microliters substrate solution (equal volumes of hydrogen peroxide and ATBS buffer (Bio-Rad) were added to each well and color as allowed to develop for 20 minutes.

The reaction was terminated by addition of 50 microliters of 0.01M oxalic acid. The color was read at absorbance (A) 410 nm on a automatic plate reader.

VACCINATION STUDIES IN SWINE. Weaned pigs (4–6 weeks old) and pregnant sows were obtained from swine herds known to be free of pseudorabies disease. Susceptibility of the test animals to pseudorabies was further verified by testing the pig serum for absence of neutralizing antibodies to pseudorabies virus (PRV). The weaned pigs and 3-to-4 day old piglets were inoculated intramuscularly with 1 ml of virum fluid containing about $10^4$ to $10^6$ infectious units ($TCID_{50}$). Animals were observed each day after vaccination for adverse reactions (clinical signs of PRV disease) and body temperatures were recorded. Samples of tonsillar secretions were obtained and cultured to determined if the vaccine virus was capable of shedding and spreading to other animals. Immunity was determined by measuring PRV serum antibody levels at weekly intervals and in some cases, by challenging the vaccinated pigs with virulent virus. In the latter case, the vaccinated animals and a group of non-vaccinated pigs were inoculated with virulent, Iowa S-62 strain PRV, using an amount of virus that caused PRV disease in at least 80% of the unvaccinated group of pigs. This was done about 28 days after vaccination. The challenged animals were observed daily for signs of disease and for increased body temperature. A necropsy was conducted on animals that dies and selected tissues were examined and cultured for PRV.

cDNA CLONING. cDNA cloning refers to the methods used to convert RNA molecules into DNA molecules following state of the art procedures. Applicants' methods are described in (57). Bethesda Research Laboratories (Gaithersburg, Md.) have designed a cDNA Cloning Kit that is very similar to the procedures used by applicants and contains the best set of reagents and protocols to duplicate our results.

PREPARATION OF RNA. For cloning virus mRNA species, a host cell line sensitive to infection by the virus was infected at 5-10 plaque forming units power cell. When cytopathic effect was evident, but before total destruction, the medium was removed and the cells were lysed in 10 mls lysis buffer (4M guanidine thiocyanate, 0.1% antifoam A, 25 mM sodium citrate pH 7.0, 0.5% N-lauroyl sarcosine, 0.1M beta-mercaptoethanol). The cell lysate was poured into a sterilized Dounce homogenizer and homogenized on ice 0-10 times until the solution was homogenous. For RNA purification, 8 mls of cell lysate were gently layered over 3.5 mls of CsCl solution (5.7M CsCl, 25 mM sodium citrate pH 7.0) in a Beckman SW41 centrifuge tube. The samples were centrifuged for 18 hours at 20° C. at 36000 rpm in a Beckman SW41 rotor. The tubes were put on ice and the supernatants from the tubes were carefully removed by aspiration to leave the RNA pellet undisturbed. The pellet was resuspended in 400 microliters glass distilled water, and 2.6 mls of guanidine solution (7.5M guanidine-HCl, 25 mM sodium citrate pH 7.0, 5 mM dithiothreitol) were added. Then 0.37 volumes of 1M acetic acid were added, followed by 0.75 volumes of cold ethanol and the sample was put at −20° C. for 18 hrs to precipitate RNA. The precipitate was collected by centrifugation in a Sorvall centrifuge for 10 min at 4° C. at 1000 rpm in a SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2M potassium acetate solution was added to the sample followed by 2 volumes of cold ethanol and the sample was put at −20° C. for 18 hrs. The precipitated RNA was collected by centrifugation in the SS34 rotor at 4° C. for 10 min at 10000 rpm. The pellet was dissolved in 1 ml distilled water and the concentration taken by adsorption at A260/280. The RNA was stored at −70° C.

POLY A SELECTION. mRNA containing polyadenylate tails (poly-A) was selected using oligo-dT cellulose (Pharmacia #27 5543-0). Three milligrams of total RNA was boiled and chilled and applied to a 100 mg oligo-dT cellulose column in binding buffer (0.1M Tris pH 7.5, 0.5M LiCl, 5 mM EDTA pH 8.0, 0.1% lithium dodecyl sulfate). The retained poly-A+ RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 microliters distilled water.

FIRST STRAND REACTION. Ten micrograms poly-A+ RNA was denatured in 20 mM methyl mercury hydroxide for 6 min at 22° C. Beta-mercaptoethanol was added to 75 mM and the sample was incubated for 5 min at 22° C. The reaction mixture for first strand cDNA synthesis in 0.25 ml contained 1 microgram oligo-dT primer (P-L Biochemicals) or 1 microgram synthetic primer, 28 units placental ribonuclease inhibitor (Bethesda Research Labs #5518SA), 100 mM Tris pH 8.3, 140 mM KCl, 10 1 mM $MgCl_2$, 0.8 mM dATP, dCTP, dGTP, and dTTP (Pharmacia), 100 microcuries $^{32}P$-labelled dCTP (New England Nuclear #NEG-013H), and 180 units AMV reverse transcriptase (Molecular Genetics Resources #MG 101). The reaction was incubated at 42° C. for 90 min, and then was terminated with an equal volume of phenol/chloroform (1:1) and precipitated with 2M ammonium acetate and 2 volumes of cold ethanol −20° C. for 3 hrs. After precipitation and centrifugation, the pellet was dissolved in 100 microliters distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions were pooled, and DNA was concentrated by lyophilization until the volume was about 100 microliters, then the DNA was precipitated with ammonium acetate plus ethanol as above.

SECOND STRAND REACTION. The entire first strand sample was used for second strand reaction which followed the Gubler and Hoffman (57) method except that 50 micrograms/ml dNTP's, 5.4 units DNA polymerase I (Boerhinger Mannheim #421-711), and 100 units/ml E. coli DNA ligase (New England Biolabs #205) in a total volume of 50 microliters were used. After second strand synthesis, the cDNA was phenol/chloroform extracted and precipitated. The DNA was resuspended in 10 microliters distilled water, treated with 1 microgram RNase A for 10 min at 22° C., and electrophoresed through a 1% agarose gel (Sigma Type II agarose) in 40 mM Tris-acetate buffer pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 microliters water.

TAILING THE DNA. Oligo-dC tails were added to the DNA to facilitate closing. The reaction contained the DNA, 100 mM potassium cacodylate pH 7.2, 0.2 mM dithiothreitol, 2 mM $CoCl_2$, 80 micromoles dCTP, and 25 units terminal deoxynucleotidyl transferase (Molecular Genetic Resources #S1001) in 50 microliters. After 30 min at 37° C., the reaction was terminated with 10 mM EDTA, and the sample was phenol/chloroform extracted and precipitated as above.

CLONING THE cDNA. The dC-tailed DNA sample was annealed to 200 ng plasmid vector pBR322 that contained oligo-dG tails (Bethesda Research Labs #5355 SA/SB) in 200 microliters of 0.01M Tris pH 7.5, 0.1M NaCl, 1 mM EDTA pH 8.0 at 65° C. for 2 min and then 57° C. for 2 hrs. Fresh competent E. coli DH-1 cells were prepared and transformed as described by Hanahan (58) using half the annealed cDNA sample in twenty 200 microliters aliquots of cells. Transformed cells were plated on L-broth agar plates plus 10 micrograms/ml tetracycline. Colonies were screened for the presence of inserts into the ampicillin gene using Ampscreen ® (Bethesda Research Labs #5537 UA), and the positive colonies were picked for analysis.

MEANS TO DETERMINE THE SUITABILITY OF GENES FOR EXPRESSION IN HERPESVIRUSES. The first step in the analysis is to determine the overall G+C content of the gene is question. For good expression of a foreign antigen in herpesviruses, the G+C content of the foreign DNA must be equal to or higher than the G+C content of competing mRNAs. Said another way, the higher the G+C content of the foreign gene, the better will be the expression. The second step is to construct a "codon bias" table for known genes of the herpesvirus using a computer program such as the IBI DNA analysis system discussed in Example 24. The resulting table of "triplet frequencies" will form the final bass for comparison of the sequence. The IBI DNA analysis package provides a way to plot the similarity of any gene to a codon bias table. One can get from this plot a relative fit of the foreign gene to a herpesvirus gene (see Example 24).

The analysis can then be used to make a prediction—will the gene be expressed well within the context of a herpesvirus genome? The higher the G+C content, and the better the fit with herpesvirus codon usage, the higher will be the expression of the gene in the herpesvirus genome and the less need to practice the methods of this invention.

From this analysis, the deficiencies in the foreign gene become apparent. If the G+C content is low, then the G+C content must be raised —this is one way to practice the invention. If raising the G+C content is to be practiced by DNA synthesis, then the method of choice in the practice of the invention is to consult the codon usage bias of the herpesvirus to utilize condons in the synthesis that best fit the herpesvirus codon usage.

FOREIGN GENES ALREADY FAVORABLE FOR HERPESVIRUS EXPRESSION. The applicants have found some genes already exist that are favorable for expression in herpesviruses. The trivial cases are those genes that are already present in the herpesvirus genome—i.e., herpesvirus genes themselves. However not all herpesvirus genes work in all of the herpesviruses. For example, the herpesvirus of turkeys (HVT) glycoprotein A gene is not well expressed in pseudorabies virus (applicants' unpublished work). This result is predicted by the above analysis—the HVT gA gene has 47% G+C content and PRV has 70% G+C and their codon usage is very different.

Applicants have used several genes that are well expressed in pseudorabies virus, and some have been tested in IBR and HVT as well. These genes include the *E. coli* beta-galactosidase gene, the neomycin resistance gene, and the HSV-1 thymidine kinase gene. These genes have a higher than average G+C content (55-60%) and by chance match the pseudorabies codon usage better than the average. A second method to practice the invention is to sue one of these genes to drive the expression of the foreign gene in herpesvirus by linking the two genes together in a fusion.

Most of the other genes that code for the antigenic proteins of animal viruses have a resultive low G+C content and do not match the herpesvirus codon usage, and their expression in herpesviruses can be improved by practicing this invention. Some examples of these viruses are swine parvovirus (37.8% G+C), swine and bovine rotavirus (34% G+C), swine transmissible gastroenteritis virus (37G+C), parainfluenza type 3 (35% G+C), bovine viral diarrhea, Newcastles disease virus (46% G+C), infectious bronchitis virus (36% G+C), to a lesser extent, and infectious bursal disease virus (53% G+C).

BETA-GALACTOSIDASE ONPG ASSAY METHOD (67). The assay method followed these steps:

1. Infect Vero or other cells at high multiplicity of infection and wait for total cytopathic effect (usually next day).

2. Add detergent NP40 to the medium in each dish to a final concentration of 1% (use 20% NP40 stock in water). Pipet to lyse cells, and pellet to clarify supernatant. Save supernatant for assay.

3. Make up Z buffer as below. Make up a sock of ONPG (o-nitrophenyl-B, D-galactopyranoside from Sigma) at a concentration of 4 mg/ml in Z buffer. Store both Z buffer and ONPG solution at 4° C. in the dark.

4. For the reaction, mix 0.7 ml Z buffer, 0.2 ml ONPG solution, and 0.1 ml supernatant sample in tube. Let reaction proceed at room temperature until yellow color forms. Intensity of yellow indicates beta-gal activity.

5. For quantitative measurement, spectrophotometer readings must be taken at A420. The first reading must be taken at +10-15 minutes of reaction as a starting point. The second reading should occur when a good yellow color is present subject to the following constraints—less than 20 hours duration of reaction, and the A420 reading must be less than 0.9 on the spectrophotometer. Within these constraints, the reaction is linear. The calculations applicants use are:

rate=[(A420 at T2)−(A420 at T1)]/(T2−T1 in minutes)

units=rate/0.0045 (1 nmole NP=0.0045)

total units=units×totals mls in supernatant×10

1 unit=1 nmole ONPG converted to NP per minute

Applicants do most of their comparisons in terms of total units. For information purposes, applicants have determined that 267 units of beta-galactosidase activity is equal to 1 microgram of active protein.

| Z Buffer per Liter | |
|---|---|
| 16.1 g Na2HPO4.7H2O | (0.06M) |
| 5.5 g NaH2PO4.H2O | (0.04M) |
| 0.75 g KCl | (0.01M) |
| 0.246 g MgSO4.7H2O | (0.001M) |
| 2.7 ml beta-mercaptoethanol | (0.05M) |
| Adjust pH to 7.3–7.6 (original reference says ph 7.0) | |
| Do not autoclave | |

PROTECTION OF VACCINATED PIGS AGAINST PARVOVIRUS VIREMIA. Weaned pigs, four to six weeks of age, were obtained from a swine herd known to be free of porcine parvovirus. Susceptibility of the pigs was verified by demonstrating the absence of serum neutralizing antibodies against parvovirus at the time of vaccination. Pigs were given two doses of vaccine containing $10^6$ PFU of virus, 21 to 28 days apart. One vaccine group was given a commercially available, inactivated parvovirus vaccine as the second dose. Serum samples were obtained weekly for evaluation of serum antibodies to pseudorabies virus and of porcine parvovirus. Twenty-one to 28 days after the second vaccination, vaccinated pigs and two, non-vaccinated, age-matched pigs were challenged oronasally with virulent parvovirus. Parvovirus viremia was the criterion used for measuring vaccine efficacy.

Parvovirus viremia was measured as follows: whole blood was collected and the cells were separated from plasma. Lymphocytes were separated by passage over a Ficoll gradient and their DNA was recovered following treatment of the cells with protease and phenol. The isolated DNA was reacted, in a slot blot assay (Schleicher & Schuell), with $^{32}$p-labeled parvovirus RNA. The slot blots were exposed to Kronex X-ray film (Kodak) and developed.

Parvovirus serum neutralizing antibody was determined by infecting swine testis cell cultures with parvovirus that had been incubated with varying dilutions of vaccinated swine serum. Three days after infection, the cell culture monolayers were fixed in acetone/methanol and incubated with a polyclonal rabbit anti-PPV serum. The fluorescent tag was goat anti-rabbit IgG (Kirkegaard & Perry). The serum antibody titer was determined to be that dilution which resulted in a 50% or greater reduction of fluorescent foci.

EXAMPLES

Example 1

S-PRV-004

Figure 1A:
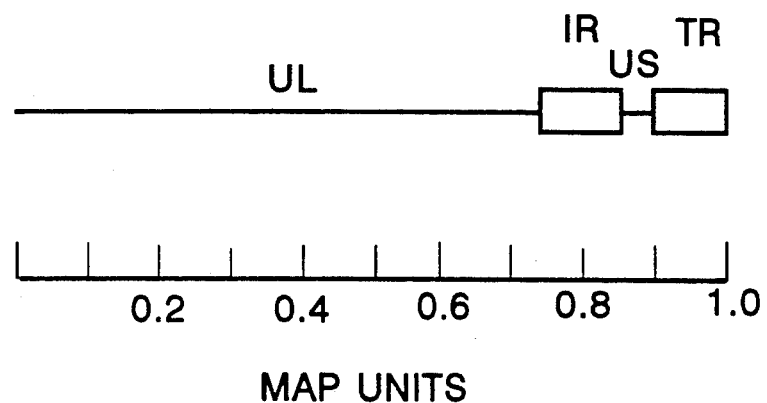
FIG. 1 Details of Wild Type Iowa S-62 A Strain.
  A. Diagram of PRV genomic DNA showing the unique long region (UL), the unique short region (US), the internal repeat region (IR), and the terminal repeat region (TR).
  B. BamHI restriction enzyme map of PRV. Fragments are numbered in order of decreasing size.
Figure 1B:
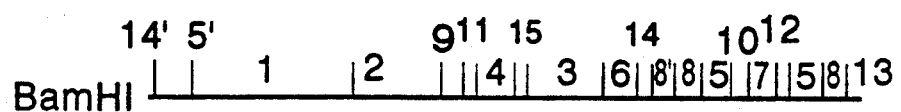
Figure 2A:
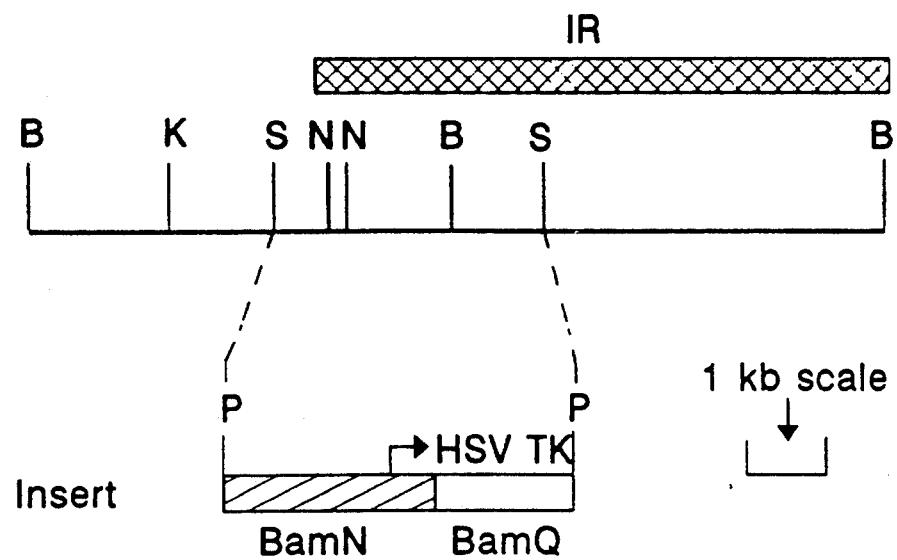
FIG. 2 Details of S-PRV-004 Construction and Map Data.
  A. Detailed map of BamHI #8' and #8. The location of the internal repeat (IR) region is shown.
  B. Detailed map of BamHI #8'-TK-8 fragment ultimately present in the recombinant virus.
  C. Diagram of the S-PRV-004 DNA genome showing the location of the HSV-1 TK gene inserted into the junction region between the UL and IR regions.
    Restriction Enzyme Legend: B=BamHI; K=KpnI; N=NdeI; P=PvuII; S=StuI.
Figure 2B:
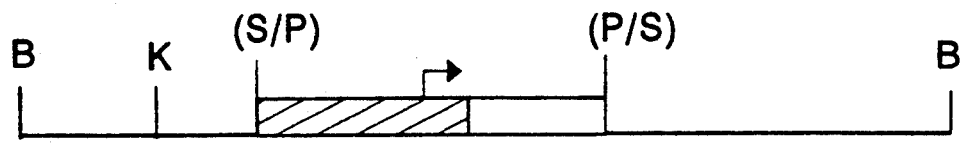
Figure 2C:
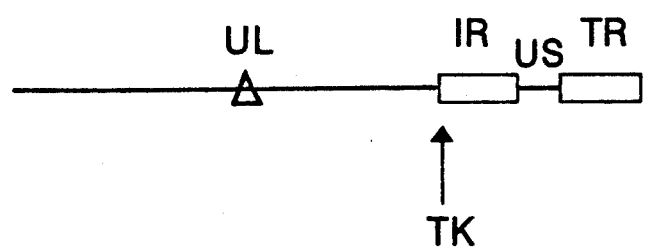
Figure 3A:
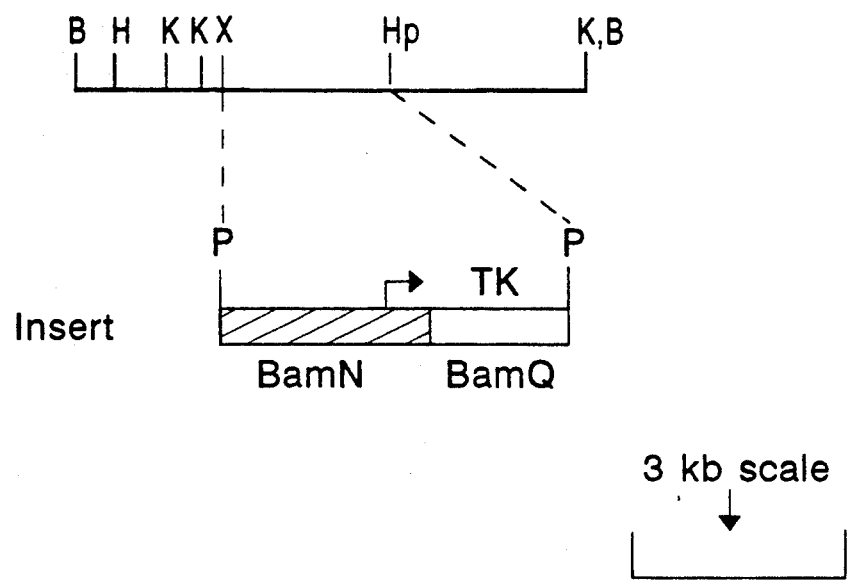
FIG. 3 Details of S-PRV-005 Construction and Map Data.
  A. Detailed map of BamHI #5. The HSV-1TK gene fused to the HSV-1 ICP4 promoter is shown on a PvuII fragment.
  B. Detailed map of BamHI #5 after the insertion of the TK gene construct.
  C. Diagram of the S-PRV-005 DNA genome showing the location of the TK gene inserted into both copies of BamHI #5 in the repeat region of the genome and the creation of new deletions.
    Restriction Enzyme Legend: B=BamHI; H=HindIII; Hp=HpaI; K=KpnI; P=PvuII; X=XbaI.
Figure 3B:
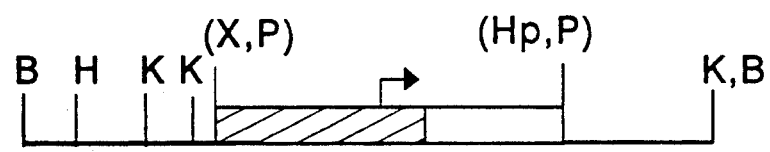
Figure 3C:
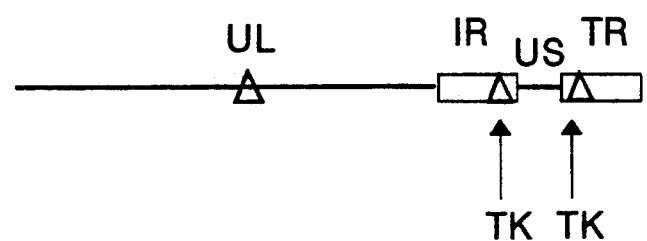
Figure 4A:
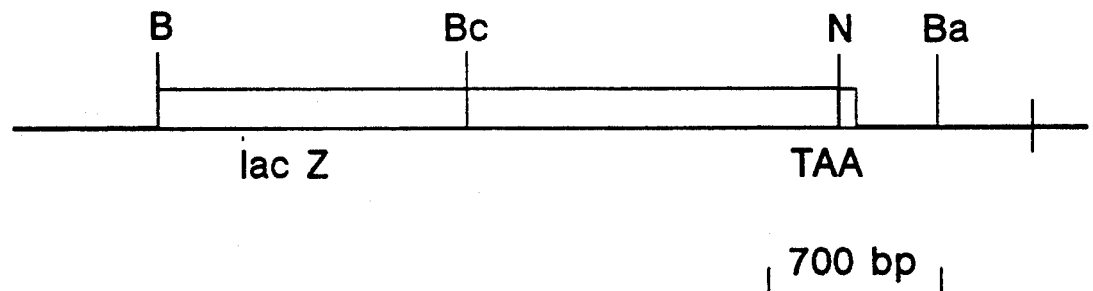
FIG. 4 Construction of the Foreign DNA insert Used in S-PRV-010.
  A. Diagram of the relevant portion of pJF751 that contains the lac Z (beta-galactosidase) gene. The position of the TAA termination codon for the polypeptide is indicated.
  B. Diagram of the promoter sequence from the HSV-1 TK gene.
  C. Diagram of the RsaI fragment of the TK gene now with BamHI modified ends.
  D. Diagram of the final plasmid that contained the lac Z gene fused to the HSV-1 TK promoter.
    Restriction Enzyme legend: B=BamHI; Ba=baII; Bc=BclI; Bg=BglII; H=HindIII; Ha =HaeIII; N=NdeI; R=RsaI; X=XbaI.
Figure 4B:
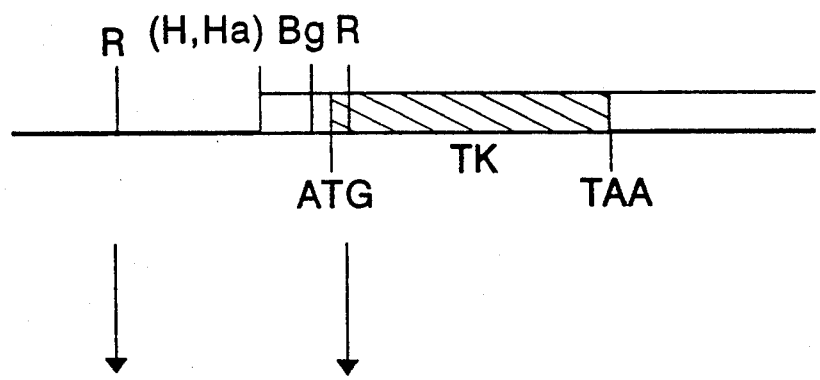
Figure 4C:
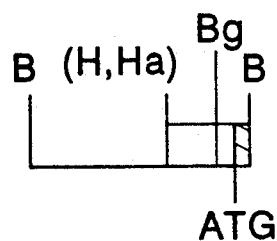
Figure 4D:
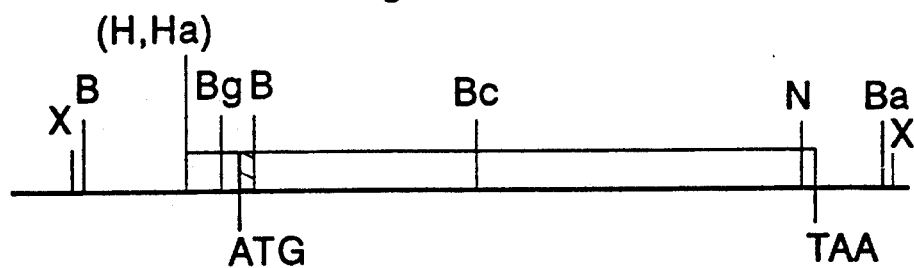

We have created a virus that has a deletion in the junction region between the unique long DNA and the internal repeat of PRV, and a deletion in the endogenous PRV thymidine kinase gene in the unique long region. Into the junction deletion we have cloned the herpes simplex type 1 (HSV-1) thymidine kinase (TK) gene under the control of the ICP4 promoter. This virus is designated S-PRV-004.

To create this virus, we first cloned the SalI #1 fragment of PRV. PRV DNA was prepared and then cut with SalI restriction enzyme. The cut DNA was electrophoresed on an agarose gel and the largest SalI band (15 kb) was purified from the gel (see PHENOL EXTRACTION OF DNA FROM AGAROSE). The purified DNA was ligated into the plasmid pSP64 (see LIGATION) and the DNA mixture was used to transform *E. coli* HB101 according to Maniatis et al. (1). The SalI #1 clone was mapped for restriction sites.

The homologous recombination procedure was used to create S-PRV-004 (see FIG. 2). The exact position of the junction region was determined by sequencing the DNA from SalI #1 fragment. It was found that the junction region was positioned between two StuI sites (FIG. 2A). Two fragments of DNA from the SalI clone were used to create the homology vector for recombination. One was a fragment from BamHI #80' from StuI to BamHI and the other was from BamHI #8 from BamHI to StuI (see FIGS. 1B and 2A). These fragments were cloned into the BamHI site of pSP64. This plasmid was cut with StuI, and a 3.8 kb PvuII fragment, obtained from B. Roizman (16), The University of Chicago, and containing the ICP4promoter on the BamHI-N fragment and the HSV-1 TK gene on the BamHI-Q fragment, fused at the BamHI/BglII sites, was ligated into the StuI site. The net result from this series of clonings was a plasmid which had suffered a deletion of 3 kb from between the StuI sites, and into which 3.8 kb of the foreign TK gene had been incorporated (see FIG. 2B). The TK gene was thus flanked by PRV DNA sequences to allow for insertion of the foreign gene into the PRV genome by homologous recombination. The plasmid DNA was transfected into rabbit skin cells along with the intact PRV DNA from S-PRV-003, which is a pseudorabies virus that has a deletion in the endogenous TK gene. The transfection stock of virus was selected in HAT medium and the virus was identified and selected by analysis of the restriction pattern of DNA isolated from the infected cells.

S-PRV-004 contained the HSV-1 TK gene and was expressing this gene as demonstrated by the incorporation of 14C-thymidine in a plaque assay describe din Tenser et al. (40) and by direct analysis of TK activity in infected cell extracts, following the procedure of Cheng et al. (41). The location of this gene in the genome of PRV is shown in FIG. 2C.

Six weaning age pigs were vaccinated with $10^{5.0}$ infectious units of S-PRV-004 and challenged with virulent PRV 28 days later, according to the VACCINATION STUDIES IN SWINE procedure. The vaccinated pigs remained healthy following vaccination and developed serum neutralizing antibody against PRV (see Table I below). Vaccine virus was not recovered from nasal or tonsillar secretions. After exposure to virulent PRV, 83% of the vaccinated swine were protected against PRV disease.

TABLE I

RESPONSES OF WEANED PIGS VACCINATED WITH S-PRV-004 AND CHALLENGED WITH VIRULENT PRV

| | | Post-Vaccination | | | | | Post-Challenge | | | |
|---|---|---|---|---|---|---|---|---|---|---|
| | | Antibody | | | | | Antibody | | | |
| Antigen Level | Pig No. | Day 14 | Day 21 | Day 28 | Clinical Signs | Virus Isolation | Day 7 | Day 14 | Clinical Signs[a] | Virus Isolation |
| $10^{5.0}$ | 1 | 32 | 32 | 16 | None | None | >64 | >64 | F | Swabs |
| | 2 | 16 | 32 | 8 | None | None | >64 | >64 | F | Swabs |
| | 3 | 8 | 16 | 4 | None | None | >64 | >64 | F | Swabs |
| | 4 | 4 | 16 | 8 | None | None | >64 | >64 | F,C | Swabs |
| | 5 | 16 | 16 | 8 | None | None | >64 | >64 | F | Swabs |
| | 6 | 8 | 8 | 4 | None | None | >64 | >64 | F | Swabs |

[a]Key to clinical signs: C = CNS, F = Febrile

EXAMPLE 2

S-PRV-005

S-PRV-005 is a pseudorabies virus that has a deletion in the repeat region and in the endogenous PRV TK gene in the long unique region, and has an insertion of the HSV-1 TK gene under the control of the ICP4 promoter incorporated into both copies of the repeat region between the XbaI site and the HpaI site in the BamHI #5 fragment (See FIG. 3).

To create this virus, we first obtained a clone of BamHI #5 fragment from PRV (FIG. 1B). The BamHI #5 fragment was cloned into the plasmid pACYC184 at the BamHI site (see LIGATION above). A map of the BamHI #5 fragment is shown in FIG. 3A.

The plasmid containing the BamHI #5 fragment was cut with XbaI and HpaI and the linearized plasmid was purified (see PHENOL EXTRACTION OF DNA FROM AGAROSE). The 3.8 kb PvuII fragment described in Example 1 and containing the TK gene and ICP4 promoter was likewise purified. The XbaI site was filled to yield a blunt end (see POLYMERASE FILL-IN REACTION), and the two DNAs were mixed and ligated together. The resulting plasmid that had incorporated the TK gene in the XbaI-HpaI deletion was selected and analyzed by restriction mapping (FIG. 3B).

The plasmid containing the TK gene flanked by PRV BamHI #5 sequences was used to transfect rabbit skin cells along with purified DNA from S-PRV-003, a pseudorabies virus that had a deletion in the endogenous TK gene. The resulting recombinant PRV that had incorporated the HSV-1 TK gene into the deletion in the repeats was screened and purified from the transfection stock by the HYBRIDIZATION SCREEN FOR RECOMBINANT HERPESVIRUS procedure without any prior selection.

S-PRV-005 recombinant PRV was shown to express the HSV-1 TK gene by incorporation of $^{14}C$-thymidine in a plaque assay (40), by analysis of the TK activity in infected cell lysates (41), and by immunodetection of the HSV-1 TK protein according to the ANTIBODY SCREEN FOR RECOMBINANT HERPESVIRUS procedure outlined above. The location of this gene in the genome of PRV is shown in FIG. 3C.

EXAMPLE 3

S-PRV-010

S-PRV-101 is a pseudorabies virus that has a deletion in the PRV TK gene in the long unique region, a deletion in the repeat region, and the insertion of the *E. coli* beta-galactosidase gene (lacZ gene) incorporated into both copies of the repeats at the XbaI site in BamHI #5 fragment (see FIG. 5A). The beta-galactosidase gene was constructed to be expressed using the HSV-1 TK gene promoter which we have shown in this construct to be active in PRV.

The method used to insert the beta-galactosidase gene into S-PRV-010 was direct ligation (see DIRECT LIGATION PROCEDURE FOR GENERATING RECOMBINANT HERPESVIRUS). The beta-galactosidase gene was on plasmid pJF751, obtained from Jim Hoch, Scripps Clinic and Research Foundation. This gene is truncated at the 5′ end with a BamHI site that has removed the AGT initiation codon, and the AvaI site in pBR322 was used at the other end (see FIG. 4A). The HSV-1 TK promoter (FIG. 4B) was taken form the McKnight TK gene as an RsaI fragment, gel purified, and ligated to a synthetic piece of DNA which contained a BamHI site within the sequence CGGATCCG (FIG. 4C). After digestion with BamHI, the fragment was cloned into the BamHI site at the start of the beta-galactosidase gene (FIG. 4D). The plasmid was constructed with the *E. coli* plasmids pSP64 and pSP65 such that XbaI sites from the polylinkers could be used to excise the entire construct for the plasmid. The ligation mixture was used to transfect *E. coli* HB101 according to published procedures (Maniatis et al. (1)). This construct was planned such that the first three amino acids of the protein were from the HSV-1 TK gene, the next three were form the synthetic linker, and the rest were from the beta-galactosidase gene. The gene contained the following sequence at the fusion between TK and lacZ:

```
5' CGT ATG GCT TCG TCG GAT CCC GTC GGT TTA ... 3'
       MET ala ser ser asp pro val val leu ...
   --------------      -----------      -------------
      TK gene         BamHI linker          lac Z
```

A pseudorabies virus construct designated S-PRV-002 which has a deletion in the PRV TK gene in the unique long region and a deletion in the repeat region was used as the recipient for the beta-galactosidase gene. Intact S-PRV-002 DNA was mixed with a 30-fold molar excess of plasmid DNA containing the beta-galactosidase gene under the control of the HSV-1 TK promoter, and this mixture was digested with XbaI restriction enzyme. The ligated DNA was used to transfect animal cells, and the transfection stock was analyzed for recombinant PRV. First, PRV DNA was prepared from cells infected with the transfection stock virus and this DNA was cut with restriction enzymes and analyzed on an agarose gel. This analysis showed that the recombinant virus was present as the major species in the transfection stock, and it was subsequently purified from other virus species by plaque assay coupled with the BLUOGAL SCREEN FOR RECOMBINANT HERPESVIRUS. Because beta-galactosidase reacted with the drug Bluogal~ to yield a product with blue color, it was possible to plaque purify the recombinant by picking blue plaques.

The final result of the purification was the recombinant PRV designated S-pRV-010. It was shown to express the enzyme beta-galactosidase by the formation of blue plaques as noted above, nd by the detection of the enzyme in infected cell extracts using the substrate O-nitrophenyl-beta-D-galactopyranoside (Sigma) following the procedure of Norton and Coffin (33). The location of this gene in the genome of PRV is shown in FIG. 5C.

Previous studies demonstrated that swine vaccinated with S-PRV-002 developed antibody to PRV and were fully protected against clinical disease following exposure to virulent PRV virus. Animal studies were conducted with S-PRV-010 to determine the utility of a recombinant pseudorabies virus as a vaccine against pseudorabies disease.

A group of weaned pigs and a litter of four-day-old piglets were vaccinated with S-PRV-010 and challenged three to four weeks later, according to VACCINATION STUDIES IN SWINE.

Responses of weaned pigs vaccinated with S-PRV-010 are shown in Table II. Administration of this virus did not cause adverse reactions in the pigs. The vaccinated animals developed PRV neutralizing antibody. Two, non-vaccinated control animals (#75 and #91) place din contact with the vaccinates did not develop PRV antibody prior to challenge, indicating the vaccine virus was not shed from vaccinates. After challenge, all ten vaccinated animals remained clinically normal and free of PRV disease. In contrast, the two in-contact control animals and three of five non-vaccinated control animals developed PRV disease and one of these pigs died of PRV.

To test further the utility of S-PRV-010 as a vaccine, the virus was inoculated into 4-day old piglets. The results, presented in Table III, demonstrated that the virus elicited an antibody response in vaccinated piglets and did not cause adverse reactions. The virus apparently was shed form vaccinates, since one (#67) out of two non-vaccinated, in-contact control piglets had developed PRV antibody by Day 24. After challenge, all vaccinated animals and the sero-positive in-contact control animal remained free of PRV disease. By comparison, the three non-vaccinated control pigs and the second in-contact control pig developed clinical signs of PRV and died.

The conclusion for the study is that S-PRV-010 given at a dosage of $10^{4.0}$ or $10^{6.0}$, elicits a protective response in vaccinated piglets or weaned pigs capable of preventing infection by virulent virus.

EXAMPLE 4

S-PRV-007

S-PRV-007 is a pseudorabies virus that has a deletion in the PRV TK gene in the unique long region, a deletion in the repeat region, and the swine rotavirus glycoprotein 38 gene under the control of the HSV-1 ICP4 promoter inserted into the repeat region.

S-PRV-005 virus described in Example 2 above was further engineered to contain the rotavirus antigen (see FIG. 6) as follows. The swine rotavirus gp38 gene was

TABLE II

SEROLOGIC AND CLINICAL RESPONSES OF WEANED PIGS FOLLOWING VACCINATION WITH S-PRV-010 AND CHALLENGE WITH WILD-TYPE PRV

| Vaccine GROUP | Pig Number | Antibody Titers[a] Post-Vaccination Day 0 | Day 14 | Day 24 | Post-Challenge Day 7 | Day 14 | Post-Challenge Clinical Signs |
|---|---|---|---|---|---|---|---|
| $10^{6.0}$ | 70 | <2 | 64 | 32 | 32 | 64 | None |
| Per | 71 | <2 | 16 | 16 | 16 | 32 | None |
| Dose | 72 | <2 | 64 | 32 | 16 | 64 | None |
| | 73 | <2 | 64 | 16 | 16 | 64 | None |
| | 74 | <2 | 16 | 8 | 4 | 4 | None |
| | 75[b] | <2 | <2 | <2 | <2 | 4 | Depressed, Dyspnea, CNS Signs[c] |
| $10^{4.0}$ | 76 | <2 | 64 | 4 | 8 | 32 | None |
| Per | 77 | <2 | 16 | 16 | 64 | 8 | None |
| Dose | 78 | <2 | 32 | 16 | 32 | 8 | None |
| | 79 | <2 | 8 | 16 | 64 | 4 | None |
| | 80 | <2 | 2 | <2 | 256 | 16 | None |
| | 81[b] | <2 | <2 | <2 | <2 | 16 | Depressed, Rhinitis, CNS Signs |
| Con- | 82 | NT | NT | <2 | <2 | 8 | None |
| trols | 83 | NT | NT | <2 | <2 | 16 | None |
| | 84 | NT | NT | <2 | <2 | 32 | CNS Signs, Depressed, Dyspnea |
| | 85 | NT | NT | <2 | <2 | 64 | CNS Signs |
| | 86 | NT | NT | <2 | <2 | — | CNS Signs Died |

[a]Determined by RIDEA
[b]In-contact Controls
[c]CNS signs include Ataxia, Incoordination, Circling, Lateral Recumbency
NT: Not Tested

TABLE III

SEROLOGIC AND CLINICAL RESPONSES OF 4-DAY-OLD PIGLETS FOLLOWING VACCINATION WITH S-PRV-010 AND CHALLENGE WITH WILD-TYPE PRV

| Vaccine GROUP | Pig Number | Antibody Titers[a] Post-Vaccination Day 0 | Day 14 | Day 24 | Post-Challenge Day 7 | Day 14 | Post-Challenge Clinical Signs |
|---|---|---|---|---|---|---|---|
| $10^{6.0}$ | 60 | <2 | 4 | 16 | 16 | 32 | None |
| Per | 61 | <2 | 64 | 8 | 64 | 8 | None |
| Dose | 62 | <2 | 32 | 2 | 16 | 16 | None |
| $10^{4.0}$ | 63 | <2 | —[b] | — | — | — | — |
| Per | 64 | <2 | 64 | 2 | 32 | 16 | None |
| Dose | 65 | <2 | 2 | 4 | 32 | 16 | None |
| In-Contact | 66 | <2 | 2 | NT | —[c] | — | Comatose, Died |
| Controls | 67 | <2 | <2 | 8 | 64 | 32 | None |
| Controls | 87 | NT | NT | <2 | —c | — | CNS Signs[d], Died |
| | 88 | NT | NT | <2 | —c | — | CNS Signs, Died |
| | 89 | NT | NT | <2 | —[c] | — | Died |

[a]Determined by RIDEA
[b]Died 8 Days Post Vaccination From Ruptured Stomach
[c]Died on or Prior to Day 7 Post-Challenge
[d]CNS Signs include Ataxia, Incoordination, Circling Lateral Recumbency
NT: Not Tested cloned into plasmid pBR322 at the PstI site by procedures previously described herein. The resulting plasmid was called pSY565 (see FIG. 7). The 1090 bp PstI fragment containing the gp38 gene was cloned into vector pUC4K at the PstI site such that it became flanked by BamHI sites in a plasmid called pSY762.

Plasmid pSY590 has had a complex origin as inferred from the flow chart. These clonings were routine in nature and are of historical interest but are not strictly required to practice the invention. Briefly this history is:

(1) The McKnight TK gene was the HSV-1 BamHI Q fragment from HaeIII at −178 relative to CAP site to BamHI at +2700 which was cloned between HindIII and BamHI in pBR327.

(2) pSY491 . . . The entire TK coding region form the BglII site at +55 (relative to CAP site) to the BamHI site at +2700 was cloned into the BamHI site in pSP65 and called pSY491.

(3) pSY481 . . . The polyA signal sequence (pA) on an 800 bp SmaI fragment from TK was subcloned into the SmaI site in PSP65 and was called pSY481.

(4) pSY583 . . . The pA 800 bp SmaI fragment from pSY481 was cloned into the HincII site in pSP65 and called PSY583.

(5) pSY429 . . . The HSV-1 BamHI N fragment was obtained from Dr. B. Roizman cloned into the BamHI site of pBR322 and was called pSY429.

(6) pSY584 . . . The 2.2 kb fragment of BamHI N from PvuII to BamHI (Ref. 16) in pSY420 was subcloned into pSP65 between HincII and BamHI in the polylinker and was called pSY584.

(7) pSY479 . . . The plasmid was constructed from pSP64 and pSP65 that contained a fused polylinker sequence. Both plasmids were cut with PstI in the polylinker and PvuI in the plasmid body. The net effect to this construct was to create a fusion plasmid called pSP66 which has a symmetrical polylinker sequence centered on the PstI site. pSY479 is the name of this plasmid and it also contained a PstI fragment cloned into the PstI site that is irrelevant for the manipulations that follow.

Figure 7:
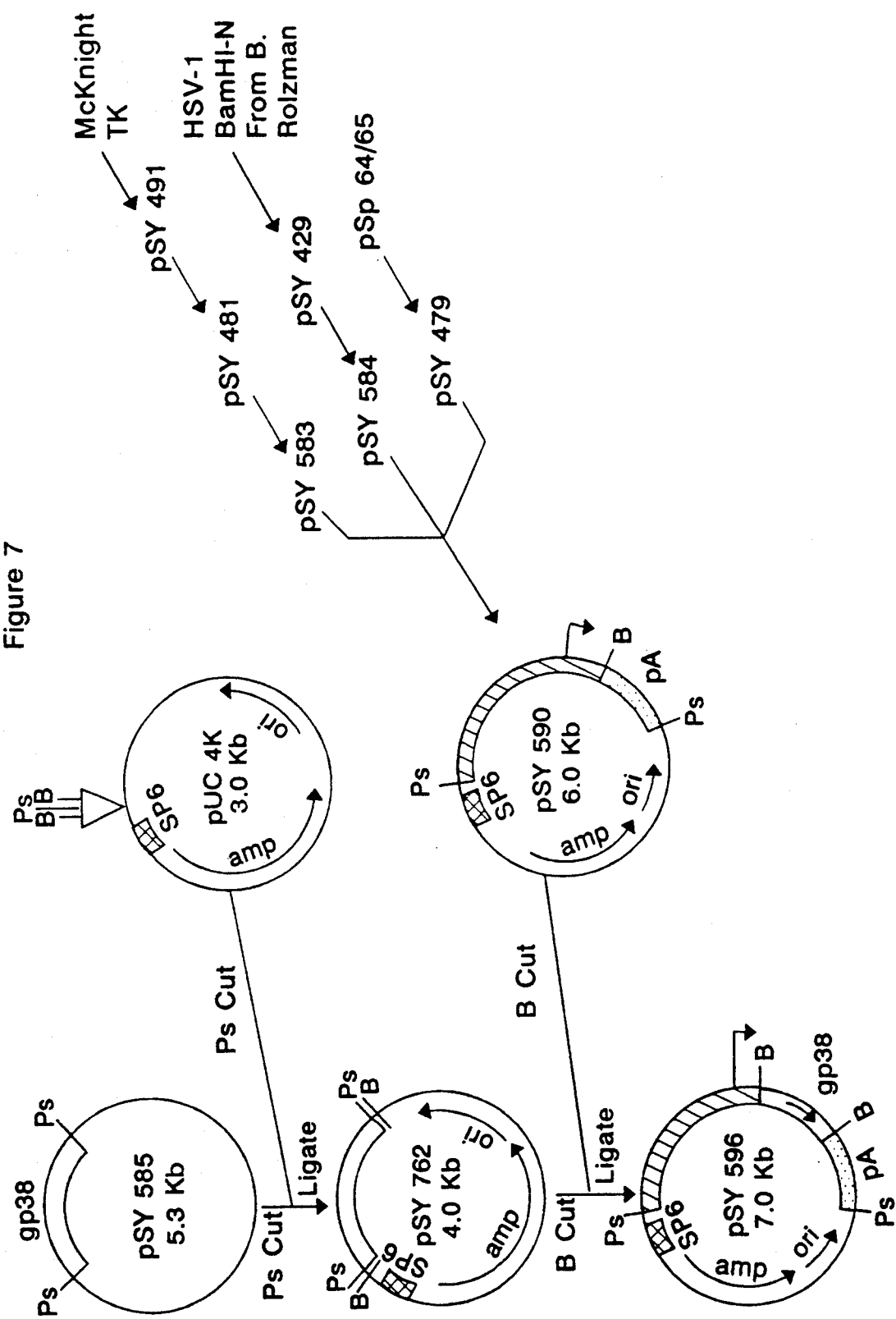
FIG. 7 Construction of the Foreign DNA Inset Used in S-PRV-007.
Figure 8A:
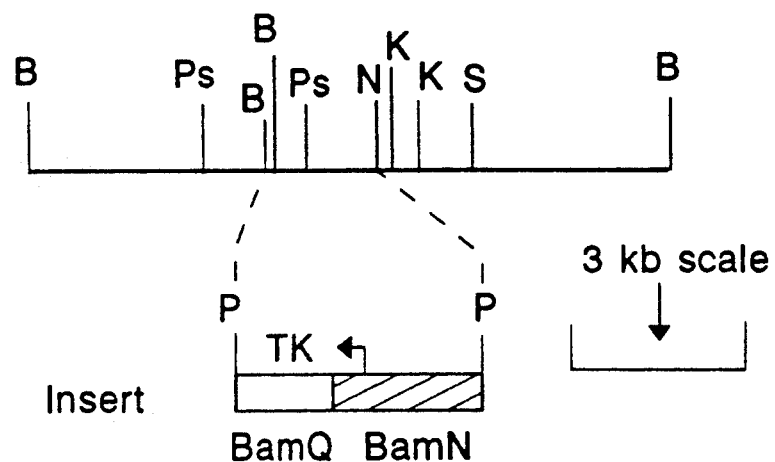
FIG. 8 Details of S-PRV-012 Construction and Map Data.
  A. Detailed map of PRV extending from BamHI #10 through BamHI #7.
  B. Detailed map of PRV extending from BamHI #10 through BamHI #7 after the insertion of the TK gene into the recombinant virus.
  C. Diagram of the S-PRV-102 DNA genome showing the location of the TK gene inserted into the gpX region and the creation of a deletion that removes most of the coding region of the gpX gene and renders the virus unable to synthesize the gpX polypeptide.
Restriction Enzyme Legend: B=BamHI; K=KpnI; N=NdeI; P=PvuII; Ps=PstI; S=StuI.
Figure 8B:
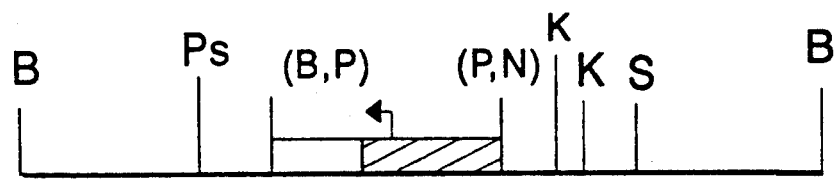
Figure 8C:
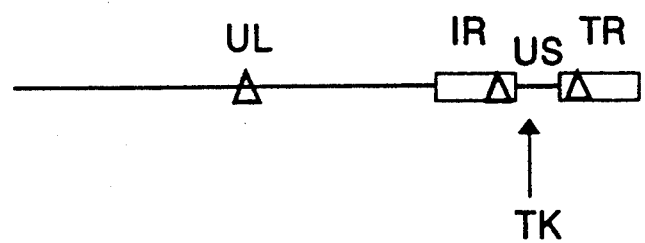

Plasmid pSY590 was created from pSY583, pSY584, and pSY479 in a three fragment ligation of the following elements: the 3 kb plasmid sequences from pSY479 (pSP66) cut with PstI, the 800 bp SmaI pA fragment cut from the polylinker in pSY583 with PstI and BamHI, and the 2200 bp BamHI N fragment cut from pSY583 with PstI and BamHI. FIG. 7 shows the final configuration of all of these DNA fragments in pSY590. There is a single BamHI site in the plasmid between the promoter in BamHI N and the TK pA signal that was used to insert the coding region of the gp38 gene.

For the creation of the homology vector used in the formation of S-PRV-007, the plasmid pSY590 was opened with BamHI, and the 1090 bp gp38 gene was removed from pSY762 by cutting with BamHI, and these two fragments were ligated together to form pSY596. The correct orientation of the gp38 gene was confirmed by diagnostic restriction enzyme digestion utilizing sites with gp38 (see FIG. 10A and 10B).

In pSY596 described above, the gp38 gene resided between two flanking HSV-1 DNA fragments. These two regions were thus homologous to similar regions on the HSV-1 TK gene in S-PRV-005,and these regions were used for the homologous recombination to create S-PRV-007 (FIG. 6A). The plasmid and S-PRV-005 DNAs were mixed and used in the DNA TRANSFECTION PROCEDURE FOR GENERATING RECOMBINANT VIRUS. A virus that had incorporated the rotavirus antigen in place of the TK gene was selected with BUDR. Recombinants from the selected virus stock that had incorporate the rotavirus DNA were screened by the HYBRIDIZATION SCREEN FOR RECOMBINANT HERPESVIRUS and by analyzing restriction digests of DNA by the SOUTHERN BLOTTING OF DNA procedure using the rotavirus cloned gp38 gene as probe.

The final result of this screening was a recombinant PRV called S-PRV-007 which had the rotavirus gp38 gene incorporated into the repeat region between the XbI and HpaI sites in PRV BamHI #5 fragment shown in FIG. 6C. The presence in a host of gp38 expressed by S-PRV-007 has not yet been detected.

EXAMPLE 5

S-PRV-012

S-PRV-012 is a pseudorabies virus that has a deletion in the PRV TK region in the unique long region, a deletion in the repeat region, and a deletion in the unique short region encoding the PRV glycoprotein X, called gpX and identified and mapped by Rea et al. (23). The HSV-1 TK gene under the control of the ICP4 promoter was inserted in place of the gpX gene.

The following procedure was used to make the deletion of gpX and the simultaneous insertion of the HSV-1 TK gene. The flanking regions for homology to PRV were from cloned fragments of BamHI #10 fragment and BamHI #7 fragment extending from NdeI to BamHI (FIG. 8). The BamHI and NdeI sites were filled in according to the POLYMERASE FILL-IN REACTION, and the PvuII fragment of HSV-1 DNA was inserted by LIGATION. This plasmid was transfected with intact S-PRV-002 DNA according to the DNA TRANSFECTION FOR GENERATING RECOMBINANT VIRUS procedure. The recombinant virus was selected by HAT SELECTION OF RECOMBINANT HERPESVIRUS procedure, and screened by the ANTIBODY SCREEN FOR RECOMBINANT HERPESVIRUS procedure using antibodies specific for the HSV-1 protein.

The recombinant virus selected by this procedure was designated S-PRV-012 and has been deposited with the ATCC under Accession No. VR-2119 and was shown by RESTRICTION MAPPING OF DNA and SOUTHERN BLOTTING OF DNA to contain the HSV-1 TK gene inserted in place of the gpX gene (FIG. 8B). The ANTIBODY SCREEN FOR RECOMBINANT HERPESVIRUS procedure showed that the virus was expressing the inserted HSV-1 TK gene. The structure of this virus is shown in FIG. 8C.

EXAMPLE 6

S-PRV-013

S-PRV-013 is a pseudorabies virus that has a deletion in the TK gene in the long unique region, a deletion in the repeat region and a deletion in the gpX coding region. The gene for *E. coli* beta-galactosidase (lacZ gene) was inserted in place of the gpX gene and is under the control of the endogenous gpX gene promoter.

The following procedures were used to construct S-PRV-013 by homologous recombination. The flanking PRV homology regions were form the cloned BamHI #10 fragment which contained the gpX promoter, and form the cloned BamHI #7 fragment extending from the NdeI site to the BamHI site (FIG. 9A). The NdeI site was filled in according to the POLY- MERASE FILL-IN REACTION, and the beta-galactosidase gene between the gpX promoter and the gpX poly A signal sequences with a deletion of almost all of the coding regions of gpX. The plasmid DNA and DNA form S-PRV-002, a PRV strain with a deletion in both repeat sequences and a deletion in the thymidine kinase gene, were mixed and transfected according to the DNA TRANSFECTION FOR GENERATING RECOMBINANT VIRUS PROCEDURE. The recombinant virus was screened and purified from the transfection stock by the BLUOGAL SCREEN FOR RECOMBINANT HERPESVIRUS PROCEDURE.

The resulting virus form this screen was designated S-PRV-013 and has been deposited with the ATCC under Accession No. VR 2120. It contained the beta-galactosidase gene in place of the gpX coding regions (FIGS. 9B and 9C) as determined by PREPARATION OF HERPESVIRUS DNA followed by SOUTHERN BLOTTING OF DNA. The expression of the Beta-galactosidase gene was confirmed by the BLUOGAL SCREEN FOR RECOMBINANT HERPESVIRUS test, and by the o-nitrophenyl-galactopyranoside substrate assay (33).

To confirm that the coding region for gpX had been removed form S-PRV-013, DNA extracted from a stock of purified S-PRV-013 was digested with BamHI and the fragments were speared on agarose gel electrophoresis and analyzed by SOUTHERN BLOT HYBRIDIZATION. The hybridization probe was the BamHI-NDE fragment of pseudorabies BamHI #7 fragment from the unique short region. This probe fragment included 90% of the coding sequences of gpX. In this analysis, the gpX region was shown to be missing form S-PRV-013.

To confirm these results, cells were infected with either wild-type pseudorabies, S-PRV-012 or S-PRV-013, and samples of media form the infected cultures were subjected to SDS-polyacrylamide gel electrophoresis. The cell was blotted and analyzed using the WESTERN BLOTTING PROCEDURE. The antiserum used was a rabbit hyper-immune serum raised against a chemically-synthesized gpX antigenic peptide linked to bovine serum albumin. As shown in FIG. 4, gpX is prominent in the media of cells infected with wild-type virus (PRV 000), but is not detected in the media of cells infected with S-RPV-012 or S-PRV-013. These results demonstrate that the pgX gene is missing from both S-RPV-012 and S-PRV-013 and the protein, gpX, is not produced in cells infected by either S-RPV-012 or S-PRV-013.

The following experiments indicate that S-PRV-013 may be used as a vaccine to protect swine against pseudorabies disease and that it produces an immune response which can readily be distinguished form wild-type infection.

In the first study, susceptible weaned pigs and four-day old piglets were vaccinated intramuscularly with S-PRV-013 as follows: 4 of each group were inoculated with $10^6$ $TCID_{50}$ and 4 were inoculated with $10^4$ $TCID_{50}$ of virus. The animals were observed, then challenged as describe din VACCINATION STUDIES WITH SWINE (see Table IV below).

TABLE IV

RESPONSES OF 4-DAY-OLD PIGLETS VACCINATED WITH S-PRV-013 AND CHALLENGED WITH VIRULENT PRV

| | | | Post-Vaccination | | | | | Post-Challenge | | |
|---|---|---|---|---|---|---|---|---|---|---|
| | | | Antibody | | | | | Antibody | | |
| Pig Group | Vaccine Dose | Pig No. | Day 14 | Day 21 | Day 28 | Clinical Signs[a] | Virus Isolation | Day 7 | Day 14 | Clinical Signs |
| WEANED | $10^6$ | 1 | 4 | 2 | 2 | NEG | NT[b] | >64 | >64 | NEG |
| | $TCID_{50}$ | 2 | 4 | 2 | 2 | NEG | NT | >64 | >64 | NEG |
| | | 3 | 2 | 2 | 2 | NEG | NT | 64 | >64 | NEG |
| | | 4 | 4 | 2 | 4 | NEG | NT | >64 | >64 | NEG |
| | $10^4$ | 5 | 2 | 2 | 2 | NEG | NT | >64 | >64 | NEG |
| | $TCID_{50}$ | 6 | <2 | <2 | 2 | NEG | NT | 64 | >64 | NEG |
| | | 7 | <2 | <2 | <2 | NEG | NT | 64 | >64 | NEG |
| | | 8 | <2 | <2 | <2 | NEG | NT | 64 | >64 | NEG |
| PIGLETS | $10^6$ | 10 | 8 | 16 | 32 | NEG | NEG | >64 | >64 | NEG |
| | $TCID_{50}$ | 11 | —[d] | — | — | NEG | NEG | — | — | — |
| | | 12 | 8 | NT | 64 | NEG | NEG | >64 | >64 | NEG |
| | | 13 | 4 | 8 | 32 | NEG | NEG | >64 | >64 | NEG |
| | $10^4$ | 14 | 4 | 8 | 32 | NEG | NEG | >64 | >64 | NEG |
| | $TCID_{50}$ | 15 | 8 | 16 | 32 | NEG | NEG | >64 | >64 | S |
| | | 16 | 2 | 2 | 8 | NEG | NEG | 64 | >64 | NEG |
| | | 17 | 4 | 16 | 32 | NEG | NEG | 64 | 64 | NEG |
| | Contact | 18 | <2 | <2 | <2 | NEG | NEG | 2 | 16 | F,C |
| | Control | 19 | —[e] | — | — | NEG | NEG | — | — | — |
| Challenge Control | | 20 | Not Applicable | | | | | <2 | — | F,C.D |
| | | 21 | | | | | | <2 | 2 | F,C |
| | | 22 | | | | | | <2 | 2 | F,C |

[a]Key to clinical signs: NEG = Negative, C = CNS, D = Death, F = Febrile, R = Respiratory, S = Scours
[b]Not tested
[c]Sacrificed Day 4 post-vaccination
[d]Sacrificed Day 7 post-vaccination; runt doing poorly Following vaccination, all animals were free of adverse reactions and all but 2 (weaned pigs) developed serum neutralizing antibody titers of 1:2 to 1:64. Virus was not recovered from tonsillar swabs of any pig or from tissues taken form the piglet (#11) sacrificed on Day 4. One of 2 contact control piglets (#19) was sacrificed 7 days into the experiment because it was a runt and doing poorly. Tissues from this piglet were negative when cultured for PRV. The other contact control remained healthy and did not develop PRV antibody prior to challenge.

After challenge, all vaccinated animals remained clinically normal and developed secondary antibody responses. The contact control piglet and the three challenge control pigs all developed typical central nervous system signs of PRv and one control died following challenge.

In a second study with S-PRV-013 using larger numbers of animals, 2 litters of susceptible 3-day-old piglets and a group of 15 susceptible weaned pigs were vaccinated with $10^4$ TCID$_{50}$ of virus, then challenged as describe din VACCINATION STUDIES WITH SWINE (see Tables V and VI below).

TABLE V

RESPONSES OF 3-DAY-OLD PIGLETS VACCINATED WITH S-PRV-O13 AND CHALLENGED WITH VIRULENT PRV

| | | Post-Vaccination | | | | | | Post-Challenge | | | |
|---|---|---|---|---|---|---|---|---|---|---|---|
| | | Antibody | | | | | | Antibody | | | |
| Group | Pig No. | Day 7 | Day 14 | Day 21 | Day 28 | Clinical Signs[a] | Virus Isolation | Day 7 | Day 14 | Clinical Signs | Virus Isolation |
| LITTER A VACCINATES | 1 | <2 | 2 | 4 | 4 | F[b] | Neg | 32 | >64 | Neg | Neg |
| | 2 | <2 | 8 | 8 | 16 | F | Neg | 64 | >64 | Neg | Neg |
| | 3 | <2 | 8 | 8 | 16 | F | Neg | 16 | 32 | Neg | Neg |
| | 4 | <2 | 8 | 16 | 16 | F | Neg | 32 | >64 | Neg | Neg |
| | 6 | <2 | 8 | 8 | 16 | F | Neg | 64 | >64 | Neg | Neg |
| Contact Control | 7 | <2 | <2 | <2 | <2 | Neg | Neg | 2 | 2 | C,F,R | Neg |
| | 8 | <2 | <2 | <2 | <2 | Neg | Neg | <2 | >64 | C,F | Neg |
| LITTER B VACCINATES | 10 | <2 | 8 | 8 | 16 | F | Neg | 16 | >64 | Neg | Neg |
| | 11 | <2 | 8 | 8 | 16 | F | Neg | 32 | >64 | Neg | Neg |
| | 12 | <2 | 8 | 32 | 32 | F | Neg | 32 | >64 | Neg | Neg |
| | 13 | <2 | 4 | 16 | 32 | F | Neg | 64 | >64 | Neg | Neg |
| | 14 | <2 | 8 | 16 | 32 | Neg | Neg | 64 | >64 | Neg | Neg |
| | 16 | <2 | 4 | 4 | 16 | F | Neg | 32 | >64 | Neg | Neg |
| | 17 | <2 | 8 | 8 | 32 | F | Neg | 64 | >64 | Neg | Neg |
| Contact Control | 18 | <2 | <2 | <2 | <2 | Neg | Neg | 2 | 2 | C,F | Neg |
| CHALLENGE CONTROLS | 19 | Not Applicable | | | <2 | Not Applicable | | <2 | 2 | C,F,R | Neg |
| | 20 | | | | <2 | | | <2 | 2 | C,F,R | Swab |
| | 21 | | | | <2 | | | 2 | <2 | C,F,R | Swab |
| | 22 | | | | <2 | | | <2 | <2 | C,F,R | Swab |
| | 23 | | | | <2 | | | <2 | Died | C,D,F R | Swab Tonsil, CNS |
| | 24 | | | | <2 | | | <2 | <2 | C,F,R | Swab |

[a]Clinical signs: NEG = Negative. C = CNS. D = Death. F = Febrile. R = Respirator
[b]A 1° F. increase in temperature was observed in day 1 in these vaccinates

TABLE VI

RESPONSE OF WEANED PIGS VACCINATED WITH S-PRV-013 AND CHALLENGED WITH VIRULENT PRV

| | | Post-Vaccination | | | | | Post-Challenge | | | |
|---|---|---|---|---|---|---|---|---|---|---|
| | | Antibody | | | | | Antibody | | | |
| Group | Pig No. | Day 0 | Day 14 | Day 21 | Clinical Signs[a] | Virus Isolation | Day 7 | Day 14 | Clinical Signs | Virus Isolation |
| VACCINATES | 35 | <2 | <2 | 4 | Neg | Neg | >64 | >64 | Neg | Neg |
| | 36 | <2 | 2 | 2 | Neg | Neg | >64 | >64 | Neg | Neg |
| | 37 | <2 | 2 | 2 | Neg | Neg | >64 | >64 | Neg | Neg |
| | 38 | <2 | <2 | 2 | Neg | Neg | >64 | >64 | Neg | Neg |
| | 39 | <2 | 2 | 2 | Neg | Neg | 64 | 64 | Neg | Neg |
| | 40 | <2 | 2 | 4 | Neg | Neg | >64 | >64 | Neg | Neg |
| | 41 | <2 | 2 | 4 | Neg | Neg | 64 | >64 | Neg | Neg |
| | 42 | <2 | 2 | 4 | Neg | Neg | >64 | >64 | F | Neg |
| | 43 | <2 | 2 | 2 | Neg | Neg | >64 | >64 | F | Neg |
| | 44 | <2 | 2 | 2 | Neg | Neg | 64 | >64 | F | Neg |
| | 45 | <2 | 2 | 4 | Neg | Neg | >64 | >64 | Neg | Neg |
| | 48 | <2 | 2 | 2 | Neg | Neg | >64 | >64 | Neg | Neg |
| | 47 | <2 | <2 | 2 | Neg | Neg | 32 | >64 | F | Neg |
| | 48 | <2 | 2 | 2 | Neg | Neg | >64 | >64 | F | Neg |
| | 49 | <2 | 2 | 2 | Neg | Neg | 64 | >64 | F | Neg |
| CONTROLS | 30 | <2 | NT[b] | <2 | Not Applicable | | <2 | 4 | C,F,R | Neg |
| | 31 | <2 | NT | <2 | | | <2 | 2 | C,F | Neg |
| | 32 | <2 | NT | <2 | | | <2 | 4 | C,F,R | Neg |
| | 33 | <2 | NT | <2 | | | <2 | Died | C,D,F,R | Tonsil, CNS |
| | 34 | <2 | NT | <2 | | | <2 | 4 | F | Neg |

[a]Clinical signs: NEG = Negative, C = CNS, D = Death, F - Febrile, R = Respiratory
[b]Not tested In this experiment, all of the vaccinated animals remained healthy following vaccination, developed serum neutralizing antibody to PRV and did not shed vaccine virus in tonsillar secretions. After challenge with virulent virus, vaccinates of both age groups remained free of PRV disease, whereas the 3 non-vaccinated contact controls and 10 of 11 of the challenge controls developed severe pseudorabies of disease.

The serum samples collected from the vaccinated and challenged swine were assayed by the gpX ELISA assay. Because the gene for gpX was deleted form S-PRV-013, it is expected that swine vaccinated with S-PRV-013 would be sero-negative in the ELISA test for this antigen. The challenge virus carrier the gpX gene. The vaccinated animals were protected by the vaccination from pseudorabies disease when challenged with the wild-type virus. However, vaccinated animals were asymptomatically super-infected by the challenge strain and would, therefore, be expected to produce antibodies to gpX upon challenge.

Figure 5A:
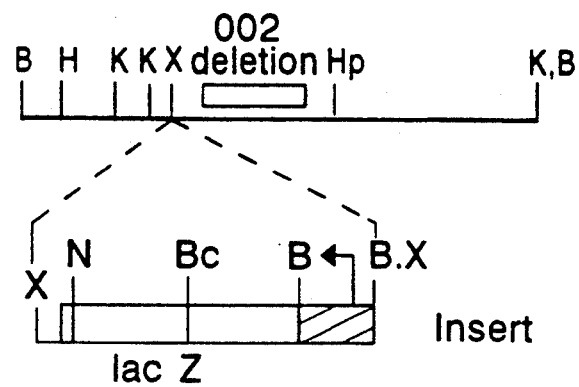
FIG. 5 Details of S-PRV-010 Construction and Map Data.
  A. Detailed map of BamHI #5. The lac Z gene (beta-galactosidase) fused to the HSV-1 TK promoter is shown on an XbaI fragment (see FIG. 4). The position of the deletion in S-PRV-002 is shown.
  Detailed map of BamHI #5 after the insertion of the lac Z gene construct.
  C. Diagram of the S-PRV-010 genome DNA showing the location of the lac Z gene into both copies of BamHI #5 in the repeat region of the genome.
    Restriction Enzyme Legend: B=BamHI; Bc=BclI; H=HindIII; Hp=HpaI; K=KpnI; N=NdeI; X=XbaI.
Figure 5B:
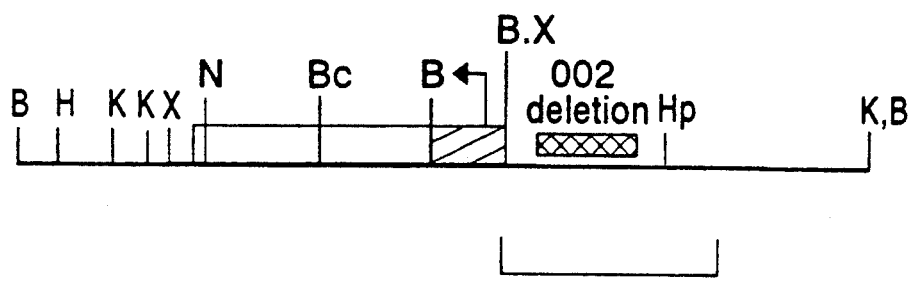
Figure 5C:
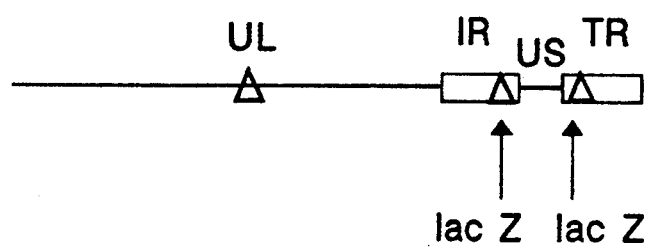
Figure 6A:
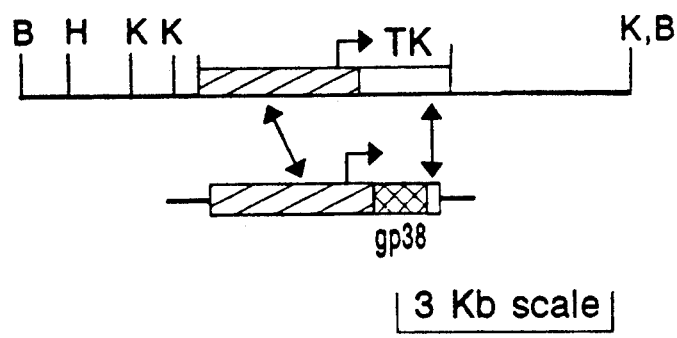
FIG. 6 Details of S-PRV-007 Construction and Map Data.
  A. Detailed map of BamHI #5 from S-PRV-005.
  B. Detailed map of BamHI #5 after the substitution of the TK gene with the swine rotavirus gp38 gene.
  C. Diagram of the S-PRV-007 DNA genome showing the location of the gp38 gene inserted into both copies of BamHI #5 in the repeat regions of the genome.
    Restriction Enzyme Legend: B=BamHI; H=HindIII; K=KpnI.
Figure 6B:
Figure 6C:
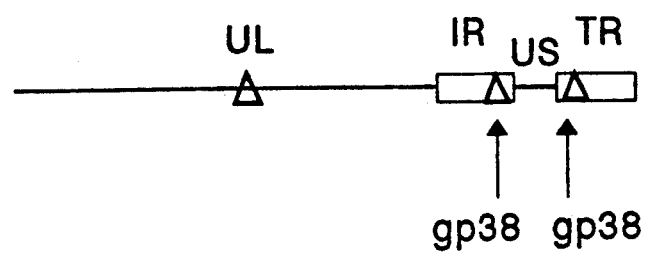

As shown in FIG. 5, serum from an animal vaccinated with S-PRV-013 remained negative for gpX until after challenge with the wild-type virus. These results indicate that S-PRV-013 is an effective vaccine strain which permits vaccinates to be distinguished form animals infected with wild-type virus by a sample serum diagnostic assay.

EXAMPLE 7

S-PRV-014

S-PRV-014 is a pseudorabies virus that has a deletion in the gpX coding region. The gene for *E. coli* beta-galactosidase was inserted in place of the gpX gene and is under the control of the endogenous gpX promoter.

The following procedures were used to create S-PRV-014 by homologous recombination. The flanking PRV homology regions were form the cloned BamHI #10 fragment which contains the gpX promoter, and form the cloned BamHI #7 fragment extending from the NdeI site to the BamHI site (FIG. 9). The NdeI site was filled in according to the POLYMERASE FILL-IN REACTION, and the beta-galactosidase gene was inserted between the BamHI #10 and BamHI #7 fragments. This construct positioned the beta-galactosidase gene behind the gpX promoter and the gpX poly A signal sequence with a deletion of almost all of the coding region of gpX. The plasmid DNA and DNA from wild-type PRV were mixed and transfected according to the DNA TRANSFECTION FOR GENERATING RECOMBINANT VIRUS procedure. The recombinant virus was screened and purified from the transfection stock by the BLUOGAL SCREEN FOR RECOMBINANT HERPESVIRUS procedure.

Figure 9A:
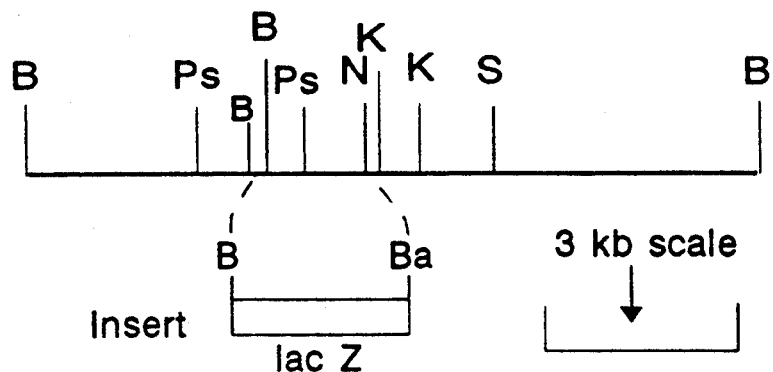
FIG. 9 Details of S-PRV-013, S-PRV-014, and S-PRV-016 Construction and Map Data.
  A. Detailed map of PRV extending from BamHI #10 through BamHI #7.
  B. Detailed map of PRV extending from BamHI #10 through BamHI #7 after the insertion of the lac Z gene into the recombinant virus.
  C. Diagram of the S-PRV-013 DNA genome showing the location of the lac Z gene inserted into the gpX region and the creation of a deletion that removed most of the coding region of the gpX gene and rendered the virus unable to synthesize the gpX polypeptide. Other deletions in the TK region and repeat regions are shown by ( ).
  D. Diagram of the S-PRV-014 DNA genome showing the location of the lac Z gene inserted into the gpX region and the creation of a deletion that removed most of the coding region of the gpX gene and rendered the virus unable to synthesize the gpX polypeptide. There are no other deletions in this virus.
  E. Diagram of the S-PRV-016 DNA genome showing the location of the lac Z gene inserted into the gpX region and the creation of a deletion that removed most of the coding region of the gpX gene and rendered the virus unable to synthesize the gpX polypeptide. Other deletions in the repeat regions are shown by ( ).
  Restriction Enzyme Legend: B=BamHI; Ba=BalI; K=KpnI; N=NdeI; Ps=PstI; S=StuI.
Figure 9B:
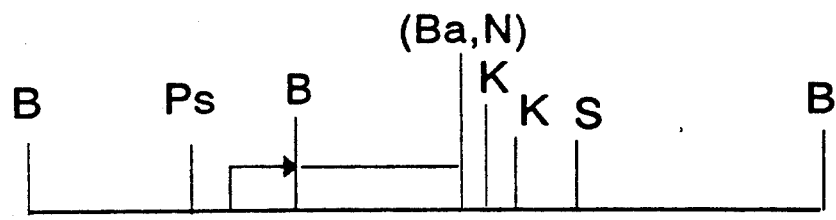
Figure 9C:
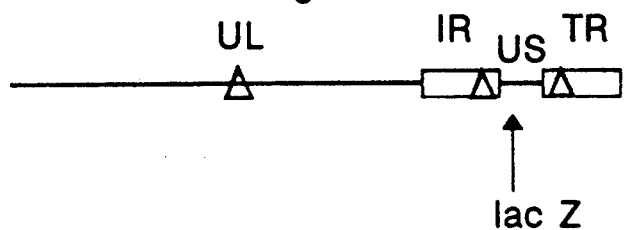
Figure 9D:
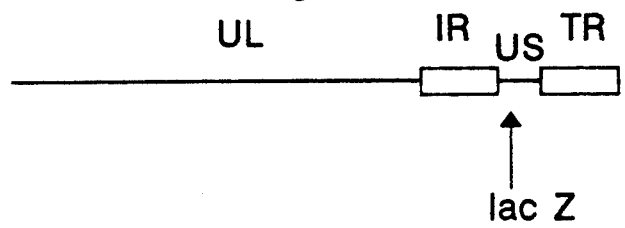

The resulting virus from this screen was designated S-PRV-014 and has been deposited with the ATCC under Accession No. VR 2135. It contains the beta-galactosidase gene in place of the gpX coding region as determined by PREPARATION OF HERPESVIRUS DNA of allowed by SOUTHERN BLOTTING DNA. The expression of the beta-galactosidase gene was confirmed by the BLUOGAL SCREEN FOR RECOMBINANT HERPESVIRUS test, and by the o-nitrophenylgalactopyranoside substrate assay (33). The structure of this virus is shown in FIG. 9D.

EXAMPLE 8

S-PRV-016

S-PRV-016 is a pseudorabies virus that has a deletion in both repeat sequences, and a deletion in the gpX coding region. The gene for *E. coli* beta-galactosidase was inserted in place of the gpX gene and is under the control of the endogenous gpX gene promoter.

the following procedures were used to construct S-PRV-016 by homologous recombination. The flanking PRV homology regions were from the cloned BamHI #10 fragment which contains the gpX promoter, and form the cloned BamHI #7 fragment extending form the NdeI site to the BamHI site (FIG. 9). The NdeI site was filled in according to the POLYMERASE FILL-IN REACTION, and the beta-galactosidase gene was inserted between the BamHI #10 and BamHI #7 fragments. The construct positioned the beta-galactosidase gene behind the gpX promoter and the gpX poly A signal sequence with a deletion of almost all of the coding region of gpX. The plasmid DNA and DNA from S-PRV-001 were mixed and transfected according to the DNA TRANSFECTION FOR GENERATING RECOMBINANT VIRUS procedure. The recombinant virus was screened and purified from the transfection stock by the BLUOGAL SCREEN FOR RECOMBINANT HERPESVIRUS procedure.

Figure 9E:
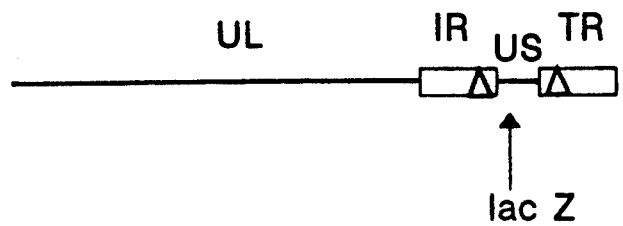
Figure 12:
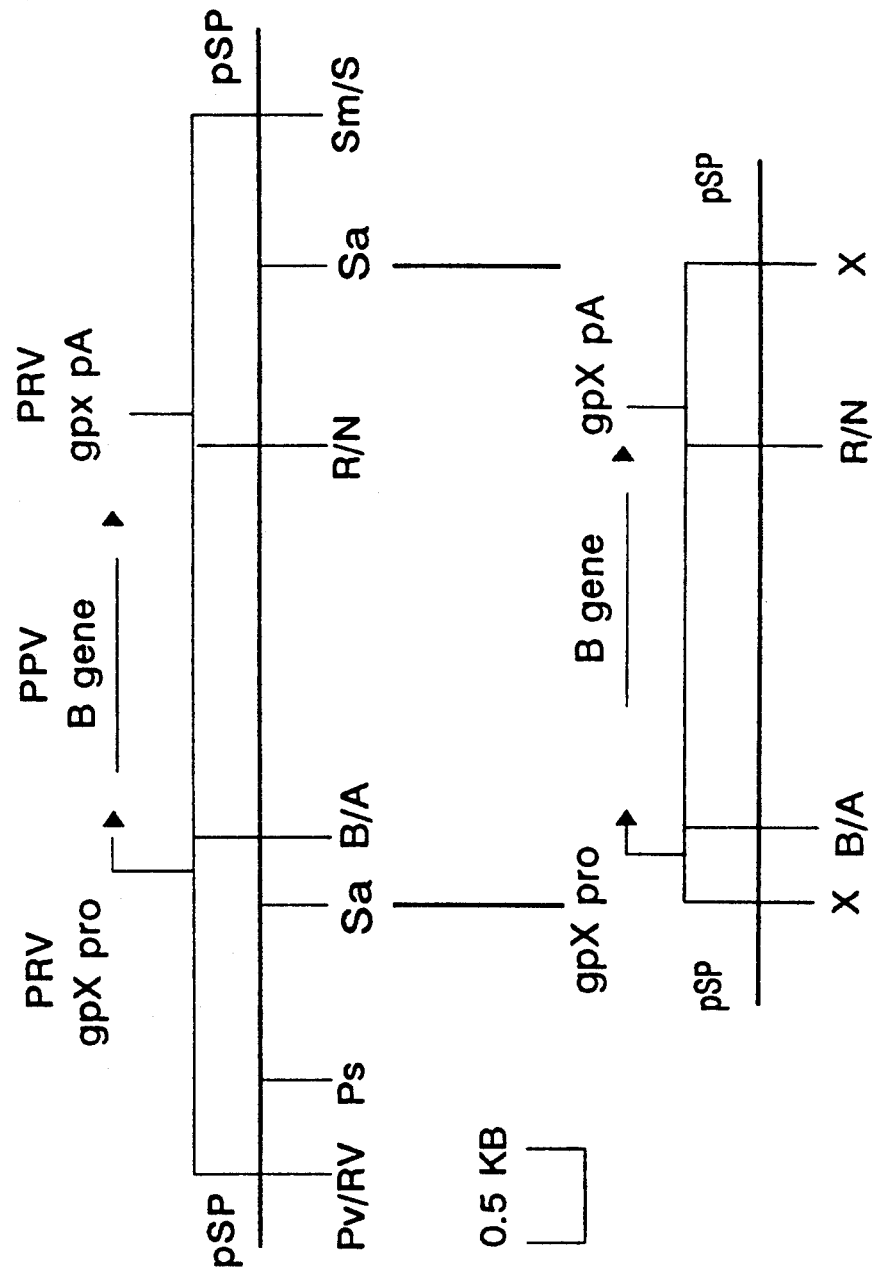
FIG. 12 Swine parvovirus B gene construction with signal sequence.
  A. pSY864 which contains the B gene from AccI at nucleotide #391 to RsaI site at nucleotide #2051 cloned between the BamHI site in BamHI #10 and the NdeI site in BamHI #7.
  B. pSY957 which contains the SalI fragment from pSY865 cloned into a polylinker in pSP65 so that XbaI sites flank the insert.
  Legend: pSP=E. coli plasmid; PRV=pseudorabies virus DNA; PPV=porcine parvovirus DNA; Pv=PvuII; RV=EcoRV; Ps=PstI; B=BamHI; A=AccI; R=RsaI; N=NdeI; Sa=SalI; Sm=SmaI; S=StuI; X=XbaI; gpX pro=glycoprotein X promoter; gpX pA= glycoprotein X polyadenylation signal sequences.
Figure 13A:
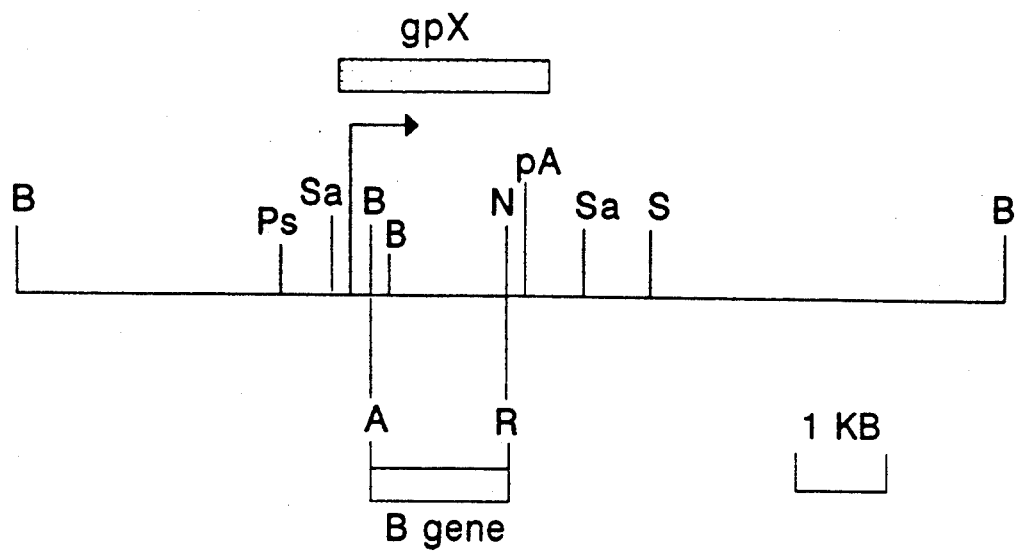
FIG. 13 Details of S-PRV-020 Construction and Map Data.
  A. Detailed map of PRV extending from BamHI #10 through BamHI #7 showing the parvovirus B gene that will replace the gpX gene.
  B. Detailed map of PRV from BamHI #10 through BamHI #7 after the insertion of the swine parvovirus B gene in place of the gpX gene.
  C. Diagram of the S-PRV-020 genome showing the location of the swine parvovirus B gene inserted into the gpX region of PRV.
  Restriction Enzyme Legend: B=BamHI; Ps=PstI; Sa=SalI; N=NdeI; S=StuI; A=AccI; R=RsaI.
Figure 13B:
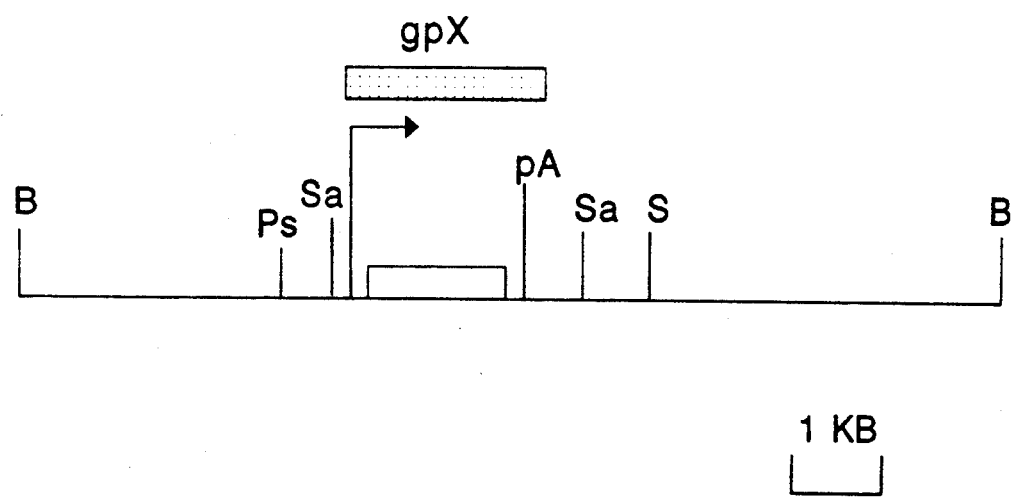
Figure 13C:
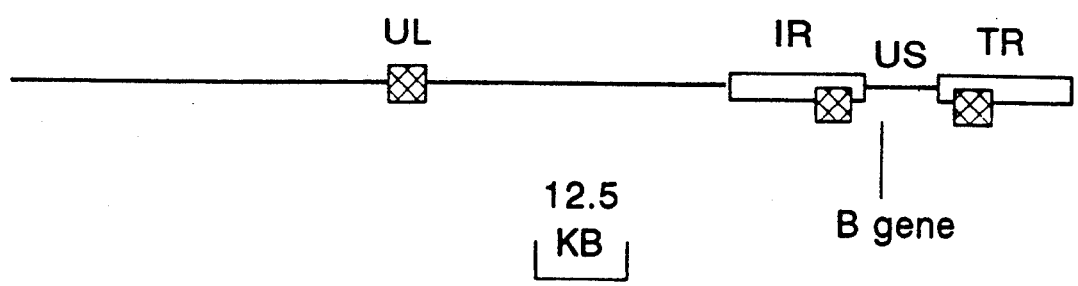
Figure 14A:
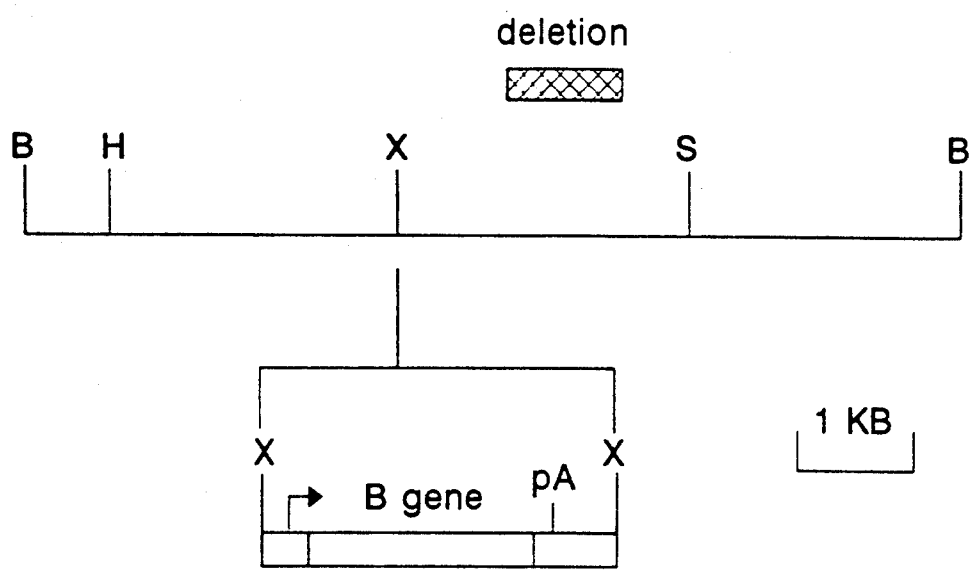
FIG. 14 Details of S-PRV-025 construction and map data.
  A. Region of S-PRV-002 starting virus showing BamHI #5 fragment. The parvovirus B gene XbaI fragment from pSY957 is diagrammed below showing how it will be inserted into the XbaI site by direct ligation.
  B. Region of BamHI #5 after insertion of the parvovirus B gene.
  C. Location of the parvovirus B gene inserted into both copies of the repeat in S-PRV-025.
  Legend: B=BamHI; H=HindIII; X=XbaI; S=SalI; pA=glycoprotein X polyadenylation signal sequences; UL=unique long region; US=unique short region; IR=internal repeat region; TR=terminal repeat region.
Figure 14B:
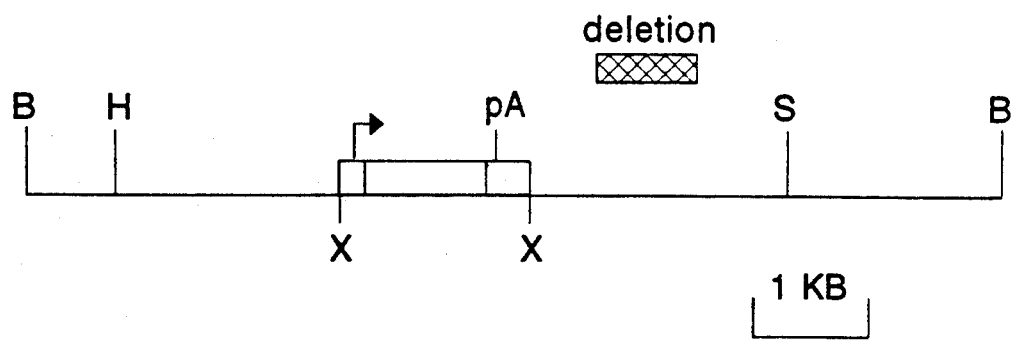
Figure 14C:
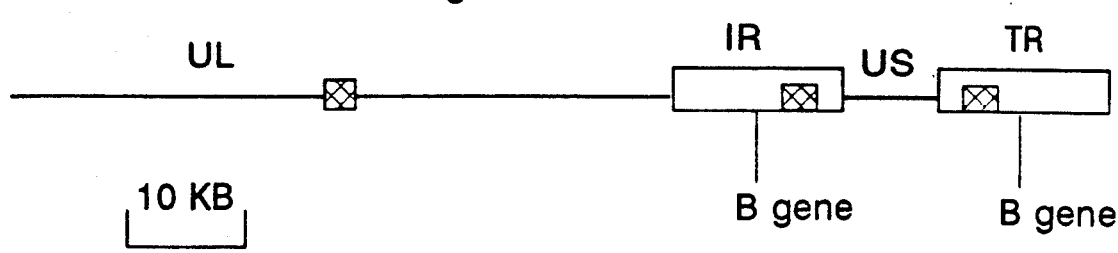
Figure 15A:
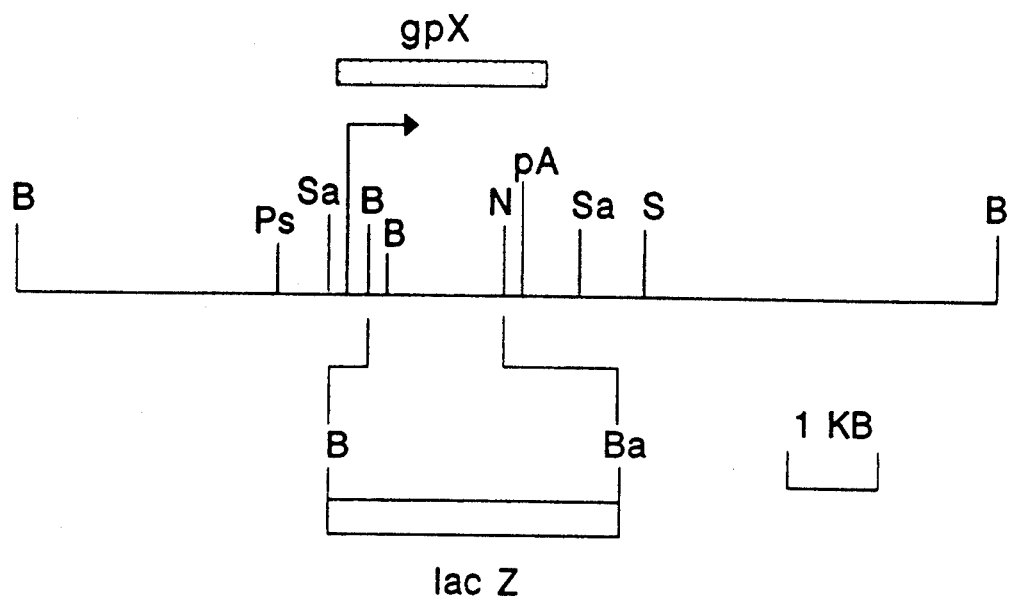
FIG. 15 Details of S-PRV-029 Construction and Map Data.
  A. Detailed map of PRV extending from BamHI #10 through BamHI #7 showing the lac Z gene that will replace the gpX gene.
  B. Detailed map of PRV extending from BamHI #8' through BamHI #8 at the junction of the unique long region and the internal repeat region (IR). The lac Z gene as a SalI fragment will replace the DNA between the StuI sites bracketing the junction.
  C. Diagram of the S-PRV-029 genome showing the locations of the lac Z genes in the gpX region and the junction region.
  Restriction Enzyme Legend: B=BamHI; Ps=PstI; Sa=SalI; N=NdeI; S=StuI; Ba=BalI; K=KpnI.
Figure 15B:
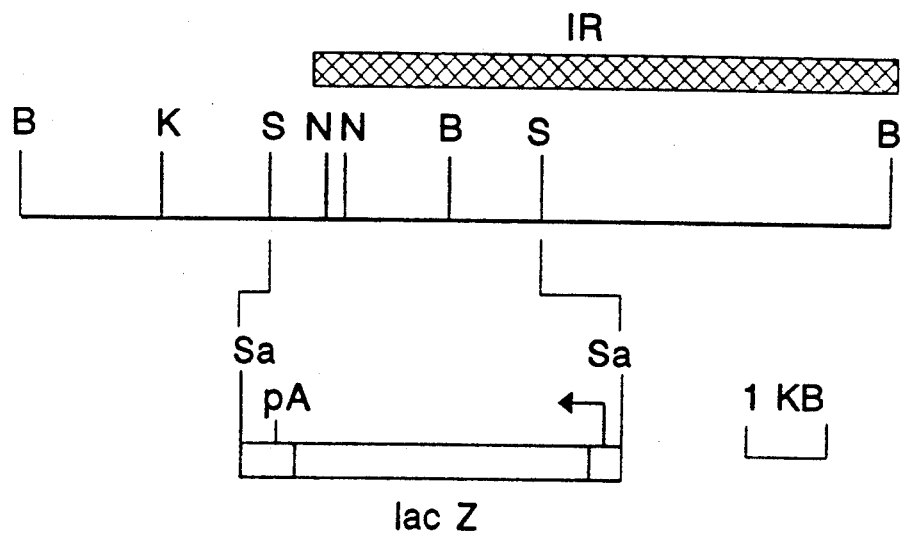
Figure 15C:
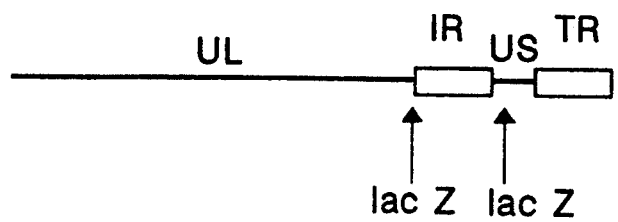
Figure 16:
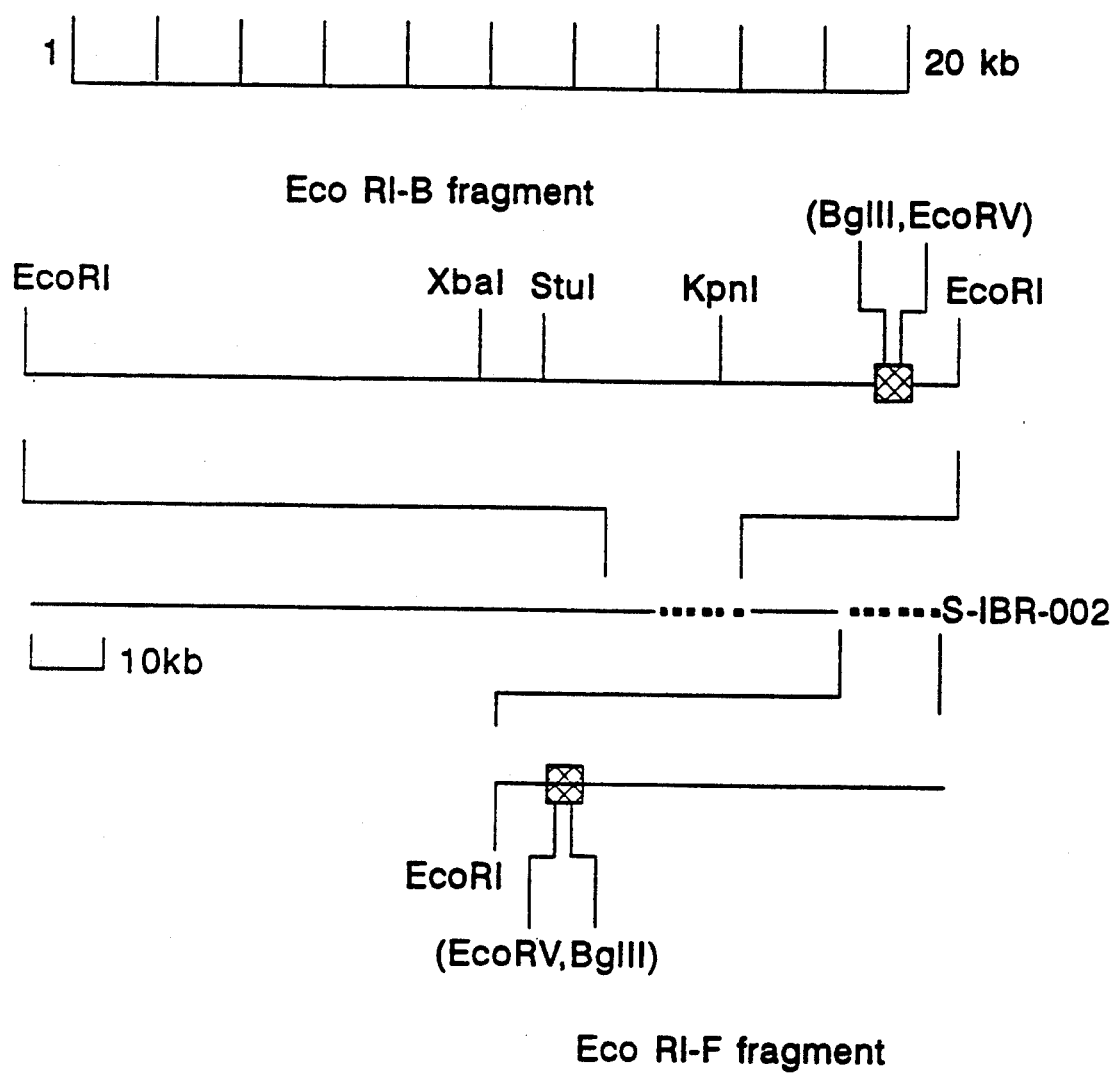
FIG. 16 Restriction Map of Deleted S-IBR-002 EcoRI B Fragment and EcoRI F Fragment.
  An 800 bp deletion including EcoRV and BGlII restriction sites was mapped in both repeat fragments.
Figure 17:
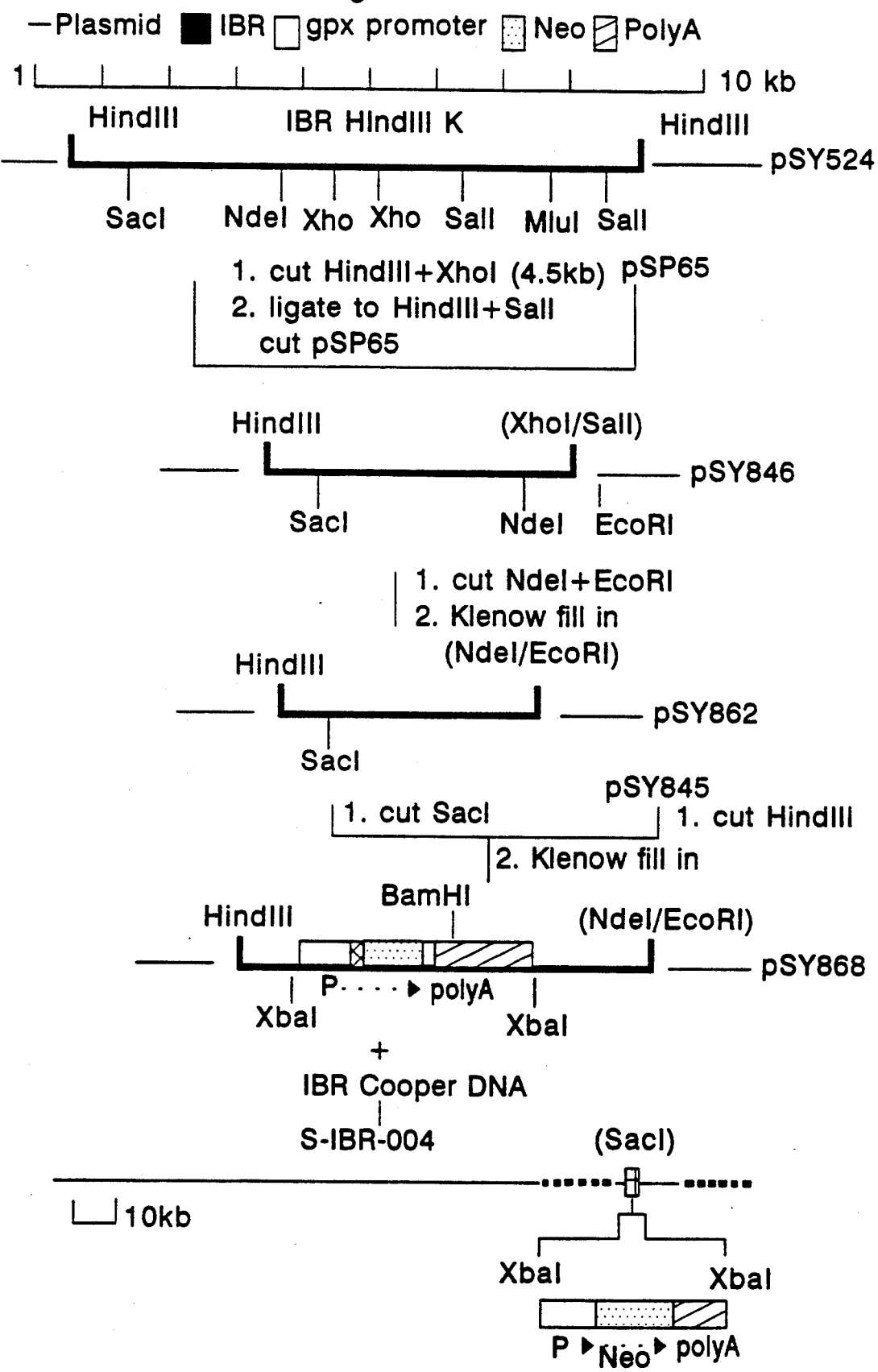
FIG. 17 Construction of Recombinant S-IBR-004 Virus.
  S-IBR-004 is an IBR recombinant virus carrying an inserted foreign gene (NEO) under the control of the PRV gpX promoter. A new XbaI site was created at the small unique region and the original SacI site was deleted.
Figure 18:
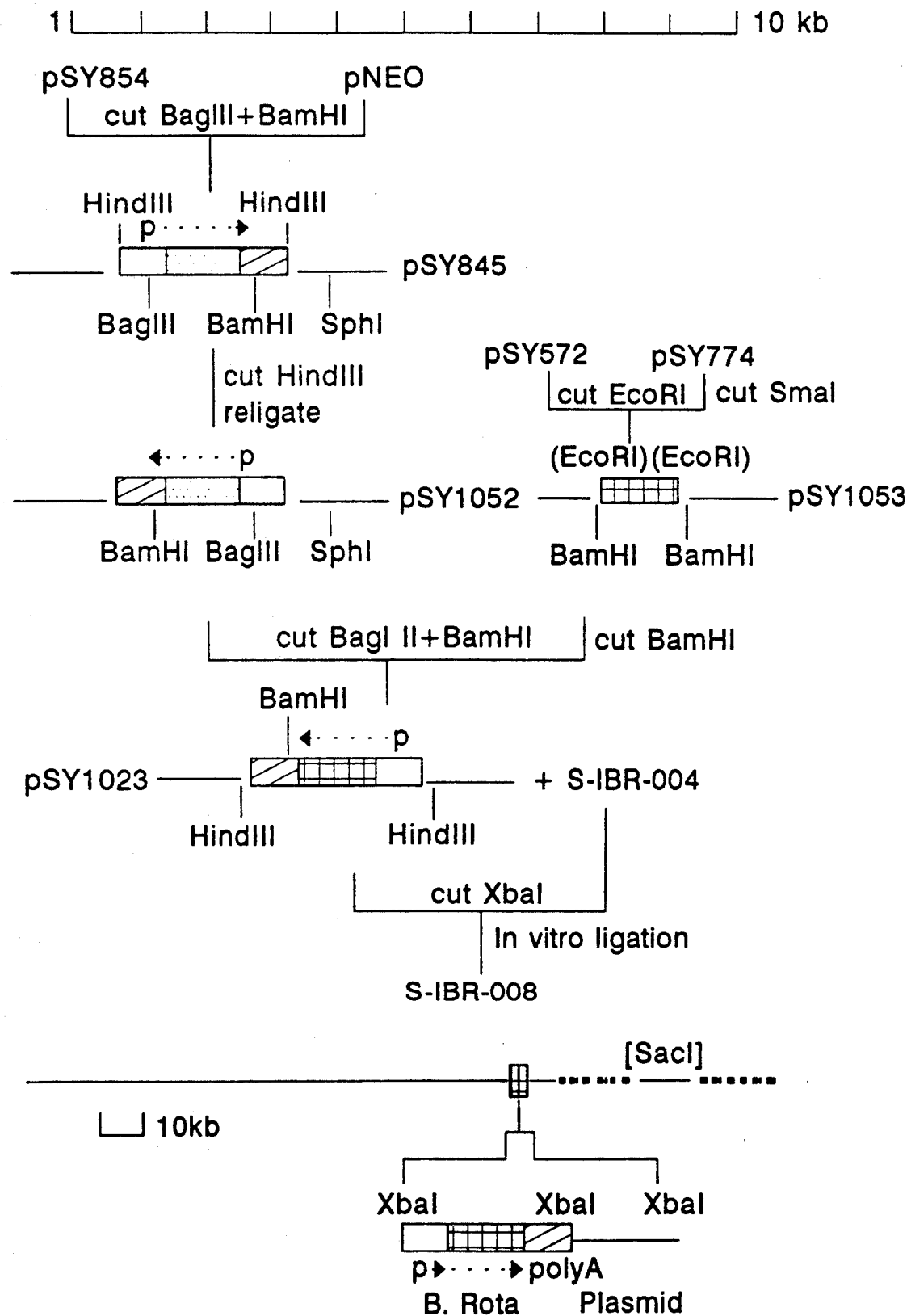
FIG. 18 Construction of Recombinant S-IBR-008 Virus.
  S-IBR-008 is a recombinant IBR virus that has a bovine rota glycoprotein gene and the plasmid vector inserted in the XbaI site on the unique long region. A site specific deletion was created at the [SacI] site due to the loss of NEO gene in the small unique region.
Figure 19A:
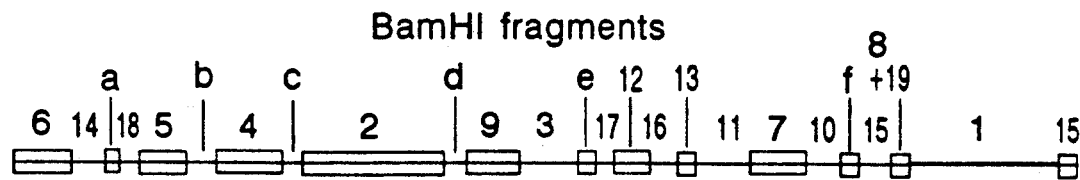
FIG. 19 Details of HVT Construction and Map Data.
  A. BamHI restriction fragment map of HVT. Fragments are numbered in order of decreasing size; letters refer to small fragments whose comparative size has not been determined.
  B. BamHI #16 fragment showing location of beta-galactosidase gene insertion in S-HVT-001.
  C. BamHI #19 fragment showing location of beta-glactosidase gene insertion.
  Legend: B=BamHI; X=XhoI; H=HindIII; P=PstI; S =SalI; N=NdeI; R=EcoRI.
Figure 19B:
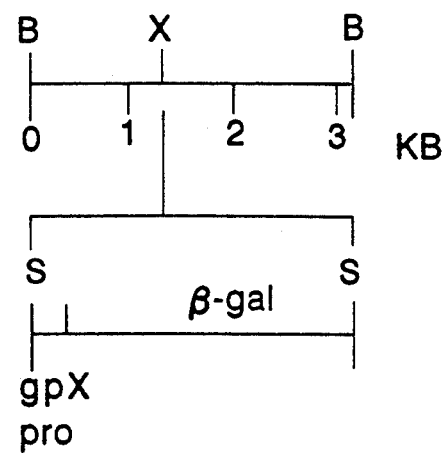
Figure 19C:
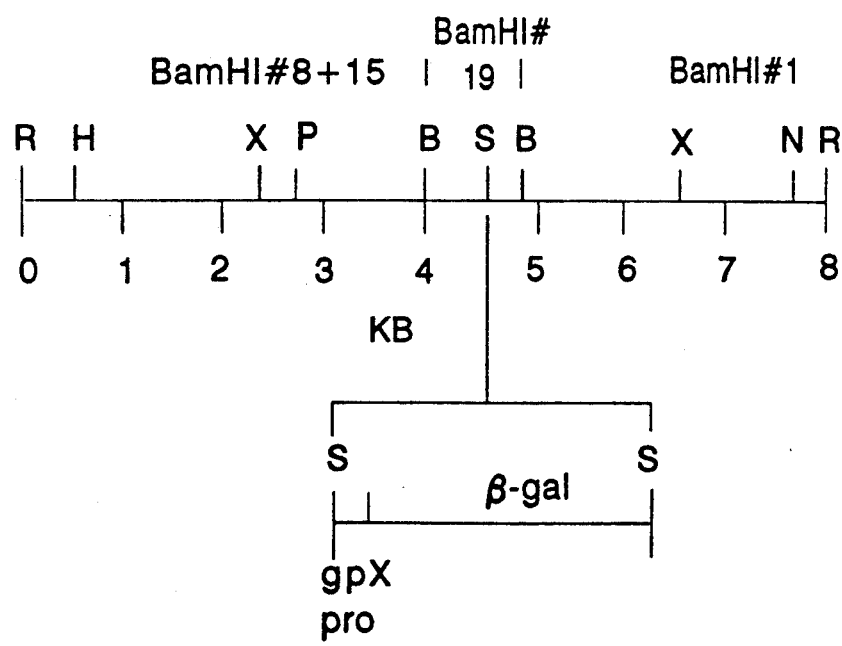
Figure 20:
FIG. 20. Western blot of proteins released into the medium of PRV infected cells, showing the absence of gpX in S-PRV-012 and S-PRV--013 but its presence in wild-type PRV-000. Lanes: (A) molecular weight markers, (B) uninfected Vero cells, (C) wild-type PRV, (D) S-PRV-012, (E) S-PRV-013.
Figure 21:
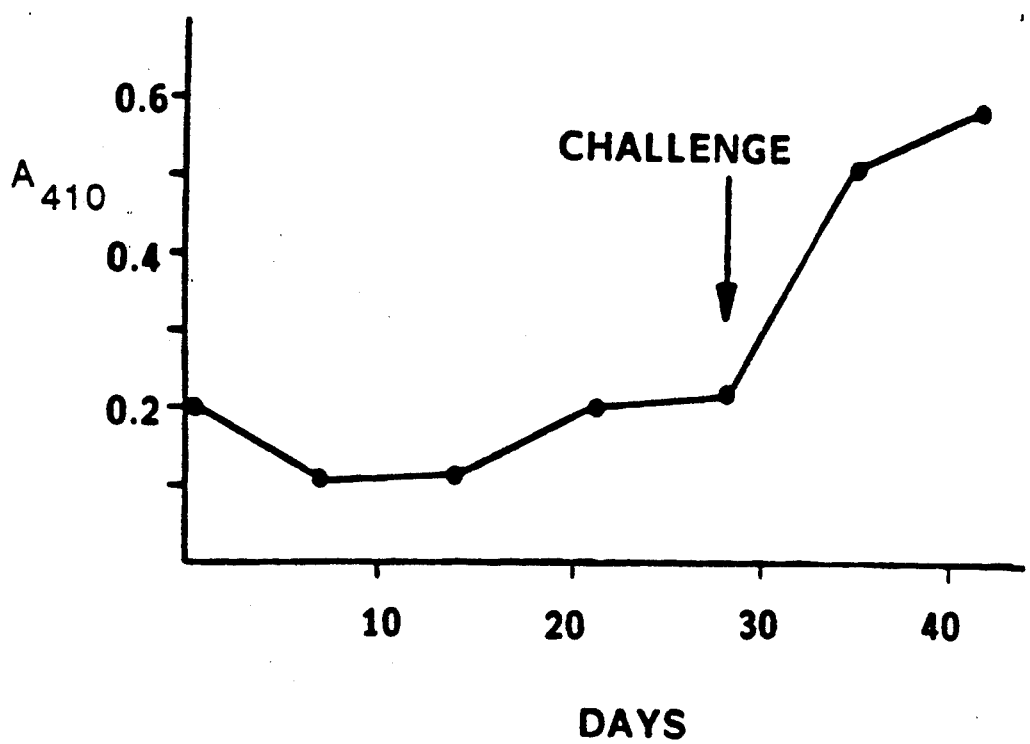
FIG. 21. Diagnostic test for the presence of antibodies against gpX in the serum of a pig vaccinated with S-PRV-013 on Day 0 and challenged with B gene contained in the fusions in S-PRV-039 and S-PRV-061 (called 039-fragment).
Figure 23A:
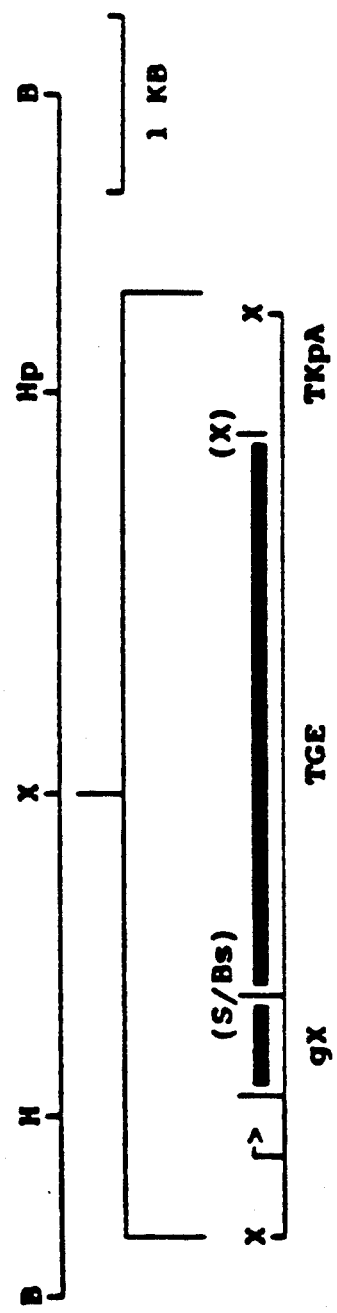
Figure 23B:
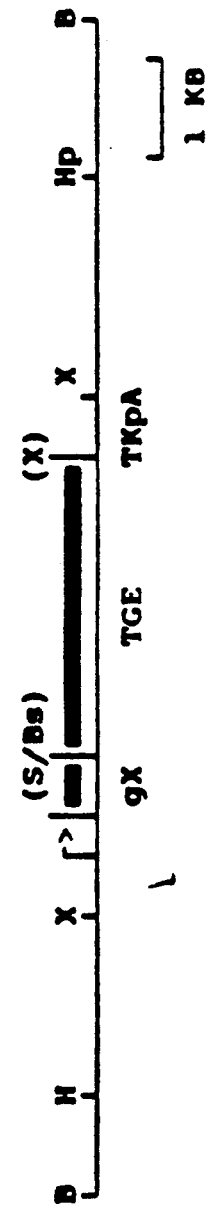
Figure 23C:

The resulting virus from this screen was designated S-PRV-016 and has been deposited with the ATCC Accession No. VR 1136. It contains the beta-galactosidase gene in place of the gpX coding region as determined by PREPARATION OF HERPESVIRUS DNA followed by SOUTHERN BLOTTING OF DNA. The expression of the beta-galactosidase gene was confirmed by the BLUOGAL SCREEN FOR RECOMBINANT HERPESVIRUS test, and by the o-nitrophenylgalactophyranoside substrate assay (33). The structure of the is virus is shown in FIG. 9E.

Example 9

S-PRV-020

S-PRV-020 is a pseudorabies virus that contains a deletion in the TK gene, a deletion in the repeat regions, and a deletion of the gpX gene, with an insertion of the swine parvovirus B capsid protein gene into the gpX region.

For cloning the swine parvovirus B gene, the NADL-8 strain double-stranded replicative-form DNA was purified from swine parvovirus infected cells and was supplied by Dr. T. Molitor, University of Minnesota. The parvovirus NADL-8 DNA was cloned into the *E. coli* plasmid pSP64 by methods detailed in (15). The DNA was partially sequenced to allow the determination of the start and the end of the major caspid protein gene, the B gene. Identification was confirmed by comparison of related sequences in the rat HI parvovirus capsid gene (28,29). The sequence of the swine parvovirus B gene is shown in FIG. 11A and 11B.

The PRV glycoprotein X (gpX) gene promoter was used to express the B gene and the gpX poly A signal sequence was used to terminate transcription. The parvovirus B gene from the AccI site at nucleotide #391 to the RsaI site at nucleotide #2051 was cloned between the BamHI and NdeI site of gpX (see FIG. 7A and B). Plasmid pSY864 contained this fragment of the parvovirus B gene flanked by the gpX signal sequence as shown in FIG. 13. It was used as the homologous DNA to promote homologous recombination between S-PRV-013 DNA and the plasmid DNA to facilitate the incorporation of the B gene into the PRV genome. The plasmid DNA and S-PRV-013 DNA were mixed and transfected together according to the DNA TRANSFECTION FOR GENERATING RECOMBINANT VIRUS procedure. The recombinant virus was screened and purified for the transfection stock by the BLUOGAL SCREEN FOR RECOMBINANT HERPESVIRUS procedure with the following modification. Because the parental S-PRV-013 contained the beta-galactosidase gene, it generated blue plaques in the screening procedure. Since the parvovirus B gene would replace the beta-galactosidase gene in the virus, the plaques with this insert would appear colorless. Therefore, colorless plaques were picked and analyzed during this screening. A virus that contained the B gene was isolated from this screening and was designated S-PRV-020. S-PRV-020 has been deposited with ATCC under Accession No. VR 2137.

DNA from S-PRV-020 was isolated by the PREPARATION OF HERPESVIRUS DNA procedure and used to confirm the insertion of the parvovirus B gene according to the SOUTHERN BLOTTING OF DNA procedure using the B gene as a probe. The test showed that the parvovirus B gene has been incorporated into the PRV genome as expected. The structure of S-PRV-020 is shown in FIG. 13C.

Example 10

S-PRV-025

The cloning of the B gene and construction of these signal sequences onto the B gene are described in Example 9 and are shown in FIG. 12.

The DIRECT LIGATION PROCEDURE FOR GENERATING RECOMBINANT HERPESVIRUS was used to insert the parvovirus B gene into PRV. The plasmid pSY957 containing the B gene mixed with S-PRV-002 DNA and they were cut with restriction enzyme XbaI. The DNA mixture was ligated as described in the method and the DNA was transfected into Vero cells. A virus that contained the B gene was isolated from the transfection stock of virus and was designated S-PRV-025. S-PRV-025 has been deposted with the ATCC under Accession No. VR 2138.

DNA from S-PRV-025 was isolated by the PREPARATION OF HERPESVIRUS DNA procedure and used to confirm the insertion of the parvovirus B gene according to the SOUTHERN BLOTTING OF DNA procedure using the B gene a probe. The test showed that the parvovirus B gene has been incorporated into the PRV genome as expected. The structure of S-PRV-025 is shown in FIG. 14.

Example 11

S-PRV-029

S-PRV-029 is a pseudorabies virus that has a deletion in the junction region between the unique long region and the internal repeat of PRV, and a deletion in the gpX gene in the unique short region. The *E. coli* beta-galactosidase gene under the control of the gpX promoter and polyadenylation signals has been inserted into both deletions in S-PRV-029.

To construct this virus, the SalI #1 fragment of PRV was first cloned. PRV DNA was prepared and then cut with SalI restriction enzyme. The cut DNA was electrophoresed on an agarose gel and the largest SalI band (15kb) was purified from the gel (see PHENOL EXTRACTION OF DNA FROM AGAROSE). The purified DNA was ligated into the plasmid pSP64 (see LIGATION) and the DNA mixture was used to transform *E. coli* HB101 according to Maniatis et al. (1). The SalI clone was mapped for restriction sites.

The homologous recombination procedure was used to create S-PRV-029. The exact position of the junction region was determined by sequencing the DNA from the SalI #1 fragment. It was found that the junction region was positioned between two StuI sites (see FIG. 15B). Two fragments of DNA from the SalI clone were used to create the homology vector for recombination. One was a fragment from BamHI #8' from StuI to BamHI and the other was from BamHI to StuI (FIG. 15B).

The *E. coli* beta-galactosidase gene was previously engineered to contain the gpX promoter and polyadenylation signals as described for S-PRV-013. To put this B-galactosidase gene into the junction region clone, a HindIII linker was first inserted into the StuI site between the BamHI #8 and BamHI #8', and into this HindIII site was cloned a HindIII fragment containing the beta-galactosidase gene with the gpX signals.

The resulting plasmid plus wild-type PRV DNA were transfected into Vero cells by the DNA TRANSFECTION FOR GENERATING RECOMBINANT VIRUS procedure. A virus was isolated from the transfection stock that contained the beta-galactosidase gene inserted into both the junction deletion (FIG. 15B) and the gpX deletion (FIG. 15A) due to the presence of homology to both of these regions in the plasmid. This virus was purified by the BLUOGAL SCREEN FOR RECOMBINANT HERPESVIRUS procedure and was designated S-PRV-029. S-PRV-029 has been deposited with the ATCC under Accession No. VR 2139.

S-PRV-029 was shown to be expressing beta-galactosidase by the BLUOGAL SCREEN FOR RECOMBINANT HERPESVIRUS procedure and the o-nitrophenylgalactopyranoside assay (33). The structure of this virus is shown in FIG. 15C.

Example 12

S-IBR-002

S-IBR-002 is an IBR virus that has a deletion of approximately 800 bp in the repeat region of the genome. This deletion removes the only two EcoRV restriction sites on the virus genome and an adjacent BglII site (FIG. 16).

To construct this virus, the DIRECT LIGATION PROCEDURE FOR GENERATING RECOMBINANT HERPESVIRUSES was performed. Purified IBR DNA (Cooper strain) digested with EcoRV restriction enzyme was mixed with FraI-restriction enzyme-digested plasmid DNA containing the beta-galactosidase gene under the control of the HSV-1 TK promoter. After ligation the mixture was used to transfect animal cells and the transfection stock was screened for recombinant IBR virus by the HYBRIDIZATION SCREEN FOR RECOMBINANT HERPESVIRUSES procedure. The final result of the purification was the recombinant IBR designated S-IBR-002. It was shown by Southern hybridization that this virus does not carry any foreign genes. Restriction enzyme analysis also showed that the insertion sites (EcoRV) at both repeats were deleted. FIG. 16 shows the restriction map of the EcoRI B fragment which contains the EcoRV restriction sites and the map of S-IBR-002 which lacks the EcoRV sites. S-IBR-002 has been deposited with the ATCC under Accession No. VR 2140.

Example 13

S-IBR-004

S-IBR-004 is an IBR recombinant virus carrying an inserted foreign gene, Tn5 NEO (aminoglycoside 3'-phosphotransferase) gene, under the control of the pseudorabies virus (PRV) glycoprotein X promoter.

To construct this virus, the HindIII K DNA fragment from wild type IBR virus was cloned into the plasmid pSP64 at the HindIII site. This plasmid was designated pSY524. A map of the HindIII K fragment is shown in FIG. 17. The DNA from the XhoI site to the HindIII site and containing the NdeI site from pSY524 was cloned into plasmid pSP65 and called pSY846. The NdeI to EcoRI fragment was removed from pSY846 by digestion with NdeI and EcoRI restriction enzymes, followed by POLYMERASE FILL-IN REACTION and LIGATION. The resulting plasmid was called pSY862. The plasmid pNEO (P.L. Biochemicals, Inc.)

contains the aminoglycoside 3'-phosphotransferase (NEO) gene and confers resistance to ampicillin and neomycin on *E. coli* hosts. The coding region of this gene (BglII-BamHI fragment) was isolated and cloned between the PRV gpX promoter and the HSV-Tk poly A sequence in a plasmid called pSY845.

The NEO gene construct in pSY845 was excised with HindIII, made blunt ended by the POLYMERASE FILL-IN REACTION, and cloned into the SacI site of plasmid pSY862. The final product was called pSY868.

Wild type IBR DNA was mixed with pSY868 DNA and the mixture was transfected into rabbit skin cells to generate recombinant IBR. The recombinant IBR virus carrying a functional NEO gene was then isolated and purified according to the SELECTION OF G418 RESISTANT VIRUS method.

S-IBR-004 recombinant IBR was shown to express the NEO gene by the fact that cells infected with this virus were resistant to the toxicity of G418. A detailed map of the plasmid construction is shown in FIG. 17. The structure of S-IBR-004 is also shown in FIG. 17. S-IBR-004 has been deposited with the ATCC under Accession No. VR 2134.

Example 14

S-IBR-008

S-IBR-008 is an IBR virus that has a deletion in the short unique region, and an insertion of the bovine rotavirus glycoprotein 38 (gp38) gene in the XbaI site in the long unique region.

First the bovine rotavirus gp38 gene was engineered to contain herpesvirus regulatory signals as shown in FIG. 18. This was accomplished by cloning the gp38 gene BamHI fragment contained in pSY1053 between the BamHI and BglII sites in pSY1052. The resulting plasmid, pSY1023, contained the PRV gpX promoter in front of the gp38 gene, and the HSV-1 TK polyadenylation signal behind the gp38 gene. The entire construct was flanked by XbaI sites to allow for the insertion of the XbaI fragment into IBR by direct ligation.

S-IBR-004 was the starting virus for the generation of S-IBR-008. S-IBR-004 DNA and pSY1023 DNA were mixed together, cut with XbaI, and transfected into rabbit skin cells according to the DIRECT LIGATION FOR GENERATING RECOMBINANT HERPESVIRUS procedure. The transfection stock was screened for recombinant virus by the ANTIBODY SCREEN FOR RECOMBINANT HERPESVIRUS procedure using antibodies prepared against the rotavirus gp38 protein.

One of the viruses purified by this screen was S-IBR-008, which has the following characteristics. It contains the rotavirus gp38 gene plus the plasmid DNA inserted into the XbaI site in the long unique region of the virus genome, but no longer contains the NEO gene of parent S-IBR-004 in the unique short region. In fact, a small deletion was created in the unique short region at the location of the NEO gene, as evidenced by the absence of an XbaI site at this location in S-IBR-008.

S-IBR-008 was shown to be expressing the rotavirus gp38 gene by analysis of RNA transcription in infected cells, and by the ANTIBODY SCREEN FOR RECOMBINANT HERPESVIRUS procedure using antibodies specific for the gp38 gene. S-IBR-008 has been deposited with the ATCC under Accession No. VR 2141, and its structure is shown in FIG. 18.

Example 15

Herpes Virus of Turkeys

Herpes virus of turkeys (HVT) is another herpesvirus that is similar in organization and structure to the other animal herpesvirus examples described above. The restriction enzyme map of HVT has been published (34). This information was used as a starting point to engineer the insertion of foreign genes into HVT. The Bam I restriction map of HVT is shown in FIG. 19A. From this data, several different regions of HVT DNA into which insertions of foreign genes could be made were targeted. The foreign gene chosen for insertion was the *E. coli* beta-galactosidase gene (beta-gal), which we have used in PRV. The promoter was the PRV gpX promoter. The beta-gal gene was inserted into the unique long region of HVT, specifically into the XhoI site in the BamHI #16 (3300 bp) fragment, and has been shown to be expressed in an HVT recombinant by the formation of blue plaques using the substrate Bluogal. Similarly, the beta-gal gene has been inserted into the SalI site in the repeat region contained within the BamHI #19 (900 bp) fragment.

These experiments show that HVT is amenable to the procedures described within this application for the insertion and expression of foreign genes in herpesviruses. In particular, two sites for insertion of foreign DNA have been identified (FIGS. 19B and 19C).

Example 16

Methods for Constructing An Attenuated Herpesvirus Containing A Foreign DNA Insert Applicants contemplate that the procedures disclosed herein which have been utilized to attenuate and insert foreign DNA sequences into PRV, IBR and HVT may be suitable for constructing other herpesviruses which are attenuated or contain inserted foreign DNA sequences which are ranslated into amino acid sequences in a host or both. Equine herpesvirus-1 (EHV), canine herpesvirus-1 (CHV), feline herpesvirus-1 (FHV) or any animal herpesvirus whose genomic structure is related to these viruses are contemplated to be amenable to these methods. More specifically, the following procedures may be followed to construct such viruses.

GROW ANIMAL HERPESVIRUS IN CELL CULTURE. Established cell lines or primary cells may be used. The methodology for the growth of these viruses exists in the literature and does not require new art. EHV grows in Vero cells, CHV grows in Madin Darby canine kidney cells and FHV grows in Crandell feline kidney cells.

PURIFY HERPESVIRUS DNA. The procedure disclosed herein for purifying herpesvirus DNA was successful for all herpesviruses tested, including PRV, IBR, HVT and cytomegalovirus, and is a general method applicable to all herpesviruses.

CLONE RESTRICTION FRAGMENTS. The cloning of herpesvirus restriction fragments is a state of the art recombinant DNA procedure and is described in Maniatis et al. (1).

MAP RESTRICTION FRAGMENTS TO GENOME. It is useful to have a restriction enzyme map of the virus genome to identify and select regions for deletion and insertion. Such maps are available for PRV and IBR, and partially for HVT. A map exists for EHV, but not for CHV or FHV. The creation of this map does not require any new technology and is detailed in Maniatis et al. (1).

IDENTIFY RESTRICTION FRAGMENTS THAT CORRESPOND TO THE REPEAT REGION. The identification of repeat regions requires the SOUTHERN BLOTTING PROCEDURE as detailed in the methods section. Clones of the repeat region hybridize to multiple bands in a restriction enzyme digest due to the fact that they are repeated in the virus genome. This feature, coupled with their location in the genome, are diagnostic of repeat regions.

MAKE DELETION IN REPEAT REGION CLONE. Genetic information in the repeat region is duplicated in the other copy of the repeat in the genome. Therefore one copy of the repeat region is nonessential for replication of the virus. Hence the repeat region is suitable for deletions and insertions of foreign DNA. After the repeat region is cloned and mapped by restriction enzymes, enzymes may be chosen to engineer the repeat deletion and to insert foreign DNA. It is obvious to one skilled in the art that enzyme sites will exist in a given stretch of DNA and that they can be found by analysis. The methodology involves RESTRICTION DIGESTION OF DNA, AGAROSE GEL ELECTROPHORESIS OF DNA, LIGATION and cloning in bacterial cells as detailed in the methods section and in Maniatis et al. (1).

MAKE INSERTION OF MARKER GENE INTO DELETION IN REPEAT REGION CLONE. The methodology of this insertion is that described in Maniatis et al. (1) for the cloning of genes into bacteria. What is not obvious prior to the present disclosure is which marker genes to use that will be active in a herpesvirus, nor which signal sequences to use for the expression of foreign genes in these herpesviruses. The E. Coli beta-galactosidase gene and neomycin resistance gene under the control of the HSV-1 ICP4 promoter, the PRV gpX promoter or the HSV-1 TK promoter have been used. The gpX promoter, in particular, works in PRV, IBR, and HVT. The other promoters have also worked in more limited testing.

TRANSFECTION WITH MARKER GENE CLONE+HERPESVIRUS DNA. The intent of this procedure is to put into the same cell the intact herpesvirus DNA and the repeat region clone with the deletion and containing the marker gene. Once these two DNAs are present in the same cell, normal mechanisms of homologous recombination ensure that a recombination will occur between the homologous regions in the clone and the same region in the herpesvirus DNA, thus substituting the marker gene for the deleted regions in the virus, with frequency of about 1%. The technique involves the TRANSFECTION PROCEDURE FOR GENERATING RECOMBINANT HERPESVIRUSES as detailed in the methods section.

PURIFY HERPESVIRUS DNA. Herpesvirus DNA may be purivied according to the methods described above.

SELECT RECOMBINANT PLAQUE. All the herpesviruses contemplated by this invention form plaques (foci of infection in cell culture) that enable their purification. A plaque results from infection by a single virus particle. Thus picking a single plaque selects for the progeny of a single recombinational event. This technical feat requires a method to identify which plaque to pick. The methods used herein include SOUTHERN BLOTTING OF DNA to pick the plaque based upon the presence of the inserted gene, ANTIBODY SCREEN FOR RECOMBINANT HERPESVIRUS to pick the plaque based upon the presence of protein made from the gene, BLUOGAL SCREEN FOR RECOMBINANT HERPESVIRUSES to pick a plaque that expresses the marker gene beta-galactosidase or G-418 SELECTION TO PURIFY RECOMBINANT HERPESVIRUSES to pick the plaque by its ability to form in the presence of the antibiotic G-418. The first two methods are applicable to any gene; the latter two are specific for the beta-galactosidase gene and neomycin resistance gene respectively. The biology of these screening and selection systems is such that they are applicable to any herpesvirus, including EHV, CHV, FHV, and any animal herpesvirus related to them.

PURIFY RECOMBINANT VIRUS. This procedure involves multiple plaque purifications in succession to completely purify the recombinant virus away from the parental virus. The screening is applied at each step to choose the plaque with which to continue. The procedures are known to those skilled in the art of virology.

Multivalent vaccines for animals may be constructed by inserting a foreign antigen gene into a herpesvirus. The procedures and methodology are very analogous to those used for the initial insertion of the marker gene into the virus and may be performed as follows.

SUBSTITUTE FOREIGN ANTIGEN GENE FOR MARKER GENE IN REPEAT CLONE. This is a cloning experiment that involves putting the antigen gene behind the same herpesvirus promoter used with the marker gene and inserting this construction into the same identical deletion in the repeat clone. The methods for this cloning are described in Maniatis et al. (1).

TRANSFECTION WITH ANTIGEN CLONE+RECOMBINANT HERPES DNA CONTAINING MARKER. The marker gene that is already present in the herpesvirus genome may be use to aid in the selection of the new recombinant. For example, it has proven useful to select white plaques instead of blue ones to test for the absence of beta-galactosidase in this step. One reason for the present of a white plaque is the replacement of the beta-galactosidase gene with the foreign antigen gene by homologous recombination (the desired outcome). Continued screening for this new recombinant by the SOUTHERN BLOT PROCEDURE or by the ANTIBODY SCREEN FOR RECOMBINANT HERPESVIRUS becomes more focused, less time-consuming and specifically identifies the recombinant of interest.

ISOLATE RECOMBINANT HERPES DNA. The transfection procedure requires intact infectious herpesvirus DNA. Recombinant herpesviruses which include an inserted marker gene may be used. The isolation of herpesvirus DNA procedure is equally applicable to these recombinant viruses.

SCREEN TRANSFECTION STOCK FOR FOREIGN GENE INSERTION. Screening methods have been described above. They are a combination of indirect methods (screening for the absence of the marker) as well as direct methods (SOUTHERN BLOT for the antigen gene, and ANTIBODY SCREEN for the expressed protein). The methods may be applied sequentially during the purification of the virus.

PURIFY RECOMBINANT VIRUSES CONTAINING FOREIGN ANTIGEN GENE. The recombinant virus containing the foreign antigen gene may be purified according to the procedures described above.

This sequence of steps, along with the methods and examples described herein, enable anyone skilled in the art to successfully practice this invention with any animal herpesvirus.

Example 17

The present invention involves the use of genetically engineered herpesviruses to protect animals against disease. It was not apparent at the outset of research which deletions in herpesviruses would serve to attenuate the viruses to the proper degree so as to render them useful as vaccines. Even testing vaccine candidates in animal models, e.g. mouse, does not serve as a valid indicator of the safety and efficacy of the vaccine in the target animal species, e.g. swine. To illustrate this point more clearly, Table VII shows summary data of the safety and efficacy of various pseudorabies viruses which were constructed and tested in swine according to the VACCINATION STUDIES IN SWINE procedure.

TABLE VII
SUMMARY OF STUDIES CONDUCTED IN PIGS WITH VARIOUS PSEUDORABIES VIRUS CONSTRUCTS

| Construct (Deletions/ Insertions)[1] | Number of Pigs | Age of Pigs | Post-Vaccination Antibody Range | Post-Vaccination Clinical Signs | Percent Protection Against Challenge |
|---|---|---|---|---|---|
| S-PRV-001 (A) | 9 | 4–6 weeks | 1:32–>1:64 | Yes (22%) | Not Done |
| S-PRV-002 (A,B) | 12 | 4–6 weeks | 1:4–1:64 | None | 100 |
| S-PRV-003 (B) | 8 | 4–6 weeks | >1:2–1:16 | None | 50 |
| S-PRV-004 (B,C) | 6 | 4–6 weeks | 1:4–1:32 | None | 64 |
| S-PRV-010 (A,B,E) | 30 | 4–16 weeks | <1:2–1:16 | None | 100 |
|  | 30 | 3–4 days | 1:4–1:64 | Yes (13%) | 100 |
| S-PRV-013 (A,B,D,E) | 23 | 4–6 weeks | <1:2–1:8 | None | 100 |
|  | 25 | 3–4 days | 1:4–1:64 | None | 100 |
| S-PRV-014 (D,E) | 5 | 4–6 weeks | 1:4–1:8 | Yes (40%) | 100 |
| S-PRV-016 (A,D,E) | 5 | 4–6 weeks | 1:4–1:8 | None | 100 |

[1]A-Repeats; B-TK; C-Junction; D-gpX; E-beta-galactosidase insert

The eight constructs that have been tested have the following deletions and insertions in the genome of the virulent Shope strain of PRV: S-PRV-001 has a deletion in both repeat regions; S-PRV-002 has a deletion in both repeat regions and in the thymidine kinase gene; S-PRV-003 has a deletion in the thymidine kinase gene; S-PRV-004, S-PRV-010, S-PRV-013, S-PRV-014 and S-PRV-016 are described in Example #'s 1, 3, 6, 7 and 8 respectively.

A superior vaccine product must not produce clinical signs in 3–4 day old piglets (the more sensitive age), and give 100% protection in pigs of all ages. From Table VII, it is apparent that each vaccine candidate provided some degree of attenuation and protection in swine, but each vaccine provided a unique response. The best vaccine candidate from this list to date is S-PRV-013, which contains three deletions; one in the repeat region; one in the TK gene, and one in the gpX gene. The utility of this combination of deletions was unexpected. These results are novel, unpredicted, and useful in the selections of a superior pseudorabies vaccine product.

Example 18

S-PRV-055

S-PRV-055 is a pseudorabies virus that has a deletion in the TK gene, a deletion in the repeat region, and an insertion of the transmissible gastroenteritis virus (TGE) gp195 gene in the XbaI site in the repeat region.

For cloning the TGE gp195 gene, the Purdue strain of TGE was grown in swine testes cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the TGE virus. The location of the gene encoding the TGE gp195 gene has been published (59) and this information was used to locate the gene in our clones. The entire open reading frame of the gp195 gene was sequenced by applicants and is given in FIG. 22.

The PRV gpX promoter was used to express the TGE gp195 gene and the HSV TK poly-A signal was used to terminate transcription. The engineering of this construct was done as shown in FIG. 23 A and B. The construct contained (5' to 3') the gX promoter, the gX TATA box, the gX cap site, the gX 5' untranslated region, the gX start codon, 28 codons of the gX gene, an in-frame fusion to the TGE gp195 gene at the BstEII site, the TGE structural gene, the TGE stop codon, a fusion within the TGE 3' untranslated region to the HSV TK 3' untranslated region, and the HSV TK poly-A signal sequence.

The TGE construction was used in the DIRECT LIGATION PROCEDURE FOR GENERATING RECOMBINANT HERPESVIRUSES. Restriction enzyme XbaI was used to cut the PRV DNA and the plasmid DNA prior to ligation. After the transfection step in the procedure, the resulting recombinant virus from the transfection stock was plaque purified by analysis of the DNA at each step. The virus that resulted from this screening was designated S-PRV-055.

S-PRV-055 contained the TGE gp195 gene inserted at the XbaI site in the repeat region as shown by the SOUTHERN BLOTTING OF DNA procedure using the TGE coding region as probe. The expression of the gp195 protein was shown by the ANTIBODY SCREEN FOR RECOMBINANT HERPESVIRUS procedure.

The structure of S-PRV-055 is shown in FIG. 23C.

Example 19

S-IBR-018

S-IBR-018 is an IBR virus that has three foreign genes inserted: the *E. coli* beta-galactosidase gene and the neomycin resistance gene in the XbaI site in the unique long region, and the parainfluenza-3 (PI-3) virus hemagglutinin gene (HN) in the HindIII site in the unique long region immediately adjacent to the XbaI site.

For cloning the PI-3 HN gene, the SF-4 strain of PI-3 was grown in MADIN-DARBY bovine kidney (MDBK) cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the human PI-3 HN gene has been published (60,61) and this information was used to locate the gene in applicants' bovine PI-3 clones. The entire open reading frame of the bovine PI-3 HN gene was sequenced by applicants and is given in FIG. 24.

Figure 25A:
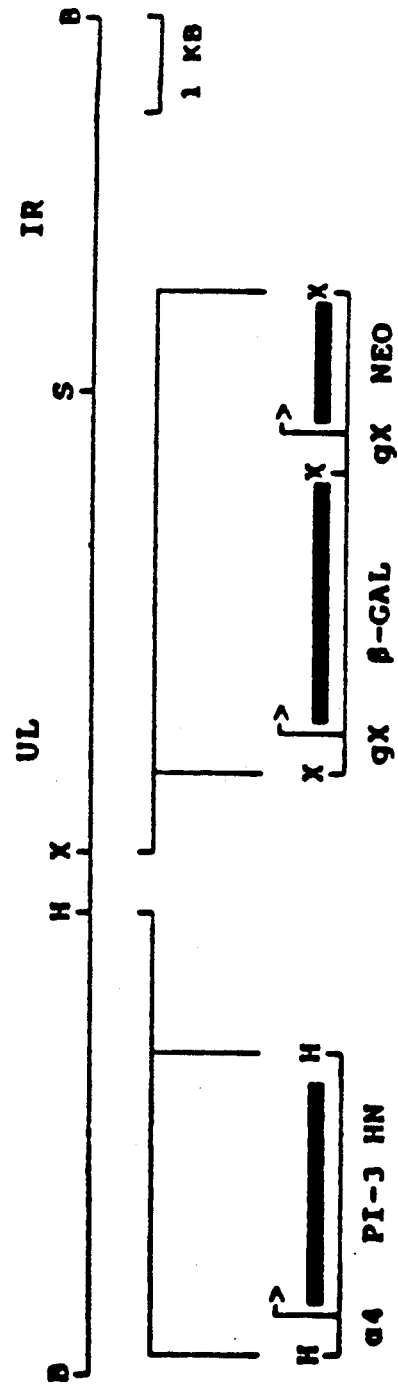
Figure 25B:
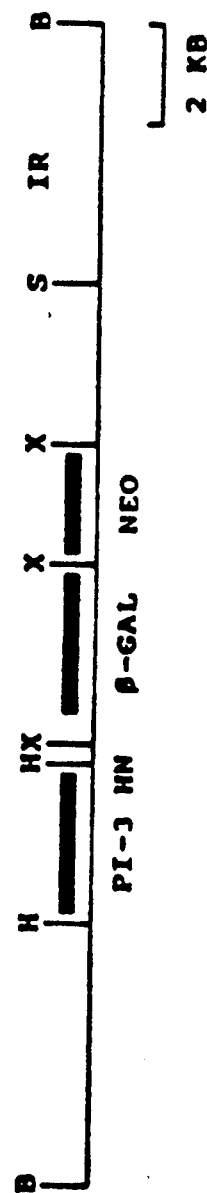

The HSV ICP4 promoter was used to express the PI-3 HN gene and the HSV TK poly-A signal was used to terminate transcription. The engineering of this construct was done as shown in FIG. 25A and B. The construct contained (5' to 3') the HSV ICP4 promoter, the ICP4 TATA box, the ICP4 cap site, a fusion within the ICP4 5' untranslated region to the PI-3 HN gene at the HhaI site, the HN gene start codon, the HN structural gene, the HN stop codon, a fusion within the HN 3' untranslated region to the HSV TK untranslated 3' region, and the HSV TK poly-A signal sequence.

This plasmid also contained the beta-galactosidase gene under the control of the PRV gpX promoter with the gpX poly-A termination signal, as well as the neomycin resistance gene under the control of the gpX promoter with the TK poly-A termination signal. These latter two genes were cloned in tandem at the XbaI site in BamHI-C fragment (FIG. 25A and B). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT HERPESVIRUS procedure, followed by the BLUOGAL SCREEN FOR RECOMBINANT HERPESVIRUS procedure, and subsequently analyzed for the insertion of the PI-3 HN gene by SOUTHERN BLOTTING OF DNA procedure. The virus that resulted from this screening was designated S-IBR-018.

Figure 25C:
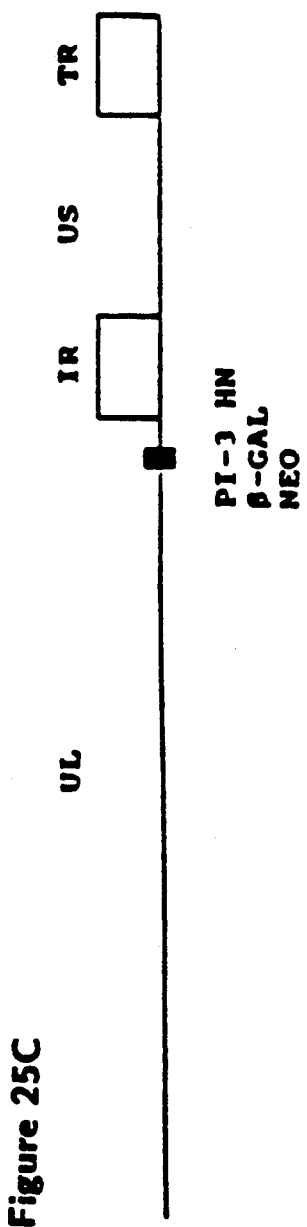

The structure of S-IBR-018 is shown in FIG. 25C.

Example 20

S-IBR-019

S-IBR-019 is an IBR virus that has three foreign genes inserted: the *E. coli* beta-galactosidase gene and the neomycin resistance gene in the XbaI site in the unique long region, and the parainfluenza-3 (PI-3) virus fusion gene (F) in the HindIII site in the long unique region adjacent to the XbaI site.

For cloning the PI-3 F gene, the SF-4 strain of PI-3 was grown in MADIN-DARBY bovine kidney (MDBK) cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the Sendai virus F gene has been published (62) and this comparative sequence information was used to locate the homologous gene in applicants' bovine PI-3 clones.

The HSV ICP4 promoter was used to express the PI-3 F gene and the HSV TK poly-A signal was used to terminate transcription. The construct contained (5' to 3') the HSV ICP4 promoter, the ICP4 TATA box, the ICP4 cap site, a fusion in the ICP4 5' untranslated region to the PI-3 F gene, the F start codon, the F structural gene, the F stop codon, a fusion in the F 3' untranslated region to the HSV TK 3' untranslated region, and the TK poly-A signal sequence.

Figure 26A:
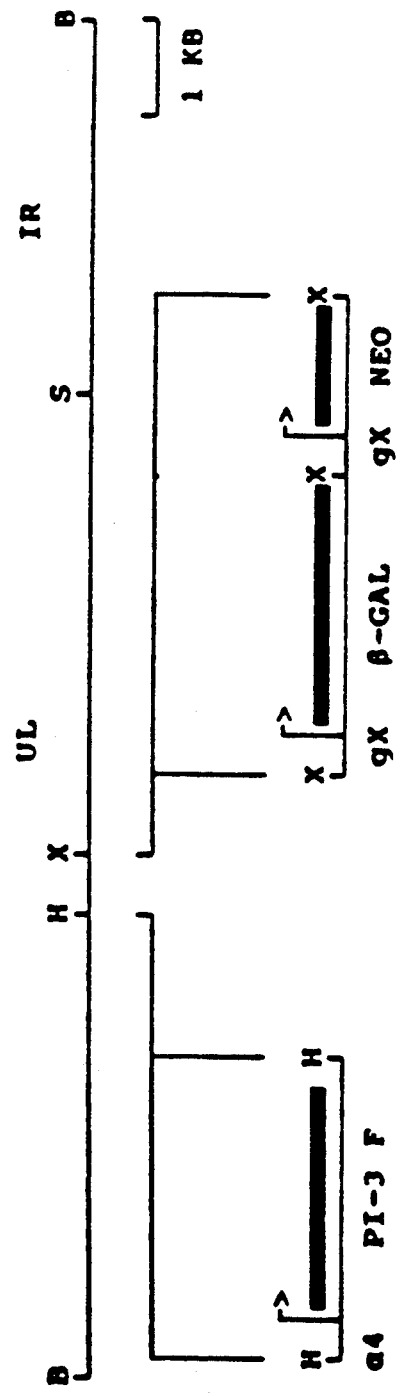
Figure 26B:
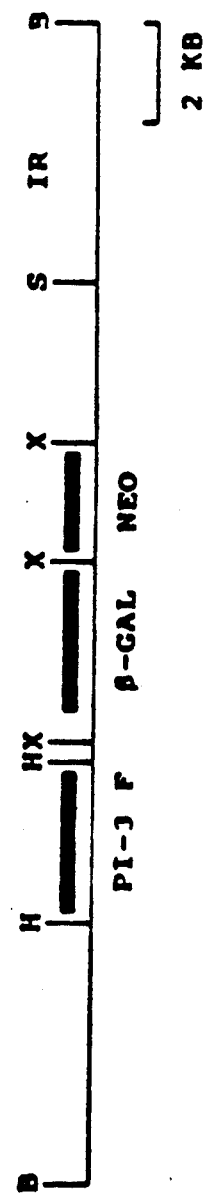

This plasmid also contained the beta-galactosidase gene under the control of the PRV gpX promoter with the gpX poly-A termination signal, as well as the neomycin resistance gene under the control of the gpX promoter with the TK poly-A termination signal. These latter two genes were cloned in tandem at the XbaI site in BamHI-C fragment (FIG. 26A and B). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT HERPESVIRUS procedure, followed by the BLUOGAL SCREEN FOR RECOMBINANT HERPESVIRUS procedure, and subsequently analyzed for the insertion of the PI-3 F gene by SOUTHERN BLOTTING OF DNA procedure. The virus that resulted from this screening was designated S-IBR-019.

Figure 26C:
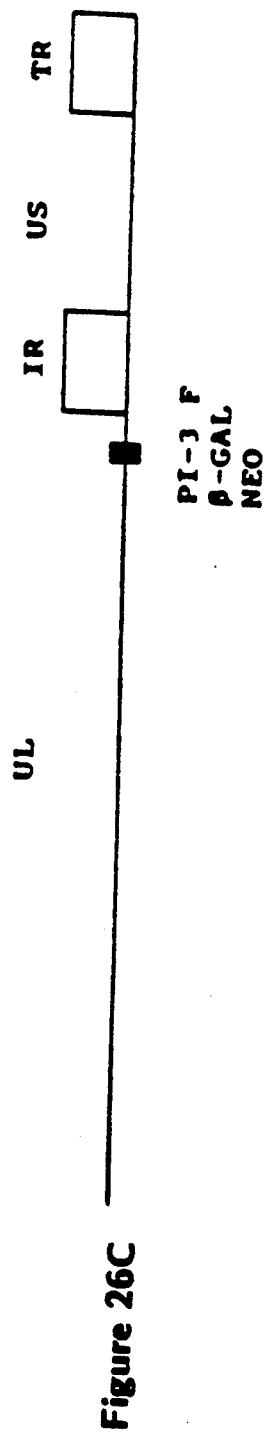
Figure 28A:
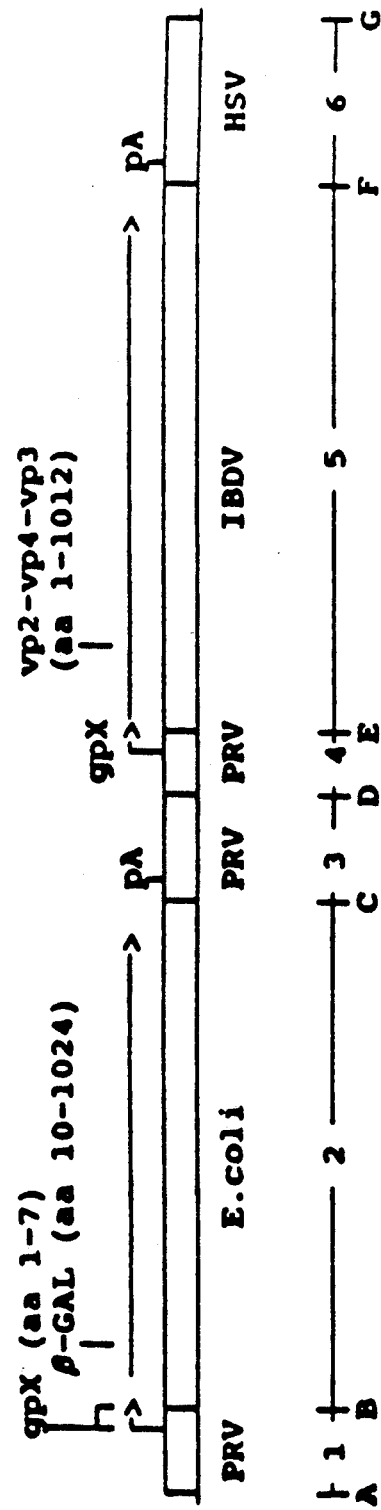
Figure 28B:
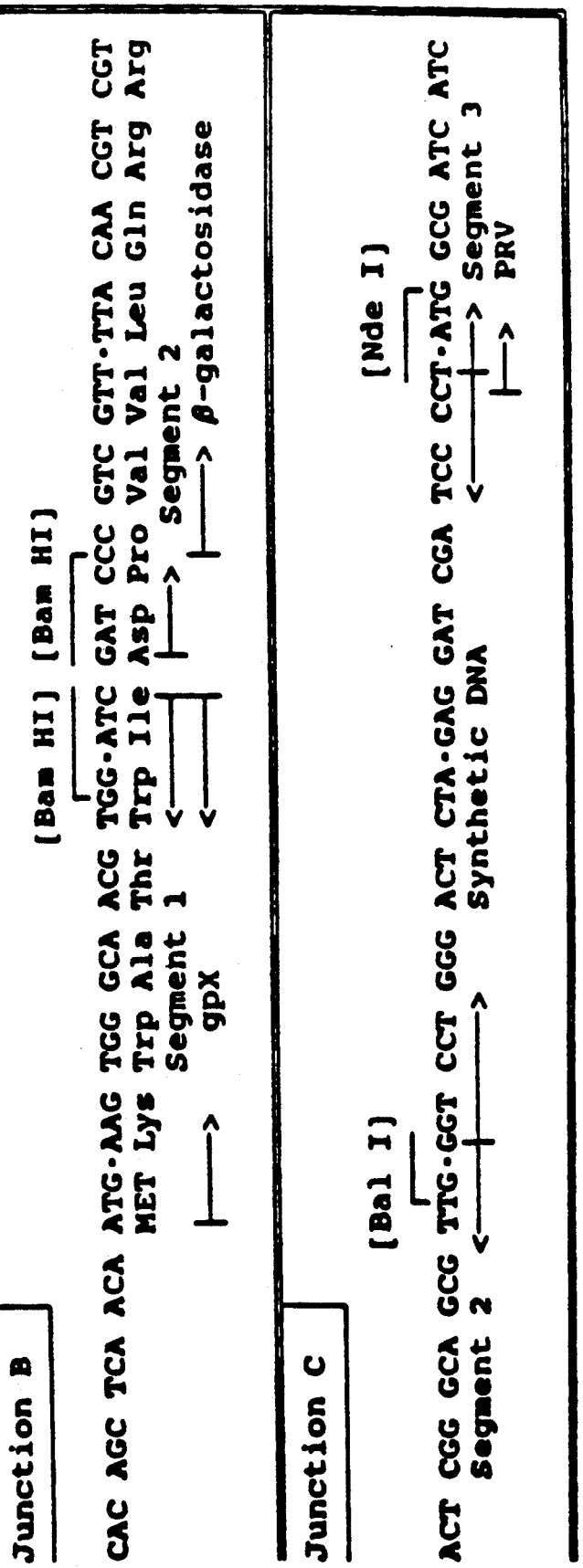
Figure 28C:
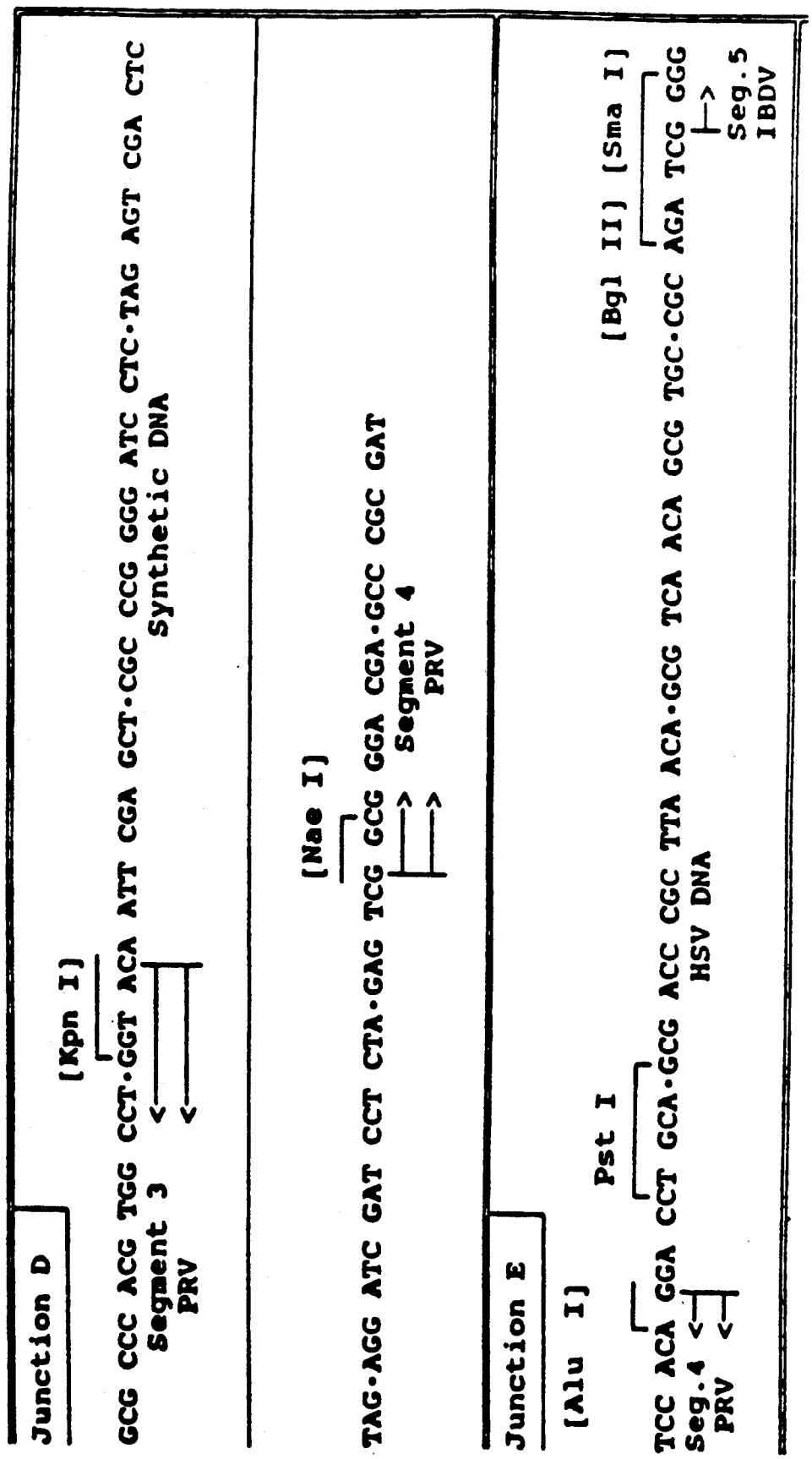
Figure 28D:
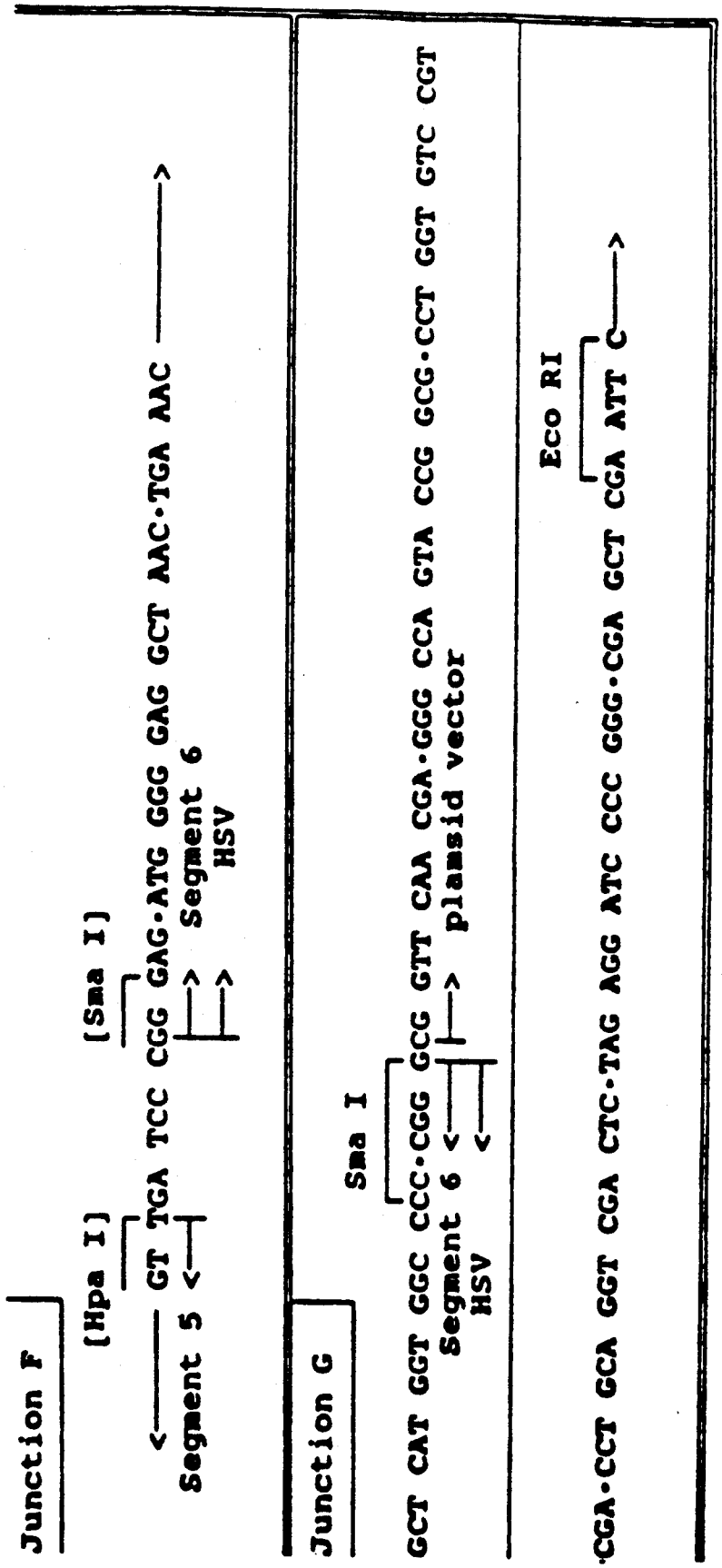

The structure of S-IBR-019 is shown in FIG. 26C.

Example 21

S-HVT-003

S-HVT-003 is a herpesvirus of turkeys (HVT) that contains the *E. coli* beta-galactosidase gene plus the infectious bursal disease virus (IBDV) strain S40747 large segment of RNA (as a cDNA copy) inserted into the unique long region of the HVT genome. This IBDV DNA contains one open reading frame that encodes three proteins (5'VP2-VP4-VP3 3'), two of which are antigens to provide protection against IBDV infections of chickens. Expression of the genes for both beta-galactosidase and the IBDV polyprotein are under the control of the pseudorabies virus (PRV) gpX gene promoter. S-HVT-003, deposited under ATCC Accession No. VR 2178, was made by homologous recombination.

The IBDV genes were cloned by the cDNA CLONING PROCEDURE. Clones representing the genome of IBDV were screened by SOUTHERN BLOTTING OF DNA procedure against blots containing authentic IBDV RNA. Positive clones were then characterized by restriction mapping to identify groups of clones. Two such clones were identified, that together were found to represent the entire coding region of the IBDV large segment of RNA (3.3 kb dsRNA). One cDNA clone (2-84) contained an approximately 2500 base pair fragment representing the first half of the IBDV gene. The second clone (2-40) contained an approximately 2000 base pair fragment representing the distal half of the IBDV gene. Plasmid 2-84/2-40, representing the entire IBDV gene, was constructed by joining clone 2-84 and 2-40 at a unique Pvu II site present in the overlapping sequences. The IBDV genome can be obtained from plasmid 2-84/2-40 as an approximately 3400 base pair Sma I to Hpa I fragment. Confirmation of the nature of the proteins encoded by the IBDV gene was obtained by expressing the clone (2-84/2-40) in *E. coli* and detecting VP3 antigen using antiserum made against purified IBDV capsid proteins on Western blots. Applicants' sequence of the large DNA segment that encodes the IBDV antigens is given in FIG. 27. This sequence shows one open reading frame that will henceforth be referred to as the IBDV gene. Recently, the sequence of an Australian IBDV strain has been published which bears close homology to applicants' sequence (63). Comparison of the amino acid differences between the two viruses revealed 29 amino acid changes within the 1012 amino acid coding region. There were only 3 amino acid differences deduced for VP4 and only 8 in VP3. In contrast, VP2 contained 18 amino acid changes, 14 of which were clustered between amino acids 139 to 332.

For insertion into the genome of HVT, the coding region for the IBDV gene was cloned between the PRV gpX promoter and the HSV TK poly-A signal sequence, creating plasmid 191-23. To aid in the identification of HVT recombinants made by homologus recombination, containing the IBDV gene, the gpX promoted IBDV fragment from plasimid 191-23 was inserted behind (in tandem to) a beta-galactosidase gene controlled by a gpX promoter. The resultant plasmid, 191-47, contains the E. coli beta-galactosidase gene and the IBDV gene under the control of individual PRV gpX promoters. In constructing plasmid 191-47, various DNA fragments were joined by recombinant DNA techniques using either naturally occurring restriction sites or synthetic linker DNA. Details concerning the construction of these genes contained in plasmid 191-47 can be seen in FIG. 28. The first segment of DNA (segment 1, FIG. 28) contains the gpX promoter region including the residues encoding the first seven amino acids of the gpX gene, and was derived from a subclone of the PRV Bam HI number 10 fragment as an approximately 800 base pair Sal I to Bam HI fragment. The second segment of DNA (segment 2, FIG. 28) contains the E. coli beta-galactosidase coding region from amino acid 10 to amino acid 1024 and was derived from the plasmid pJF751 (obtained from Jim Hoch, Scripps Clinic and Research Foundation) as an approximately 3300 base pair Bam HI to Bal I fragment followed by an approximately 40 base pair Ava I to Sma I fragment. The third segment of DNA (segment 3, FIG. 28) contains the gpX poly A signal sequence and was derived from a subclone of the PRV Bam HI number 7 fragment as an approximately 700 base pair Nde I to Stu I fragment. Segment three was joined to segment two by ligating the Nde I end which had been filled in according to the POLYMERASE FILL-IN REACTION, to the Sma I site. The fourth segment of DNA (segment 4, FIG. 28) contains the gpX promoter (TATA box and cap site) and was derived from a subclone of the PRV Bam HI number 10 fragment as an approximately 330 base pair Nae I to Alu I fragment. Additionally, segment four contains approximately 36 base pairs of HSV TK 5′untranslated leader sequence as a Pst I to Bgl II fragment in which the Pst I site has been joined to the Alu I site through the use of a synthetic DNA linker (64). DNA segments four through six were inserted as a unit into the unique Kpn I site of segment three which is located 3′ of the gpX poly A signal sequence. The fifth segment of DNA (segment 5, FIG. 28) contains the entire coding region of the IBDV large segment of RNA (cDNA clone) as an approximately 3400 base pair Sma I to Hpa I fragment. The Sma I site of segment five was fused to the Bgl II site of segment four which had been filled in according to the POLYMERASE FILL IN REACTION. Expression of the IBDV gene (5′VP2-VP4-VP3 3′) is under the control of the gpX promoter (segment 4), but utilizes its own natural start and stop codons. The sixth segment of DNA (segment 6, FIG. 28) contains the HSV TK poly-A signal sequence as an approximately 800 base pair Sma I fragment (obtained from Bernard Roizman, Univ. of Chicago). The Hpa I site of segment five was fused to the Sma I site of segment six through the use of a synthetic DNA liner.

In summary, the construct used to create S-HVT-003 (plasmid 191-47) contains (5′ to 3′) the PRV promoter, the gpX TATA box, the gpX cap site, the first seven amino acids of gpx, the E. coli beta-galactosidase gene, the PRV poly-A signal sequence, the PRV gpX promoter, the gpX TATA box, the gpX cap site, a fusion within the gpX untranslated 5′ leader to the IBDV gene, IBDV start codon, a fusion within the IBDV untranslated 3′ end to HSV TK untranslated 3′ end, and the TK poly-A signal sequence. The cassette containing these genes was engineered such that it was flanked by two Eco RI restriction endonuclease sites. As a result, an approximately 9100 base pair fragment containing both beta-galactosidase and the IBDV gene can be obtained by digestion with Eco RI. Henceforth, the 9161 base pair Eco RI fragment will be referred to as the IBDV/b-gal cassette.

Figures 29A, 29B:
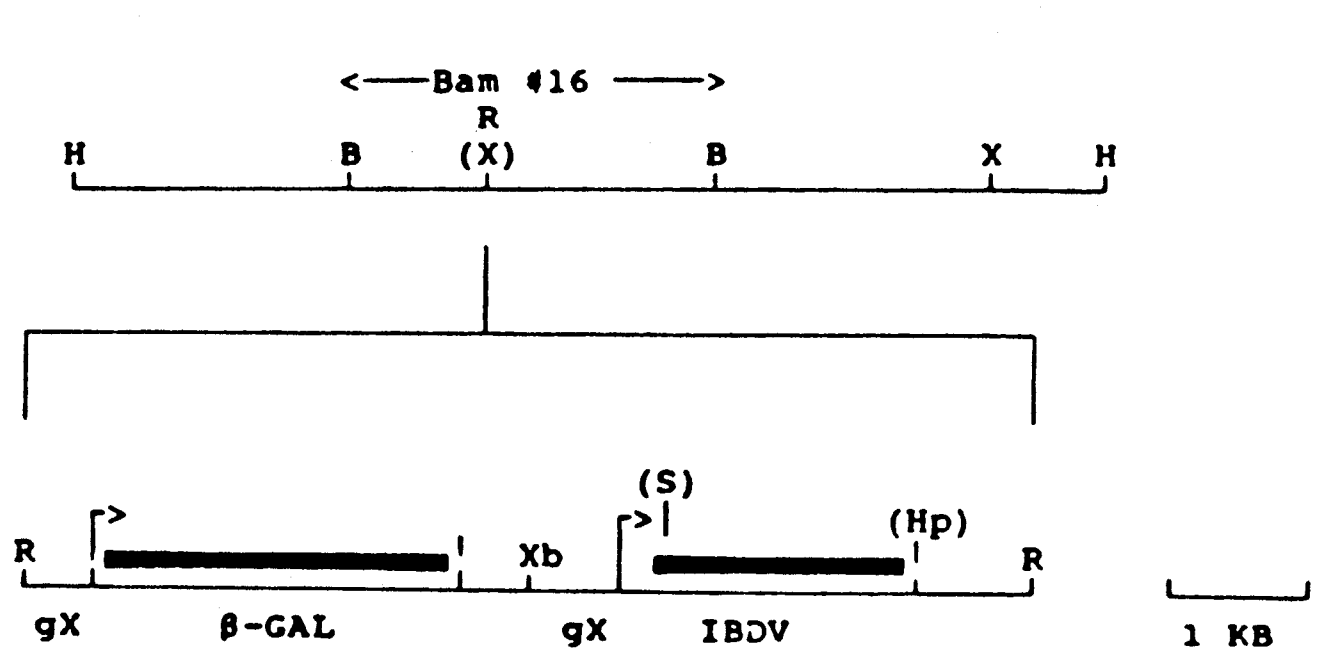
Figure 29C:
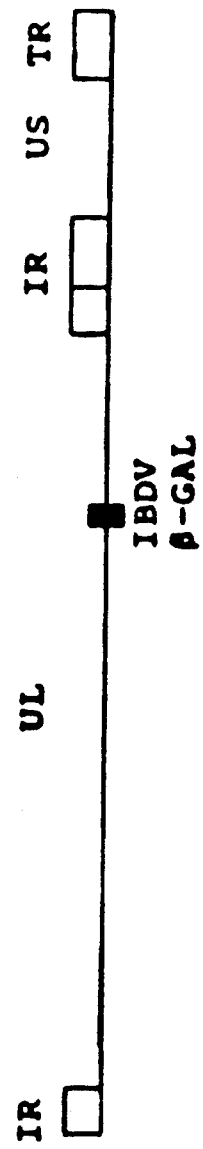

The following procedures were used to construct S-HVT-003 by homologous recombination. The IBDV/b-gal cassette was inserted into the unique Xho I site present within a subclone of the HVT Bam HI number 16 fragment. To achieve this, the Xho I site was first changed to an Eco RI site through the use of an Eco RI liner. This site had previously been shown to be nonessential in HVT by the insertion of beta-galactosidase (S-HVT-001). It was also shown that the flanking homology regions in Bam HI number 16 were efficient in homologous recombination. Shown in FIG. 29, the genomic location of the Bam HI number 16 fragment maps within the unique long region of HVT. The complete nucleotide sequence of the approximately 3329 base pair Bam HI number 16 fragment is presented in FIG. 30. HVT DNA was prepared by the PREPARATION OF HERPES VIRUS OF TURKEY DNA procedure. Cotransfections of HVT DNA and plasmid DNA into primary chick embryo fibroblast (CEF) cells were done according to the DNA COTRANSFECTION FOR GENERATING RECOMBINANT HVT VIRUS procedure. The recombinant virus resulting from the cotransfection stock was purified by three successive rounds of plaque purification using the BLUOGAL SCREEN FOR RECOMBINANT HERPESVIRUS procedure. When 100% of the plaques were blue, the DNA was analyzed for the presence of the IBDV gene by the SOUTHERN BLOTTING OF DNA procedure. Southern blots, probing Eco RI digested S-HVT-003 DNA with an IBDV specific nick translated probe (plasmid 2-84/2-40), confirmed the presence of the 9100 base pair Eco RI fragment. This result confirmed that S-HVT-003 contained both the beta-galactosidase gene and the IBDV gene incorporated into its genome. Additional Southern blots, using a probe specific for Bam HI #16, confirmed that the homologous recombination occurred at the appropriate position in Bam 16 and that no deletions were created. No differences in the growth of S-HVT-003 compared to wild type virus (S-HVT-000) were observed in vitro.

Figure 31:
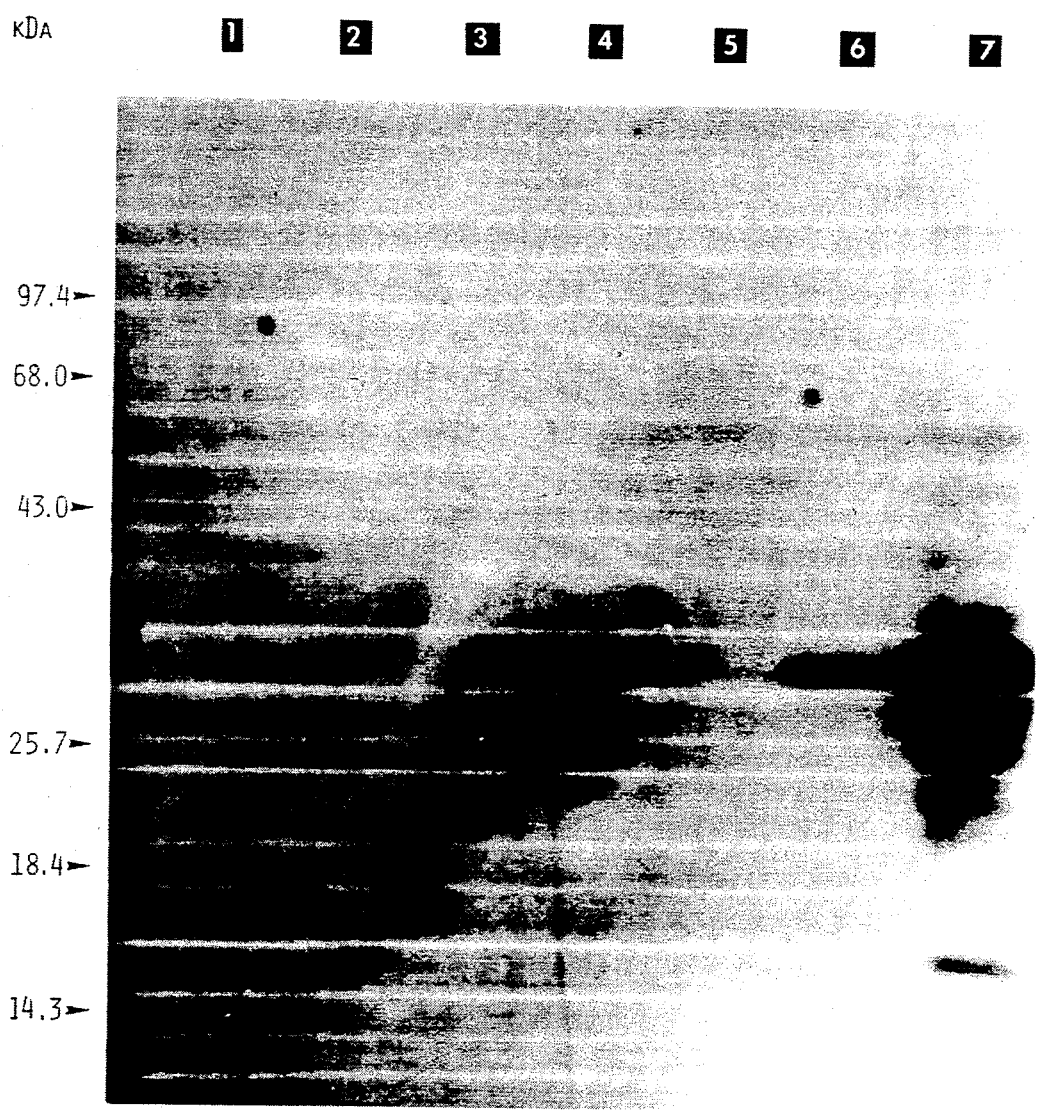

Expression of IBDV specific proteins from S-HVT-003 were assayed in vitro using the WESTERN BLOTTING PROCEDURE. Cellular lysates were prepared as described in PREPARATION OF HERPESVIRUS CELL LYSATES. Briefly, the proteins contained in the cellular lysates of S-HVT-003 were separated by polyacrylamide gel electrophoresis, transferred to nitrocellulose, and probed with either an antiserum made against denatured purified IBDV capsid proteins or antiserum made against a synthetic peptide corresponding to a predicted imuno dominant region of the IBDV 40 kd (VP2) capsid protein. The filters were washed and treated with [$^{125}$I] protein A to detect the position of the bound antibodies. FIG. 31 shows the results obtained using the antiserum made against denatured purified IBDV capsid proteins, which have been shown by the applicants to primarily react with VP3 (32 kd protein). As seen, S-HVT-003 produces a protein which is immunologically indistinguishable from the authentic VP3 species that comigrates with the authentic VP3 protein. Recent evidence using an Australian IBDV strain indicates that VP4 is involved in the processing of the precursor polyprotein into mature VP2 and VP3 protein species (65).

Figure 32:
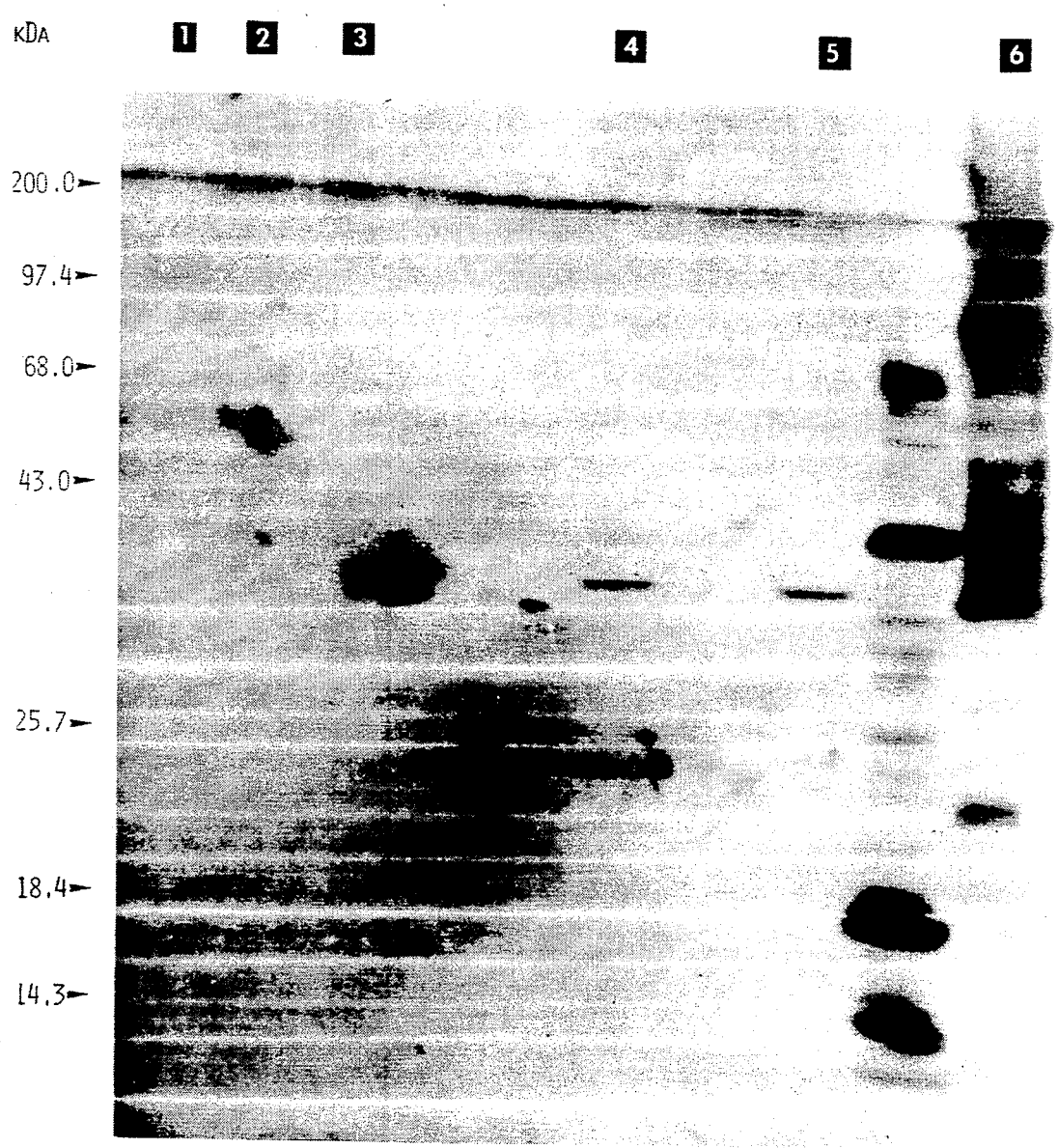

FIG. 32 shows the results obtained using a rabbit antiserum raised against a synthetic peptide that is homologous to a 14 amino acid region of the IBDV VP2 (40 kd) capsid protein. As seen, S-HVT-003 produces a protein that is immunologically indistinguishable from the authentic viral VP2 protein. In addition, the VP2 protein produced from S-HVT-003 comigrates with the 40 kd species of VP2 isolated from intact IBDV virions. This species represents a major component of infectious (complete) viral particles.

In summary, analysis of the expression of IBDV specific proteins from S-HVT-003 has shown that the polyprotein is processed in CEF cell culture, producing proteins of the appropriate size that react to immunological reagents specific for either VP2 or VP3 proteins on Western blots.

The following set of experiments was carried out in chickens to analyze the in vivo expression of the IBDV genes contained within S-HVT-003 as determined by seroconversion data, serum neutralization results, and protection from IBDV challenge.

The first experiment was designed to show the seroconversion of chickens to IBDV upon being vaccinated with S-HVT-003. Eleven 11-week-old chickens, seronegative to HVT and IBDV were obtained from SPAFAS Inc. Six birds were vaccinated subcutaneously in the abdominal region with one-half milliliter of a cellular suspension of CEF cells containing S-HVT-003 (40,000 PFU per milliliter). Serum samples were obtained every seven days for eight weeks for all birds in this study. On day 28 (4th week), three of these birds received a boost of S-HVT-003, while the other three birds received one-half milliliter of an inactivated IBDV vaccine inoculated subcutaneously in the cervical region. Three additional birds were given only the inactivated vaccine on day 28. Two birds served as contact controls and received no vaccinations. On day 56, all birds were sacrificed and necropsied. Table VIII shows the results of the serum neutralization assay against IBDV. No detectable SN activity was observed in the birds given only S-HVT-003. Additionally, only one of the three birds that were given only the inactivated vaccine demonstrated low but detectable SN activity. SN titers were also detected in one of the three birds that received the S-HVT-003 followed by the inactivated IBDV vaccine boost; these titers were at a much higher level than with the inactivated IBDV vaccine alone. These results suggest that S-HVT-003 is priming the chicken for a secondary response against IBDV. In vitro analysis of the serum samples by WESTERN BLOTTING confirmed the seroconversion of the chickens to IBDV upon vaccination with S-HVT-003 both prior to and after boosts administered on day 28.

TABLE VIII

| | | DAY | | | | | | |
|---|---|---|---|---|---|---|---|---|
| | | 28 | 31 | 35 | 38 | 42 | 49 | 56 |
| HVT-003 | 265 | <2 | <2 | <2 | <2 | <2 | <2 | ND |
| HVT-003 | 266 | <2 | <2 | <2 | <2 | <2 | <2 | |
| | 267 | <2 | <2 | <2 | <2 | <2 | <2 | |
| HVT-003 | 260 | <2 | <2 | <2 | <2 | <2 | <2 | |
| Vac-IBDV | 264 | <2 | <2 | <2 | 1:64 | 1:256 | 1:512 | |
| | 269 | <2 | <2 | <2 | <2 | <2 | <2 | |
| C | 261 | <2 | <2 | <2 | <2 | <2 | <2 | |
| Vac-IBDV | 262 | <2 | <2 | <2 | <2 | 1:4 | 1:4 | |
| | 263 | <2 | <2 | <2 | <2 | <2 | <2 | |
| C | 270 | <2 | <2 | <2 | <2 | <2 | <2 | |
| | 271 | <2 | <2 | <2 | <2 | <2 | <2 | |

In the second experiment, twenty five 1-day old SPF chicks were vaccinated with S-HVT-003 (20 with 0.2 ml subcutaneously and 5 by bilateral eyedrop). Twenty chicks were kept as controls. On days four and seven postinfection, five vaccinates and two control birds were bled, sacrificed and their spleens removed for virus isolation. Spleen cell suspensions were made by standard method, and $\sim 1 \times 10^6$ cells in 3 ml of chick embryo fibroblast (CEF) growth media were inoculated directly onto secondary cells. Cultures were incubated for 6–7 days and then scored for cytopathic effects (CPE) as determined by observing cell morphology. The cultures were passed a second time, and again scored for CPE. The results are shown in table IX. All nonvaccinated control birds remained negative for HVT for both day 4 and 7 spleen cell isolations. Four out of the five birds vaccinated with S-HVT-003 were positive for HVT at day 4 for both the first and second passages. One bird did not produce virus, this may represent a vaccination failure. Five out of five birds were positive for HVT on day 7 at both passage one and two. Overall, the vector recovery experiment demonstrates that S-HVT-003 replicates as well as wild type HVT virus in vivo and that insertion of the IBDV/beta-galactosidase cassette into the Xho I site of Bam HI #16 does not result in detectable attenuation of virus. Subsequent experiments examining the recovered virus by the BLUOGAL SCREEN FOR RECOMBINANT HERPESVIRUS procedure confirmed the in vivo stability of S-HVT-003, by demonstrating beta-galactosidase expression in 100% of the viruses.

TABLE IX

| | Harvest Date | | | |
|---|---|---|---|---|
| | Day 4 | | Day 7 | |
| Sample | P1 | P2 | P1 | P2 |
| N1 | − | − | | |
| N2 | − | − | | |
| N3 | | | − | − |
| N4 | | | − | − |
| T1 | − | − | | |
| T2 | 2+ | 2+ | | |
| T3 | 2+ | 2+ | | |
| T4 | + | 4+ | | |
| T5 | 3+ | 3+ | | |
| T6 | | | 2+ | contaminated |
| T7 | | | + | 5+ |
| T8 | | | + | 5+ |
| T9 | | | +· | 5+ |
| T10 | | | + | 5+ |

N = control, T = vaccinated.
CPE ranged from negative (−) to 5+

At days 0, 4, 7, 14, 21, and 27 postinfection, blood samples were obtained from the rest of the chickens for determining serum ELISA titers against IBDV and HVT antigens as well as for virus neutralizing tests against IBDV. Additionally, at 21-days postinfection five control and fourteen vaccinated chicks were challenged with virulent IBDV by bi-lateral eyedrop ($10^{3.8}$EID$_{50}$). All birds were sacrificed 6-days post challenge and bursa to body weight ratios were calculated. A summary of the results is shown in tables X and XI, respectively. As presented in table X, no antibodies were detected against HVT antigens by ELISA prior to 21–27 days post vaccination. In chickens, the immune response during the first two weeks post hatch is both immature and parentally suppressed, and therefore these results are not totally unexpected. In contrast, IBDV ELISA's were negative up to day 21 postvaccination, and were only detectable after challenge on day 27. The ELISA levels seen on day 27 postvaccination indicate a primary response to IBDV. Table XI comparing the Bursa-to-Body weight ratios for challenged controls and vaccinated/challenged groups show no significant differences. Vaccination with S-HVT-003 under these conditions did not prevent infection of the vaccinated birds by IBDV challenge, as indicated by the death of four vaccinated birds following challenge

TABLE X

| Sample Group | ELISA | | VN |
|---|---|---|---|
| | HVT | IBDV | IBDV |
| C-0 (n = 3) | 0 | 0 | <100 |
| C-4 (n = 2) | 0 | 0 | nd |
| T-4 (n = 5) | 0 | 0 | nd |
| C-7 (n = 2) | 0 | 0 | <100 |
| T-7 (n = 5) | 0 | 0 | <100 |
| C-14 (n = 5) | 0 | 0 | nd |
| T-14 (n = 14) | 0 | 0 | <100 |
| C-21 (n = 5) | 0 | 0 | nd |
| T-21 (n = 14) | 1 | 0 | <100 |
| C-27 (n = 5) | 0 | 0 | nd |
| CC-27 (n = 5) | 0 | 5 | nd |
| CT-27 (n = 10) | 3.2 | 2 | nd |

C = control, T = vaccinated, CC = challenged control, CT = Challenged & vaccinated. ELISA titers are GMTs and they range from 0–9.

TABLE XI

| Sample Group | Body wt. | Bursa wt. | BBR |
|---|---|---|---|
| Con. (n = 5) | 258.8 | 1.5088 | .0058 |
| Chall. Con (n = 5) | 209 | 0.6502 | .0031 |
| Chall. Treated (n = 10) | 215.5 | 0.5944 | .0027 |

Values are mean values. Body weights are different in control group because challenged birds did not feed well. Four challenged-treated birds died.

A third experiment was conducted repeating Experiment 2 but using immunologically responsive chicks (3 weeks of age). Six three week old SPF leghorn chickens were vaccinated intraperitoneally with 0.2 ml of S-HVT-003 (one drop in each eye). Serum samples were obtained every seven days for six-weeks and the birds were challenged with the virulent USDA standard challenge IBDV virus on day 43 postvaccination. Six days post challenge, the control, vaccinated-challenged, and challenged groups were sacrificed and bursas were harvested for probing with anti-IBDV monoclonal antibodies (MAB) (provided by Dr. David Snyder, Virginia-Maryland Regional College of Veterinary Medicine). Bursal homogenates were prepared by mixing 1 ml of 0.5% NP40 with one bursa. Bursa were then ground and briefly sonicated. Supernatants from the homogenates were reacted with the R63 MAB which had been affixed to 96-well Elisa plates via a protein A linkage. After incubation, a biotin labeled preparation of the R63 MAB was added. After washing, an avidin-horse radish peroxidase conjugate was added and incubated. Tests were developed with Tris-malcate buffer (TMB)+$H_2O_2$ substrate. The test results are presented in table XII. The data show the presence of high levels of IBDV antigen in all bursa in the vaccinated-challenged group and in the challenged group. No IBDV antigen was detected in the controls. IBDV specific antigen could be detected at dilutions of over 1/1000, and there does not appear to be differences between vaccinated and non-vaccinated challenged groups. HVT titers as determined by ELISA were first detectable at day 7 in four out of the six birds vaccinated. By day 14, six out of six vaccinated birds showed titers to HVT. All six birds continued to show HVT titers throughout the experiment. No IBDV SN titers were seen prior to the challenge. In contrast, analysis of these same serum samples by the WESTERN BLOTTING procedure demonstrated the seroconversion of chickens vaccinated with S-HVT-003 to IBDV prior to administration of the virus challenge. The level of response, however, remains small unless boosted by challenge. Comparison between the vaccinated/challenged and challenged only groups clearly demonstrates that the level of reactivity by Western blots is much higher in the vaccinated/challenged group. These results show that S-HVT-003 is seroconverting vaccinated birds to IBDV, and suggest that the level of IBDV specific expression are not high enough to induce a neutralizing response in the birds.

S-HVT-003 shows the merit of the vaccine approach the applicants have invented. HVT has been engineered to simultaneously express the foreign antigens (b-galactosidase and IBDV antigens) that are recognized in the host by an immune response directed to these proteins. Applicants' invention will enable progression towards a product based on this technology.

TABLE XII

| | Serology: Herpes/IBDV ELISA titer | | | | | | |
|---|---|---|---|---|---|---|---|
| | Bleed Date | | | | | | |
| | 11/3 | 11/10 | 11/14 | 11/24 | 12/1 | 12/8 | 12/15 | 12/22 |
| Bird # | | | | | | | | |
| Vacc. Chal | | | | | | | | |
| 221 | 0/0 | 7/0 | 5/0 | 6/0 | 5/0 | 5/0 | 5/0 | 3/3 |
| 41 | 0/0 | 4/0 | 4/0 | 1/0 | 1/0 | 1/0 | 1/0 | 1/3 |
| 42 | 0/0 | 3/0 | 2/0 | 1/0 | 5/0 | 5/0 | 5/0 | 3/2 |
| 43 | 0/0 | 0/0 | 5/0 | 5/0 | 5/0 | 5/0 | 3/0 | 3/2 |
| 44 | 0/0 | 2/0 | 5/0 | 1/0 | 2/0 | 1/0 | 1/0 | 2/4 |
| 45 | 0/0 | 0/0 | 1/0 | 1/0 | 1/0 | 1/0 | 1/0 | 1/3 |
| Control | | | | | | | | |
| 28 | 0/0 | | | | | | | 0/0 |
| 38 | 0/0 | | | | | | | 0/0 |
| 73 | 0/0 | | | | | | | 0/0 |
| 75 | 0/0 | | | | | | | 0/0 |

TABLE XII-continued

| | Serology: Herpes/IBDV ELISA titer | | | | | | | |
|---|---|---|---|---|---|---|---|---|
| | Bleed Date | | | | | | | |
| | 11/3 | 11/10 | 11/14 | 11/24 | 12/1 | 12/8 | 12/15 | 12/22 |
| Chal only | | | | | | | | |
| 40 | 0/0 | | | | | | | 0/3 |
| 74 | 0/0 | | | | | | | 0/5 |
| 39 | 0/0 | | | | | | | 0/3 |
| 72 | 0/0 | | | | | | | 0/3 |

Maximum titer level is 9

Example 22

S-HVT-004

S-HVT-004 is a recombinant herpesvirus of turkeys that contains the Marek's disease virus (MDV) glycoprotein A (gpA) gene inserted into the long unique region, and the beta-galactosidase gene also inserted in the long unique region. The MDV antigen is more likely to elicit the proper antigenic response than the HVT equivalent antigen.

The MDV gpA gene was cloned by standard DNA cloning gpA procedures. An EcoRI restriction fragment had been reported to contain the MDV gpA gene (66) and this fragment was identified by size in the DNA clones. The region of the DNA reported to contain the gpA gene was sequenced by applicants and found to contain a glycoprotein gene as expected. The DNA from this gene was used to find the corresponding gene in HVT by the SOUTHERN BLOTTING OF DNA procedure, and a gene in HVT was identified that contained a very similar sequence. This gene is the same gene previously called gpA (66).

Figures 33A, 33B:
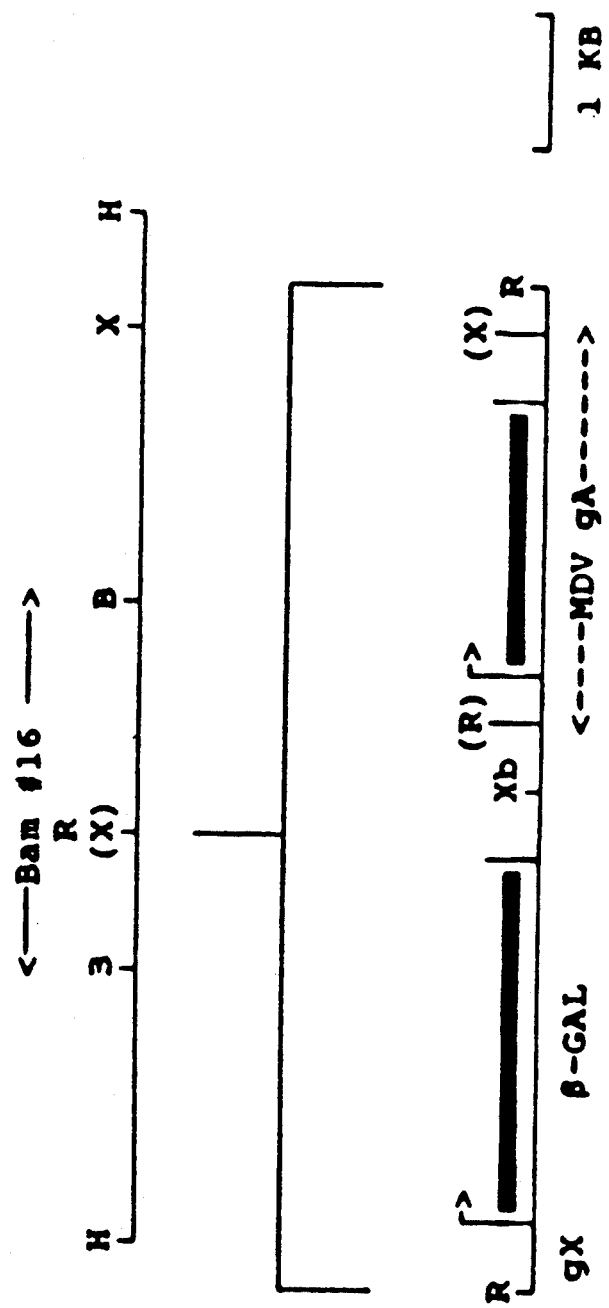

For insertion into the genome of HVT, the MDV gpA gene was used intact because it would have good herpesvirus signal sequences already. The beta-galactosidase gene was inserted into the XhoI fragment in BamHI fragment #16, and the MDV gpA gene was inserted behind beta-gal as shown in FIG. 33A and B. Flanking regions in BamHI #16 were used for the homologous recombination. HVT DNA and plasmid DNA were co-transfected according to the DNA TRANSFECTION FOR GENERATING RECOMBINANT VIRUS procedure into primary chick embryo fibroblast (CEF) cells. The virus from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the MDV gpA gene. S-HVT-004 is a recombinant virus that contains both the beta-galactosidase gene and the MDV gpA gene incorporated into the genome.

Figure 33C:
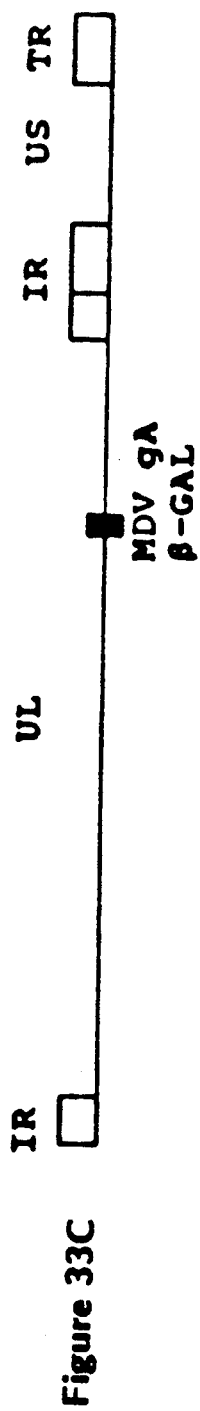

FIG. 33 C shows the structure of S-HVT-004.

Example 22

BOVINE CORONAVIRUS

Bovine coronavirus (BCV) is closely related to TGE virus in overall structure. We have closed the major neutralizing antigens from BCV for use in a herpesvirus delivery system (Infectious bovine rhinotracheitis virus, IBR).

The procedures that we have utilized for the construction of herpesvirus signal sequences for expression are being applied to BCV. It is contemplated that the procedures that have been used to express TGE in PRV and PI-3 in IBR and are disclosed herein are also applicable to BCV.

NEWCASTLE'S DISEASE VIRUS

Newcastle's disease virus (NDV) is closely related to PI-3 in overall structure. We have cloned the hemagglutinin (HN) and fusion (F) genes from NDV for use in the herpesvirus delivery system (Herpesvirus of turkeys, HVT).

The procedures that we have utilized for the construction of herpesvirus signal sequences for expression are being applied to NDV. It is contemplated that the procedures that have been used to express IBDV in HVT and PI-3 in IBR and are disclosed herein are also applicable to NDV.

INFECTIOUS BRONCHITIS VIRUS

Infectious bronchitis virus (IBV) is a virus of chickens closely related in overall structure to TGE. We have closed the major neutralizing antigens from three strains of IBV: Massachusetts, Connecticut, and Arkansas-99 for use in a herpesvirus delivery system (HVT).

The procedures that we have utilized for the construction of herpesvirus signal sequences for expression are being applied to IBV. It is contemplated that the procedures that have been used to express IBDV in HVT and TGE in PRV and are disclosed herein are also applicable to IBV.

BOVINE VIRAL DIARRHEA

Bovine viral diarrhea (BVD) is a virus of cattle. We have cloned the major neutralizing antigen of BVD for use in a herpesvirus delivery system (IBR).

The procedures that we have utilized for the construction of herpesvirus signal sequences for expression are being applied to BVD. It is contemplated that the procedures that have been used to express TGE in PRV and PI-3 in IBR and are disclosed herein are also applicable to BVD.

Example 24

Synthetic sequences of DNA may be used to provide the favored triplet frequencies for expression within the herpesvirus genome. The herpesvirus is pseudorabies virus of swine (PRV) and the foreign gene is a fragment of DNA from the swine parvovirus B gene. This fragment of parvovirus DNA is small, but it illustrates dramatically the effect even such a short unfavorable sequence has on expression, and it is small enough that a synthetic DNA sequence can be readily synthesized for it. Larger unfavorable sequences have an even more dramatic effect on expression, and they too can be made synthetically at some cost of materials and manpower.

FIG. 34 shows the sequence of the entire parvovirus B gene, with the sequence of the fragment (hereinafter called 039-fragment) overlined. FIG. 35A shows the amino acids that are coded for by the 039-fragment in the parvovirus B protein.

The design of the synthetic DNA fragment starts with the amino acid sequence of the authentic gene. This amino acid sequence is "reverse translated" back to DNA using a computer program. One such program is sold by International Biotechnologies, Inc., New Haven, Conn., and is called the IBI DNA/protein Sequence Analysis System. In constructing a new gene, changes can be incorporated into the synthetic DNA at any point using alternative codons for any amino acid. The next level of analysis is to approximate a new synthetic DNA based upon G+C content. The 039-fragment has a G+C content of 34%, while the herpesvirus PRV has a G+C content of about 70%. Therefore codons that are richer in G+C need to be substituted wherever possible into the synthetic DNA. The next step is to compare potential synthetic DNA pieces for the 039-fragment with actual coding regions from PRV to assign the best new sequence. This is accomplished by another program in the same computer package, which first creates a "codon bias" table for known PRV genes. Using this table, the synthetic DNA which best fits the PRV codon usage can be determined. This is the synthetic DNA of choice since it "looks most like" a PRV gene.

FIG. 35B shows the synthetic DNA fragment (called 039-synthetic) that was made to match the 039-fragment in amino acid sequence. It is a requirement of the invention that the amino acids encoded by both the natural and the synthetic DNA remain substantially the same. In practice some amino acids may be changed in order to create convenient restriction sites for the subsequent use of the synthetic DNA in constructions. Usually these changes can be limited to the addition of extra amino acids at the ends of the sequence of interest. Other changes within the body of the synthetic DNA are contemplated as well and are included within the scope of this invention, but they are in the main unnecessary in the practice of this invention.

Figure 36:
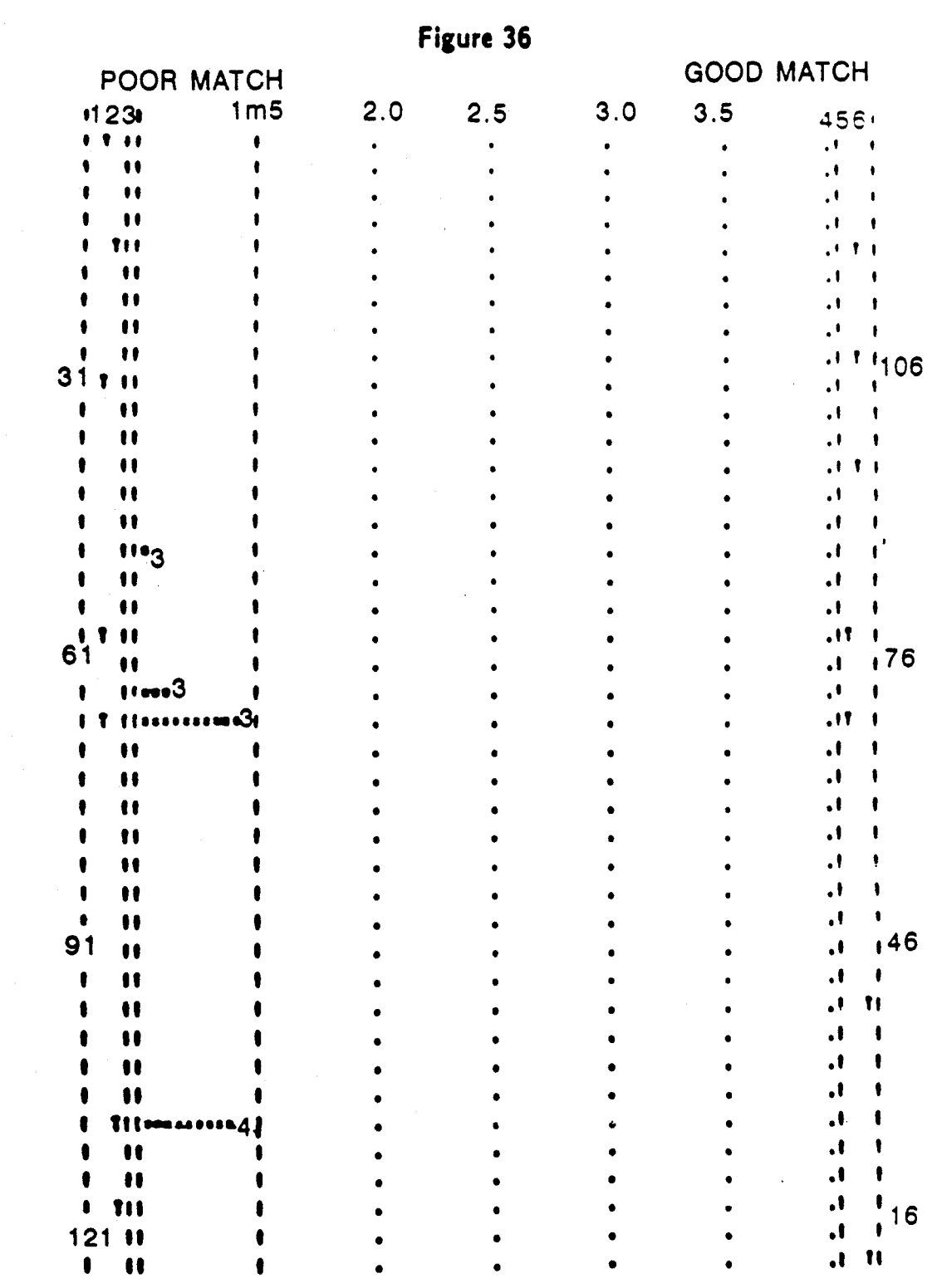
Figure 37:
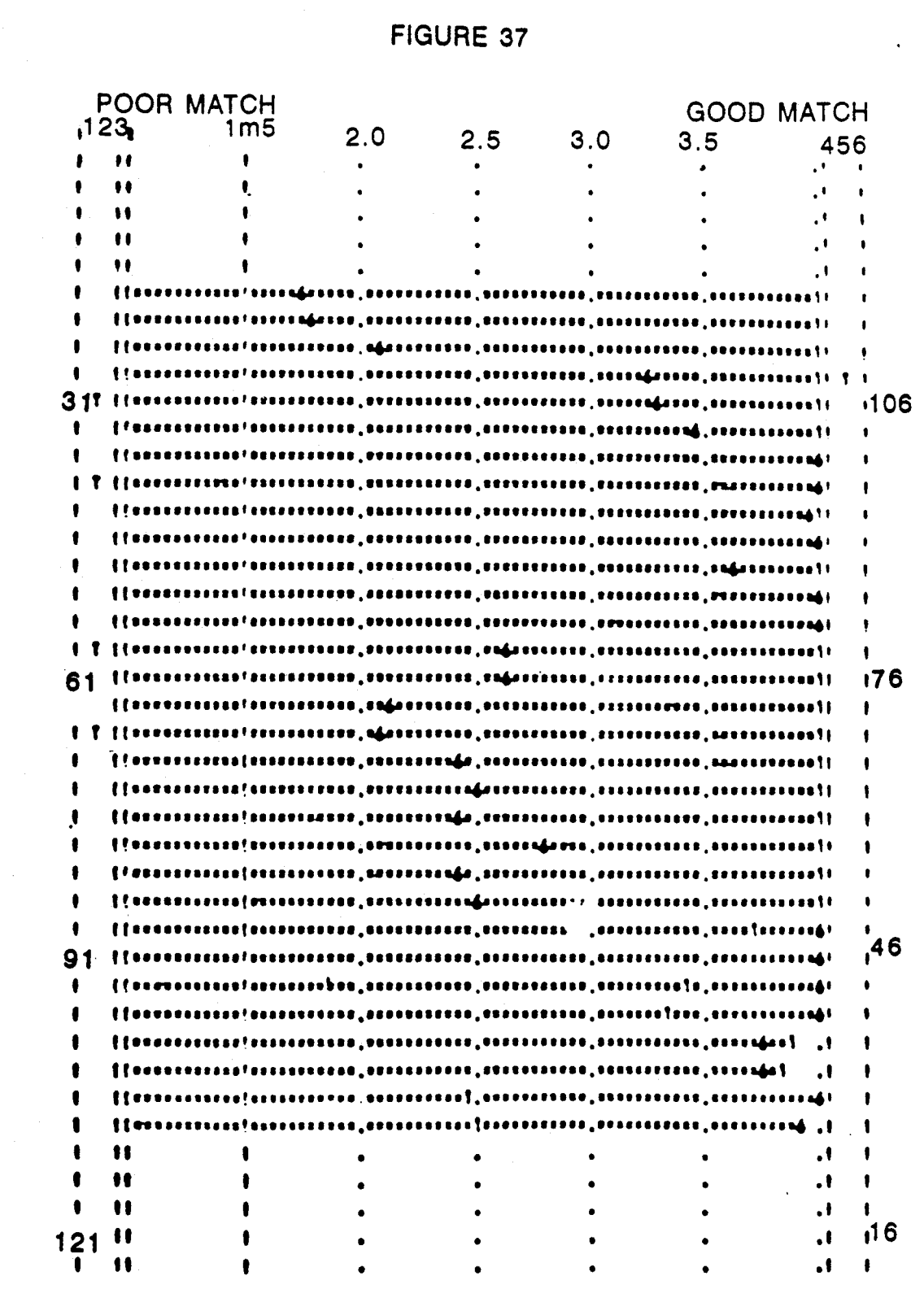

FIGS. 36 and 37 illustrate the degree to which the natural 039-fragment and the synthesized 039-synthetic match the codon bias of a PRV gene. These figures dramatically show that the synthetic DNA has been optimized for PRV codon usage and G+C content.

Example 25

A fusion protein may be used to provide the foreign antigen with the necessary triplet nucleotide frequencies to get expression in the herpesvirus genome. In this case, the fusion protein was the *E. coli* beta-galactosidase (beta-gal) gene which is efficiently expressed in the pseudorabies virus genome and which has a high G+C content and a triplet nucleotide frequency that is sufficiently similar to a real herpesvirus gene.

To demonstrate the improvement aspects of the present invention, the applicants have made both amino terminal fusions of the parvovirus B-gene to beta-gal (which are not the invention) and carboxy terminal fusions to beta-gal (which are the invention) and have compared their expression in pseudorabies virus. FIG. 38 shows the construction details of the amino terminal fusions made to beta-gal, and FIG. 39 shows the construction details of the carboxy terminal fusions made to beta-gal. Representative examples of these fusions were tested for the expression level of beta-gal made from the fusion. The method of testing the expression was the BETA-GALACTOSIDASE ONPG ASSAY METHOD given in the Methods section. In addition, the WESTERN BLOTTING METHOD was used to measure the amount of beta-gal present in the infected lysate, which did not rely upon active beta-gal expression. In all cases the amount of beta-gal determined enzymatically and the amount determined immunologically were the same. The size of the beta-gal fusion protein on Western blots showed that the protein contained the parvovirus amino acid sequence attached to the beta-gal.

Table XIII shows the results of analysis of the expression of beta-gal in representative examples of the fusions. The results are normalized to a control for beta-gal expression, S-PRV-043, which contains no parvovirus sequences. Clearly, putting the parvovirus B-gene sequences in front of beta-gal (at the amino terminus) drastically reduced expression of beta-gal. Conversely, putting the parvovirus sequence behind beta-gal (at the carboxy terminus) resulted in significantly better expression of both the beta-gal part of the fusion (Table XIII) and the parvovirus part of the fusion) as determined by the size and amount of the fusion protein on Western blots). The best direct comparison to see this effect is to compare S-PRV-039 (6% expression) with S-PRV-061 (72% expression), where the same 44 amino acids of parvovirus are involved (Table XIII).

This example provides a demonstration of the second method of expressing a gene in herpesvirus. To practice the invention, a fusion should be made by putting at the amino terminus a gene that is well expressed, and putting at the carboxy terminus a gene that is less well expressed. The order of these two genes must not be altered to benefit from the invention.

TABLE XIII

| EXPRESSION OF BETA-GAL IN FUSIONS WITH PARVOVIRUS B-GENE | | |
|---|---|---|
| VIRUS | INSERT | EXPRESSION OF B-GAL |
| control | | |
| S-PRV-043 | β-GAL ALONE | 100% |
| amino fusions | | |
| S-PRV-039 | 44aaPPV/β-gal | 6% |
| S-PRV-049 | 212aaPPV/β-gal | 0.2% |
| carboxy fusions | | |
| S-PRV-061 | β-gal/4 aaPPV | 72% |
| S-PRV-060 | β-gal/260aaPPV | 68% |
| S-PRV-065 | β-gal/666aaPPV | 58% |

Example 26

S-PRV-065

S-PRV-065 is a pseudorabies virus that has a deletion in the TK gene in the long unique region, and a deletion in the repeat region. A gene coding for a fusion protein between *E.coli* beta-galactosidase (lacZ gene) and the swine parvovirus A capsid was inserted into the repeat regions.

This virus is an example of a unique method for expressing foreign antigens from a herpesvirus vector. This method involves the construction of herpesvirus containing a gene which codes for the foreign antigen as a carboxyl-terminal fusion to *E.coli* beta-galactosidase. This method has several advantages over previously known approaches. First and foremost this method often results in a dramatic increase in the absolute amount of antigen produced from the recombinant virus. Second the method as performed here results in an enzymatically active fusion protein, which allows the recombinant virus to be purified by the BLUOGAL SCREEN FOR RECOMBINANT HERPESVIRUS procedure. Third the resulting protein can easily be characterized by the WESTERN BLOTTING procedure using commercially available antibody to E.coli beta-galactosidase.

Figure 41:
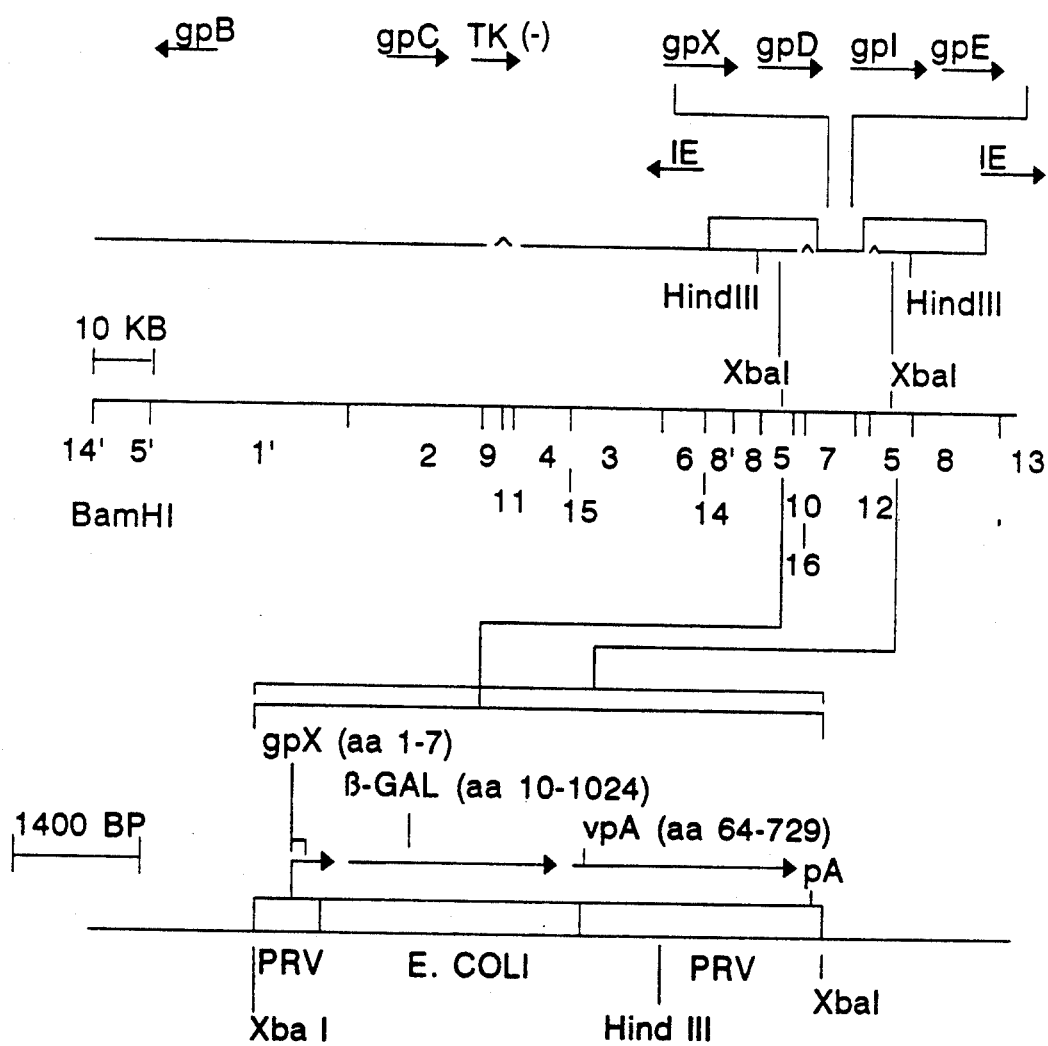

The DIRECT LIGATION PROCEDURE FOR GENERATING RECOMBINANT HERPESVIRUS was used to construct PRV-065. This procedure requires a parental virus DNA, a parental plasmid DNA, and a specific restriction enzyme. The parental virus DNA was from PRV-002 deposited under ATCC Accession No. VR2107 and described in parent application U.S. Ser. No. 773,043, filed Sep. 6, 1985. The parental plasmid DNA was from 244-25.3D (see FIG. 40) and the restriction enzyme used was Xba I. The plasmid 244-24.3D contains an E. coli beta-galactosidase-swine parvovirus fusion gene as an Xba I fragment in the plasmid vector pSP65. Several segments of NDA were linked together utilizing either naturally occurring restriction sites or synthetic linker DNA. The detailed structure of this gene is shown in FIG. 40. The first segment of DNA (segment 1 in FIG. 40) contains the gpX promoter including the first seven amino acids of the gpX coding region and was derived from a subclone of the PRV Bam HI number 10 fragment as an approximately 400 base pair Sal I to Bam HI fragment. The second segment of DNA (segment 2 in FIG. 40) contains the E.coli beta-galactosidase coding region from amino acid 10 to amino acid 1024 and was derived from the plasmid pJF571 (obtained from Jim Hoch, Scripps Clinic and Research Foundation) as two fragments of DNA, an approximately 3000 base pair BAM HI to Nde I fragment followed by an approximately 55 base pair Nde I to Pvu II fragment. The third segment of DNA (segment 3 in FIG. 40) contains the swine parvovirus capsid A coding region from amino acid 64 to amino acid 729 and can be derived from swine parvovirus replicative form DNA (68) as two fragments of DNA, an approximately 1600 base pair Pvu II to Nde I fragment followed by an approximately 450 base pair Nde I to Rsa I fragment. These segments were assembled as indicated in FIG. 40. The recombinant virus resulting from this construction was purified by the BLUOGAL SCREEN FOR RECOMBINANT HERPESVIRUS and confirmed by restriction analysis of viral DNA prepared from the purified virus. This virus was designated S-PRV-065 and has been deposited with the ATCC under Accession No. VR 2215. The structure of PRV-065 is shown in FIG. 41.

Figure 42:

Expression of the parvovirus antigen was assayed in vitro utilizing the WESTERN BLOTTING PROCEDURE. Cell lysates were prepared as described in PREPARATION OF HERPESVIRUS CELL LYSATES. FIG. 42 shows that a band of the expected size (185 kilodaltons) for a beta-galactosidase-swine parvovirus capsid A fusion protein reacts specifically with an antibody directed against beta-galactosidase. Based on comparisons to known amounts of purified beta-galactosidase protein it is estimated that ~30 ng of parvovirus capsid A are produced from an infection of a 60 mm petri dish of vero cells with S-PRV-065. Expression of the parvovirus antigen was also assayed in vitro using the ELISA ASSAY FOR PARVOVIRUS ANTIGEN. Table XIV shows that S-PRV-065 expresses antigen which reacts specifically with antibody directed against parvovirus protein.

Results of an experiment in which weaned pigs were vaccinated with S-PRV-065 as shown in Table XV, indicate that S-PRV-065 may be used as a vaccine to protect swine against parvovirus infection. Following vaccination all animals were free of adverse reactions and five out of five pigs developed serum neutralizing antibodies to swine parvovirus. After challenge vaccinated animals exhibited a significant reduction in viremia relative to non vaccinated control animals.

TABLE XIV

| SAMPLE LYSATE | MEAN ABSORBANCE VALUE |
|---|---|
| Uninfected cells | 0.181 |
| PRV-013 | 0.074 |
| PRV-040 | 0.300 |
| PRV-065 | 0.511 |
| PRV-086 | 0.440 |
| PRV-098 | 0.598 |

ELISA ASSAY FOR PARVOVIRUS ANTIGEN A sandwhich ELISA was conducted by coating a microwell plate with polyclonal rabbit antiserum made against cesium chloride-purified porcine parvovirus. Lysates of infected cells were added to the coated plates and reacted for 90 minutes. The wells were washed and reacted with a polyclonal mouse antiserum against porcine parvovirus. A biotin/avidin anti-mouse IgG, conjugated to horse radish peroxidase, was then added and the reaction was read at 405 nm.

TABLE XV

| VACCINE GROUP | PIG NO. | PPV SN - DAYS POST VACCINATION | | | | PPV VIREMIA DAYS POST CHALLENGE* | | | | | | |
|---|---|---|---|---|---|---|---|---|---|---|---|---|
| | | 0 | 28 | 35 | 42 | 1 | 2 | 3 | 4 | 5 | 6 | 7 |
| PRV-065 DOSE 1 DAY 0 | 120 | <2 | 2 | 2 | 4 | − | − | − | + | − | + | − |
| | 121 | <2 | 2 | 2 | 2 | − | − | − | − | + | + | + |
| | 122 | <2 | 2 | 4 | 2 | − | − | − | − | − | + | − |
| DOSE 2 DAY 28 | 123 | <2 | 4 | 4 | 2 | − | − | − | − | + | + | − |
| | 124 | <2 | 32 | 8 | 32 | + | − | − | − | − | − | − |
| CONTROLS | E-11 | NOT APPLICABLE** | | | | − | − | + | + | + | + | − |
| | E-12 | | | | | − | + | − | + | + | + | + |

*Challenge administred on day 56
**Pigs were added to the study at the time of challenge
−Lymphocytes negative for PPV
+Lymphocytes positive for PPV Example 27

S-PRV-086

S-PRV-086 is a pseudorabies virus that has a deletion in the TK gene in the long unique region, a deletion in the repeat region and a deletion in the gpX coding region. A gene coding for a fusion protein between E.coli beta-galactosidase (lacZ gene) and the swine parvovirus A capsid was inserted into the deletion in the gpX coding region.

This virus is an example of combining the unique method of expression of a foreign antigen described for PRV-065 (Example 26) with increased safety and negative sero-logical marker described for PRV-013 (Example 6).

Figure 43B:
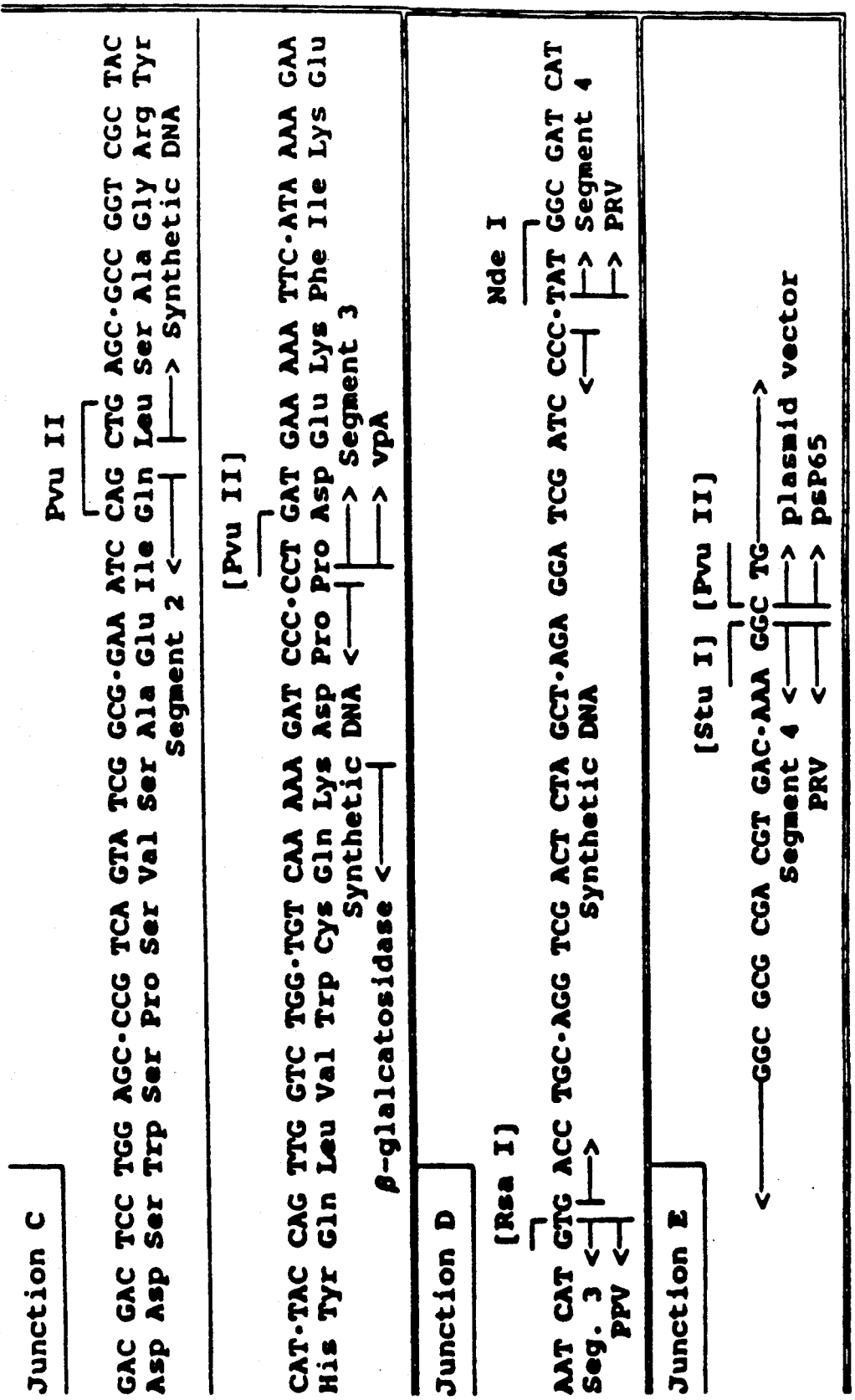

S-PRV-086 was constructed by homologous recombination using the DNA TRANSFECTION FOR GENERATING RECOMBINANT PRV. This procedure requires a parental virus DNA and a homologous recombination plasmid DNA. The parental virus DNA was from PRV-002 deposited under ATCC Accession No. VR2107 and described in U.S. Ser. No. 773,403, filed Sep. 6, 1985, and the homologous recombination plasmid was 244-49.2H (see FIG. 43). The plasmid 244-49.2H contains an E.coli beta-galactosidase-swine parvovirus fusion gene flanked by PRV DNA homologous to the gpX region cloned in the plasmid vector pSP65. Several segments of DNA were linked together utilizing either naturally occurring restriction sites and/or synthetic linker DNA. The detailed structure of this gene is shown in FIG. 43. The first segment of DNA (segment 1 in FIG. 43) contains the gpX promoter including the first seven amino acids of the gpX coding region and was derived from a subclone of the PRV Bam HI number 10 fragment as an approximately 1400 base pair Eco RV to Bam HI fragment. The second segment of DNA (segment 2 in FIG. 43) contains the E.coli beta-galactosidase coding region from amino acid 10 to amino acid 1024 and was derived from the plasmid pJF751 (obtained from Jim Hoch, Scripps Clinic and Research Foundation) as two fragments of DNA, an approximately 3000 base pair Bam HI to Nde I fragment followed by an approximately 55 base pair Nde I to Pvu II fragment. The third segment of DNA (segment 3 in FIG. 43) contains the swine parvovirus capsid A coding region from amino acid 64 to amino acid 729 and can be derived from swine parvovirus replicative form DNA (68) as two fragments of DNA, an approximately 1600 base pair Pvu II to Nde I fragment followed by an approximately 450 base pair Nde I to RSA I fragment. The fourth segment (segment 4 in FIG. 43) contains the gpX poly A addition signal and was derived from a sub-clone of the PRV Bam HI fragment number 7 as an approximately 1800 base pair Nde I to Stu I fragment. These segments were assembled as indicated in FIG. 43. The recombinant virus resulting from this construction was purified by the BLUOGAL SCREEN FOR RECOMBINANT HERPESVIRUS and confirmed by restriction analysis of viral DNA prepared from the purified virus. This virus was designated S-PRV-086 and has been deposited with the ATCC under Accession No. VR 2216. The structure of PRV-086 is shown in FIG. 44.

Expression of the parvovirus antigen was assayed in vitro utilizing the WESTERN BLOTTING PROCEDURE. Cell lysates were prepared as described in PREPARATION OF HERPESVIRUS CELL LYSATES. FIG. 42 shows that a band of the expected size (180 kilodaltons) for a beta-galactosidase-swine parvovirus capsid A fusion protein reacts specifically with an antibody directed against beta-galactosidase. Based on comparisons to known amounts of purified beta-galactosidase protein it is estimated that ~15 ng of parvovirus capsid A are produced from an infection of a 60 mm petri dish of vero cells with S-PRV-086.

Results of an experiment in which weaned pigs were vaccinated with S-PRV-086 as shown in Table XVI, indicate that S-PRV-086 may be used as a vaccine to protect swine against parvovirus infection. Following vaccination all animals were free of adverse reactions and two out of three pigs developed serum neutralizing antibodies to swine parvovirus. After challenge vaccinated animals exhibited a significant reduction in viremia relative to non vaccinated control animals.

TABLE XVI

| VACCINE GROUP | PIG NO. | PPV SN POST VAC | | PPV VIREMIA DAYS POST CHALLENGE* | | | | | |
|---|---|---|---|---|---|---|---|---|---|
| | | 0 | 42 | 2 | 4 | 6 | 8 | 10 | 12 |
| PRV-040 DAY 0 | 34 | <2 | 4 | − | − | + | − | + | − |
| | 36 | <2 | 2 | − | − | − | − | − | − |
| PRV-040 DAY 21 | 37 | <2 | <2 | − | − | − | − | − | − |
| PRV-086 DAY 0 | 38 | <2 | 2 | − | + | − | − | − | − |
| | 39 | <2 | 4 | + | + | + | − | − | − |
| PRV-086 DAY 21 | 40 | <2 | <2 | − | + | + | + | − | − |
| CONTROLS | 41 | | <2 | + | + | + | + | + | − |
| | 42 | <2 | | + | + | − | + | + | − |

*Challenge administred on day 42
−Lymphocytes negative for PPV
+Lymphocytes positive for PPV Example 28

S-PRV-040

S-PRV-040 is a pseudorabies virus that has a deletion in the TK gene in the long unique region and a deletion in the repeat region. A gene coding for a fusion protein between the pseudorabies gpX secretion signal sequence and the swine parvovirus A capsid was inserted into the repeat regions.

This virus is an example of a unique method for expressing foreign antigens from a herpesvirus vector. This method involves the construction of herpesvirus containing a gene which codes for the foreign antigen as a carboxyl-terminal fusion to a herpesvirus secretion signal sequence. This method has several advantages over previously known approaches. First, this method often results in an increase in the absolute amount of antigen produced from the recombinant virus. Second, the method often results in the secretion of the foreign antigen from cells infected with the herpesvirus vector. Third, the secretion signal is often cleaved from the fusion protein resulting in a protein more closely resembling the unfused antigen.

The DIRECT LIGATION PROCEDURE FOR GENERATING RECOMBINANT HERPESVIRUS was used to construct PRV-040. This procedure requires a parental virus DNA, a parental plasmid DNA, and a specific restriction enzyme. The parental virus DNA was from PRV-002 deposited under ATCC Accession No. VR2107 and described in U.S. Ser. No. 773,403, filed Sep. 6, 1985, the parental plasmid DNA was from 167-72.54G (see FIG. 45) and the restriction enzyme used was Xba I. The plasmid 167-72.54G contains a PRV gpX secretion signal-swine parvovirus fusion gene as an Xba I fragment in the plasmid vector pSP65. Several segments of DNA were linked together utilizing either naturally occurring restriction sites and/or synthetic linker DNA. The detailed structure of this gene is shown in FIG. 45. The first segment of DNA (segment 1 in FIG. 45) contains the gpX promoter including the first twenty-seven amino acids of the gpX coding region and was derived from a subclone of the PRV Kpn J' fragment as an approximately 500 base pair Sal I to Sac I fragment. The second segment of DNA (segment 2 in FIG. 45) contains the swine parvovirus capsid A coding region from amino acid 64 to amino acid 729 and can be derived from swine parvovirus replicative form DNA (68) as two fragments of DNA, an approximately 1600 base pair Pvu II to Nde I fragment followed by an approximately 450 base pair Nde I to Rsa I fragment. These segments were assembled as indicated in FIG. 45. A recombinant virus transfection stock generated using the DIRECT LIGATION PROCEDURE FOR GENERATING RECOMBINANT HERPESVIRUS was plated out. Twelve plaques were picked and analyzed for the presence of the approximately 2600 base pair parvovirus DNA containing Xba I fragment. Two of the viruses contained the expected Xba I fragment. One of these viruses was designated S-PRV-040 and has been deposited with the ATCC under Accession No. VR2214. The structure of PRV-040 is shown in FIG. 46.

Results of an experiment in which weaned pigs were vaccinated with S-PRV-040 as shown in Table XVI indicate that S-PRV-040 may be used as a vaccine to protect swine against parvovirus infection. Following vaccination all animals were free of adverse reactions and two out of three pigs developed serum neutralizing antibodies to swine parvovirus. After challenge vaccinated animals exhibited a significant reduction in viremia relative to non vaccinated control animals.

Example 29

S-PRV-098

S-PRV-098 is a pseudorabies virus that has a deletion in the TK gene in the long unique region, a deletion in the repeat region and a deletion in the gpX coding region. A gene coding for a fusion protein between E.coli beta-galactosidase (lacZ gene) and the swine parvovirus A capsid was inserted into the deletion in the gpX ending region. A second gene coding for a fusion protein between the pseudorabies gpX secretion signal sequence and the swine parvovirus A capsid was inserted into the repeat regions.

This virus is an example of combining the unique methods for expression of a foreign antigen described for PRV-065 (Example 26) and for PRV-040 (Example 28) with increased safety and negative sero-logical marker described for PRV-013 (Example 6).

Figure 45B:
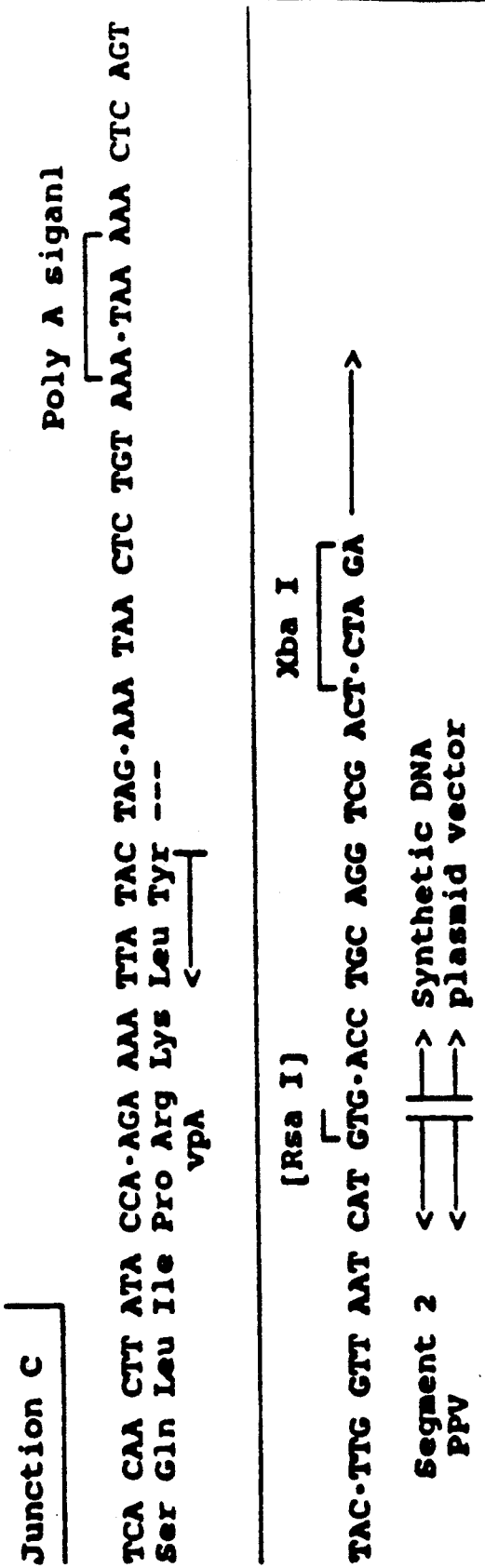

The DIRECT LIGATION PROCEDURE FOR GENERATING RECOMBINANT HERPESVIRUS was used to construct PRV-098. This procedure requires a parental virus DNA, a parental plasmid DNA, and a specific restriction enzyme. The parental virus DNA was from PRV-086 (Example 27), the parental plasmid DNA was from 167-72.54G (see FIG. 45) and the restriction enzyme used was Xba I. The plasmid 167-72.54G contains a PRV gpX secretion signal-swine parvovirus fusion gene as an Xba I fragment in the plasmid vector pSP65.

A virus containing this XbaI insert was purified as described for PRV-040 (Example 28). This virus was designated S-PRV-098 and has been deposited with the ATCC under accession No. VR 2219. The structure of PRV-098 is shown in FIG. 47.

Expression of the parvovirus antigen was assayed in vitro utilizing the ELISA ASSAY FOR PARVOVIRUS ANTIGEN. Table XIV shows that S-PRV-098 expresses the parvovirus antigen which reacts specifically with antibody directed against authentic parvovirus protein.

Example 30

S-PRV-066

S-PRV-066 is a pseudorabies virus that has a deletion in the TK gene in the long unique region, and a deletion in the repeat region. A gene coding for a fusion protein between the pseudorabies gpX secretion signal sequence and the plasmodium falciparum (P.fal.) circumsporozoite protein (CSP) was inserted into the repeat regions.

This virus is an example of a unique method for expressing foreign antigens from a herpesvirus vector. This method involves the construction of herpesvirus containing a gene which codes for the foreign antigen as a carboxyl-terminal fusion to a herpesvirus secretion signal sequence. This method has several advantages over previously known approaches. First, this method often results in an increase in the absolute amount of the antigen produced from the recombinant virus. Second, the method often results in the secretion of the foreign antigen from cells infected with the herpesvirus vector. Third, the secretion signal is often cleaved from the fusion protein resulting in a protein more closely resembling the unfused antigen.

Figure 48B:
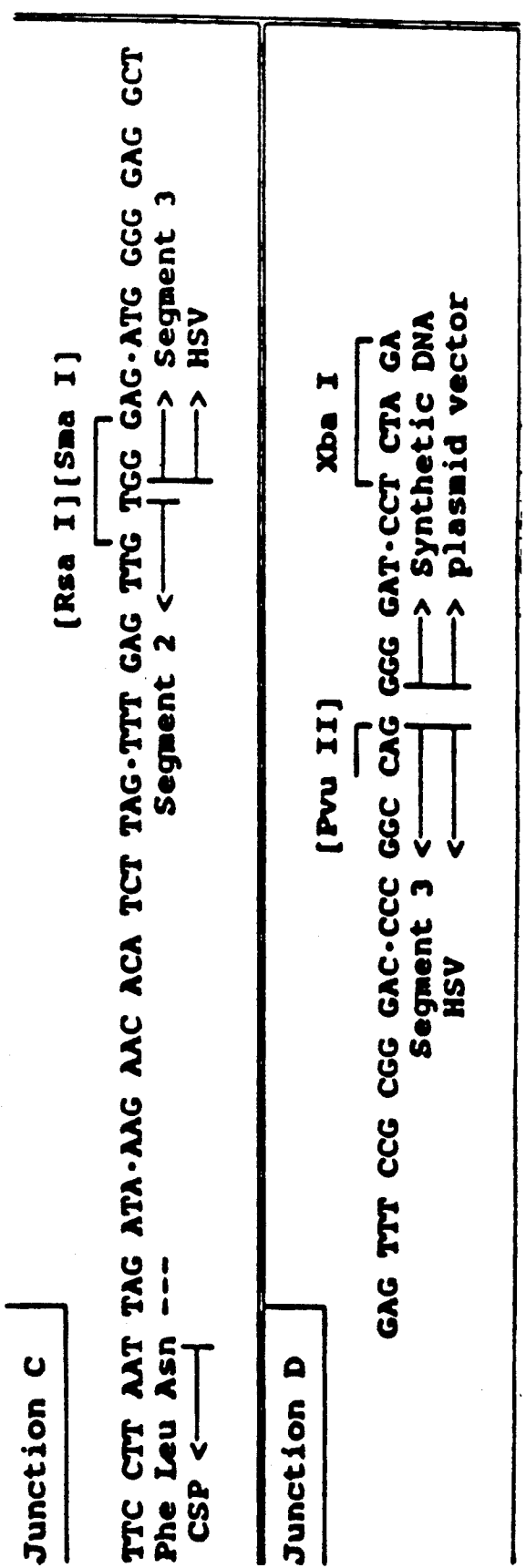
FIG. 48 Description of the DNA insertion in plasmid 181-42.2. Restriction enzymes indicated are those present in the source DNAs mentioned in the text. Restriction enzymes enclosed in brackets indicate sites which were destroyed in the creation of segment junctions.

The DIRECT LIGATION PROCEDURE FOR GENERATING RECOMBINANT HERPESVIRUS was used to construct PRV-066. This procedure requires a parental virus DNA, a parental plasmid DNA, and a specific restriction enzyme. The parental virus DNA was from PRV-002 deposited under ATCC Accession No. VR2107 and described in parent application U.S. Ser. No. 773,403, filed Sep. 6, 1985, the parental plasmid DNA was from 181-42.2 (see FIG. 48) and the restriction enzyme used was Xba I. The plasmid 181-42.2 contains a PRV gpX secretion signal-P.fal.CSP fusion gene as an Xba I fragment in the plasmid vector pSP18. Several segments of DNA were linked together utilizing either naturally occurring restriction sites and/or synthetic linker DNA. The detailed structure of this gene is shown in FIG. 48. The first segment of DNA (segment 1 in FIG. 48) contains the gpX promoter including the first twenty-seven amino acids of the gpX coding region and was derived from a subclone of the PRV Kpn J' fragment as an approximately 500 base pair Sal I to Sac I fragment. The second segment of DNA (segment 2 in FIG. 48) contains the P.fal. CSP coding region from amino acid 19 to amino acid 412 and was derived from plasmid pUC8-/lambda mpf5 (obtained from Institute of Immunology, dept. of the Army, Walter Reed Army Institute of Research) as an approximately 1200 base pair Stu I to Rsa I fragment. The third segment of DNA (segment 3 in FIG. 48) contains the herpes simplex virus (HSV) thymidine kinase (TK) poly A addition signal and was derived from plasmid D 5'-0.20 (68) as an approximately 600 bas pair Sma I to Pvu II fragment. These segments were assembled as indicated in FIG. 48 and used in the DIRECT LIGATION PROCEDURE FOR GENERATING RECOMBINANT HERPESVIRUS. A virus containing the expected Xba I insert was purified as described for PRV-040 (Example 28). This virus was designated S-PRV-066. The structure of PRV-066 shown in FIG. 49.

Expression of the CSP antigen was assayed in vitro utilizing the WESTERN BLOTTING PROCEDURE. Cell lysates were prepared as described in PREPARATION OF HERPESVIRUS CELL LYSATES. FIG. 60 shows that a band of the expected size (~46 kilodaltons) for a gpX secretion signal sequence-P.fal. CSP fusion protein reacts specifically with an antibody directed against the repeat portion of the CSP protein. Based on comparisons to known amounts of purified CSP protein it is estimated that ~2 ng of CSP are produced from an infection of a 60 mm petri dish of vero cells with S-PRV-066.

The potential for PRV-066 to induce an immune response in vivo was assayed. These weaned pigs were vaccinated, and on day 21 post infection one of the pigs demonstrated a clear sero-conversion to the CSP antigen based on ELISA titers (69). This experiment demonstrates the utility of this expression approach to induce an immune response to the CSP antigen in a host animal.

Example 31

S-PRV-088

S-PRV-088 is a pseudorabies virus that has a deletion in the TK gene in the long unique region, a deletion in the repeat region and a deletion in the gpX coding region. A gene for *E.coli* beta-galactosidase (lacZ gene) was inserted into the deletion in the gpX coding region. A second gene coding for an embedded fusion protein between the PRV gpX and the P.fal.CSP was inserted into the repeat regions.

This virus is an example of a unique method for expression of the antigenic determinate of a foreign antigen. This method involves the construction of a herpesvirus containing a gene which codes for a herpesvirus protein in which an antigenic determinate of the herpesvirus protein has been replaced with an antigenic determinant from the foreign antigen. Such a gene contains the foreign determinate as an embedded fusion in the herpesvirus protein. This method has several advantages over previously known approaches. First, this method often results in a dramatic (as much as 5000 fold) increase in the absolute amount of antigenic determinant produced from the recombinant virus. Second, the foreign antigenic determinate often acquires advantageous properties of the herpesvirus protein, such as localization (secreted, surface, or intracellular) and stimulation of the host immune system. Third, the high level of expression of this construct in vitro makes it feasible to purify this antigen from tissue culture for use as a subunit vaccine.

Figure 51B:
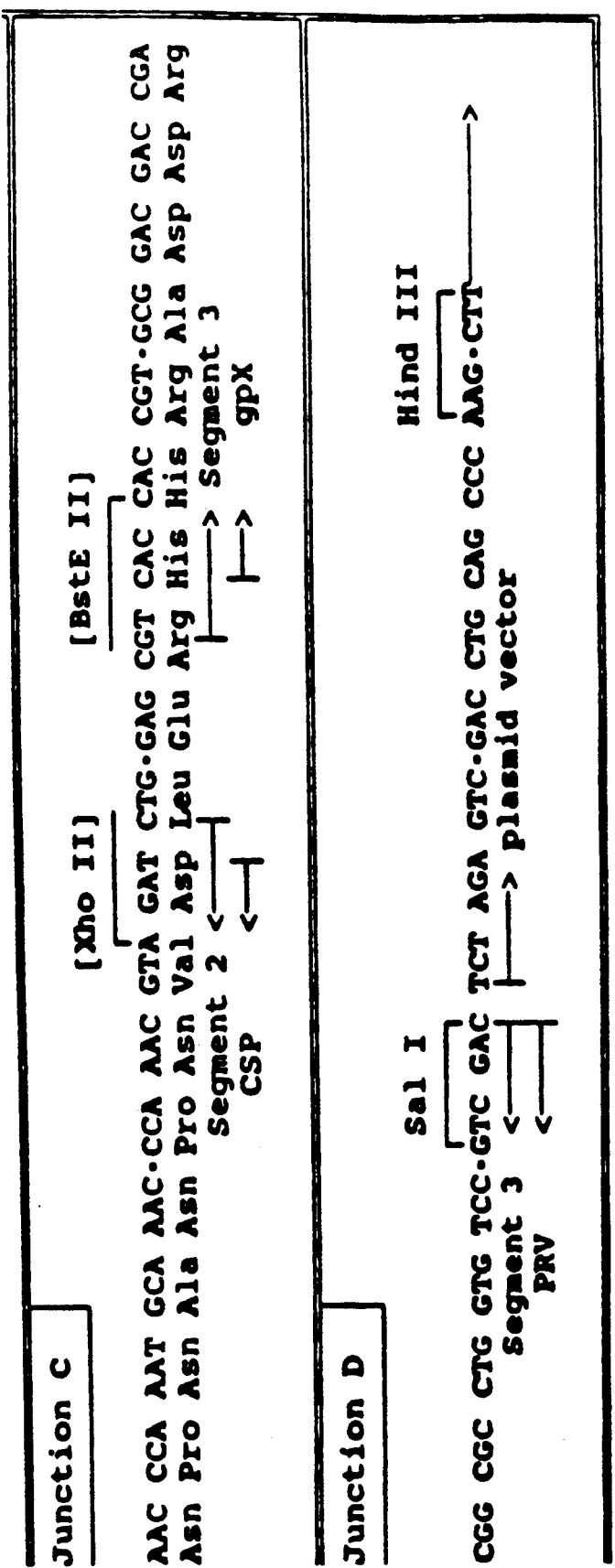
Figure 52:
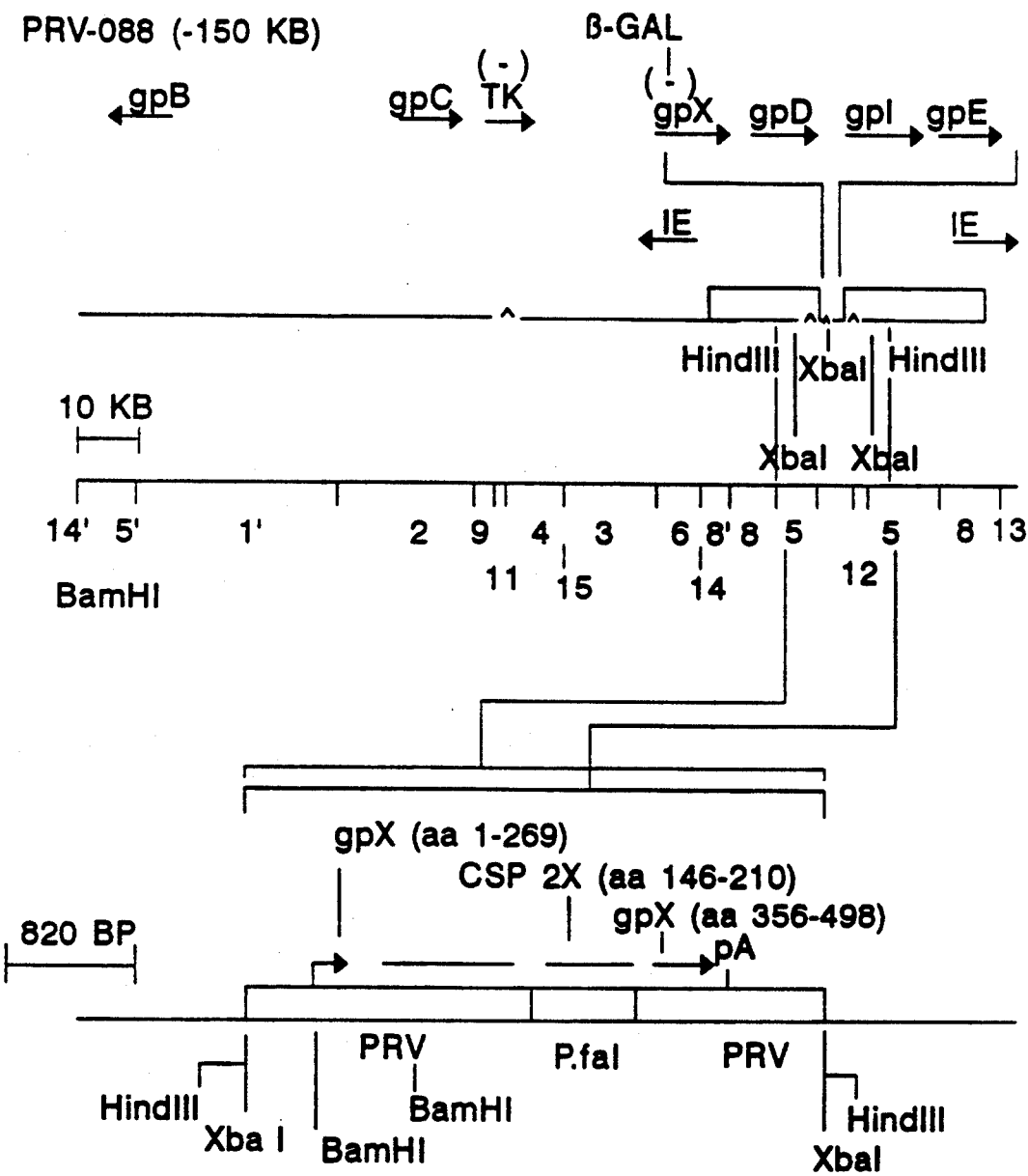
Figures 53A, 53B:
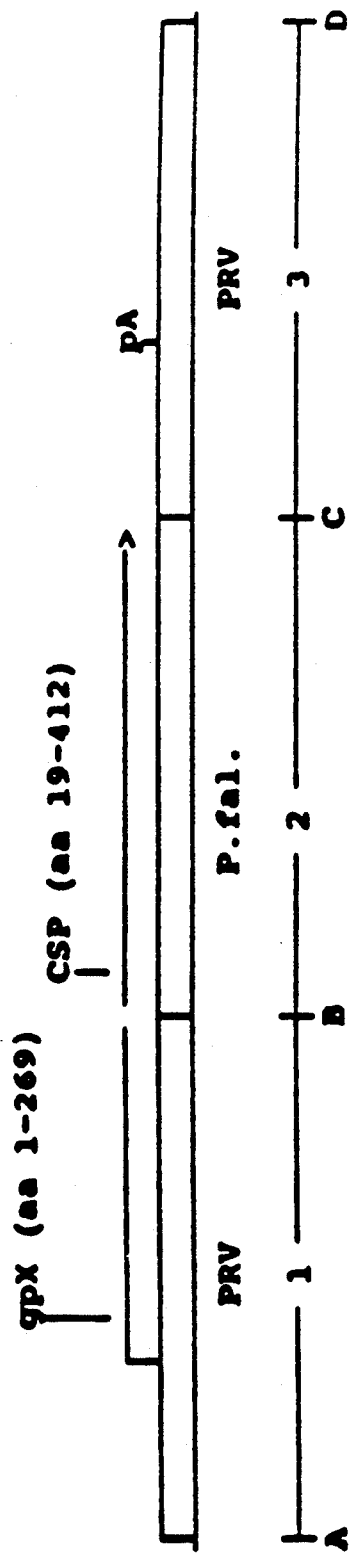
Figure 53B:
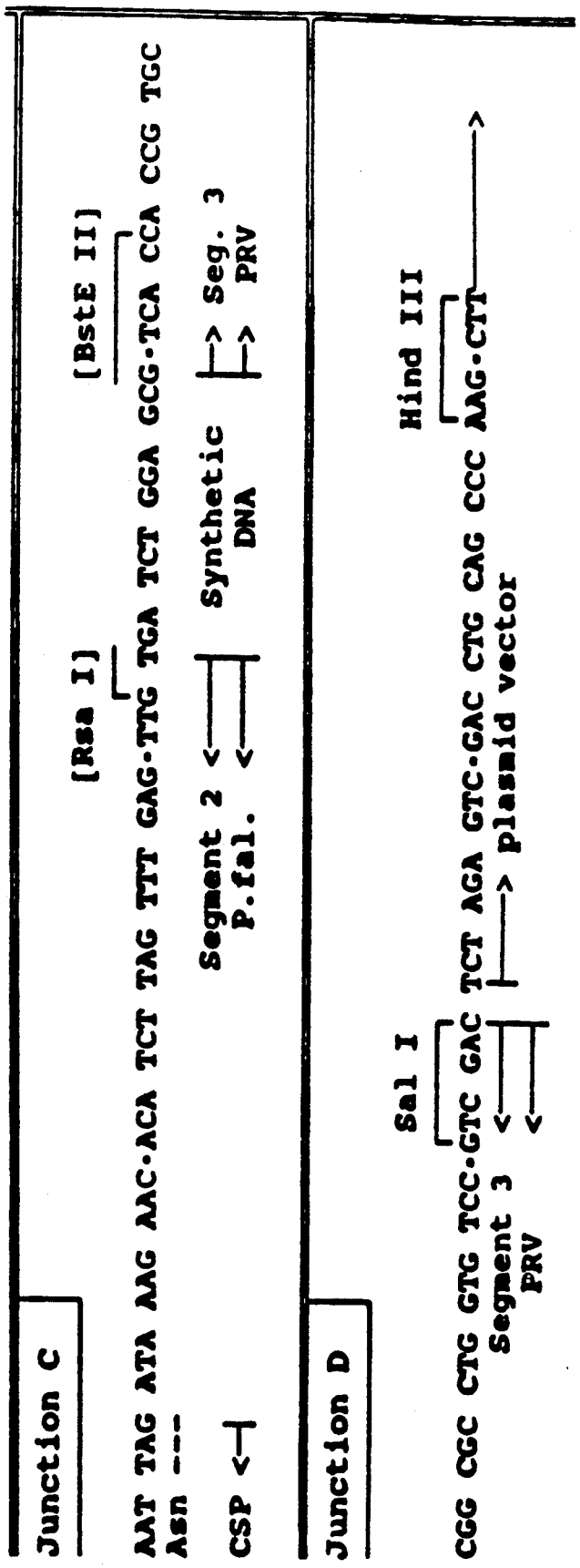

The DIRECT LIGATION PROCEDURE FOR GENERATING RECOMBINANT HERPESVIRUS was used to construct PRV-088. This procedure requires a parental virus DNA, a parental plasmid DNA, and a specific restriction enzyme. The parental virus DNA was from PRV-013 (example 2), the parental plasmid DNA was from PSY1373 (see FIG. 51) and the restriction enzyme used was Hind III. The plasmid PSY1373 contains a PRV gpX-P.fal.CSP embedded fusion gene as a Hind III fragment in the plasmid vector pSP65. The antigenic determinate to be replaced in gpX as identified by computer analysis of the gpX amino acid sequence. The site was confirmed by raising rabbit anti-serum against a chemically-synthesized peptide (peptide 85.12 amino acids 299 to 316) and showed that anti-serum to react specifically with the naturally synthesized gpX protein (see example 2, FIG. 4). The antigenic determinant of the P.fal.CSP was determined by Dame, et al. (69) and is composed of tandem repeats of the tetrapeptide asn-ala-asn-pro. In order to construct the appropriate embedded fusion several segments of DNA were linked together utilizing either naturally occurring restriction sites and/or synthetic linker DNA. The detailed structure of this gene is shown in FIG. 51. The first segment of DNA (segment 1 in FIG. 51) contains the gpX promoter and the first two hundred and sixty-nine amino acids of the gpX coding region and was derived from a subclone of the PRV Kpn J′ fragment as an approximately 12000 base pair Sal I to BstE II fragment. The second segment of DNA (segment 2 in FIG. 51) contains the P.fal. antigenic determinate as ~32 tandem repeats of the tetrapeptide and can be derived from plasmid pUC8/lambda mpf5 (obtained from Institute of Immunology, Dept. of the Army, Walter Reed Army Institute of Research) as two copies of approximately 200 base pair Xho II to Xho II fragment of DNA (note this fragment when ligated at its Xho II ends in the same translational orientation retains the reading frame of the CSP). The third segment (segment 3 in FIG. 51) contains the C-terminal region of gpX (amino acids 356 to 498) including the poly A addition signal and can be derived from a subclone of the PRV BAM HI number 10 fragment as an approximately 1100 base pair BstE II to Sal I fragment of DNA.

These segments were assembled as indicated in FIG. 31A and used in the DIRECT LIGATION PROCEDURE FOR GENERATING RECOMBINANT HERPESVIRUS. A virus containing the expected Hind III insert was purified as described for PRV-040 (Example 28). This virus was designated S-PRV-088 and has been deposited with the ATCC under Accession No. VR 2217. The structure of PRV-088 is shown in FIG. 52.

Expression of CSP antigen was assayed in vitro utilizing the WESTERN BLOTTING PROCEDURE. Cell lysates were prepared as described in PREPARATION OF HERPESVIRUS CELL LYSATES. FIG. 50 shows that a band of the expected size (~60 kilodaltons) for the gpX-P.fal. CSP embedded fusion protein reacts specifically with an antibody directed against the repeat portion of the CSP protein. Based on comparisons to known amounts of purified CS protein it is estimated that ~25 lg of CSP are produced from an infection of a 60 mm petri dish of vero cells with S-PRV-088.

Example 32

S-PRV-093

S-PRV-093 is a pseudorabies virus that has a deletion in the TK gene in the long unique region, a deletion in the repeat region and a deletion in the gpX coding region. A gene for *E.coli* beta-galactosidase (lacZ gene) was inserted into the deletion in the gpX coding region. A second gene coding for a hybrid protein between the PRV gpX and the P.fal CSP was inserted into the repeat regions.

This virus is an example of a unique method for expression of a foreign antigen. This method involves the construction of a herpesvirus containing a gene which codes for a hybrid protein the amino terminal portion of which is a herpesvirus protein and the carboxyl-terminal portion of which is the foreign antigen. This method has several advantages over previously known approaches. First, this method often results in an increase in the absolute amount of antigen produced from the recombinant virus. Second, the foreign antigen often has advantageous properties of both the herpesvirus protein and the foreign antigen. These properties may include localization (secreted, surface, or intracellular) and stimulation of the host immune system.

The DIRECT LIGATION PROCEDURE FOR GENERATING RECOMBINANT HERPESVIRUS was used to construct PRV-093. This procedure requires a parental virus DNA was from PRV-013 (Example 2), the parental plasmid DNA was from 181-66.26 (see FIG. 53) and the restriction enzyme used was Hind III. The plasmid 181-66.26 contains a PRV gpX-P.fal.CSP hybrid gene as a HIND III fragment in the plasmid vector pSP65. In order to construct the appropriate hybrid fusion several segments of DNA were linked together utilizing either naturally occurring restriction sites and/or synthetic linker DNA. The detailed structure of this gene is shown in FIG. 53. The first segment of DNA (segment 1 in FIG. 53) contains the gpX promoter and the first two hundred and sixty-nine amino acids of the gpX coding region and was derived from a subclone of the PRV Kpn J' fragment as an approximately 12000 base pair Sal to BstE II fragment. The second segment of DNA (segment 2 in FIG. 53) contains the P.fal.CSP coding region from amino acid 19 to amino acid 412 and was derived from plasmid pUC8/lambda mpf5 (obtained from Institute of Immunology, Dept. of the Army, Walter Reed Army Institute of Research) as an approximately 1200 base pair Stu I to Rsa I fragment. The third segment (segment 3 in FIG. 53) contains the gpX poly A addition signal and can be derived from a subclone of the PRV Bam HI number 10 fragment as an approximately 1100 base pair BstE II to Sal I fragment of DNA. These segments were assembled as indicated in FIG. 53 and used in the DIRECT LIGATION PROCEDURE FOR GENERATING RECOMBINANT HEPESVIRUS. A virus containing the expected Hind III insert was purified as described for S-PRV-040 (example 28). This virus was designated S-PRV-093 and has been deposited with the ATCC under Acession No. VR 2218. The structure of PRV-093 is shown in FIG. 54.

Expression of the CSP antigen was assayed in vitro utilizing the WESTERN BLOTTING PROCEDURE. Cell lysates were prepared as described in PREPARATION OF HERPESVIRUS CELL LYSATES. FIG. 50 shows that a band of the expected size (~72 kilodaltons) for the gpX-P.fal. CSP hybrid protein reacts specifically with an antibody directed against the repeat portion of the CSP protein. Based on comparisons to known amounts of purified CS protein it is estimated that ~600 ng of CSP are produced from an infection of a 60 mm petri dish of vero cells with S-PRV-093.

REFERENCES

1. Maniatis et al., Molecular Cloning: A Laboratory Manual, Cold Spring Harbor Laboratory Press (1982).
2. S. L. Mansour, et al., Proceeding of the National Academy of Science U.S.A. 82, 1359–1363 (1985).
3. C. Thummel, et al., Cell, 33, 455–464 (1983).
4. D. Scolnick, Cell, 24, 135–143 (1981).
5. C. Thummel et al., Cell 23, 825–836 (1981).
6. M. Mackett et al., Proc. Natl. Acad. Sci. USA, 79, 7415–7419 (1982).
7. D. Panicali and E. Paoletti, Proc. Natl. Acad. Sci. USA, 79, 4927–4931 (1982).
8. E. Paoletti et al., Proc. Natl. Acad. Sci. USA, 81, 193–197 (1984).
9. G. L. Smith et al., Nature, 302, 490–495 (1983).
10. D. Pancicali et al., Proc. Natl. Acad. Sci. USA, 80, 5364–5368 (1983).
11. G. L. Smith et al., Proc. Natl. Acad. Sci. USA, 80, 7155–7159 (1983).
12. G. L. Smith et al., Science, 224, 397–399 (1984).
13. M. Mackett et al., Science, 227, 433–435 (1985).
14. D. M. Knipe et al., Proc. Natl. Acad. Sci. USA, 75, 3896–3900 (1978).
15. E. S. Mocarski et al., Cell, 22, 243–255 (1980).
16. L. E. Post et al., Cell, 24, 555–565 (1981).
17. L. E. Post and B. Roizman, Cell, 25, 227–232 (1981).
18. K. L. Poffenberger et al., Proc. Natl. Acad. Sci. USA, 80, 2690–2694 (1981).
19. M. G. Gibson and P. G. Spear, Journal of Virology, 48, 396–404 (1983).
20. G. T.-Y. Lee et al., Proc. Natl. Acad. Sci. USA, 79, 6612–6616 (1982).
21. M. -F. Shih et al., Proc. Natl. Acad. Sci. USA, 81, 5867–5870 (1984).
22. R. Desrosiers et al., Ninth Annual Herpesvirus Meeting, Seattle, Abstract #280 (1984).
23. T. J. Rea, et al., Journal of Virology 54: 21–29 (1984).
24. S. Ihara et al., Virology, 122, 268–278 (1982).
25. S. Kit et al., American Journal of Veterinary Research 46, 1359–1367 (1985).
26. A Berns et al., J. Virology, 53, 89–93 (1985).
27. B. Lomniczi et al., J. Virology, 49, 970–979 (1984).
28. Y. Haj-Ahmed and F. L. Graham, J. Virology, 57, 267–274 (1986).
29. J. H. Gillespie et al., J. Clin. Microbiology, 23, 283–288 (1986).
30. M. Arsenakis and B. Roizman, in "The High Technology Route to Virus Vaccines", American Society for Microbiology, Washington, D.C., 1985 (Proceedings of the First Annual Southwest Foundation for Biomedical Research Internatinal Symposium, Houston, Tex., Nov. 8–10, 1984).
31. L. E. Post et al., Tenth International Herpesvirus Workshop, Ann Arbor, August, 1985.
32. F. L. Graham and A. Van der Eb, Virology, 52, 556–567, 1973.
33. P. A. Norton and J. M. Coffin, Molecular and Cellular Biology 5, 281–290, 1985.
34. T. Igarashi, et al., 10th International Herpesvirus Workshop, Abstract No. 17, Ann Arbor, Mich., August 1985.
35. J. Campione - Piccardo, et al., J. Virology 31, 281–287, 1979.
36. L. Villarreal and P. Berg, Science 196, 183–185 (1977).
37. S. B. Mohanty and S. K. Dutta, *Veterinary Virology*, Lea and Febiger, pubs., Philadelphia (1981).
38. R. Crandell in *Current Veterinary Therapy*, pages 543–546, W. B. Saunders, pubs., Philadelphia (1981).
39. H. Ludwig in *The Herpesviruses*, Vol. 2, B. Roizman, ed., Plenum Press (1983).
40. R. B. Tenser et al., k J. Clinical Microbiol. 17; 122–127 (1983).
41. Y-C. Cheng et al., J. Virological Methods 5, 209–217 (1982).
42. U. K. Laemmli, Nature 227, 680–685 (1970).
43. K. Fukuchi, et al., J. of Virology 51, 102–109, (1984).
44. M. A. Richardson et al., J. Virology 51, 860, 1985.
45. R. W. Price and A. Kahn, Infection and Immunity 34, 571–580, 1981.
46. P. B. Tenser, et al., Journal of General Virology 64, 1369–1373, 1983.
47. S. Kit, et al., Ninth International Herpesvirus Workshop, Seattle, Aug. 24–29, 1984.
48. Roizman, et al., Coldspring Harbor Conference on New Aproaches to Viral Vaccines, September, 1983.
49. R. L. Thompson, et al., Virology 131, 180–192, 1983.
50. K. Fukuchi, et al., Proc. Natl. Acad. Sci. (USA) 82, 751–754, 1985.
51. J. M. Koomey, et al., Journal of Virology 50, 662–665, 1984.
52. T. C. Holland, et al., Journal of Virology, 52, 566–574, 1984.
53. A. E. Churchill, et al., Journal of General Virology 4, 557–563, 1969.
54. M. W. Wathan and L. M. K. Wathan, Journal of Virology 58, 173–178, 1986.
55. T. C. Mettenleiter, et al., Journal of Virology 56, 307–311, 1985.

56. J. T. Van Oirschot, et al., Journal of General Virology 67, 1179-1182, 1986.
57. Gubler, U., and Hoffman, B. J., Gene 25, 263-269, 1983.
58. Hanahan, D., Molecular Biology 166, 557-580, 1983.
59. Hu, S., et al., in *Modern Approaches to Vaccines,* R. M. Chanock and R. A. Lerner, eds., 219-223, Cold Spring Harbor Press (1984).
60. N. Elango, et al., Journal of Virology, 57, 481-489 (1986).
61. M. K. Spriggs and P. L. Collins, Journal of Virology, 59, 646-654 (1986).
62. B. M. Blumberg, et al., Journal of General Virology, 66, 317-331 (1985).
63. P. J. Hudson, et al., Nucleic Acid Research, 14, 5001-5012 (1986).
64. McKnight, S. L. and Kingbury, R., Science 217, 316-324.
65. Jagadish, M. N., et al., J. of Virol, 62, 1084-1087 (1988).
66. R. J. Isfort, et al., Ninth International Herpesvirus Workshop, Abstract #146, Seattle, Wash., August 1984.
67. Miller, J. H. (Ed.), *Experiments in Molecular Genetics,* 362-355, Cold Spring Harbor Laboratory Press (1972).
68. Hirt, B., J. Mol. Biol. 26:365-369 (1967).
69. McKnight, S. L. and Gravis, E. R., Nucleic Acids Research, 8, 3931-3949 (1980).
70. Dame, J. B., et al., Science 225, 593-599 (1984).

What is claimed is:

1. An attenuated, hybrid, nonprimate herpesvirus, designated S-PRV-055 and deposited under ATCC Accession No. VR 2179.

2. An attenuated, pseudorabies virus designated S-PRV-065 and deposited under ATCC Accession No. VR 2215.

3. An attenuated, hybrid, nonprimate herpesvirus designated S-PRV-086 and deposited under ATCC No. VR 2216.

4. An attenuated, hybrid, nonprimate herpesvirus designated S-PRV-040 and deposited under ATCC No. VR 2214.

5. An attenuated, hybrid, nonprimate herpesvirus designated S-PRV-098 and deposited under ATCC No. VR 2219.

6. An attenuated, hybrid, nonprimate herpesvirus designated S-PRV-088 and deposited under ATCC No. VR 2217.

7. An attenuated, hybrid, nonprimate herpesvirus designated S-PRV-093 and deposited under ATCC No. VR 2218.

* * * * *